US011414707B2

(12) United States Patent
Modlin et al.

(10) Patent No.: US 11,414,707 B2
(45) Date of Patent: Aug. 16, 2022

(54) METHODS FOR COLON CANCER DETECTION AND TREATMENT

(71) Applicant: Liquid Biopsy Research LLC, Charlestown (KN)

(72) Inventors: Irvin Mark Modlin, Woodbridge, CT (US); Mark Kidd, New Haven, CT (US); Ignat Drozdov, Warwick (GB)

(73) Assignee: Liquid Biopsy Research LLC, Charlestown (KN)

( * ) Notice: Subject to any disclaimer, the term of this patent is extended or adjusted under 35 U.S.C. 154(b) by 432 days.

(21) Appl. No.: 16/253,697

(22) Filed: Jan. 22, 2019

(65) Prior Publication Data

US 2019/0226030 A1 Jul. 25, 2019

Related U.S. Application Data

(60) Provisional application No. 62/620,015, filed on Jan. 22, 2018.

(51) Int. Cl.

*C12Q 1/68* (2018.01)
*C12Q 1/6886* (2018.01)
*A61P 35/00* (2006.01)
*G16B 20/20* (2019.01)
*G16B 40/00* (2019.01)
*A61K 31/496* (2006.01)
*A61K 31/513* (2006.01)
*A61K 31/7072* (2006.01)
*C07K 16/28* (2006.01)
*C12Q 1/6827* (2018.01)
*C12Q 1/686* (2018.01)

(52) U.S. Cl.

CPC .......... *C12Q 1/6886* (2013.01); *A61K 31/496* (2013.01); *A61K 31/513* (2013.01); *A61K 31/7072* (2013.01); *A61P 35/00* (2018.01); *C07K 16/2803* (2013.01); *C12Q 1/686* (2013.01); *C12Q 1/6827* (2013.01); *G16B 20/20* (2019.02); *G16B 40/00* (2019.02); *C12Q 2600/106* (2013.01); *C12Q 2600/112* (2013.01); *C12Q 2600/158* (2013.01)

(58) Field of Classification Search

None

See application file for complete search history.

(56) References Cited

FOREIGN PATENT DOCUMENTS

| EP | 2 169 078 A1 | 3/2010 |
|---|---|---|
| WO | WO 2010/061996 A1 | 6/2010 |
| WO | WO 2012/103250 A2 | 8/2012 |

OTHER PUBLICATIONS

Kalinin et al; Future Medicine, vol. 19, pp. 629-650, 2018.*
Liu et al; PLOS One, vol. 10, pp. 1-11, 2015.*
Amri, R. et al. (2013) "Preoperative Carcinoembryonic Antigen as an Outcome Predictor in Colon Cancer" *J Surg Oncol*, 108:14-18.
Chen, V.W. et al. (Dec. 1, 2014) "Analysis of Stage and Clinical/Prognostic Factors for Colon and Rectal Cancer From SEER Registries: AJCC and Collaborative Stage Data Collection System" *Cancer*, 120(23 Suppl):3793-3806.
Chen, W. et al. (2009) "Knockdown of the novel proteasome subunit *Adrml* located on the 20q13 amplicon inhibits colorectal cancer cell migration, survival and tumorigenicity" *Oncology Reports*, 21:531-537.
Ferlay, J. et al. (2013) "Cancer incidence and mortality patterns in Europe: Estimates for 40 countries in 2012" *Eur J Cancer*, 49:1374-1403.
Fritzmann, J. et al. (2009) "A Colorectal Cancer Expression Profile That Includes Transforming Growth Factor β Inhibitor BAMBI Predicts Metastatic Potential" *Gastroenterology*, 137:165-175.
Garcia-Bilbao, A. et al. (2012) "Identification of a biomarker panel for colorectal cancer diagnosis" *BMC Cancer*, 12:43, 13 pages.
Heald, R.J. and Lockhart-Mummery, H.E. (Jan. 1972) "The Lesion of the Second Cancer of the Large Bowel" *Brit J Surg*, 59(1):16-19.
Jansen, N. and Coy, J.F. (2013) "Diagnostic use of epitope detection in monocytes blood test for early detection of colon cancer metastasis" *Future Oncol*, 9(4):605-609.
Locker, G.Y. et al. "ASCO 2006 Update of Recommendations for the Use of Tumor Markers in Gastrointestinal Cancer" *J Clin Oncol*, 24(33):5313-5327.
Mead, R. et al. (2011) "Circulating tumour markers can define patients with normal colons, benign polyps, and cancers" *Br J Cancer*, 105:239-245.
Mishaeli, M. et al. (1998) "Initial TPS Serum Level as an Indicator of Relapse and Survival in Colorectal Cancer" *Anticancer Res*, 18:2101-2106.
Mokhles, S. et al. (2016) "Meta-analysis of colorectal cancer follow-up after potentially curative resection" *BJS*, 103:1259-1268.
Molnar, B. et al. (2008) "Elevation in peripheral blood circulating tumor cell number correlates with macroscopic progression in UICC stage IV colorectal cancer patients" *Disease Markers*, 24:141-150.
Parkkila, S. et al. (2008) "The calcium-binding protein S100P in normal and malignant human tissues" *BMC Clin Pathol*, 8:2, 9 pages.
Piepoli, A. et al. (Mar. 3, 2009) "Promoter methylation correlates with reduced NDRG2 expression in advanced colon tumour" *BMC Medical Genomics*, 2:11, 12 pages.
Siegel, R.L. et al. (2017) "Cancer Statistics, 2017" *CA Cancer J Clin*, 67:7-30.
Thomas, S.N. et al. (Jun. 6, 2008) "Carcinoembryonic Antigen and CD44 Variant Isoforms Cooperate to Mediate Colon Carcinoma Cell Adhesion to E- and L-selectin in Shear Flow" *J Biol Chem*, 283(23):15647-15655.
Uzozie, A. et al. (2014) "Sorbitol Dehydrogenase Overexpression and Other Aspects of Dysregulated Protein Expression in Human Precancerous Colorectal Neoplasms: A Quantitative Proteomics Study" *Mol Cell Proteomics*, 13:1198-1218.

(Continued)

*Primary Examiner* — Jehanne S Sitton
(74) *Attorney, Agent, or Firm* — Cooley LLP; Ivor R. Elrifi; Matthew Pavao

(57) ABSTRACT

The present invention is directed to methods for detecting a colon cancer, methods for determining whether a colon cancer is stable or progressive, methods for determining a risk for disease relapse, and methods for determining a response by a subject having a colon cancer to a therapy.

9 Claims, 8 Drawing Sheets

Specification includes a Sequence Listing.

(56) References Cited

OTHER PUBLICATIONS

Warren, J.D. et al. (2011) "Septin 9 methylated DNA is a sensitive and specific blood test for colorectal cancer" *BMC Medicine*, 9:133, 9 pages.

Genbank Accession No. NM_000075.3 (Nov. 4, 2018) "*Homo sapiens* cyclin dependent kinase 4 (CDK4), mRNA" National Center for Biotechnology Information, U.S. National Library of Medicine [online]. Retrieved from: www.ncbi.nlm.nih.gov/nuccore/NM_000075.3; retrieved on Apr. 24, 2019, 5 pages.

Genbank Accession No. NM_000181.3 (Jul. 8, 2018) "*Homo sapiens* glucuronidase beta (GUSB), transcript variant 1, mRNA" National Center for Biotechnology Information, U.S. National Library of Medicine [online]. Retrieved from: www.ncbi.nlm.nih.gov/nuccore/NM_000181.3; retrieved on Apr. 24, 2019, 5 pages.

Genbank Accession No. NM_000194.2 (Sep. 16, 2018) "*Homo sapiens* hypoxanthine phosphoribosyltransferase 1 (HPRT1), mRNA" National Center for Biotechnology Information, U.S. National Library of Medicine [online]. Retrieved from: www.ncbi.nlm.nih.gov/nuccore/NM_000194.2; retrieved on Apr. 24, 2019, 4 pages.

Genbank Accession No. NM_000291.3 (Oct. 20, 2018) "*Homo sapiens* phosphoglycerate kinase 1 (PGK1), mRNA" National Center for Biotechnology Information, U.S. National Library of Medicine [online]. Retrieved from: www.ncbi.nlm.nih.gov/nuccore/NM_000291.3; retrieved on Apr. 24, 2019, 7 pages.

Genbank Accession No. NM_000373.3 (Nov. 11, 2018) "*Homo sapiens* uridine monophosphate synthetase (UMPS), transcript variant 1, mRNA" National Center for Biotechnology Information, U.S. National Library of Medicine [online]. Retrieved from: www.ncbi.nlm.nih.gov/nuccore/NM_000373.3; retrieved on Apr. 24, 2019, 6 pages.

Genbank Accession No. NM_000754.3 (Apr. 23, 2019) "*Homo sapiens* catechol-O-methyltransferase (COMT), transcript variant 1, mRNA" National Center for Biotechnology Information, U.S. National Library of Medicine [online]. Retrieved from: www.ncbi.nlm.nih.gov/nuccore/NM_000754.3; retrieved on Apr. 24, 2019, 4 pages.

Genbank Accession No. NM_001002.3 (Oct. 20, 2018) "*Homo sapiens* ribosomal protein lateral stalk subunit P0 (PLP0), transcript variant 1, mRNA" National Center for Biotechnology Information, U.S. National Library of Medicine [online]. Retrieved from: www.ncbi.nlm.nih.gov/nuccore/NM_001002.3; retrieved on Apr. 24, 2019, 5 pages.

Genbank Accession No. NM_001020658.1 (Apr. 13, 2019) "*Homo sapiens* pumilio RNA binding family member 1 (PUM1), transcript variant 1, mRNA" National Center for Biotechnology Information, U.S. National Library of Medicine [online]. Retrieved from: www.ncbi.nlm.nih.gov/nuccore/NM_001020658.1; retrieved on Apr. 24, 2019, 9 pages.

Genbank Accession No. NM_001101.4 (Oct. 21, 2018) "*Homo sapiens* actin beta (ACTB), mRNA" National Center for Biotechnology Information, U.S. National Library of Medicine [online]. Retrieved from: www.ncbi.nlm.nih.gov/nuccore/NM_001101.4; retrieved on Apr. 24, 2019, 4 pages.

Genbank Accession No. NM_001127204.1 (Feb. 21, 2019) "*Homo sapiens* oxygenase 2 (HMOX2), transcript variant 1, mRNA" National Center for Biotechnology Information, U.S. National Library of Medicine [online]. Retrieved from: www.ncbi.nlm.nih.gov/nuccore/NM_001127204.1; retrieved on Apr. 24, 2019, 4 pages.

Genbank Accession No. NM_001163817.1 (Feb. 23, 2019) "*Homo sapiens* 7-dehydrocholesterol reductase (DHCR7), transcript variant 2, mRNA" National Center for Biotechnology Information, U.S. National Library of Medicine [online]. Retrieved from: www.ncbi.nlm.nih.gov/nuccore/NM_001163817.1; retrieved on Apr. 24, 2019, 5 pages.

Genbank Accession No. NM_001265603.1 (Jun. 11, 2018) "*Homo sapiens* mortality factor 4 like 1 (MORF4L1), transcript variant 3, mRNA" National Center for Biotechnology Information, U.S. National Library of Medicine [online]. Retrieved from: www.ncbi.nlm.nih.gov/nuccore/NM_001265603.1; retrieved on Apr. 24, 2019, 4 pages.

Genbank Accession No. NM_001287031.1 (Feb. 10, 2019) "*Homo sapiens* stomatin like 2 (STOML2), transcript variant 2, mRNA" National Center for Biotechnology Information, U.S. National Library of Medicine [online]. Retrieved from: www.ncbi.nlm.nih.gov/nuccore/NM_001287031.1; retrieved on Apr. 24, 2019, 4 pages.

Genbank Accession No. NM_002046.6 (Oct. 21, 2018) "*Homo sapiens* glyceraldehyde-3-phosphate dehydrogenase (GAPDH), transcript variant 1, mRNA" National Center for Biotechnology Information, U.S. National Library of Medicine [online]. Retrieved from: www.ncbi.nlm.nih.gov/nuccore/NM_002046.6; retrieved on Apr. 24, 2019, 9 pages.

Genbank Accession No. NM_003104.5 (Jun. 24, 2018) "*Homo sapiens* sorbitol dehydrogenase (SORD), transcript variant 1, mRNA" National Center for Biotechnology Information, U.S. National Library of Medicine [online]. Retrieved from: www.ncbi.nlm.nih.gov/nuccore/NM_003104.5; retrieved on Apr. 24, 2019, 4 pages.

Genbank Accession No. NM_003234.3 (Apr. 20, 2019) "*Homo sapiens* transferrin receptor (TFRC), transcript variant 1, mRNA" National Center for Biotechnology Information, U.S. National Library of Medicine [online]. Retrieved from: www.ncbi.nlm.nih.gov/nuccore/NM_003234.3; retrieved on Apr. 24, 2019, 7 pages.

Genbank Accession No. NM_003406.3 (Mar. 25, 2019) "*Homo sapiens* tyrosine 3-monooxygenase/tryptophan 5-monooxygenase activation protein zeta (YWHAZ), transcript variant 1, mRNA" National Center for Biotechnology Information, U.S. National Library of Medicine [online]. Retrieved from: www.ncbi.nlm.nih.gov/nuccore/NM_003406.3; retrieved on Apr. 24, 2019, 6 pages.

Genbank Accession No. NM_003681.4 (Oct. 20, 2018) "*Homo sapiens* pyridoxal kinase (PDXK), transcript variant 1, mRNA" National Center for Biotechnology Information, U.S. National Library of Medicine [online]. Retrieved from: www.ncbi.nlm.nih.gov/nuccore/NM_003681.4; retrieved on Apr. 24, 2019, 6 pages.

Genbank Accession No. NM_004048.2 (Mar. 29, 2018) "*Homo sapiens* beta-2 -microglobulin (B2M), mRNA" National Center for Biotechnology Information, U.S. National Library of Medicine [online]. Retrieved from: www.ncbi.nlm.nih.gov/nuccore/NM_004048.2; retrieved on Apr. 24, 2019, 4 pages.

Genbank Accession No. NM_004168.3 (Oct. 21, 2018) "*Homo sapiens* succinate dehydrogenase complex flavoprotein subunit A (SDHA), transcript variant 1, mRNA" National Center for Biotechnology Information, U.S. National Library of Medicine [online]. Retrieved from: www.ncbi.nlm.nih.gov/nuccore/NM_004168.3; retrieved on Apr. 24, 2019, 8 pages.

Genbank Accession No. NM_004526.3 (Nov. 4, 2018) "*Homo sapiens* minichromosome maintenance complex component 2 (MCM2), transcript variant 1, mRNA" National Center for Biotechnology Information, U.S. National Library of Medicine [online]. Retrieved from: www.ncbi.nlm.nih.gov/nuccore/NM_004526.3; retrieved on Apr. 24, 2019, 8 pages.

Genbank Accession No. NM_004596.4 (Oct. 21, 2018) "*Homo sapiens* small nuclear ribonucleoprotein polypeptide A (SNRPA), mRNA" National Center for Biotechnology Information, U.S. National Library of Medicine [online]. Retrieved from: www.ncbi.nlm.nih.gov/nuccore/NM_004596.4; retrieved on Apr. 24, 2019, 4 pages.

Genbank Accession No. NM_005837.2 (Jun. 24, 2018) "*Homo sapiens* POP7 homolog, ribonuclease P/MRP subunit (POP7), mRNA" National Center for Biotechnology Information, U.S. National Library of Medicine [online]. Retrieved from: www.ncbi.nlm.nih.gov/nuccore/NM_005837.2; retrieved on Apr. 24, 2019, 3 pages.

Genbank Accession No. NM_005877.5 (Jun. 3, 2018) "*Homo sapiens* splicing factor 3a subunit 1 (SF3 A1), mRNA" National Center for Biotechnology Information, U.S. National Library of Medicine [online]. Retrieved from: www.ncbi.nlm.nih.gov/nuccore/NM_005877.5; retrieved on Apr. 24, 2019, 6 pages.

Genbank Accession No. NM_005980.2 (Jun. 17, 2018) "*Homo sapiens* S100 calcium binding protein P (S100P), mRNA" National Center for Biotechnology Information, U.S. National Library of Medicine [online]. Retrieved from: www.ncbi.nlm.nih.gov/nuccore/NM_005980.2; retrieved on Apr. 24, 2019, 3 pages.

Genbank Accession No. NM_007002.3 (Oct. 21, 2018) "*Homo sapiens* adhesion regulating molecule 1 (ADRM1), transcript variant 1, mRNA" National Center for Biotechnology Information, U.S.

(56) References Cited

OTHER PUBLICATIONS

National Library of Medicine [online]. Retrieved from: www.ncbi.nlm.nih.gov/nuccore/NM_007002.3; retrieved on Apr. 24, 2019, 5 pages.

Genbank Accession No. NM_012423.3 (Oct. 20, 2018) "*Homo sapiens* ribosomal protein L13a (RPL13A), transcript variant 1, mRNA" National Center for Biotechnology Information, U.S. National Library of Medicine [online]. Retrieved from: www.ncbi.nlm.nih.gov/nuccore/NM_012423.3; retrieved on Apr. 24, 2019, 7 pages.

Genbank Accession No. NM_014763.3 (Nov. 11, 2018) "*Homo sapiens* mitochondrial ribosomal protein L19 (MRPL19), mRNA" National Center for Biotechnology Information, U.S. National Library of Medicine [online]. Retrieved from: www.ncbi.nlm.nih.gov/nuccore/NM_014763.3; retrieved on Apr. 24, 2019, 6 pages.

Genbank Accession No. NM_021130.4 (Nov. 18, 2018) "*Homo sapiens* peptidylprolyl isomerase A (PPIA), transcript variant 1, mRNA" National Center for Biotechnology Information, U.S. National Library of Medicine [online]. Retrieved from: www.ncbi.nlm.nih.gov/nuccore/NM_021130.4; retrieved on Apr. 24, 2019, 5 pages.

Genbank Accession No. NM_153001.2 (Apr. 14, 2019) "*Homo sapiens* proteasome 26S subunit, ATPase 4 (PSMC4), transcript variant 2, mRNA" National Center for Biotechnology Information, U.S. National Library of Medicine [online]. Retrieved from: www.ncbi.nlm.nih.gov/nuccore/NM_153001.2; retrieved on Apr. 24, 2019, 4 pages.

Genbank Accession No. X03205.1 (Dec. 16, 1994) "Human 18S ribosomal RNA" National Center for Biotechnology Information, U.S. National Library of Medicine [online]. Retrieved from: www.ncbi.nlm.nih.gov/nuccore/X03205.1; retrieved on Apr. 24, 2019, 3 pages.

* cited by examiner

METHODS FOR COLON CANCER DETECTION AND TREATMENT

CROSS-REFERENCE TO RELATED APPLICATIONS

This application claims priority to, and the benefit of, U.S. Provisional Application No. 62/620,015, filed Jan. 22, 2018, the contents of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Jan. 21, 2019, is named "LBIO-004_001US.txt" and is TO BE ADDED 111 KB in size.

FIELD OF THE INVENTION

The present invention relates to colon cancer detection.

BACKGROUND OF THE INVENTION

Colorectal cancer (CRC) is one of the most commonly diagnosed cancers worldwide. In the US, CRC is the second leading cause of death as it is in Europe, after lung cancer. Worldwide, it is the fourth most common cause of cancer death. Although surgical resection followed by chemotherapy is the leading treatment option, approximately half eventually die due to distant metastases. Currently, the 5-year overall survival rate of patients with primary CRC can be up to 90%, but it will be reduced to ~50% in patients with advanced non-metastatic tumors, and can be further decreased to <10% in patients in whom the disease is resected at its earliest stages, owing to an incomplete understanding of the molecular mechanisms underpinning its pathogenesis.

Overall survival is associated with the disease stage at the time of diagnosis, suggesting that early detection of disseminated disease is of considerable significance. Consequently, the development of new diagnostic methods that better define disease stage and can better monitor disease progression is critical.

Surveillance remains a cornerstone approach to detect recurrence at an early stage and plan further therapeutic strategies. After potentially curative resection, monitoring can be undertaken through measurement of blood biomarkers and/or imaging like CT to detect asymptomatic metastatic disease earlier. Pooled data from randomized trials published from 1995 to 2016, however, identifies that a benefit from surgical treatment resulting from earlier detection of metastases, does not occur. This likely reflects the poor sensitivity of current biomarkers.

The current biomarker is carcinoembryonic antigen (CEA), a glycoprotein involved in cell adhesion that is not generally expressed in adult tissues except in heavy smokers. Its specialized sialofucosylated glycoforms serve as functional colon carcinoma L-selectin and E-selectin ligands, which may play a role in metastatic dissemination of colon carcinoma cells. CEA is principally used to monitor colorectal carcinoma treatment, to identify recurrences after surgical resection, for staging or to localize cancer spread through measurement of biological fluids. There are, however, significant limitations. While preoperative CEA levels have shown an association with (disease-free) survival, this was chiefly because it was a surrogate for metastatic presentation. Extrapolating the predictive value of preoperative CEA has, however, been shown to be of limited significance for predictions of long-term outcomes in individual cases. This has been independently supported by a prospective analysis, which identified that levels of CEA, and other biomarkers like CA19-9, does not indicate metastasis even at a time-point where clinical signs and imaging techniques has already demonstrated metastasis.

While the molecular basis for the colorectal cancer disease has been well-characterized e.g., microsatellite instability, K-RAS mutations etc., the development of diagnostic and prognostic markers e.g., in urine or stool or as circulating-free DNA that captures this information, remains nascent but have begun to be developed. Examples include measurements of methylation of septin 9, a tumor suppressor involved in cytokinesis during cellular division. This has been used to detect colon cancer; the metrics range between 60-70%. Assessment of circulating free DNA (Line 1 and Alu-based PCR) has a predictive value of 81% with a ROC of 0.86 as a diagnostic, while measurements of circulating tumor cells are also considered useful. TPS (tissue polypeptide specific antigen) can be used as a monitor of colon cancer as can TAG-72 (tumor-associated glycoprotein) but measurements of other single analytes, like CEA or CA19-9, are non-specific.

SUMMARY OF THE INVENTION

Among other things, disclosed herein is a 14-gene expression tool for colon cancer detection.

In one aspect, the present disclosure provides a method for detecting a colon cancer in a subject in need thereof, comprising: (a) determining the expression level of at least 14 biomarkers from a test sample from the subject by contacting the test sample with a plurality of agents specific to detect the expression of the at least 14 biomarkers, wherein the 14 biomarkers comprise ADRM1, CDK4, COMT, DHCR7, HMOX2, MCM2, PDXK, POP7, S100P, SNRPA, SORD, STOML2, UMPS, and a housekeeping gene; (b) normalizing the expression level of each of ADRM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADRM1, CDK4, COMT, DHCR7, HMOX2, MCM2, PDXK, POP7, S100P, SNRPA, SORD, STOML2, and UMPS; (c) inputting each normalized expression level into an algorithm to generate a score; (d) comparing the score with a predetermined cutoff value; and (e) identifying the presence of a colon cancer in the subject when the score is equal to or greater than the predetermined cutoff value or identifying the absence of a colon cancer in the subject when the score is less than the predetermined cutoff value.

In one aspect, the present disclosure provides a method for detecting a colon cancer in a subject in need thereof, the method comprising: (a) determining the expression level of at least 14 biomarkers from a test sample from the subject by contacting the test sample with a plurality of agents specific to detect the expression of the at least 14 biomarkers, wherein the 14 biomarkers comprise ADRM1, CDK4, COMT, DHCR7, HMOX2, MCM2, PDXK, POP7, S100P, SNRPA, SORD, STOML2, UMPS, and a housekeeping gene; (b) normalizing the expression level of each of ADRM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADRM1, CDK4, COMT, DHCR7, HMOX2, MCM2, PDXK, POP7, S100P, SNRPA, SORD, STOML2, and UMPS; (c) inputting each normalized expression level into an algorithm to generate a score; (d) comparing the score with a first predetermined cutoff value; and (e) producing a report, wherein the report identifies the presence of a colon cancer in the subject when the score is equal to or greater than the first predetermined cutoff value or identifies the absence of a colon cancer in the subject when the score is less than the first predetermined cutoff value, wherein the first predetermined cutoff value is 50% on a scale of 0-100%.

In one aspect, the present disclosure provides a method for determining whether a colon cancer in a subject is stable or progressive, the method comprising: (a) determining the expression level of at least 14 biomarkers from a test sample from the subject by contacting the test sample with a plurality of agents specific to detect the expression of the at least 14 biomarkers, wherein the 14 biomarkers comprise ADRM1, CDK4, COMT, DHCR7, HMOX2, MCM2, PDXK, POP7, S100P, SNRPA, SORD, STOML2, UMPS, and a housekeeping gene; (b) normalizing the expression level of each of ADRM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADRM1, CDK4, COMT, DHCR7, HMOX2, MCM2, PDXK, POP7, S100P, SNRPA, SORD, STOML2, and UMPS; (c) inputting each normalized expression level into an algorithm to generate a score; (d) comparing the score with a predetermined cutoff value; and (e) identifying that the colon cancer in the subject is progressive when the score is equal to or greater than the predetermined cutoff value or identifying that the colon cancer in the subject is stable when the score is less than the predetermined cutoff value.

In one aspect, the present disclosure provides a method for determining whether a colon cancer in a subject is stable or progressive, the method comprising: (a) determining the expression level of at least 14 biomarkers from a test sample from the subject by contacting the test sample with a plurality of agents specific to detect the expression of the at least 14 biomarkers, wherein the 14 biomarkers comprise ADRM1, CDK4, COMT, DHCR7, HMOX2, MCM2, PDXK, POP7, S100P, SNRPA, SORD, STOML2, UMPS, and a housekeeping gene; (b) normalizing the expression level of each of ADRM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADRM1, CDK4, COMT, DHCR7, HMOX2, MCM2, PDXK, POP7, S100P, SNRPA, SORD, STOML2, and UMPS; (c) inputting each normalized expression level into an algorithm to generate a score; (d) comparing the score with a second predetermined cutoff value; and (e) producing a report, wherein the report identifies that the colon cancer is progressive when the score is equal to or greater than the second predetermined cutoff value or identifies that the colon cancer is stable when the score is less than the second predetermined cutoff value, wherein the second predetermined cutoff value is 60% on a scale of 0 to 100%.

In one aspect, a method for determining the completeness of surgery in a subject having a colon cancer, the method comprising: (a) determining the expression level of at least 14 biomarkers from a test sample from the subject after the surgery by contacting the test sample with a plurality of agents specific to detect the expression of the at least 14 biomarkers, wherein the 14 biomarkers comprise ADRM1, CDK4, COMT, DHCR7, HMOX2, MCM2, PDXK, POP7, S100P, SNRPA, SORD, STOML2, UMPS, and a housekeeping gene; (b) normalizing the expression level of each of ADRM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADRM1, CDK4, COMT, DHCR7, HMOX2, MCM2, PDXK, POP7, S100P, SNRPA, SORD, STOML2, and UMPS; (c) inputting each normalized expression level into an algorithm to generate a score; (d) comparing the score with a predetermined cutoff value; and (e) identifying that the colon cancer in the subject is not completely removed when the score is equal to or greater than the predetermined cutoff value or identifying that the colon cancer in the subject is completely removed when the score is less than the predetermined cutoff value.

In one aspect, the present disclosure provides a method for determining the completeness of surgery in a subject having a colon cancer, the method comprising: (a) determining the expression level of at least 14 biomarkers from a test sample from the subject after the surgery by contacting the test sample with a plurality of agents specific to detect the expression of the at least 14 biomarkers, wherein the 14 biomarkers comprise ADRM1, CDK4, COMT, DHCR7, HMOX2, MCM2, PDXK, POP7, S100P, SNRPA, SORD, STOML2, UMPS, and a housekeeping gene; (b) normalizing the expression level of each of ADRM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADRM1, CDK4, COMT, DHCR7, HMOX2, MCM2, PDXK, POP7, S100P, SNRPA, SORD, STOML2, and UMPS; (c) inputting each normalized expression level into an algorithm to generate a score; (d) comparing the score with a first predetermined cutoff value; and (e) producing a report, wherein the report identifies that the colon cancer is not completely removed when the score is equal to or greater than the first predetermined cutoff value or identifies that the colon cancer is completely removed when the score is less than the first predetermined cutoff value, wherein the first predetermined cutoff value is 50% on a scale of 0-100%.

In one aspect, the present disclosure provides a method comprising: (a) determining the expression level of at least 14 biomarkers from a test sample from a subject by contacting the test sample with a plurality of agents specific to detect the expression of the at least 14 biomarkers, wherein the 14 biomarkers comprise ADRM1, CDK4, COMT, DHCR7, HMOX2, MCM2, PDXK, POP7, S100P, SNRPA, SORD, STOML2, UMPS, and a housekeeping gene; (b) normalizing the expression level of each of ADRM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADRM1, CDK4, COMT, DHCR7, HMOX2, MCM2, PDXK, POP7, S100P, SNRPA, SORD, STOML2, and UMPS; (c) inputting each normalized expression level into an algorithm to generate a score; (d) comparing the score with a predetermined cutoff value; and (e) administering a first therapy to the subject when the score is equal to or greater than the predetermined cutoff value.

In one aspect, the present disclosure provides a method for evaluating the response of a subject having a colon cancer to a first therapy, the method comprising: (1) at a first time point: (a) determining the expression level of at least 14 biomarkers from a first test sample from the subject by contacting the first test sample with a plurality of agents specific to detect the expression of the at least 14 biomarkers, wherein the 14 biomarkers comprise ADRM1, CDK4, COMT, DHCR7, HMOX2, MCM2, PDXK, POP7, S100P, SNRPA, SORD, STOML2, UMPS, and a housekeeping gene; (b) normalizing the expression level of each of ADRM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADRM1, CDK4, COMT, DHCR7, HMOX2, MCM2, PDXK, POP7, S100P, SNRPA, SORD, STOML2, and UMPS; (c) inputting each normalized expression level into an algorithm to generate a first score; (2) at a second time point, wherein the second time point is after the first time point and after the administration of the therapy to the subject: (a) determining the expression level of at least 14 biomarkers from a second test sample from the subject by contacting the second test sample with a plurality of agents specific to detect the expression of the at least 14 biomarkers, wherein the 14 biomarkers comprise ADRM1, CDK4, COMT, DHCR7, HMOX2, MCM2, PDXK, POP7, S100P, SNRPA, SORD, STOML2, UMPS, and the housekeeping gene; (b) normalizing the expression level of each of ADRM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADRM1, CDK4, COMT, DHCR7, HMOX2, MCM2, PDXK, POP7, S100P, SNRPA, SORD, STOML2, and UMPS; (c) inputting each normalized expression level into the algorithm to generate a second score; (3) comparing the first score with the second score; and (4) identifying that the subject is responsive to the first therapy when the second score is significantly decreased as compared to the first score or identifying that the subject is not responsive to the first therapy when the second score is not significantly decreased as compared to the first score.

In one aspect, the present disclosure provides a method for evaluating the response of a subject having a colon cancer to a therapy, the method comprising: (1) at a first time point, performing the following steps that include (a) determining the expression level of at least 14 biomarkers from a first test sample from the subject by contacting the first test sample with a plurality of agents specific to detect the expression of the at least 14 biomarkers, wherein the 14 biomarkers comprise ADRM1, CDK4, COMT, DHCR7, HMOX2, MCM2, PDXK, POP7, S100P, SNRPA, SORD, STOML2, UMPS, and a housekeeping gene; (b) normalizing the expression level of each of ADRM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADRM1, CDK4, COMT, DHCR7, HMOX2, MCM2, PDXK, POP7, S100P, SNRPA, SORD, STOML2, and UMPS; (c) inputting each normalized expression level into an algorithm to generate a first score; and (2) at a second time point, performing the following steps that include (d) determining the expression level of at least 14 biomarkers from a second test sample from the subject by contacting the second test sample with a plurality of agents specific to detect the expression of the at least 14 biomarkers, wherein the 14 biomarkers comprise ADRM1, CDK4, COMT, DHCR7, HMOX2, MCM2, PDXK, POP7, S100P, SNRPA, SORD, STOML2, UMPS, and the housekeeping gene; (e) normalizing the expression level of each of ADRM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADRM1, CDK4, COMT, DHCR7, HMOX2, MCM2, PDXK, POP7, S100P, SNRPA, SORD, STOML2, and UMPS; (f) inputting each normalized expression level into the algorithm to generate a second score, wherein the second time point is after the first time point and after the administration of the therapy to the subject; (3) comparing the first score with the second score; and (4) producing a report, wherein the report identifies that the subject is responsive to the therapy when the second score is significantly decreased as compared to the first score or identifies that the subject is not responsive to the therapy when the second score is not significantly decreased as compared to the first score.

In some aspects, a method of the present disclosure can further comprise continuing to administer a first therapy to a subject when a second score is significantly decreased as compared to a first score.

In some aspects, a method of the present disclosure can further comprise discontinuing administration of a first therapy to a subject when a second score is not significantly decreased as compared to a first score.

In some aspects, a method of the present disclosure can further comprise administering a second therapy to a subject when a second score is not significantly decreased as compared to a first score.

In some aspects, a second score is significantly decreased as compared to a first score when the second score is at least 25% less than the first score.

In some aspects, a predetermined cutoff value can be 50% on a scale of 0-100%. A predetermined cutoff value can be 60% on a scale of 0-100%.

In some aspects of any one of the methods disclosed herein, a housekeeping gene can be selected from the group consisting of MRPL19, PSMC4, SF3A1, PUM1, ACTS, GAPD, GUSB, RPLP0, TFRC, MORF4L1, 18S, PPIA, PGK1, RPL13A, B2M, YWHAZ, SDHA, and HPRT1. For example, the housekeeping gene can be MORF4L1.

In some aspects, a method of the present disclosure can have a sensitivity greater than 85%. In some aspects, a method of the present disclosure can have a specificity of greater than 85%.

In some aspects, a biomarker can comprise RNA, cDNA, protein or any combination thereof.

In some aspects, wherein when the biomarker is RNA, the RNA can be reverse transcribed to produce cDNA, and the produced cDNA expression level can be detected.

In some aspects, a biomarker or the expression of a biomarker can be detected by forming a complex between the biomarker and a labeled probe or primer.

In some aspects, when a biomarker is protein, the protein can be detected by forming a complex between the protein and a labeled antibody.

In some aspects, when a biomarker is RNA or cDNA, the RNA or cDNA can be detected by forming a complex between the RNA or cDNA and a labeled nucleic acid probe or primer. A complex between the RNA or cDNA and the labeled nucleic acid probe or primer can be a hybridization complex.

In some aspects, a predetermined cutoff value can be derived from a plurality of reference samples obtained from subjects not having or not diagnosed with a neoplastic disease. The neoplastic disease can be colon cancer.

In some aspects, an algorithm can be XGBoost (XGB), Random Forest (RF), glmnet, cforest, Classification and Regression Trees for Machine Learning (CART), treebag, K-Nearest Neighbors (kNN), neural network (nnet), Support Vector Machine radial (SVM-radial), Support Vector Machine linear (SVM-linear), Naïve Bayes (NB), multilayer perceptron (mlp) or any combination thereof.

In some aspects, the methods of the present disclosure can further comprise administering to a subject a first therapy when a score is equal to or greater than a predetermined cutoff.

In some aspects, a first time point can be prior to the administration of a first therapy to the subject. A first time point can be after the administration of the first therapy to the subject.

In some aspects, a therapy can comprise anti-cancer therapy, surgery, chemotherapy, targeted drug therapy, radiation therapy, immunotherapy or any combination thereof.

In some aspects, surgery can comprise removing a polyp during a colonoscopy, endoscopic mucosal resection, a partial colectomy, an ostomy, removing at least one cancerous lesion from the liver, or any combination thereof.

In some aspects, chemotherapy can comprise FOLFOX, FOLFIRI, a combination of 5-FU and leucovorin, capecitabine, irinotecan, CapeOx or any combination thereof.

In some aspects, targeted drug therapy can comprise bevacizumab, cetuximab, panitumumab, regorafenib, a combination of trifluridine and tipiracil, a EGFR TKI inhibitor or any combination thereof.

In some aspects, anti-cancer therapy can comprise anti-colon cancer therapy.

In some aspects, immunotherapy can comprise pembrolizumab, nivolumab or a combination of pembrolizumab and nivolumab.

In some aspects, a test sample can be blood, serum, plasma, neoplastic tissue or any combination thereof. A reference sample can be blood, serum, plasma, non-neoplastic tissue or any combination thereof.

Any of the above aspects can be combined with any other aspect.

Unless otherwise defined, all technical and scientific terms used herein have the same meaning as commonly understood by one of ordinary skill in the art to which this disclosure belongs. In the Specification, the singular forms also include the plural unless the context clearly dictates otherwise; as examples, the terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although methods and materials similar or equivalent to those described herein can be used in the practice or testing of the present disclosure, suitable methods and materials are described below. All publications, patent applications, patents, and other references mentioned herein are incorporated by reference in their entirety. The references cited herein are not admitted to be prior art to the claimed invention. In the case of conflict, the present Specification, including definitions, will control. In addition, the materials, methods, and examples are illustrative only and are not intended to be limiting. Other features and advantages of the disclosure will be apparent from the following detailed description and claim.

DETAILED DESCRIPTION OF THE INVENTION

Figure 1A:
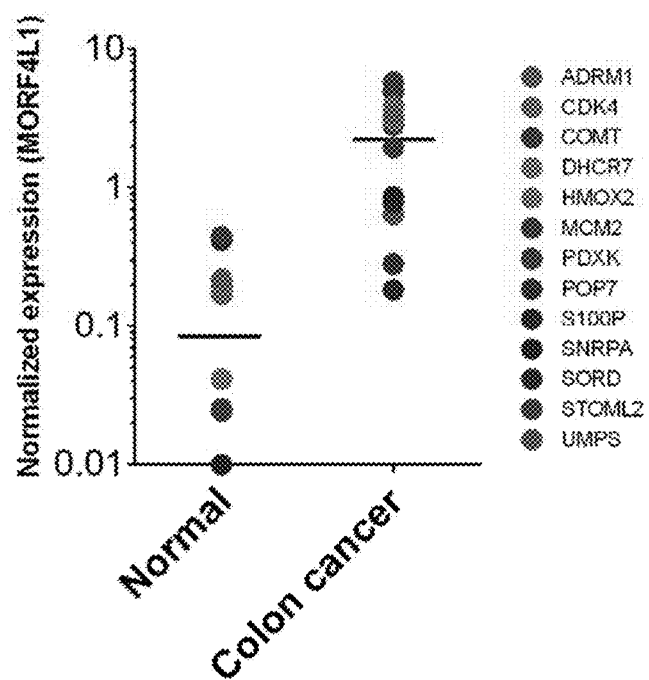
FIGS. 1A-1B are graphs showing normalized gene expression of the 13 gene signature in colon mucosa (FIG. 1A) and cell lines (FIG. 1B). Gene expression was significantly ($p<0.0001$) elevated in colon cancer samples (n=7) compared to matched normal mucosa (n=7). Levels were ~20-fold elevated in colon cancer tumor tissue than in normal mucosa. All genes were expressed in three different colon cancer cell lines. Levels were ~1000× elevated compared to normal mucosa. Horizontal lines identify median normalized expression of the 13 genes.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Colon cancer is cancer of the large intestine (colon). Symptoms of colon cancer include, but are not limited to: (a) a change in bowel habits, (b) rectal bleeding or blood in the stool, (c) persistent abdominal discomfort, such as cramps, gas or pain, (d) a feeling that the bowel doesn't empty completely, (e) weakness or fatigue, and (f) unexplained weight loss.

Described herein are methods to quantitate (score) the circulating colon cancer molecular signature with high sensitivity and specificity for purposes including, but not limited to, detecting a colon cancer, determining whether a colon cancer is stable or progressive, determining the completeness of surgery, and evaluating the response to a colon cancer therapy. Specifically, the present invention is based on the discovery that the expression levels of ADRM1, CDK4, COMT, DHCR7, HMOX2, MCM2, PDXK, POP7, S100P, SNRPA, SORD, STOML2, and UMPS, normalized by the expression level of a housekeeping gene such as MORF4L1, are elevated in subjects having colon cancers as compared to healthy subjects.

Accordingly, the present disclosure provides a method for detecting a colon cancer in a subject in need thereof, the method comprising: (a) determining the expression level of at least 14 biomarkers from a test sample from the subject by contacting the test sample with a plurality of agents specific to detect the expression of the at least 14 biomarkers, wherein the 14 biomarkers comprise ADRM1, CDK4, COMT, DHCR7, HMOX2, MCM2, PDXK, POP7, S100P, SNRPA, SORD, STOML2, UMPS, and a housekeeping gene; (b) normalizing the expression level of each of ADRM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADRM1, CDK4, COMT, DHCR7, HMOX2, MCM2, PDXK, POP7, S100P, SNRPA, SORD, STOML2, and UMPS; (c) inputting each normalized expression level into an algorithm to generate a score; (d) comparing the score with a first predetermined cutoff value; and (e) identifying the presence of a colon cancer in the subject when the score is equal to or greater than the predetermined cutoff value or identifying the absence of a colon cancer in the subject when the score is less than the predetermined cutoff value.

In some aspects of the preceding method, step (e) can comprise producing a report, wherein the report identifies the presence of a colon cancer in the subject when the score is equal to or greater than the first predetermined cutoff value or identifies the absence of a colon cancer in the subject when the score is less than the first predetermined cutoff value.

In some aspects, the preceding method can further comprise administering to the subject a first therapy. The preceding method can further comprise administering to the subject a first therapy when the score is equal to or greater than the predetermined cutoff.

The present disclosure also provides a method for determining whether a colon cancer in a subject is stable or progressive, the method comprising: (a) determining the expression level of at least 14 biomarkers from a test sample from the subject by contacting the test sample with a plurality of agents specific to detect the expression of the at least 14 biomarkers, wherein the 14 biomarkers comprise ADRM1, CDK4, COMT, DHCR7, HMOX2, MCM2, PDXK, POP7, S100P, SNRPA, SORD, STOML2, UMPS, and a housekeeping gene; (b) normalizing the expression level of each of ADRM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADRM1, CDK4, COMT, DHCR7, HMOX2, MCM2, PDXK, POP7, S100P, SNRPA, SORD, STOML2, and UMPS; (c) inputting each normalized expression level into an algorithm to generate a score; (d) comparing the score with a second predetermined cutoff value; and (e) identifying that the colon cancer in the subject is progressive when the score is equal to or greater than the predetermined cutoff value or identifying that the colon cancer in the subject is stable when the score is less than the predetermined cutoff value.

In some aspects of the preceding method, step (e) can comprise producing a report, wherein the report identifies that the colon cancer is progressive when the score is equal to or greater than the second predetermined cutoff value or identifies that the colon cancer is stable when the score is less than the second predetermined cutoff value.

In some aspects, the preceding method can further comprise administering to the subject a first therapy. The preceding method can further comprise administering to the subject a first therapy when the score is equal to or greater than the predetermined cutoff.

In some aspects, the method further comprises treating the subject with a progressive colon cancer with surgery, chemotherapy, targeted drug therapy, radiation therapy, immunotherapy, or a combination thereof.

The present disclosure also provides a method for determining the completeness of surgery in a subject having a colon cancer, the method comprising: (a) determining the expression level of at least 14 biomarkers from a test sample from the subject after the surgery by contacting the test sample with a plurality of agents specific to detect the expression of the at least 14 biomarkers, wherein the 14 biomarkers comprise ADRM1, CDK4, COMT, DHCR7, HMOX2, MCM2, PDXK, POP7, S100P, SNRPA, SORD, STOML2, UMPS, and a housekeeping gene; (b) normalizing the expression level of each of ADRM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADRM1, CDK4, COMT, DHCR7, HMOX2, MCM2, PDXK, POP7, S100P, SNRPA, SORD, STOML2, and UMPS; (c) inputting each normalized expression level into an algorithm to generate a score; (d) comparing the score with a first predetermined cutoff value; and (e) identifying that the colon cancer in the subject is not completely removed when the score is equal to or greater than the predetermined cutoff value or identifying that the colon cancer in the subject is completely removed when the score is less than the predetermined cutoff value.

In some aspects of the preceding method, step (e) can comprise producing a report, wherein the report identifies that the colon cancer is not completely removed when the score is equal to or greater than the first predetermined cutoff value or identifies that the colon cancer is completely removed when the score is less than the first predetermined cutoff value.

In some aspects, the preceding method can further comprise administering to the subject a first therapy. The preceding method can further comprise administering to the subject a first therapy when the score is equal to or greater than the predetermined cutoff.

The present disclosure also provides a method comprising: (a) determining the expression level of at least 14 biomarkers from a test sample from a subject by contacting the test sample with a plurality of agents specific to detect the expression of the at least 14 biomarkers, wherein the 14 biomarkers comprise ADRM1, CDK4, COMT, DHCR7, HMOX2, MCM2, PDXK, POP7, S100P, SNRPA, SORD, STOML2, UMPS, and a housekeeping gene; (b) normalizing the expression level of each of ADRM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADRM1, CDK4, COMT, DHCR7, HMOX2, MCM2, PDXK, POP7, S100P, SNRPA, SORD, STOML2, and UMPS; (c) inputting each normalized expression level into an algorithm to generate a score; (d) comparing the score with a predetermined cutoff value; and (e) administering a first therapy to the subject when the score is equal to or greater than the predetermined cutoff value.

The response of a subject having a colon cancer to a therapy can also be evaluated by comparing the scores determined by the same algorithm at different time points of the therapy. For example, the first time point can be prior to or after the administration of the therapy to the subject; the second time point is after the first time point and after the administration of the therapy to the subject. A first score is generated at the first time point, and a second score is generated at the second time point. When the second score is significantly decreased as compared to the first score, the subject is considered to be responsive to the therapy.

Accordingly, the present disclosure provides a method for evaluating the response of a subject having a colon cancer to a first therapy, the method comprising: (1) at a first time point: (a) determining the expression level of at least 14 biomarkers from a first test sample from the subject by contacting the first test sample with a plurality of agents specific to detect the expression of the at least 14 biomarkers, wherein the 14 biomarkers comprise ADRM1, CDK4, COMT, DHCR7, HMOX2, MCM2, PDXK, POP7, S100P, SNRPA, SORD, STOML2, UMPS, and a housekeeping gene; (b) normalizing the expression level of each of ADRM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADRM1, CDK4, COMT, DHCR7, HMOX2, MCM2, PDXK, POP7, S100P, SNRPA, SORD, STOML2, and UMPS; (c) inputting each normalized expression level into an algorithm to generate a first score; (2) at a second time point, wherein the second time point is after the first time point and after the administration of the therapy to the subject: (a) determining the expression level of at least 14 biomarkers from a second test sample from the subject by contacting the second test sample with a plurality of agents specific to detect the expression of the at least 14 biomarkers, wherein the 14 biomarkers comprise ADRM1, CDK4, COMT, DHCR7, HMOX2, MCM2, PDXK, POP7, S100P, SNRPA, SORD, STOML2, UMPS, and the housekeeping gene; (b) normalizing the expression level of each of ADRM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADRM1, CDK4, COMT, DHCR7, HMOX2, MCM2, PDXK, POP7, S100P, SNRPA, SORD, STOML2, and UMPS; (c) inputting each normalized expression level into the algorithm to generate a second score; (3) comparing the first score with the second score; and (4) identifying that the subject is responsive to the first therapy when the second score is significantly decreased as compared to the first score or identifying that the subject is not responsive to the first therapy when the second score is not significantly decreased as compared to the first score.

In some aspects of the preceding method, step (4) can comprise producing a report, wherein the report identifies that the subject is responsive to the first therapy when the second score is significantly decreased as compared to the first score or identifies that the subject is not responsive to the first therapy when the second score is not significantly decreased as compared to the first score.

In some aspects of the preceding method, the second score is significantly decreased as compared to the first score when the second score is at least about 10% less than the first score, or at least about 20% less than the first score, or at least about 25% less than the first score, at least about 40% less than the first score, at least about 50% less than the first score, or at least about 60% less than the first score, or at least about 70% less than the first score, or at least about 75% less than the first score, or at least about 80% less than the first score, or at least about 90% less than the first score, or at least about 95% less than the first score or at least about 95% less than the first score. In some aspects, when the second score is not significantly decreased as compared to the first score, the subject is considered to be not responsive to the therapy.

In some aspects of the preceding method, a first time point can be prior to the administration of a first therapy to the subject. A first time point can be after the administration of a first therapy to the subject.

In some aspects, the preceding method can further comprise continuing to administer the first therapy to the subject when the second score is significantly decreased as compared to the first score.

In some aspects, the preceding method can further comprise discontinuing administration of the first therapy to the subject when the second score is not significantly decreased as compared to the first score.

In some aspects, the preceding method can further comprise administering a second therapy to the subject when the second score is not significantly decreased as compared to the first score.

In some aspects of the methods of the present disclosure, a predetermined cutoff value can be about 50% on a scale of 0-100%. A predetermined cutoff value can be about 60% on a scale of 0-100%. A predetermine cutoff value can be about 10%, or about 20%, or about 30%, or about 40%, or about 70%, or about 80%, or about 90% on a scale of 0-100%.

In some aspects of the methods of the present disclosure, a test sample can be any biological fluid obtained from the subject. A test sample can be blood, serum, plasma, neoplastic tissue or any combination thereof. In some aspects, the test sample is blood. In some aspects, the test sample is serum. In some aspects, the test sample is plasma.

In some aspects of the methods of the present disclosure, a housekeeping gene can comprise, but is not limited to, MRPL19, PSMC4, SF3A1, PUM1, ACTB, GAPD, GUSB, RPLP0, TFRC, MORF4L1, 18S, PPIA, PGK1, RPL13A, B2M, YWHAZ, SDHA, and HPRT1. In some aspects, the housekeeping gene is MORF4L1.

The methods of the present disclosure can have a sensitivity of at least about 50%, or at least about 60%, or at least about 70%, or at least about 75%, or at least about 80%, or at least about 85%, or at least about 90%, or at least about 95%, or at least about 99%. The methods of the present disclosure can have a sensitivity of greater than about 50%, or greater than about 60%, or greater than about 70%, or greater than about 75%, or greater than about 80%, or greater than about 85%, or greater than about 90%, or greater than about 95%, or greater than about 99%.

The methods of the present disclosure can have a specificity of at least about 50%, or at least about 60%, or at least about 70%, or at least about 75%, or at least about 80%, or at least about 85%, or at least about 90%, or at least about 95%, or at least about 99%. The methods of the present disclosure can have a specificity of greater than about 50%, or greater than about 60%, or greater than about 70%, or greater than about 75%, or greater than about 80%, or greater than about 85%, or greater than about 90%, or greater than about 95%, or greater than about 99%.

The methods of the present disclosure can have an accuracy of at least about 50%, or at least about 60%, or at least about 70%, or at least about 75%, or at least about 80%, or at least about 85%, or at least about 90%, or at least about 95%, or at least about 99%. The methods of the present disclosure can have an accuracy of greater than about 50%, or greater than about 60%, or greater than about 70%, or greater than about 75%, or greater than about 80%, or greater than about 85%, or greater than about 90%, or greater than about 95%, or greater than about 99%.

In some aspects of the methods of the present disclosure, a predetermined cutoff value can be derived from a plurality of reference samples obtained from subjects not having or not diagnosed with a neoplastic disease. In some aspects, the neoplastic disease can be colon cancer.

The plurality of reference samples can comprise about 2-500, 2-200, 10-100, or 20-80 reference samples. Each reference sample produces a score using the algorithm, and the first predetermined cutoff value can be an arithmetic mean of these scores. Each reference sample can be blood, serum, plasma, or non-neoplastic tissue. In some aspects, each reference sample is blood. In some aspects, each reference sample is of the same type as the test sample.

Each of the biomarkers disclosed herein may have one or more transcript variants. The methods disclosed herein can measure the expression level of any one of the transcript variants for each biomarker.

The expression level can be measured in a number of ways, including, but not limited to: measuring the mRNA encoded by the selected genes; measuring the amount of protein encoded by the selected genes; and measuring the activity of the protein encoded by the selected genes.

In some aspects of the methods of the present disclosure, a biomarker can be RNA, cDNA, protein or any combination thereof. When the biomarker is RNA, the RNA can be reverse transcribed to produce cDNA (such as by RT-PCR), and the produced cDNA expression level can be detected. The expression level of a biomarker can be detected by forming a complex between the biomarker and a labeled probe or primer. When the biomarker is RNA or cDNA, the RNA or cDNA can be detected by forming a complex between the RNA or cDNA and a labeled nucleic acid probe or primer. The complex between the RNA or cDNA and the labeled nucleic acid probe or primer can be a hybridization complex.

In some aspects of the methods of the present disclosure, gene expression can be detected by microarray analysis. Differential gene expression can also be identified, or confirmed using the microarray technique. Thus, the expression profile biomarkers can be measured in either fresh or fixed tissue, using microarray technology. In this method, polynucleotide sequences of interest (including cDNAs and oligonucleotides) are plated, or arrayed, on a microchip substrate. The arrayed sequences are then hybridized with specific DNA probes from cells or tissues of interest. The source of mRNA typically is total RNA isolated from a biological sample, and corresponding normal tissues or cell lines may be used to determine differential expression.

In some aspects of microarray techniques, PCR amplified inserts of cDNA clones are applied to a substrate in a dense array. In some aspects, at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the microarray chip is scanned by a device such as, confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. Microarray analysis can be performed by commercially available equipment, following manufacturer's protocols.

In some aspects of the methods of the present disclosure, the biomarkers can be detected in a biological sample using qRT-PCR. The first step in gene expression profiling by RT-PCR is extracting RNA from a biological sample followed by the reverse transcription of the RNA template into cDNA and amplification by a PCR reaction. The reverse transcription reaction step is generally primed using specific primers, random hexamers, or oligo-dT primers, depending on the goal of expression profiling. The two commonly used reverse transcriptases are avilo myeloblastosis virus reverse transcriptase (AMV-RT) and Moloney murine leukemia virus reverse transcriptase (MLV-RT).

In some aspects of the methods of the present disclosure, when the biomarker is a protein, the protein can be detected by forming a complex between the protein and a labeled antibody. The label can be any label for example a fluorescent label, chemiluminescence label, radioactive label, etc. Exemplary methods for protein detection include, but are not limited to, enzyme immunoassay (EIA), radioimmunoassay (MA), Western blot analysis and enzyme linked immunoabsorbant assay (ELISA). For example, the biomarker can be detected in an ELISA, in which the biomarker antibody is bound to a solid phase and an enzyme-antibody conjugate is employed to detect and/or quantify biomarker present in a sample. Alternatively, a western blot assay can be used in which solubilized and separated biomarker is bound to nitrocellulose paper. The combination of a highly specific, stable liquid conjugate with a sensitive chromogenic substrate allows rapid and accurate identification of samples.

In some aspects of the methods of the present disclosure, the methods described herein can have a specificity, sensitivity, and/or accuracy of at least 75%, 80%, 85%, 90%, 91%, 92%, 93%, 94%, 95%, 96%, 97%, 98%, or 99%.

In some aspects of the methods of the present disclosure, a labeled probe, a labeled primer, a labeled antibody or a labeled nucleic acid can comprise a fluorescent label.

Any algorithm that can generate a score for a sample by assessing where that sample value falls onto a prediction model generated using different techniques, e.g., decision trees, can be used in the methods disclosed herein. The algorithm analyzes the data (i.e., expression levels) and then assigns a score. In some aspects, the algorithm can be a machine-learning algorithm. Exemplary algorithms that can be used in the methods disclosed herein can include, but are not limited to, XGBoost (XGB), Random Forest (RF), glmnet, cforest, Classification and Regression Trees for Machine Learning (CART), treebag, K-Nearest Neighbors (kNN), neural network (nnet), Support Vector Machine radial (SVM-radial), Support Vector Machine linear (SVM-linear), Naïve Bayes (NB), multilayer perceptron (mlp) or any combination thereof.

In some aspects of the methods of the present disclosure, the algorithm can be XGB (also called XGBoost). XGB is an implementation of gradient boosted decision trees designed for speed and performance.

In some aspects of the methods of the present disclosure, a therapy can comprise anti-cancer therapy, surgery, chemotherapy, targeted drug therapy, radiation therapy, immunotherapy, or any combination thereof.

In some aspects of the methods of the present disclosure, surgery can comprise removing a polyp during a colonoscopy, endoscopic mucosal resection, a partial colectomy, an ostomy, removing at least one cancerous lesion from the liver, or any combination thereof.

In some aspects of the methods of the present disclosure, anti-cancer therapy can comprise anti-colon cancer therapy.

In some aspects of the methods of the present disclosure, chemotherapy can comprise FOLFOX, FOLFIRI, a combination of 5-FU and leucovorin, capecitabine, irinotecan, CapeOx or any combination thereof.

In some aspects of the methods of the present disclosure, targeted drug therapy can comprise bevacizumab, cetuximab, panitumumab, regorafenib, a combination of trifluridine and tipiracil, an EGFR TKI inhibitor or any combination thereof.

In some aspects of the methods of the present disclosure, immunotherapy can comprise pembrolizumab, nivolumab or a combination of pembrolizumab and nivolumab.

For early-stage colon cancer, a minimally invasive approach to surgery can be used to remove the cancer. For example, if the cancer is completely contained within a polyp, the polyp can be removed during a colonoscopy. Endoscopic mucosal resection can be performed to remove larger polyps. Polyps that cannot be removed during a colonoscopy may be removed using laparoscopic surgery.

If the cancer has grown into or through the colon, partial colectomy can be performed to remove the part of the colon that contains the cancer, along with a margin of normal tissue on either side of the cancer. When it's not possible to reconnect the healthy portions of the colon or rectum, an ostomy can be performed to create an opening in the wall of the abdomen from a portion of the remaining bowel for the elimination of stool into a bag that fits securely over the opening. Lymph node removal can also be performed.

For advanced colon cancer, an operation to relieve a blockage of the colon or other conditions can also be performed. In specific cases where the cancer has spread only to the liver, surgery to remove the cancerous lesion from the liver can be performed.

For chemotherapies, either the FOLFOX (5-FU, leucovorin, and oxaliplatin) or CapeOx (capecitabine and oxaliplatin) regimens are used most often, but some patients may get 5-FU with leucovorin or capecitabine alone based on their age and health needs. Irinotecan can also be used as a chemotherapeutic agent for treating a colon cancer.

Targeted drug therapies target specific malfunctions that allow cancer cells to grow. These therapies include, but are not limited to, bevacizumab, cetuximab, panitumumab, ramucirumab, regorafenib, ziv-aflibercept, a combination of trifluridine and tipiracil, and an EGFR TKI inhibitor.

Immunotherapies for colon cancer include, but are not limited to, pembrolizumab (Keytruda®) and nivolumab (Opdivo®).

The sequence information of the colon cancer biomarkers and housekeepers is shown in Table 1.

TABLE 1

Colon Cancer Biomarker/Housekeeper Sequence Informatton

| Gene Name | RefSeq Accession | Sequence | SEQ ID NO: |
|---|---|---|---|
| ADRM1 | NM_007002.3 | gttagagccggctgcgcggcttacggggctcaatcggcggcgagagcggcaggcgggg<br>cgggccgaacgcgggtttccggcggggcccggcaggcgccgaggaggaagagcgagc<br>ccggacggcgcctctcgaacgagtgtgggcgcgaggcaggatgacgacctcaggcgcg<br>ctctttccaagcctggtgccaggctctcggggcgcctccaacaagtacttggtggagtttcgg<br>gcgggaaagatgtccctgaaggggaccaccgtgactccggataagcggaaagggctggt<br>gtacattcagcagacggacgactcgcttattcacttctgctggaaggacaggacgtccggga<br>acgtggaagacgacttgatcatcttccctgacgactgtgagttcaagcgggtgccgcagtgc<br>cccagcgggagggtctacgtgctgaagttcaaggcagggtccaagcggcttttcttctggat<br>gcaggaacccaagacagaccaggatgaggagcattgccggaaagtcaacgagtatctga<br>acaacccccgatgcctggggcgctgggggccagcggaagcagcggccacgaactctct<br>gcgctaggcggtgagggtggcctgcagagcctgctgggaaacatgagccacagccagct<br>catgcagctcatcggaccagccggcctcggaggactgggtgggctgggggccctgactg<br>gacctggcctggccagcttactggggagcagtgggcctccagggagcagctcctcctcca | 1 |

TABLE 1 -continued

Colon Cancer Biomarker/Housekeeper Sequence Informatton

| Gene Name | RefSeq Accession | Sequence | SEQ ID NO: |
|---|---|---|---|
| | | gctcccggagccagtcggcagcggtcaccccgtcatccaccacctcttccacccgtgccac<br>cccagccccttctgctccagcagctgcctcagcaactagcccgagccccgcgcccagttcc<br>gggaatggagccagcacagcagccagcccgacccagcccatccagctgagcgacctcc<br>agagcatcctggccacgatgaacgtaccagccgggccagcaggcggccagcaagtgga<br>cctggccagtgtgctgacgccggagataatggctcccatcctcgccaacgcggatgtccag<br>gagcgcctgcttccctacttgccatctggggagtcgctgccgcagaccgcggatgagatcc<br>agaataccctgacctcgccccagttccagcaggccctgggcatgttcagcgcagccttggc<br>ctcggggcagctgggcccctcatgtgccagttcggtctgcctgcagaggctgtggaggcc<br>gccaacaagggcgatgtggaagcgtttgccaaagccatgcagaacaacgccaagcccga<br>gcagaaagagggcgacacgaaggacaagaaggacgaagaggaggacatgagcctgga<br>ctgagccacgcgccgtcctccgaggaactgggcgcttgcagtgcgttgcacaccctcacct<br>cccacccactgattattaataaagtcttttcttttacctgccaaaaaaaaaaaaaaaaaa | |
| CDK4 | NM_000075.3 | cacctcctgtccgcccctcagcgcatgggtggcggtcacgtgcccagaacgtccggcgttc<br>gccccgccctcccagtttccgcgcgcctctttggcagctggtcacatggtgagggtggggg<br>tgagggggcctctctagcttgcggcctgtgtctatggtcgggccctctgcgtccagctgctcc<br>ggaccgagctcgggtgtatggggccgtaggaaccggctccggggccccgataacgggc<br>cgcccccacagcaccccgggctggcgtgagggtctcccttgatctgagaatggctacctct<br>cgatatgagccagtggctgaaattggtgtcggtgcctatgggacagtgtacaaggcccgtg<br>atccccacagtggccactttgtggccctcaagagtgtgagagtccccaatggaggaggagg<br>tggaggaggccttcccatcagcacagttcgtgaggtggctttactgaggcgactggaggctt<br>ttgagcatcccaatgttgtccggctgatggacgtctgtgccacatcccgaactgaccgggag<br>atcaaggtaaccctggtgtttgagcatgtagaccaggacctaaggacatatctggacaaggc<br>acccccaccaggcttgccagccgaaacgatcaaggatctgatgcgccagtttctaagaggc<br>ctagatttccttcatgccaattgcatcgttcaccgagatctgaagccagagaacattctggtga<br>caagtggtggaacagtcaagctggctgactttggcctggccagaatctacagctaccagatg<br>gcacttacacccgtggttgttacactctggtaccgagctcccgaagttcttctgcagtccacat<br>atgcaacacctgtggacatgtggagtgttggctgtatctttgcagagatgtttcgtcgaaagcc<br>tctcttctgtggaaactctgaagccgaccagttgggcaaaatctttgacctgattgggctgcct<br>ccagaggatgactggcctcgagatgtatccctgccccgtggagcctttcccccagagggc<br>cccgcccagtgcagtcggtggtacctgagatggaggagtcgggagcacagctgctgctgg<br>aaatgctgacttttaacccacacaagcgaatctctgcctttcgagctctgcagcactcttatcta<br>cataaggatgaaggtaatccggagtgagcaatggagtggctgccatggaaggaagaaaag<br>ctgccatttcccttctggacactgagagggcaatctttgcctttatctctgaggctatggagggt<br>cctcctccatctttctacagagattactttgctgccttaatgacattcccctcccacctctccttttg<br>aggcttctccttctccttcccatttctctacactaaggggtatgttccctcttgtccctttccctacc<br>tttatatttggggtcctttttttatacaggaaaaacaaaacaaagaaataatggtctttttttttttttta<br>atgtttcttcctctgtttggctttgccattgtgcgatttggaaaaaccacttggaagaagggactt<br>tcctgcaaaaccttaaagactggttaaattacagggcctaggaagtcagtggagccccttga<br>ctgacaaagcttagaaaggaactgaaattgcttctttgaatatggattttaggcggggcgtggt<br>ggctcacgcctataatcccagcacgttgggaggccaacgcgggtggatcacctgaggtca<br>ggagttcgagaccagcctgactaacatggtgaaaccctgtctctactaaaaatacaaaattag<br>tcaggcgtggtggtgcacacctgtaatcccagctacttgggagactgaggcaggaggatcg<br>cttgaacccgggaggcagaggttgcggtgagccgagatcatgccattgcactccagcctg<br>ggcaacagagcaagactctgtgtcaaaaaaaaaaaaaagaatatagattttaaatggcaaaa<br>aaaaaaaaaaaaaa | 2 |
| COMT | NM_000754.3 | cggcctgcgtccgccaccggaagcgccctcctaatccccgcagcgccaccgccattgccg<br>ccatcgtcgtggggcttctggggcagctagggctgcccgccgcgctgcctgcgccggacc<br>ggggcgggtccagtcccgggcgggccgtcgcgggagagaaataacatctgctttgctgcc<br>gagctcagaggagaccccagacccctcccgcagccagagggctggagcctgctcagag<br>gtgctttgaagatgccggaggccccgcctctgctgttggcagctgtgttgctgggcctggtg<br>ctgctggtggtgctgctgctgcttctgaggcactggggctggggcctgtgccttatcggctg<br>gaacgagttcatcctgcagcccatccacaacctgctcatgggtgacaccaaggagcagcg<br>catcctgaaccacgtgctgcagcatgcggagcccgggaacgcacagagcgtgctggagg<br>ccattgacacctactgcgagcagaaggagtgggccatgaacgtgggcgacaagaaaggc<br>aagatcgtggacgccgtgattcaggagcaccagccctccgtgctgctggagctgggggcc<br>tactgtggctactcagctgtgcgcatggcccgcctgctgtcaccaggggcgaggctcatca<br>ccatcgagatcaaccccgactgtgccgccatcacccagcggatggtggatttcgctggcgt<br>gaaggacaaggtcacccttgtggttggagcgtcccaggacatcatcccccagctgaagaa<br>gaagtatgatgtggacacactggacatggtcttcctcgaccactggaaggaccggtacctgc<br>cggacacgcttctcttggaggaatgtggcctgctgcggaaggggacagtgctactggctga<br>caacgtgatctgcccaggtgcgccagacttcctagcacacgtgcgcgggagcagctgcttt<br>gagtgcacacactaccaatcgttcctggaatacagggaggtggtggacggcctggagaag<br>gccatctacaagggcccaggcagcgaagcagggccctgactgcccccccggcccccctc<br>tcgggctctctcacccagcctggtactgaaggtgccagacgtgctcctgctgaccttctgcg<br>gctccgggctgtgtcctaaatgcaaagcacacctcggccgaggcctgcgccctgacatgct<br>aacctctctgaactgcaacactggattgttctttttaagactcaatcatgacttctttactaacac<br>tggctagctatattatcttatatactaatatcatgttttaaaaatataaaatagaaattaagaatcta<br>aatatttagatataactcgacttagtacatccttctcaactgccattcccctgctgcccttgacttg<br>ggcaccaaacattcaaagctccccttgacggacgctaacgctaagggcggggcccctagc<br>tggctgggttctgggtggcacgcctggcccactggcctcccagccacagtggtgcagaggt<br>cagccctcctgcagctaggccaggggcacctgttagccccatggggacgactgccggcct<br>gggaaacgaagaggagtcagccagcattcacacctttctgaccaagcaggcgctggggac | 3 |

TABLE 1 -continued

Colon Cancer Biomarker/Housekeeper Sequence Informatton

| Gene Name | RefSeq Accession | Sequence | SEQ ID NO: |
|---|---|---|---|
| | | aggtggaccccgcagcagcaccagcccctctgggccccatgtggcacagagtggaagca<br>tctccttccctactccccactgggccttgcttacagaagaggcaatggctcagaccagctccc<br>gcatccctgtagttgcctccctggcccatgagtgaggatgcagtgctggtttctgcccaccta<br>cacctagagctgtccccatctcctccaaggggtcagactgctagccacctcagaggctcca<br>agggcccagttcccaggcccaggacaggaatcaaccctgtgctagctgagttcacctgcac<br>cgagaccagcccctagccaagattctactcctgggctcaaggcctggctagcccccagcca<br>gcccactcctatggatagacagaccagtgagcccaagtggacaagtttggggccacccag<br>ggaccagaaacagagcctctgcaggacacagcagatgggcacctgggaccacctccacc<br>cagggccctgccccagacgcgcagaggcccgacacaagggagaagccagccacttgtg<br>ccagacctgagtggcagaaagcaaaaagttcattgctgctttaatttttaaattttcttacaaaa<br>atttaggtgtttaccaatagtcttattttggcttatttttaa | |
| DHCR7 | NM_001163817.1 | aatcgctgacatcatccgggggcgggcgcccctgccctgcgggtgactccgacccctggc<br>tagagggtaggcggcgtggagcagcgcgcgcaagcgaggccaggggaaggtgggcgc<br>aggactttagccggttgagaaggatcaagcaggcatttggagcacaggtgtctagaaactttt<br>aaggggccggttcaagaaggaaaagttcccttctgctgtgaaactatttggcaagaggctgg<br>agggcccaatggctgcaaaatcgcaacccaacattcccaaagccaagagtctagatggcgt<br>caccaatgacagaaccgcatctcaagggcagtggggccgtgcctgggaggtggactggtt<br>ttcactggcgagcgtcatcttcctactgctgttcgccccttcatcgtctactacttcatcatggc<br>ttgtgaccagtacagctgcgccctgactggccctgtggtggacatcgtcaccggacatgctc<br>ggctctcggacatctgggccaagactccacctataacgaggaaagccgcccagctctatac<br>cttgtgggtcaccttccaggtgcttctgtacacgtctctccctgacttctgccataagtttctacc<br>cggctacgtaggaggcatccaggagggggccgtgactcctgcaggggttgtgaacaagta<br>tcagatcaatggcctgcaagcctggctcctcacgcacctgctctggtttgcaaacgctcatct<br>cctgtcctggttctcgcccaccatcatcttcgacaactggatcccactgctgtggtgcgccaa<br>catccttggctatgccgtctccaccttcgccatggtcaagggctacttcttccccaccagcgc<br>cagagactgcaaattcacaggcaatttcttttacaactacatgatgggcatcgagtttaaccct<br>cggatcgggaagtggtttgacttcaagctgttcttcaatgggcgccccgggatcgtcgcctg<br>gaccctcatcaacctgtccttcgcagcgaagcagcgggagctccacagccatgtgaccaat<br>gccatggtcctggtcaacgtcctgcaggccatctacgtgattgacttcttctggaacgaaacc<br>tggtacctgaagaccattgacatctgccatgaccacttcgggtggtacctgggctggggcga<br>ctgtgtctggctgccttatctttacacgctgcagggtctgtacttggtgtaccaccccgtgcag<br>ctgtccaccccgcacgccgtgggcgtcctgctgctgggcctggtgggctactacatcttccg<br>ggtggccaaccaccagaaggacctgttccgccgcacggatgggcgctgcctcatctgggg<br>caggaagcccaaggtcatcgagtgctcctacacatccgccgatgggcagaggcaccaca<br>gcaagctgctggtgtcgggcttctggggcgtggcccgccacttcaactacgtcggcgacct<br>gatgggcagcctggcctactgcctggcctgtggcggcggccacctgctgccctacttctac<br>atcatctacatggccatcctgctgacccaccgctgcctccgggacgagcaccgctgcgcca<br>gcaagtacggccgggactgggagcgctacaccgccgcagtgccttaccgcctgctgcctg<br>gaatcttctaagggcacgccctagggagaagccctgtggggctgtcaagagcgtgttctgc<br>caggtccatgggggctggcatcccagctccaactcgaggagcctcagtttcctcatctgtaa<br>actggagagagcccagcacttggcaggtgtccagtacctaatcacgctctgttccttgcttttg<br>ccttcaagggaattccgagtgtccagcactgccgtattgccagcacagacggattttctctaat<br>cagtgtccctggggcaggaggatgacccagtcacctttactagtcctttggagacaatttacc<br>tgtattaggagcccaggccacgctacactctgcccacactggtgagcaggaggtcttccca<br>cgccctgtcattaggctgcatttactcttgctaaataaaagtgggagtggggcgtgcgcgttat<br>ccatgtattgcctttcagctctagatcccccttccccctgcctgctctgcagtcgtgggtggggcc<br>cgtgcgccgtttctccttggtagcgtgcacggtgttgaactgggacactggggagaaaggg<br>gctttcatgtcgtttccttcctgctcctgctgcacagctgccaggagtgctctgcctggagtctg<br>cagacctcagagaggtcccagcaccggctgtggcctttcaggtgtaggcaggtgggctctg<br>cttcccgattccctgtgagcgcccaccctctcgaaagaattttctgcttgccctatgactgtgca<br>gactctggctcgagcaacccggggaacttcaccctcaggggcctcccacaccttctccagc<br>gaggaggtctcagtcccagcctcgggagggcacctccttttctgtgctttcttccctgaggca<br>ttcttcctcatccctagggtgttgtgtagaactctttttaaactctatgctccgagtagagttcatct<br>ttatattaaacttcccctgttcaaataa | 4 |
| HMOX2 | NM_001127204.1 | catctctaggccccgccccgcgctgcgtgcccacgttgcgccggcctcgcgccagtccgct<br>gggctgcagggactgcggcgcctgagggagtcgctgacgggcacgctgactggaggct<br>ggcggacaggcgacagcgacctgcggcagagtcttgctgcgacacccaggctggagtgc<br>aatggcgctatctcggctcactgcaacctccgcttcccggattcaagcgattctcctgcctca<br>gcctcccgagtaggtgggactacaggaccagaggagcgagagcagcaagaaccacacc<br>cagcagcaatgtcagcggaagtggaaacctcagagggggtagacgagtcagaaaaaaag<br>aactctggggccctagaaaaggagaaccaaatgagaatggctgacctctcggagctcctga<br>aggaagggaccaaggaagcacacgaccgggcagaaaacacccagtttgtcaaggacttc<br>ttgaaaggcaacattaagaaggagctgtttaagctggccaccacggcactttacttcacatac<br>tcagccctcgaggaggaaatggagcgcaacaaggaccatccagcctttgcccctttgtactt<br>ccccatggagctgcaccggaaggaggcgctgaccaaggacatggagtatttctttggtgaa<br>aactgggaggagcaggtgcagtgccccaaggctgcccagaagtacgtggagcggatcca<br>ctacatagggcagaacgagccggagctactggtggcccatgcatacacccgctacatggg<br>ggatctctcgggggggccaggtgctgaagaaggtggcccagcgagcactgaaactcccca<br>gcacaggggaagggacccagttctacctgtttgagaatgtggacaatgcccagcagttcaa<br>gcagctctaccgggccaggatgaacgccctggacctgaacatgaagaccaaagagagga<br>tcgtggaggaggccaacaaggcttttgagtataacatgcagatattcaatgaactggaccag<br>gccggctccacactggccagagagaccttggaggatgggttccctgtacacgatgggaaa | 5 |

TABLE 1 -continued

| Gene Name | RefSeq Accession | Sequence | SEQ ID NO: |
|---|---|---|---|
| Colon Cancer Biomarker/Housekeeper Sequence Informatton | | | |
| | | ggagacatgcgtaaatgccctttctacgctgctgaacaagacaaaggtgccctggagggca<br>gcagctgtcccttccgaacagctatggctgtgctgaggaagcccagcctccagttcatcctg<br>gccgctggtgtggccctagctgctggactcttggcctggtactacatgtgaagcacccatcat<br>gccacaccggtaccctcctcccgactgaccactggcctacccctttctccagccctgactaa<br>actaccacctcaggtgactttttaaaaatgctgggtttaagaaaggcaaccaataaaagcca<br>gatgctagagcctctgcctgacagcatcctctctatgggccatattccgcactgggcacagg<br>ccgtcaccctgggagcagtcggcacagtgcagcaagcctggcccccgacccagctctact<br>ccaggcttccacacttctgggccctaggctgcttccggtagtccctgtttttgcagtacatggg<br>tgactatctcccctgttggaggtgagtggcctgtaagtccaagctgtgcgagggggccttgct<br>ggatgctgctgtacaacttctgggcctctcttggaccctgggagtgagggtgggtgtgggtg<br>gaagcctcagaggccttgggagctcatccctctcacccagaatccctctaaccccttgggtg<br>cggtttgctcagccccagcttatctcctcctccgcgctgtgtaaatgctccagcactcaataaa<br>gtgggctttgcaagctaaaaaaaaaaaaaaaaaaaaaaaa | |
| MCM2 | NM_004526.3 | atgacgtcgcgttccgtagggctcttcccgggctttggtgggtcacgtgaaccacttttcgcg<br>cgaaacctggttgttgctgtagtggcggagaggatcgtggtactgctatggcggaatcatcg<br>gaatccttcaccatggcatccagcccggcccagcgtcggcgaggcaatgatcctctcacct<br>ccagccctggccgaagctcccggcgtactgatgccctcacctccagccctggccgtgacct<br>tccaccatttgaggatgagtccgaggggctcctaggcacagaggggcccctggaggaaga<br>agaggatggagaggagctcattggagatggcatggaaagggactaccgcgccatcccag<br>agctggacgcctatgaggccgagggactggctctggatgatgaggacgtagaggagctga<br>cggccagtcagagggaggcagcagagcgggccatgcggcagcgtgaccgggaggctg<br>gccggggcctgggccgcatgcgccgtgggctcctgtatgacagcgatgaggaggacgag<br>gagcgccctgcccgcaagcgccgccaggtggagcgggccacggaggacggcgagga<br>ggacgaggagatgatcgagagcatcgagaacctggaggatctcaaaggccactctgtgcg<br>cgagtgggtgagcatggcgggcccccggctggagatccaccaccgcttcaagaacttcct<br>gcgcactcacgtcgacagccacggccacaacgtcttcaaggagcgcatcagcgacatgtg<br>caaagagaaccgtgagagcctggtggtgaactatgaggacttggcagccagggagcacgt<br>gctggcctacttcctgcctgaggcaccggcggagctgctgcagatctttgatgaggctgccc<br>tggaggtggtactggccatgtaccccaagtacgaccgcatcaccaaccacatccatgtccg<br>catctcccacctgcctctggtggaggagctgcgctcgctgaggcagctgcatctgaaccag<br>ctgatccgcaccagtggggtggtgaccagctgcactggcgtcctgccccagctcagcatgg<br>tcaagtacaactgcaacaagtgcaatttcgtcctgggtcctttctgccagtcccagaaccagg<br>aggtgaaaccaggctcctgtcctgagtgccagtcggccggccccttgaggtcaacatgga<br>ggagaccatctatcagaactaccagcgtatccgaatccaggagagtccaggcaaagtggc<br>ggctggccggctgccccgctccaaggacgccattctcctcgcagatctggtggacagctgc<br>aagccaggagacgagatagagctgactggcatctatcacaacaactatgatggctccctca<br>acactgccaatggcttccctgtctttgccactgtcatcctagccaaccacgtggccaagaagg<br>acaacaaggttgctgtaggggaactgaccgatgaagatgtgaagatgatcactagcctctcc<br>aaggatcagcagatcggagagaagatctttgccagcattgctccttccatctatggtcatgaa<br>gacatcaagagaggcctggctctggccctgttcggaggggagcccaaaaacccaggtgg<br>caagcacaaggtacgtggtgatatcaacgtgctcttgtgcggagaccctggcacagcgaag<br>tcgcagtttctcaagtatattgagaaagtgtccagccgagccatcttcaccactggccagggg<br>gcgtcggctgtgggcctcacggcgtatgtccagcggcaccctgtcagcagggagtggacc<br>ttggaggctggggccctggttctggctgaccgaggagtgtgtctcattgatgaatttgacaag<br>atgaatgaccaggacagaaccagcatccatgaggccatggagcaacagagcatctccatct<br>cgaaggctggcatcgtcacctccctgcaggctcgctgcacggtcattgctgccgccaaccc<br>cataggagggcgctacgacccctcgctgactttctctgagaacgtggacctcacagagccc<br>atcatctcacgctttgacatcctgtgtgtggtgagggacaccgtggacccagtccaggacga<br>gatgctggcccgcttcgtggtgggcagccacgtcagacaccaccccagcaacaaggagg<br>aggagggggctggccaatggcagcgctgctgagcccgccatgcccaacacgtatggcgtg<br>gagcccctgccccaggaggtcctgaagaagtacatcatctacgccaaggagagggtccac<br>ccgaagctcaaccagatggaccaggacaaggtggccaagatgtacagtgacctgaggaa<br>agaatctatggcgacaggcagcatccccattacggtgcggcacatcgagtccatgatccgc<br>atggcggaggcccacgcgcgcatccatctgcgggactatgtgatcgaagacgacgtcaac<br>atggccatccgcgtgatgctggagagcttcatagacacacagaagttcagcgtcatgcgca<br>gcatgcgcaagacttttgcccgctacctttcattccggcgtgacaacaatgagctgttgctctt<br>catactgaagcagttagtggcagagcaggtgacatatcagcgcaaccgctttggggcccag<br>caggacactattgaggtccctgagaaggacttggtggataaggctcgtcagatcaacatcca<br>caacctctctgcattttatgacagtgagctcttcaggatgaacaagttcagccacgacctgaa<br>aaggaaaatgatcctgcagcagttctgaggccctatgccatccataaggattccttgggattc<br>tggtttggggtggtcagtgccctctgtgctttatggacacaaaaccagagcacttgatgaact<br>cggggtactagggtcagggcttatagcaggatgtctggctgcacctggcatgactgtttgttt<br>ctccaagcctgctttgtgcttctcacctttgggtgggatgccttgccagtgtgtcttacttggttg<br>ctgaacatcttgccacctccgagtgctttgtctccactcagtaccttggatcagagctgctgag<br>ttcaggatgcctgcgtgtggtttaggtgttagccttcttacatggatgtcaggagagctgctgc<br>cctcttggcgtgagttgcgtattcaggctgcttttgctgcctttggccagagagctggttgaag<br>atgtttgtaatcgttttcagtctcctgcaggtttctgtgcccctgtggtggaagagggcacgac<br>agtgccagcgcagcgttctgggctcctcagtcgcaggggtgggatgtgagtcatgcggatt<br>atccactcgccacagttatcagctgccattgctccctgtctgtttccccactctcttatttgtgcat<br>tcggtttggtttctgtagttttaatttttaataaagttgaataaaatataaaaaaaaaaaaaaaaaa<br>a | 6 |

TABLE 1 -continued

Colon Cancer Biomarker/Housekeeper Sequence Informatton

| Gene Name | RefSeq Accession | Sequence | SEQ ID NO: |
|---|---|---|---|
| PDXK | NM_003681.4 | cggaactcgcgggttcggagccgcccgctgaggtcagaaggaggcgtctgcgctgatcg<br>ggtccgccgcgcgccagagccagagtcgcagccgaggggagccggggccggagccc<br>gagcccgagccgagccggagcccgagcgagcggcggagaccgtgcccccgcctcggc<br>cccgcgccgccgcggccaggcccggcatggaggaggagtgccgggtgctctccataca<br>gagccacgtcatccgcggctacgtgggcaaccgggcggccacgttcccgctgcaggtttt<br>gggatttgagattgacgcggtgaactctgtccagttttcaaaccacacaggctatgcccactg<br>gaagggccaagtgctgaattcagatgagctccaggagttgtacgaaggcctgaggctgaa<br>caacatgaataaatatgactacgtgctcacaggttatacgagggacaagtcgttcctggccat<br>ggtggtggacattgtgcaggagctgaagcagcagaaccccaggctggtgtacgtgtgtgat<br>ccagtcttgggtgacaagtgggacggcgaaggctcgatgtacgtcccggaggacctccttc<br>ccgtctacaaagaaaaagtggtgccgcttgcagacattatcacgcccaaccagtttgaggcc<br>gagttactgagtggccggaagatccacagccaggaggaagccttgcgggtgatggacatg<br>ctgcactctatgggccccgacaccgtggtcatcaccagctccgacctgccctccccgcagg<br>gcagcaactacctgattgtgctggggagtcagaggaggaggaatcccgctggctccgtggt<br>gatggaacgcatccggatggacattcgcaaagtggacgccgtctttgtgggcactggggac<br>ctgtttgctgccatgctcctggcgtggacacacaagcaccccaataacctcaaggtggcctg<br>tgagaagaccgtgtctaccttgcaccacgttctgcagaggaccatccagtgtgcaaaagccc<br>aggccggggaaggagtgaggcccagccccatgcagctggagctgcggatggtgcagag<br>caaaagggacatcgaggacccagagatcgtcgtccaggccacggtgctgtgagggcccc<br>gccgcttgcccgtgacacgcagcgcgttggtgtctccgtgtttgtccctgtgaaaacatgtaa<br>cgtctgccttagagccatgaccgaaacttgatatttttttctttcatgagtgtccggcatctgctg<br>gtcttcattgtgaaacgtgccagtcgtgctttgtgaaaaataacaaagtggtcacagaaatttgt<br>gatctgaaaacccggctcccttccccacaaggctcctgggcctccgggaagacgggcccc<br>tgtttgccatctcgggggtgttccctgtgggagggtgagtgggtgaggccgagcctgctgc<br>gtgtggagcctcgagtgggccctggctgccactaccgtacagaggccgtgtcgcgctggg<br>ctgggcctgggtggcctctgtctttgcatctctgagaaggagtcgggtggtaacggttgggg<br>tcaggaagaattctgccaagtatctttactgtcattctgaccatagcctctttgttcccgcattcg<br>aacttttggttcttactttgctgctcgtttagtccctggggatttcagatcttaggctgttgtttcac<br>cgtatgggagggttgatgtgagcttgcttggagacacacggtgcagcatcagggaccttcc<br>caggccccagcaaattcaagtcggtctgcagacctctcagctacccgcgggacctcttgtaa<br>cccatcggcatcttccaggaatccgccgagtgacttgaggaagatgctaacgcagtaaggt<br>ctgtgctgggccaagagcagctttgaagctccagagaaccaccccgtcaggttccttgtgga<br>agctcccctcatccgtggtgcagcaggctgagcactgcgcgtttgccacgtgctgcccgtg<br>acagcacattgagccacagcatttgtagacaggacagaggggtgcctgccccctgcccctg<br>ctggcacatttaacccttgtcccctgacctcagttctgtgccccaccaaatgcccaggggcaa<br>gaggccaccctggaagctgccaatcttccaaggtgggtgtggggcacggtgggggcggg<br>cagctcccaggcccttgggcaggctggggtgacggcagaggccacagcaccagctctga<br>caagtcctatcatcctctgctcagcagtgacctccctggccccactttgcccagagtttggggt<br>ccccccaggtatagctataggcggcagtgcctgtccctggcctgccttgatttcagccacac<br>ccctgcagccctgcatcccagctctggggtgtgcagaggtttgtgtctccagggaacccac<br>ggctggagagaaatagggagatgcaggaagtgggggcccatggggcccccaagaagcg<br>gactctccaaggggtaccccaccccgctaccttccccacggacggcccctcctggagc<br>ccataccctcctgtgaggccattccagtgtcttctagaaagactcgcttgccaggagtgcgtt<br>ctttgttgaaaaatgccctgaagcgaaaagatgcaggtttatatggaacccccacccccctccc<br>ccactctcccactctgttcgttctgaatgtcttcacgagcgtgcatcagggcgcctggctcccc<br>cacctcagccagtgagtcagacacgggtttcgcagccatgtttcctggctccgaggacacg<br>ggtggcaggcccgttgcagcccagagccactggtccctacagggcgccgccacaccagc<br>aggaaggaggatggctgtgtccggagcctggcggggaggcggcctccccagtatgtgag<br>tgcagggatctgccagaaccacctggccctctgtagggcgtttaactggaaataccctcact<br>gccaagtggagactggggcgtgtgccacattgccagccaccaggaaagcttttctttttctttt<br>ttttttttttttaaacaccaagagcacgtatagcatgggggaaagaacctaaatgtctctctgtcc<br>tgtgagctggtgaaaaacccagcatgagaacgcagtgtcaggtgtgggactccttctgccc<br>ctgcagtgggtgttacgggcggtgtgccctggcgagcaagctttgattcttggttctttgagct<br>cgtttcagaggctgagtccccacatcagctttagttcttggacttccctgtattaagcaagaatt<br>aggagaatggctgtccctgcaggcgcctcccgtaaatcctgagctctctggcgcaatctgaa<br>acttctcttctgtttttctttggctgtatcagccgaaccaggagaggcctgggctgcgactaagg<br>agaaagaaatcgggggtttctgagagcagatggtgcctttgtgggtgcagggcttttgtgga<br>aattgtcagcctctacgggcagagtccggcatcccctccccagactgcctgctgtcaaacca<br>cggagcagctggagcctgccctgtccacggcccgtttccacccgggcatgttcgtctctcat<br>gacttcggcagaggcccctggtggccttcagtttcagtttctcatccaggaaggtaaccttgg<br>gcattggcagtgggtttccctatggcttggatccagattagaattgatctttgttttcactttccat<br>agttaataacatgcaaaataatgagaagaatttattttaaggtgacagctatactggtccaacat<br>cgcctgcttattgtcagggtacagaagtttaatactttcttaatccagtttttcaaacttctccctgt<br>agaccgtaaggatgaattccacaataggatccttttttaaaatcgattttaaattgttgcctagtcc<br>tgccaaggttattatgtgcatctgttatttttccaatacatgtaaacagttgcagcatgatgctttg<br>tttaatgtcctgttcttaagctcgttagagccagttttgaaacgtttggtcttaccgtgaacggag<br>gctggcttggcttagccacgctgatgagtaagtgagggatgtctccatcttgagatcaccag<br>gcaagagagttgcctgcaccaggtaagaggccaaagcccctggggtaacagtccccacc<br>gctacccgaggtaaaacaataaaagctatgtggttgagctcaggcctctcgtgcctggtgtc<br>agagaaggcagagcccacagtaggtgcacggtgcaaggccctgggagggcactggcca<br>gggaaggtggtatagatggccctcagattgcggggccccgagcagctccccactctgccc<br>gtccaccttccctggctccagcctcattctctctttagtttaactatgcaaagagaggaggttga<br>gagtgttctggcagctggagctcttttccttgtccttcctgccctccgatggggccacctgtgtc | 7 |

TABLE 1 -continued

Colon Cancer Biomarker/Housekeeper Sequence Informatton

| Gene Name | RefSeq Accession | Sequence | SEQ ID NO: |
|---|---|---|---|
| | | ggggcagcagtgtccatgtttatggagatcagaggtgtccccactgtgtggctggactgtact<br>ctgctgcccgggtagccaggagtctctccctctctcccctgccgcctgcctggtctcatggg<br>cctccttcacacacccctccctgtggatcgcctgcctgggcccagagcaggggaactggag<br>tttgtgagtgagcagagcaggttatgtgcagacagggaaacgagaactttggacctggcttt<br>ctgagtccaggtgagagctgtgtggcccccgatgccactctgcccgccggagggatgtg<br>cctgctgagccttttccttccacgccgcctctcactgccaggccagcggcttccgctgagact<br>cgctggagaggcggctcccgtgtccgtccaccgagcactcagatggatgctgatcaccag<br>ggccgaggggctcccagaaggaccccaggccctggggagggtggctgtgggaggcc<br>aagtccactgcccggaagtcttgtcagccctaagccagggaagcctggagcgtggcctgg<br>cgggtctgggtggacaccgtccccactccggactcccagcacaggggaggatacctgag<br>cctgtatggccctgtagccctgggcagagctgggcctgtcgtgtgttcctgcctggcaggtg<br>caggtgctggccatctgcaggtggaaggaggtgggaatcttggatttttgtttttttttgttttttt<br>ttttttgagatgaagtctcgctctgacacccaggctggcgtgcagtggtgtgatctcggctcac<br>tgcaaactccgcttcctgggttcaagtggttctcctgccccagcctcccaagtagctgggatt<br>acaggcatgcgccaccacgctcagctgatttttgtatttttagtagagatggggtttcaccatgt<br>tggccaagctggtctcaaactcctgacctcaagtgatctgcccgcctcggcctcccagagtg<br>ctgggattacaggcatgagccagtgcacccggcggaatcttggaatttttatagacagcacc<br>tcagtttctgactccagccgcacacctcctgcctctgccagcaggggttgccgccagaccag<br>agccagggccaggtccctgcgtccatcccccccggtaggatggacgtgagccatccttcta<br>ggggactttttttcagtgtgcgactcgtctctgttaggtggtaggagccagtttgtgtggcctgtg<br>ccacgctccacagtgcgtggctgggctctgtgtgtggcctgtgtcccctgtccctgcaggac<br>ccagcaggcatcgtggcgtgacagctgtgtccaagccactgcccgggcatcccatcaccc<br>accagggtgcacggtctctcctgctgggggctttctgtcgcatgtgtgtctcctgtcgactctg<br>cagtttgttctcagagcagaatgtttcctgttctcagtgcacaaagacactggttttcaatcggc<br>gtctaaaaccacgttcctgcctttcattgcaacacggtgtgttcatttgtttaaaacagtttaatga<br>gtaagtttagatgactggtcaatatcttaaaaatgtatattagtaagaagttcttcctggaatttttc<br>tttcgattctggcagaataaacaggtgtttttagtttcccactgtctgagccaagcaggaccct<br>gtcccagagcaagagatgtccccttccatctctgacccttgcctgggacaagctttgatggg<br>gggccccagcttcaaggctgtggtgggaacagcacccccaaatgccagcctctcctttcttc<br>ccatccaccagtatactgcggggccatttctggtctttgtccaacaggaaacccatttctggtg<br>ggatatgccttccagtgccacagggccactcaccccatgcatctctgtcctgcccgtcagtg<br>ctgggacggacagcaagggcaagcccagtgtctggcggataggtgggtgggaacagag<br>aggggagaatgccgtcctaagcttctgcttggggatcccccacacgacctgggtactgcct<br>gggaaacctgtcctaagtaaaactatggacctcgcctcgcccaccggcctgcgaagccag<br>catctccgtgaaggtggatggaagcgcctttgtcctcattttgagctgcaagctgggtcagcg<br>gctctgaagccctcgagtgactttctaacccaagacccagcccctggcaggaggagggtg<br>ggtgcagggctggtgggacaaaaagaggcctcagcaggcctggaagacccttccagtac<br>atcccacagcgtgtcgagcagctgggagaacctgtgtcaagctcgagccgtcataggtccc<br>catgaggtgtctgaagccccttcttggtgatgggaggcagaggtgctgacgttctggagcat<br>ggacgtgagtcctcagctggctccgcgtgggcccttggagggtgccaggtgtgtggtgacc<br>ttctggatgcctttaacttcatggctgcgtcattcctgatttagaactttaaccggagcttcatcta<br>gtgattgcaaaactggaccaatgggaggacggcggcgcagcccgctccctccgtggaatg<br>gagctcagctcttcggaggcatcaaagcacctgtcgcctccgtggtcccccctgctgaggga<br>gtgcggcctctgcaaggttcgggggtggcttcgtttgcctggagtggccggccctgcttgtg<br>ccatgtggatgtttgtgagcctcggtcctacagcactgtgtaggctgcatctgtttcgtgctggt<br>cctgttgacttgtatgatatccacaaataaatattttcatggcggtcgtgttgaaaaaaaaaa | |
| POP7 | NM_005837.2 | ggaaggggcggggcgaacggaagccgggaaggcgattcatagctcgcggggtacggg<br>cgcgcgtgcgcactccgcagcccgttcaggaccccggcgcgggcagggcgcccacgag<br>ctggctggctgcttgcacccacatccttctttctctgggacctggggtcgcggttacttgggct<br>ggccggcgaacccttgagtggcctggcggggagcgggcctcgcgcgcctggagggccc<br>tgtggaacgaagagaggcacacagcatggcagaaaccgagagccccgcggtgctgtg<br>gaggctgaactggatccagtggaatacacccttaggaaaggcttcccagccgcctgcccc<br>ggagacccaatgacatttatgtcaacatgaagacggactttaaggcccagctggcccgctg<br>ccagaagctgctggacggagggcccggggtcagaacgcgtgctctgagatctacattca<br>cggcttgggcctggccatcaaccgcgccatcaacatcgcgctgcagctgcaggcgggca<br>gcttcgggtccttgcaggtggctgccaatacctccaccgtggagcttgttgatgagctggag<br>ccagagaccgacacacgggagccactgactcggatccgcaacaactcagccatccacatc<br>cgagtcttcagggtcacacccaagtaattgaaaagacactcctccacttatcccctccgtgat<br>atggctcttcgcatgctgagtactggacctcggaccagagccatgtaagaaaaggcctgttc<br>cctggaagcccaaaggactctgcattgagggtgggggtaattgtctcttggtgggcccagtt<br>agtgggccttcctgagtgtgtgtatgcggtctgtaactattgccatataaataaaaaatcctgtt<br>gcactagtgtcctgccatcccaaaaaaaaaaaaaaaaaa | 8 |
| S100P | NM_005980.2 | tgaggctgccttataaagcaccaagaggctgccagtgggacattttctcggccctgccagcc<br>cccaggaggaaggtgggtctgaatctagcaccatgacggaactagagacagccatgggc<br>atgatcatagacgtcttttcccgatattcgggcagcgagggcagcacgcagaccctgacca<br>agggggagctcaaggtgctgatggagaaggagctaccaggcttcctgcagagtggaaaa<br>gacaaggatgccgtggataaattgctcaaggacctggacgccaatggagatgcccaggtg<br>gacttcagtgagttcatcgtgttcgtggctgcaatcacgtctgcctgtcacaagtactttgaga<br>aggcaggactcaaatgatgccctggagatgtcacagattcctggcagagccatggtcccag<br>gcttcccaaaagtgtttgttggcaattattcccctaggctgagcctgctcatgtacctctgattaa<br>taaatgcttatgaaatga | 9 |

TABLE 1 -continued

Colon Cancer Biomarker/Housekeeper Sequence Informatton

| Gene Name | RefSeq Accession | Sequence | SEQ ID NO: |
|---|---|---|---|
| SNRPA | NM_004596.4 | ggcggggccaggagagaaagctttgtggtttggtctcagggaagtagcaggcgccggttg<br>agagaactacggccctgtcggaaggtaacctccggtgcaaacgaccatcggcggcaggc<br>gagcggtacgcttggcgtccgggccttcctgggcccgtctgaggaaacttgctgctcgagg<br>ccaggctgcctaggacctgtccctttttttctatactggctcccacatccgggttttttctccggg<br>acggcccttcggatgcttgggccaatgggaatcgccatttagggtgctccgcccaccgggt<br>cgcgtagagcatcctggaagtcgtagtaaatctctcgagagttctctccgcacgcgggctgg<br>agaagcgggtcctacgcacgctttgttgtcgcgctttgcctccgtccttgcccctactcccgc<br>cttacctgacttccttttcggaggaagatccttgagcagccgacgttgggacaaaggatttgg<br>agaaacccagggctaaagtcacgtttttcctcctttaagacttacctcaacacttcactccatgg<br>cagttcccgagacccgccctaaccacactatttatatcaacaacctcaatgagaagatcaag<br>aaggatgagctaaaaaagtccctgtacgccatcttctcccagtttggccagatcctggatatc<br>ctggtatcacggagcctgaagatgaggggccaggcctttgtcatcttcaaggaggtcagca<br>gcgccaccaacgccctgcgctccatgcagggtttccctttctatgacaaacctatgcgtatcc<br>agtatgccaagaccgactcagatatcattgccaagatgaaaggcaccttcgtggagcggga<br>ccgcaagcgggagaagaggaagcccaagagccaggagaccccggccaccaagaagg<br>ctgtgcaaggcgggggagccaccccgtggtgggggctgtccaggggcctgtcccgggc<br>atgccgccgatgactcaggcgccccgcattatgcaccacatgccgggccagccgccctac<br>atgccgccccctggtatgatcccccgccaggccttgcacctggccagatcccaccaggg<br>gccatgcccccgcagcagcttatgccaggacagatgccccctgcccagcctctttctgaga<br>atccaccgaatcacatcttgttcctcaccaacctgccagaggagaccaacgagctcatgctg<br>tccatgcttttcaatcagttccctggcttcaaggaggtccgtctggtacccgggcggcatgac<br>atcgccttcgtggagtttgacaatgaggtacaggcaggggcagctcgcgatgccctgcagg<br>gctttaagatcacgcagaacaacgccatgaagatctcattgccaagaagtagcaccttttcc<br>ccccatgcctgccccttcccctgttctggggccacccctttccccccttggctcagcccccctga<br>aggtaagtcccccccttgggggccttcttggagccgtgtgtgagtgagtggtcgccacacag<br>cattgtacccagagtctgtccccagacattgcacctggcgctgttaggccggaattaaagtg<br>gctttttgaggtttggtttttcacaatcaaaaaaaaaaaaaaaaa | 10 |
| SORD | NM_003104.5 | ctccacgctagcgccgcccaggctggcacaaaggaggaagcctagtcccgcccctgcgt<br>gcggcgcttctcccaggccccaccttccatccagtgccctggaccctcggctgggtagcgc<br>caccagagcgaccaaacgtcccgcgccttccaggccgcactccagagccaaaagagctc<br>catggcggcggcggccaagcccaacaacctttccctggtggtgcacggaccgggggactt<br>gcgcctggagaactatcctatccctgaaccaggcccaaatgaggtcttgctgaggatgcatt<br>ctgttggaatctgtggctcagatgtccactactgggagtatggtcgaattgggaattttattgtg<br>aaaaagcccatggtgctgggacatgaagcttcgggaacagtcgaaaaagtgggatcatcg<br>gtaaagcacctaaaaccaggtgatcgtgttgccatcgagcctggtgctccccgagaaaatg<br>atgaattctgcaagatgggccgatacaatctgtcaccttccatcttcttctgtgccacgccccc<br>cgatgacgggaacctctgccggttctataagcacaatgcagccttttgttacaagcttcctgac<br>aatgtcacctttgaggaaggcgccctgatcgagccactttctgtggggatccatgcctgcag<br>gagaggcggagttaccctgggacacaaggtccttgtgtgtggagctgggccaatcgggat<br>ggtcactttgctcgtggccaaagcaatgggagcagctcaagtagtggtgactgatctgtctg<br>ctacccgattgtccaaagccaaggagattggggctgatttagtcctccagatctccaaggag<br>agccctcaggaaatcgccaggaaagtagaaggtcagctggggtgcaagccggaagtcac<br>catcgagtgcacgggggcagaggcctccatccaggcgggcatctacgccactcgctctgg<br>tgggaacctcgtgcttgtggggctgggctctgagatgaccaccgtacccctactgcatgcag<br>ccatccgggaggtggatatcaagggcgtgtttcgatactgcaacacgtggccagtggcgatt<br>tcgatgcttgcgtccaagtctgtgaatgtaaaacccctcgtcacccataggtttcctctggaga<br>aagctctggaggcctttgaaacatttaaaaagggattggggttgaaaatcatgctcaagtgtg<br>accccagtgaccagaatccctgatgttaatgggctctgccctcatccccacagtcttgggatc<br>tcagggcacaatggctggacatgggtgggctctgatgcagaactttctcttttgaatgttaaga<br>ataactaatacaattcattgtgaacagaagtccttaagcagaggaattggtgtgccttaaagat<br>acaatctgggatagtttgggggaacttgtagccagaatgccctgttcatgctgagcaaagttc<br>agcaagtagagcagagtttggcaggcaggtgccaggaactccccttcttcctggagtgcctt<br>cattgaggaaggaaatctggcccttgggtttcctggttccactgctactgacccagaggga<br>atgagggctgagttatgaaaagataacttcatgaagacttaactggcccagaagctgatttc<br>atgaaaatctgccactcagggtctgggatgaaggcttgtcagcacttccagtttagaacgcaa<br>tgtttctagagacatattggctgtttgtttgatgataaaggagaataagaaaaggcatcacttt<br>cctggatccaggataatttttaaaccaatcaaatgaaaaaaacaaacaaacaaaaaaggaaa<br>tgtcatgtgaggttaaaccagtttgcattcccctaatgtggaaaaagtaagaggactactcag<br>cactgtttgaagattgcctcttctacagcttctgagaattgtgttatttcacttgccaagtgaagg<br>acccccctccccaacatgccccagcccacccctaagcatggtcccttgtcaccaggcaacca<br>ggaaactgctacttgtggacctcaccagagaccaggagggtttggttagctcacaggacttc<br>ccccaccccagaagattagcatcccatactagactcatactcaactcaactaggctcatactc<br>aattgatggttattagacaattccatttctttctggttattataaacagaaaatattcctcttctcatt<br>accagtaaaggctcttggtatctttctgttggaatgatttctatgaacttgtcttattttaatggtgg<br>gtttttttttctggtaagatttagacctaaatcgcatcatgccaacttgtgactttgagactattcatc<br>aagaatgaggatatagtagccatgacatagcttgagctatagcctttaattccttactttggctat<br>gggtggagggtgagtttgaagaggttctgattttcttgtaacctgggaaagccatgaccttgtg<br>cccgattctttcagattgctttgggtaataaatattggtggtggtatctgactcatgctgctgttta<br>tggtcctgtttagtggggaatggactcaggttacccatttcccagagggaaggatcccagga<br>tttttgaaggttacatattttctgtaccaaatataatttcattgacatgaattatctctaatcctcatg<br>acaagccacatacacaatcattttgtagataaagaagatataaatgccagaggagaccttaa<br>gattgtcttacaacacaacccttcagttaacgagagagg | 11 |

TABLE 1 -continued

Colon Cancer Biomarker/Housekeeper Sequence Informatton

| Gene Name | RefSeq Accession | Sequence | SEQ ID NO: |
|---|---|---|---|
| STOML2 | NM_001287031.1 | tccgggggagcggaactgcaagaggaaaggctcgggtaggcttctgggagcgaccgctc<br>cgctcgtctcgttggttccggaggtcgctgcggcggtgggaaatgctggcgcgcgcggcg<br>cggggcactggggcccttttgctgaggggctctctactggcttctggccgcgctccgcgcc<br>gcgcctcctctggattgccccgaaacaccgtggtactgttcgtgccgcagcaggaggcctg<br>ggtggtggagcgaatgggccgattccaccggatcctggagcctggtttgaacatcctcatcc<br>ctgtgttagaccggatccgatatgtgcagagtctcaaggaaattgtcatcaacgtgcctgagc<br>agtcggctgtgactctcgacaatgtaactctgcaaatcgatggagtcctttacctgcgcatcat<br>ggacccttacaaggcaagctacggtgtggaggaccctgagtatgccgtcacccagctagct<br>caaacaaccatgagatcagagctcggcaaactctctctggacaaagtcttccgggtggagg<br>cagagcggcggaaacgggccacagttctagagtctgaggggacccgagagtcggccatc<br>aatgtggcagaagggaagaaacaggcccagatcctggcctccgaagcagaaaaggctga<br>acagataaatcaggcagcaggagaggccagtgcagttctggcgaaggccaaggctaaag<br>ctgaagctattcgaatcctggctgcagctctgacacaacataatggagatgcagcagcttca<br>ctgactgtggccgagcagtatgtcagcgcgttctccaaactggccaaggactccaacactat<br>cctactgccctccaaccctggcgatgtcaccagcatggtggctcaggccatgggtgtatatg<br>gagccctcaccaaagccccagtgccagggactccagactcactctccagtgggagcagca<br>gagatgtccagggtacagatgcaagtcttgatgaggaacttgatcgagtcaagatgagttag<br>tggagctgggcttggccagggagtctgggaacaaggaagcagattttcctgattctggctct<br>agcttccctgccaagattttggtttttattttttatttgaactttagtcgtgtaataaactcaccagt<br>ggcaaaccagaaactgtcctctttgattggggaatgaagttgggaaagtcactagcattttcct<br>tggatccagtcctgtcagcatgatgcctccatgaataagagtgaacttcttgtaaagtgaaact | 12 |
| UMPS | NM_0003104.3 | ctgcagacgaggcaggcggaagaggcgggacttcgcgggtgacgtcatcggggcgccg<br>gaggcccggggcgcctgggaatttgaagcaaacaggcagcgcgcgacaatggcggtcg<br>ctcgtgcagctttggggccattggtgacgggtctgtacgacgtgcaggctttcaagtttgggg<br>acttcgtgctgaagagcgggctttcctcccccatctacatcgatctgcggggcatcgtgtctc<br>gaccgcgtcttctgagtcaggttgcagatattttattccaaactgcccaaaatgcaggcatcag<br>ttttgacaccgtgtgtggagtgccttatacagctttgccattggctacagttatctgttcaaccaa<br>tcaaattccaatgcttattagaaggaaagaaacaaaggattatggaactaagcgtcttgtaga<br>aggaactattaatccaggagaaacctgtttaatcattgaagatgttgtcaccagtggatctagt<br>gttttggaaactgttgaggttcttcagaaggagggcttgaaggtcactgatgccatagtgctgt<br>tggacagagagcagggaggcaaggacaagttgcaggcgcacgggatccgcctccactca<br>gtgtgtacattgtccaaaatgctggagattctcgagcagcagaaaaaagttgatgctgagac<br>agttgggagagtgaagaggtttattcaggagaatgtctttgtggcagcgaatcataatggttct<br>cccctttctataaaggaagcacccaaagaactcagcttcggtgcacgtgcagagctgccca<br>ggatccacccagttgcatcgaagcttctcaggcttatgcaaaagaaggagaccaatctgtgt<br>ctatctgctgatgtttcactggccagagagctgttgcagctagcagatgctttaggacctagta<br>tctgcatgctgaagactcatgtagatattttgaatgattttactctggatgtgatgaaggagttga<br>taactctggcaaaatgccatgagttcttgatatttgaagaccggaagtttgcagatataggaaa<br>cacagtgaaaaagcagtatgaaggaggtatctttaaaatagcttcctgggcagatctagtaaa<br>tgctcacgtggtgccaggctcaggagttgtgaaaggcctgcaagaagtgggcctgcctttg<br>catcgggggtgcctccttattgcggaaatgagctccaccggctccctggccactggggact<br>acactagagcagcggttagaatggctgaggagcactctgaatttgttgttggttttatttctggc<br>tcccgagtaagcatgaaaccagaatttcttcacttgactccaggagttcagttggaagcagga<br>ggagataatcttggccaacagtacaatagcccacaagaagttattggcaaacgaggttccga<br>tatcatcattgtaggtcgtggcataatctcagcagctgatcgtctggaagcagcagagatgta<br>cagaaaagctgcttgggaagcgtatttgagtagacttggtgtttgagtgcttcagatacatttt<br>cagatacaatgtgaagacattgaagatatgtggtcctcctgaaagtcactggctggaaataat<br>ccaattattcctgcttggattcttccacagggcctgtgtaagaatgggttctggagttctcatgg<br>tctttaggaaatattgagtaatttgtaatcaccgcattgatactataataagttcattcttaagcttg<br>ctttttttgagactggtgtttgttagacagccacagtcctgtctgggttagggtcttccacatttga<br>ggatccttcctatctctccatgggactagactgctttgttattctatttatttttaatttttttcgaga<br>caggatctcactctgttgcccaggatggagtgcagtggtgagatcacggctcattgcagcct<br>cgacctcccaggtgatcctcccacctcagcttccagattagctggtgctataggcatgcacca<br>ccacgtccatctaaatttctttattatttgtagagatgaggtcttgccatgttacccaggctggtct<br>caactcctgggctcaagcgatcctcctgcctcagtctctcaaagtgctgggattacaggtgtg<br>agccactgtgcccagcctaattgcagtaagacaaaaattctagggcaccaagaggctaaag<br>tcagcacagcttttcttgtgtcctgtattctctgtctaatgtgttgcccaaataatacctaattgtta<br>gccattcccctccatctctggcctaaaagtgatagtccaggtatccacatgggctggttccca<br>gaactgccattgctcactctccaaagaggggaaggtggggaaggggaaggtgactatagc<br>tcagctcctgagctagtatctggctgttatttcaacaaccggagttggggtttgggctcatttttt<br>cccctagccagcaattatggaccagtagtaacacaagtgacagcttcctgtgactgacttcac<br>aattaggaggtctaagattccatttgggtatttgcttaaggatcccacataattgtcccaacggt<br>cattagtagaggggaggtaagccttcattaataataaagagaaagcccacattcaaggtggt<br>gtttgagcaggggcagggtgagggctgtcccggtgctcattgcaccagcacactcacattc<br>cttctcatttggggcccacctgcaggaagtggcacaggatcagccatttccccacccttgtca<br>gctgatggcccactgttctttaatgactcagaggaatgcctaggattttttttttttttgagacag<br>aatctcactgtcgcccaggctggagttcagtggcacgatctcggctcactgcaacttctgcct<br>ctctggttcaagcagttctcctgcctcagcctcccgagtagctgggactacaagcctaggatt<br>tttaactcaggtttttattatattccctcctgaagtttttacttcaagagcttctgctctaaagtccaa<br>tttgggcttcatgtccccagtgctgcatctccagggaaatgctgtctgtgggagagaccaact<br>ctcaaggaagaagtggccacagaaggagcaggaagggagttggccctcagggctactct<br>ggggaagccaaaagtcatgaaggggagaagaattttctgacaaaaacttgcaggaatctctt<br>aggtgtcttcagtgttggagtgatatgttgagaggcctttggagtgatgtgctgaggtctcagg | 13 |

TABLE 1 -continued

| Colon Cancer Biomarker/Housekeeper Sequence Informatton | | | |
|---|---|---|---|
| Gene Name | RefSeq Accession | Sequence | SEQ ID NO: |
| | | cgcccacctccctggctgtcacttccatgtgtcagtggttctcccactttagcaggtatcagag<br>tcacctggagtcttgtcaaaacaggtaccagccccacccgcagcgtttctgactctgggtag<br>ctctgggatggggcttgagaatttgcgtttccaaaaaggtcccaggtgatgctgcggttgcct<br>gcgcagggactggactttgagaaccacttcactggttattcacatttctgcctctgcagtgaga<br>cagccttgaggtctgcctcctgctaagagtcacatgctcctgtcctttagaaatgtgggctcct<br>gccatctccaggacgcaggcactgttcctgttgatgaaccctatttcacaggacccctgctaa<br>ggtgatttgaggggaaatgagaggaggctcaaataatcacccagcccctgccacttactga<br>aagtgtaggtccttgtgccccacaccatcagagtttctgcgttagcagatttgtggtttgccca<br>gcagcctgggcgtgtgcatttctaatgggtgcctcaagtgatctgtttctgatttgtatttctattg<br>tgaagagtcagcccagtactgcaggcctcttacctaagcagaatcccagtctggcatcaaag<br>ctttagaggacaagttgattcaggcagagaagaacttgggctatacaagcgctgttcttcagc<br>attgaagtattttggaggcattagatagtttaaccctttctcagtcaaggaatatttacagaacat<br>gatctctgggcattgtaactcctggtcttagtggggaatatagggaccccatgtctccatggg<br>gtgcacagaatgtctgtgagactgatggagtggagaacgccatcccccagcctctccagct<br>actcgaggcattctgtagaacataagcccatagattgtgtgtgtgtgtgtgtgtgtgtgtgtg<br>tgtgtgtgtgtgcatgcgcgcgcgtgcgcactggaggaacctaagaaactatttggtgcactt<br>cctcttattttagagctcccaaagtgtagctccagaatcgtaaagggatatgctcagtctcaca<br>gccagcctgtggatctcagtcccaacactcacccttgtgctactgagtcagctctaagaaaat<br>ctgccaaaagtaggccgagggctggtttttgttttgttttgtttgtttgatacagggtcttcactct<br>gttgcccaggctggagtatatcatggctcactgcaaccttgacttgggctcaagcgatccgct<br>caagtagctggaactactctcaagtagctctcaagagcctctcgagtggctggaactacagg<br>cgtgcaccaccacagctggttaattttaaaatttttgtagagacggtggaggaggttctcact<br>gtgactcagtgtgtgcccgacagcagagcccacaccactccagttgcagtggttgccatctg<br>ggtcatcagacctggctgtcaggggtgcagccacaggagagccaacagcagagggtgct<br>ggccgctgagctagctgctaatgctggcctgggtgcagttctcatccaaagtacccggtggg<br>tgggagtcactcagtaccagttccgagcctgaacccaaactctcgtgtttctgctcacccctct<br>ctggcttctgccaccacatgggaagaatatgccctggttagcccatggcttctgaagagcaa<br>gagaaagtagagcagagcctactccagcctcccccgtccaatgtatgaaagccccagctga<br>tctgtaagcctgggagcgtgataaatgcttagtagtgcatgccatggagttccagggtggttt<br>attacacggcaatatctagctaaatacatttaacttgctgcagctctctggatccagcctggtta<br>ccaggaagacaaaaactgggctccaccaggaaccagtcttctgccttcccaaccatcacct<br>ctggctgcatcagcgatctctcccagcgaaatagctgcttggtcttgtgtgaatcctgtacttta<br>acacagtggaccaagtgtcagtcattgaaaatgaccatgagtaaccctgtggactctctgca<br>gcttggttcctttgccccttaacaggtgggtatgaatcgtgtcttcagtgccagggctgaatga<br>gaaagggcattcctttttgaaggaatctgatactaaacacaaagcatgagaaaaatcaggact<br>tgttggagttatatttttaaaatatatattttaacagttatatatattagatataatatataatagtatat<br>ataaataatactatattgcccaggctggtctcgaactccttagctcaagtgatcctcctgccttg<br>gcttcccaaagtgctaggattacaggtgtgagccactgctcccggcctgttggagttctttaca<br>tttattttataatcaatgctgttttattaaatgcggattttattttggattacaggatgtagaatgcca<br>tatttttcttagatcatagggcctttcacatttgtaatttggccttgtatgagttaccctgcaatccc<br>tttgttttccccataacccttccaaaggaaggccgcaatagaaatacaaagagaaacaaaata<br>attagaatatttttttaacttctaaagttcaaggttttggcataagtctggtttagaagcacatttgcc<br>tagccctttccttcccaccaaggggaaagtcttcctctagacaagaggcagagggctcctc<br>agagtcagatcctggtgtgggctctcacgtgctgctgctgaatcccagggaaggagggag<br>gaagggcagttgacacccaaaataagggtggggaactgtcagcagaggaggtctgtgtca<br>tgtttttcagcgctggggttggggggagcccaggagagcaggaagatccagagatccctc<br>gccccagctcggccatgtgtgtctgggacagagcctgaggtggcctgagcttcctgtggct<br>ccagagtaacattatagagaagctgaattctcctgtttttctgaaaagggcatgggagttagct<br>gagaagcagacctggtgggcctgagagtctcaatcgtcaggtaaggacagtcagtgggaa<br>gtggacgggccgcacaaccaaggttctcatgaggacaaccatgtcttcggggggtgcccttg<br>tgcacagacagctccatagtcctgcctccaatgtcccaacactgcattgtctccctgcacttag<br>cagccctgcagggtgagacttggggaggatcctgaaatgattgtatttaacaagacatgctgt<br>ccttgtttacctggaacctagcaatgttgttttctgccacaacttgaatagatacttgaagcaga<br>gatgatgttgagttaaaaaaaatatatacataaaaatatgggttcttttcaacctgaatagatgg<br>cctaaaaattcaaa | |
| MORF4L1 | NM_001265603.1 | cggcgtgccctggggcggcgcgggcgcaggggcgcgtgcgcggcgggctgtcgttggc<br>tggagcagcggctgcgcgggtcgcggtgctgtgaggtctgcgggcgctggcaaatccgg<br>cccaggatgtagagctggcagtgcctgacggcgcgtctgacgcggagttgggtggggtag<br>agagtagggggcggtagtcgggggtggtgggagaaggaggaggcggcgaatcacttata<br>aatggcgccgaagcaggacccgaagcctaaattccaggaggttgggatgaatgggttccg<br>gagagcagagtactcaaatacgtggacaccaatttgcagaaacagcgagaacttcaaaaag<br>ccaatcaggagcagtatgcagaggggaagatgagaggggctgccccaggaaagaagac<br>atctggtctgcaacagaaaaatgttgaagtgaaaacgaaaaagaacaaacagaaaacacct<br>ggaaatggagatggtggcagtaccagtgagacccctcagcctcctcggaagaaagggc<br>ccgggtagatcctactgttgaaaatgaggaaacattcatgaacagagttgaagttaaagtaaa<br>gattcctgaagagctaaaaccgtggcttgttgatgactgggacttaattaccaggcaaaaaca<br>gctcttttatcttcctgccaagaagaatgtggattccattcttgaggattatgcaaattacaagaa<br>atctcgtggaaacacagataataaggagtatgcggttaatgaagttgtggcagggataaaag<br>aatacttcaacgtaatgttgggtacccagctactctataaatttgagagaccacagtatgctga<br>aattcttgcagatcatcccgatgcacccatgtcccaggtgtatggagcgccacatctcctgag<br>attatttgtacgaattggagcaatgttggcttatacacctctggatgagaagagccttgctttatt<br>actcaattatcttcacgatttcctaaagtacctggcaaagaattctgcaactttgttcagtgccag<br>cgattatgaagtggctcctcctgagtaccatcggaaagctgtgtgagaggcactctcactcac | 14 |

TABLE 1 -continued

Colon Cancer Biomarker/Housekeeper Sequence Informatton

| Gene Name | RefSeq Accession | Sequence | SEQ ID NO: |
|---|---|---|---|
| | | ttatgtttggatctccgtaaacacattttttgttcttagtctatctcttgtacaaacgatgtgctttgaa<br>gatgttagtgtataacaattgatgtttgttttctgtttgattttaaacagagaaaaaataaaaggg<br>ggtaatagctcctttttttcttctttcttttttttttttcatttcaaaattgctgccagtgttttcaatgatgg<br>acaacagagggatatgctgtagagtgttttattgcctagttgacaaagctgcttttgaatgctgg<br>tggttctattcctttgacactacgcacttttataatacatgttaatgctatatgacaaaatgctctga<br>ttcctagtgccaaaggttcaattcagtgtatataactgaacacactcatccatttgtgcttttgtttt<br>tttttatggtgcttaaagtaaagagcccatcctttgcaagtcatccatgttgttacttaggcatttta<br>tcttggctcaaattgttgaagaatggtggcttgtttcatggtttttgtatttgtgtctaatgcacgttt<br>taacatgatagacgcaatgcattgtgtagctagttttctggaaaagtcaatcttttaggaattgttt<br>ttcagatcttcaataaatttttctttaaatttcaaagaacaaaaaaaaaaaaaaa | |
| MRPL19 | NM_014763.3 | gtagtcttgacgtgagctagctggcatggcggcctgcattgcagcggggcactgggctgca<br>atgggcctaggccggagtttccaagccgccaggactctgctcccccgccggcctctatcg<br>cctgcagggtccacgcggggcctgtccggcagcagagcactgggccttccgagcccggt<br>gcgttccaaccgccgccgaaaccggtcatcgtggacaagcaccgccccgtggaaccgga<br>acgcaggttcttgagtcctgaattcattcctcgaaggggaagaacagatcctctgaaatttcaa<br>atagaaagaaaagatatgttagaaaggagaaaagtactccacattccagagttctatgttgga<br>agtattcttcgtgttactacagctgacccatatgccagtggaaaaatcagccagtttctgggga<br>tttgcattcagagatcaggaagaggacttggagctactttcatccttaggaatgttatcgaagg<br>acaaggtgtcgagatttgctttgaactttataatcctcgggtccaggagattcaggtggtcaaa<br>ttagagaaacggctggatgatagcttgctatacttacgagatgcccttcctgaatatagcacttt<br>tgatgtgaatatgaagccagtagtacaagagcctaaccaaaaagttcctgttaatgagctgaa<br>agtaaaaatgaagcctaagccctggtctaaacgctgggaacgtccaaattttaatattaaagg<br>aatcagatttgatctttgtttaactgaacagcaaatgaaagaagctcagaagtggaatcagcc<br>atggcttgaatttgatatgatgagggaatatgatacttcaaaaattgaagctgcaatatggaag<br>gaaattgaagcgtcgaaaaggtcttgattctgagaatgaatttggttagttgcagaagatacat<br>tggctctaagaggatatattttgagaccaatttaatttcatttataagaacatagtaattaagtgaa<br>ctaagcattcattgttttattaatactttttttctaaaataaaacttgtacaccagtttattactctaaa<br>aagagaattacacatgccaaatggaccaatgtccatttgcttattggaggcaaagctacaata<br>gaagtcagagcatcaccagaatggtctttaatgagcatggaacctgagcaaagggaatagg<br>tgggatgaattttttttttaattgtgaaacaattcataagcacaatatgatttacagaataataaac<br>attcatgtacccactatcaggttaagaaatagaacatttattaatatgtaggaatgttaagaaata<br>aaacatttaataagatctcagaagactccagtaaatctgcaattgtatctctctcctttttaaatgt<br>aaatatcatcttgacttgttaattattcccttgcatttcttttagtttactgccaacacatatattcttc<br>aacaatatatttaattttgaaaaacctgaaaaaaaaaacctgttagcaagtataaaggggcagt<br>attactattattgcatgaaggcttcaagggaaacgttacagtctttgggtcatagtctggcttca<br>gcttcctctgagagtttacagaggccaattttgagcaaattcatggctaaggttatgagtgagtt<br>ctgctaaacagaaggctcaccacaaggtatctggcaggattatactgggtagctggatgttg<br>cagaaatgtggttagaggaagtaaactgtttttgatgctcacagcatgatgaatcaaactctgt<br>atcttaggattaggttaaaacaatacctttggtatgatatgagtgttgttgctgatccatgcagca<br>tggattggaaagctggggtataagcacacatgctaaagaaaaacatgtaatttggtccatact<br>cacctggatatactgttcctcaggttaaaaaatacagtactatcctaaatcttgaaggcaactct<br>cagcctatccattgagttaccttcagatctgccctctggttcctagctgtcttgggactaacttct<br>ttcctgcgctcagctgttttctggattccatgttttccattttattgagtactaacttgttttgctgca<br>gcacatcctttggtagcttctagaggaagtttgtgtggaggtaaaatttttgagaccttgcatgt<br>ctcatgtttgattgatactttatacgtttaggtaggaggtaattttccttcaggactttaaaaatatt<br>gttgctccatttctttgtttctattgttgtattgagaaatccaatgccattttgatttccccatcataa<br>atttcatgatgatgtgtcttggtgtgggtctatatttatccattgtattgggttttaggtgaaccctt<br>ccagatagtaactcatttctgtcagttctgggaaacacttagcattggttgatgatttattctctgc<br>tgctttgttctcccaactattatttggatgttggatatccagcactgggtatctattttcttacctcc<br>ctcccttgaccccagtctctgtttttttagctctttagctcaatcttccaactctttgctattgtattta<br>aaatcttaagaccccttcttgatttgtagaagttcctttttcttacaaccaaaaagcctttatctatg<br>gatttgttcacagataaggggtattcaatatagtgtattttttttttcatttaaaattgtttgcgcatct<br>atttcctccaaatttctttctgtatttatttttttgttgtctatatttcagacttttccaggatatctgataa<br>tctttggctgtcttcttatggttgaaagagggactaaaaagcttggaaagcctttgggttgtggg<br>aaggggctgtctttaggattatctgaatgggctttttttgggagtcccctcctccacatgaatattt<br>tggttttgtcagattccctagaatagaggcttccaatctccttcctggaggggtctgtccagga<br>aggagattgtctaggggtctgtcagacagcagctttcagctacttccttgatctttttcactaatg<br>attatatagtcatctaactactgtcaacaagtaatagatatcctatccttcacttgtttagattatttg<br>ctgagataacctctcaaaagaacctctcaaaataaaaggttaacaagagcctatatcttatattt<br>ttcttctctttatcttgttagaagatagctattaaaacctgttctttttctgtcttgataaacacacttc<br>aatcttggtagaatggtagatgggacagtatattttaggacctaaagctctgcaaatgtatgat<br>cagcttgtaagtacaggtgctcaaaaacatgtaaacaatcatgcttttttactctgtaggaatatc<br>tttaaaattcttgtgaatttttccccagaagtaaagcaaatcttcccccagaaataaaattaaatg<br>tgcataatctaaagctttttttttttattgtggtaggatatatatataaaacataatttgccattgtaa<br>acattttaaatttacaagtcagaggcattaattacatcacaatgttgtgaaattattactactatttc<br>caaaattttctcatcaccccaaactgaaactctgtaactgttgagcaataacctcattcctgtatc<br>tctcccaaccccaggtaacctcaaatctttcttttttatctttgagacaaggtctcattctatcactc<br>aggtaggagtgcagtggtgtgatcatagctcattgcagcctcaaaatcctgggctcaagcaa<br>tcctccttgagtagctaagactataggcacacattaactgcgcctggctgattttgtttttttgtag<br>agatgtggtcttgctatgtttcccatgctggtcttgagttcctggcctcaagcagtccttaagatt<br>catccatgttgtggcatgtgtcagaatttcatttgtttttatgactaaataatattccattgtatgtat<br>atacattttgttcatccatcttctgatgaacactgggatatgtctaccttttggctattgtgaataat<br>gctgcagtaaacattgacataacaagtatgtatttgattgcctgtttctaagttcttttgggtatac | 15 |

TABLE 1 -continued

Colon Cancer Biomarker/Housekeeper Sequence Informatton

| Gene Name | RefSeq Accession | Sequence | SEQ ID NO: |
|---|---|---|---|
| | | atcttgagtagaattgctagataatgtcatgttttatttctcttgtgatttcttcttcgatcccctggtt<br>gagtgtgttaatttctacatgtttatgaatttcccactgtttttttgttattgatttccaagttcattcca<br>ttgtgattagagaagatacttagtatgattttaatgtttttgagaattggtgtgtggcctgatagat<br>ggtctgtcctggagaatgttcctcatacacttgagcaaaatatttatcatgctattgttgactgta<br>gttttctatatgtctcttaggtcaaggtggtttacaatgtgttaaggttctctttttttaaaaaaatttt<br>gcacagagtatctttttctatgtgttccatgtatttgtgtctttggagctatagtctcttgtagacag<br>catatcactatcttgttttgttttgtttttctgtccattctgccaatttctgccttttgattggaaaattt<br>aatccatttgcatttaaagtaattaaggaaggactttcttctaccatttaacacttcttctatatgtc<br>atatactttttggcccctcatttcctctttatggccttcttttctgtttttttgtagtgaactagtctgat<br>tctctttccactcccctttgtgtatatttgttagatgttttatttgtggttgctatggggattatagtta<br>acatcctacacttaaaacaatctaatttaaactgataccaatttaccttcaatagcatacaaaatc<br>tctactcctgtaaagctctgcccctgccccccttatgttattgatggcacaaattgcctaataaat<br>aatttatagttatttgtatgagtttgtcttttaaatcatttaggaaataaaaagtggagttagaaaac<br>agtatgatagtaatactgacttttatatttgtcaatatatttatcttattttggatccttatttcattatat<br>agatttgagttactgtctagtgcccttccatttcggcccaaaggattcccttatgcatttcttgca<br>gggcaagtctaattgtaataaactccctcagcttttgttttatctgagaatgtcttgatttctccctt<br>atttttgatggataattttgccagatacatgaatttttggtaacagtatttttctttcagcactttaaat<br>atgtcatcccactaccttctgacttcatggtttctcatgagatattagatgttataaaatttgagga<br>ttcctcattcttgatgagtcagttctgtcttattgcttttcggatttgctcagcttttgtcttttgacag<br>tttgattataacgcggctcagtgtgggtctctgagtttatcccacttagagtttgttgagtttcttg<br>gagtcatagatttatgtcttttatcaaattttggacatatttggctattatttcttcaatttttttcactg<br>cttctttcttttccttctgaaatattcttaatgtatatgttggtctgtttgatgctgtctcaccagtttctt<br>aggctgtgttctcttttgttcctcagacttgattattgcagttgcccttctttttatttttttcaagtttgt<br>tgattcttctccctgttcagatcaactgttgaactcctctagtgaatttatttcagttactgtactttt<br>cagctccaagatttatctttggttcctttttataacgtctgtgtctttattgatattctcattttgttcat<br>atgtctctttcttcctttagttctttgtccatgttttcctttagctctttgggcttatttaagacaattgtt<br>taaagtctttgcatagtaagtccaatgtctgtgtttcttcagggatggttttcattattttgttttcaat<br>gagccatactttcctgtgtctttgtatgctgtctttttgttgttgaaaactgtatgtttgaacatcata<br>acgtggtggccctgaaaatcagatattccccccttcctgagagttagttttatttttattattgaag<br>attgtagcagtctattgctacatgtgcagtcatttccaaactatttttgcaaagactgtattccttct<br>gtgtgtcatcactgaagtctctgttccttagtttgtgtttaatagtttgacatagatttccttgaaag<br>gagttaaaactagcagaaaaatctctctcccagtctttccagtctttgtagattggttctgtgctg<br>ggcttttccattaatacttagccaggcttgtactgagcctaacaatcaggcccaaaagcgtag<br>ggtctttgcagatcttgtctgagcatgcttcttgctgtgtatgcacgtagttttctaaatctccctgt<br>atgtgctgttgaatattctaatttcccaaagaaactcattgcagctttttctcacagaacatagat<br>ggtttttttggatatcttgaccatagtattcgacccaggtgtttgcggttgttagttcaccttacact<br>tttttcaagcattgcctactgcttacgatgagtgctctgtcaatcctttaagtagccccagacag<br>gctaccagagacttaaacaagaatttgtaagttctgctcagcttcctctagaaatggggatcag<br>ggtccaagacagaatgcagttgctgatttcaagactgctgcaacaccagggagcttgtggg<br>ggaagggcaagcagaaatgtcacaaagctttcttgccattttaaagttgcctgttcttgactca<br>gcatttgcttcattgctataaactttttactgtttttcagagttctgataaaattggctatgcctgttc<br>ctgctttaaaaaatatatatatatttttttagggattggggtctcactatactgaccaggctggtctt<br>gaacttctggcctcaagccatcctctcatttcagcttcccaaagtgctgcaattacacgcgtga<br>accaccacacccagcccctgcttgtttttcaatgtgcctactccaccatgttgctcaagtatgta<br>tattttctaaactaccttgtagtgttgtgatgggaaataaatccctgagccttttgaataactcag<br>agagatcaaaaacttagtttatcctattcgaaggattagaaaaatgatatatattcactttttcag<br>ggataggctcctcattagaaggctcctatgtgccgatgctgtacaagacatttcatttctcttaat<br>gtttacaacaagcttgttgccaaggctgatcttgaactcctggcctcaaacgatcctcccagct<br>cagtctcacaaagtgttgggatgtctggccaactaatgactatcttaactcttgtgtttcaatgttt<br>atgccttcttttatcttgactgattgtatgactatgtcttctagaacaatgttgaacagaaatggtg<br>agagcagacatccttgctttaatatttcaccattatatatgatgttaggtatagatttttctcacag<br>atgccttttatcagattgaggaatttatattcctactttgccgaaaggtttttgtagtatgaggggg<br>tgctgaattttgtcaaacactttttcggtaataattgagatgattggttctgcagtcatcgagatgt<br>ggattttctcctttattctgttcgtgagtgattacactggttgactaatgttaaaacaaccttacttt<br>ccaggaataaaccctattatctttttttataca | |
| PSMC4 | NM_153001.2 | tgcgggtacggacagcgcatgagcttatgttgagggcggagcccagaccagcccttcgtc<br>ctatcctgcccttccagcacctctcagccgtaacttaaactacacttcccagaagcctcctcag<br>ccagggacttccgttgtcgtcagcggaagcggtgacagatcatcccaggccacacagagg<br>ccggcttggtcactatggaggagataggcatcttggtggagaaggctcaggatgagatccc<br>agcactgtccgtgtcccggccccagaccggcctgtccttcctgggccctgagcctgaggac<br>ctggaggacctgtacagccgctacaaggaggaggtgaagcgaatccaaagcatcccgctg<br>gtcatcggacaatttctggaggctgtggatcagaatacagccatcgtgggctctaccacagg<br>cagtggccctccacaagcacagcaatgcactggtggacgtgctgcccccccgaagccgaca<br>gcagcatcatgatgctcacctcagaccagaagccagatgtgatgtacgcggacatcggag<br>gcatggacatccagaagcaggaggtgcgggaggccgtggagctcccgctcacgcatttcg<br>agctctacaagcagatcggcatcgatccccccccgaggcgtcctcatgtatggcccacctgg<br>ctgtgggaagaccatgttggcaaaggcggtggcacatcacacaacagctgcattcatccgg<br>gtcgtgggctcggagtttgtacagaagtatctgggtgagggcccccgcatggtccgggatg<br>tgttccgcctggccaaggagaatgcacctgccatcatcttcatagacgagattgatgccatcg<br>ccaccaagagattcgatgctcagacaggggccgacagggaggttcagaggatcctgctgg<br>agctgctgaatcagatggatggatttgatcagaatgtcaatgtcaaggtaatcatggccacaa<br>acagagcagacaccctggatccggccctgctacggccaggacggctggaccgtaaaattg<br>aatttccacttcctgaccgccgccagaagagattgattttctccactatcactagcaagatgaa | 16 |

TABLE 1 -continued

Colon Cancer Biomarker/Housekeeper Sequence Informatton

| Gene Name | RefSeq Accession | Sequence | SEQ ID NO: |
|---|---|---|---|
| | | cctctctgaggaggttgacttggaagactatgtggcccggccagataagatttcaggagctg<br>atattaactccatctgtcaggagagtggaatgttggctgtccgtgaaaaccgctacattgtcct<br>ggccaaggacttcgagaaagcatacaagactgtcatcaagaaggacgagcaggagcatg<br>agttttacaagtgacccttcccttccctccaccacaccactcaggggctggggcttctctcgc<br>acccccagcacctctgtcccaaaacctcattccctttttctttacccaggattggtttcttcaata<br>aatagataagatcgaatccatttaatttcttcttagaagtttaactcctttggagaatgtgggcctt<br>gaataggatcctctgggtccctcttaatctgacagatgagcagacgaggtgcatggcctggg<br>ttgcagcttgagagaaccaaaatattcaaaccagatgacttccaaaatgtggggaaagggat<br>ggaaaatgaacctgagatggagtccttaatcacgggataaagccctgtgcatctccctcattt<br>cctacaggtaaaagacagtaaagaaattcaggtcacaggccttgggagttcataggaagga<br>gatgtccagtgctgtccagtagaacttt | |
| SF3A1 | NM_005877.5 | ggtcccggaagtgcgccagtcgtaccttcgcggccgcaactcgctcggccgccgccatctt<br>gcgagctcgtcgtactgaccgagcggggaggctgtcttgaggcggcaccgctcaccgaca<br>ccgaggcggactggcagccctgagcgtcgcagtcatgccggccggacccgtgcaggcg<br>gtgcccccgccgccgcccgtgcccacggagcccaaacagcccacagaagaagaagcat<br>cttcaaaggaggattctgcaccttctaagccagttgtggggattatttaccctcctccagaggt<br>cagaaatattgttgacaagactgccagctttgtggccagaaacgggcctgaatttgaagcta<br>ggatccgacagaacgagatcaacaaccccaagttcaactttctgaaccccaatgacccttac<br>catgcctactaccgccacaaggtcagcgagttcaaggaagggaaggctcaggagccgtcc<br>gccgccatccccaaggtcatgcagcagcagcagcagaccacccagcagcagctgcccca<br>gaaggtccaagcccaagtaatccaagagaccatcgtgcccaaagagcctcctcctgagttt<br>gagttcattgctgatcctccctctatctcagccttcgacttggatgtggtgaagctgacggctc<br>agtttgtggccaggaatgggcgccagtttctgacccagctgatgcagaaagagcagcgcaa<br>ctaccagtttgactttctccgcccacagcacagcctcttcaactacttcacgaagctagtggaa<br>cagtacaccaagatcttgattccacccaaaggtttattttcaaagctcaagaaagaggctgaa<br>aacccccgagaagttttggatcaggtgtgttaccgagtggaatgggccaaattccaggaac<br>gtgagaggaagaaggaagaagaggagaaggagaaggagcgggtggcctatgctcagat<br>cgactggcatgatttgtggtggtggaaacagtggacttccaacccaatgagcaagggaact<br>tccctccccccaccacgccagaggagctgggggcccgaatcctcattcaggagcgctatg<br>aaaagtttggggagagtgaggaagttgagatggaggtcgagtctgatgaggaggatgaca<br>aacaggagaaggcggaggagcctccttcccagctggaccaggacacccaagtacaagat<br>atggatgagggttcagatgatgaagaagaagggcagaaagtgcccccacccccagagac<br>acccatgcctccacctctgcccccaactccagaccaagtcattgtccgcaaggattatgatcc<br>caaagcctccaagcccttgcctccagcccctgctccagatgagtatcttgtgtcccccattact<br>ggggagaagatccccgccagcaaaatgcaggaacacatgcgcattggacttcttgaccctc<br>gctggctggagcagcgggatcgctccatccgtgagaagcagagcgatgatgaggtgtacg<br>caccaggtctggatattgagagcagcttgaagcagttggctgagcggcgtactgacatcttc<br>ggtgtagaggaaacagccattggtaagaagatcggtgaggaggagatccagaagccaga<br>ggaaaaggtgacctgggatggccactcaggcagcatggcccggacccagcaggctgccc<br>aggccaacatcaccctccaggagcagattgaggccattcacaaggccaaaggcctggtgc<br>cagaggatgacactaaagagaagattggccccagcaagcccaatgaaatccctcaacagc<br>caccgccaccatcttcagccaccaacatccccagctcggctccacccatcacttcagtgccc<br>cgaccacccacaatgccacctccagttcgtactacagttgtctccgcagtacccgtcatgccc<br>cggcccccaatggcatctgtggtccggctgcccccaggctcagtgatcgcccccatgccgc<br>ccatcatccacgcgcccagaatcaacgtggtgcccatgcctccctcggcccctcctattatg<br>gcccccgcccacccccatgattgtgccaacagcctttgtgcctgctccacctgtggcacc<br>tgtcccagctccagccccaatgccccctgtgcatcccccacctcccatggaagatgagccc<br>acctccaaaaaactgaagacagaggacagcctcatgccagaggaggagttcctgcgcaga<br>aacaagggtccagtgtccatcaaagtccaggtgcccaacatgcaggataagacggaatgg<br>aaactgaatgggcaggtgctggtcttcaccctcccactcacggaccaggtctctgtcattaag<br>gtgaagattcatgaagccacaggcatgcctgcagggaaacagaagctacagtatgagggt<br>atcttcatcaaagattccaactcactggcttactacaacatggccaatggcgcagtcatccac<br>ctggccctcaaggagagaggcgggaggaagaagtagacaagaggaacctgctgtcaagt<br>ccctgccattttgcctctcctgtctcccacccccctgccccagacccaggagccccccctgagg<br>ctttgccttgcctgcatatttgtttcgctcttactcagtttgggaattcaaattgtcctgcagaggtt<br>cattcccctgaccctttccccacattggtaagagtagctgggttttctaagccactctctggaat<br>ctctttgtgttagggtctcgatttgaggacattcatttcttcagcagcccattagcaactgagag<br>cccagggatgtcctacaggatagtttcatagtgacaggtggcacttggctaatagaatatggc<br>tgatattgtcattaatcattttgtaccttgacatgggttgtctaataaaactcggacccttcttgtga<br>aatcagttaaataagacttgtctcggtcacctgtgccctgtccagactcgaggcagtggtaac<br>actgcacagtgctatgtggcttctctttgaggattttgggttttgtaactaaattcttgctgccctc<br>atactttttatgtattagaatcatattcgtattgcccttttaaaacattgggatcctccaaaggcct<br>gccccatgtatttaacagtaatacaggaagcatggcaggcaccatgcaaaccaaggatgga<br>tggtgcagtccctgtgtcagtgggcggtggtttcctgctggcctggaatcactcatcacctgat<br>tgattggctctgtggtcctgggcaggtgcctcataggtgtgtggatatgatgacgtttctttaaa<br>atgtatgtatttaacaaatacttaattgtattaaggtcatgtaccaaggatttgataaagtttaaat<br>aatttactctctacttttatccattttatccattttaactcatgtaatcctcatgtgagtattcctgttta<br>acacttgagtaaactgaggcacagagaacataagttgcatgccatagtcacacactgtgaaa<br>gtgaaaagagaatgtgtgcaaaacacgtcacagtcctggtttctgagtaaaggcaggctgtt<br>atctttagaatcaagctatcacagggagataggcaatgctgtgggtgttggaggaaggtgag<br>agcctgttgctaacaatttcctggttttaaagctaaggctgattttattgggaagatctcacatgt<br>gtgtggcccctgagagttcccagtgccttttatttgcagtccttccatttggacctcctagctgc<br>cccatcaggtcatctccagggctcagaggggtgagaccatttcccaaggtcacagaaccag | 17 |

TABLE 1 -continued

Colon Cancer Biomarker/Housekeeper Sequence Informatton

| Gene Name | RefSeq Accession | Sequence | SEQ ID NO: |
|---|---|---|---|
| | | ctctctagtcaccaccctgcctctccctctcacccagagtcagtaccagttttatggctttattac<br>aaactgctgggtccctcccattttcaacttgattgatgggatgtcatcccttatcctgtctgacat<br>ttgcctctggcctggttgctagaagtttgccccaggggcaagagttgaaatttggcttcctgag<br>gtgggctttgtggtttgcgtccctaaagtgagcccactactggttgcttgtccatggccaacac<br>cagaaatcccctgagcactacctgggtctcattccaagaaggaagagggtcaggagacctg<br>gggagtctcatattccaagttcttctttctttctgggagcagtgggcagttcatggtgttagggc<br>actcacccccacagactggcaaaccctgcaggacttccgtggctgaggctgtgaccggag<br>gccaggaatgccgttgggtggattgtgagtgaatgggccctttgagctgccctctagagagc<br>aaatccagtttcctggagctcctgaatgaatatctgtactggctcgctcagatgcagaagctcc<br>attgaccatgaggccttgtgaacatcagtggccacaggcccagtgtgctgcttggcactgca<br>ctagtttaggacctgcagcatgtaggtagcgtcctagtgtttataatacaaagctgctctgcac<br>agcttttctgattcttcttgcaatctcctgaggattatctgccccatttttaaaacgaggtggaata<br>cccaaggtcatgtagccagtgagtgctctggaaagccaaagcagctcatcccttcctgggg<br>accacactgctctgctccaccagaccacactatgaaataggaataagtgctcctgttgcagg<br>actgctgggaaaacaggtggtgtgggacttaagtcaccataattttgaagacttgcatgcaga<br>gggctccaggaattgtagacattaaggaatttcactttcagttctacccactacttaagtacttgt<br>catgtactcttagaggaggccagtaatgatcagaaccattttactttaaaattaataatattgtatt<br>agagaatatattaaatggttatattgggttatgttaggatatatacttgaatggaaatacatgtact<br>attagcaatcatatttcatttatccctgtaattagacaagaaagcataatatagctctactcatgg<br>gtacacataccagtgtataagatttttagaagtttactttttaaaaataaaagcaaaatgtaagat<br>cttaaaaaaaaaaaaaaaaa | |
| PUM1 | NM_001020658.1 | agtgggccgccatgttgtcggagtgaaaggtaagggggagcgagagcgccagagagag<br>aagatcgggggctgaaatccatcttcatcctaccgctccgcccgtgttggtggaatgagcg<br>ttgcatgtgtcttgaagagaaaagcagtgctttggcaggactctttcagcccccacctgaaac<br>atcaccctcaagaaccagctaatcccaacatgcctgttgttttgacatctggaacagggtcgc<br>aagcgcagccacaaccagctgcaaatcaggctcttgcagctgggactcactccagccctgt<br>cccaggatctataggagttgcaggccgttcccaggacgacgctatggtggactacttctttca<br>gaggcagcatggtgagcagcttgggggaggaggaagtggaggaggcggctataataata<br>gcaaacatcgatggcctactggggataacattcatgcagaacatcaggtgcgttccatggat<br>gaactgaatcatgattttcaagcacttgctctggagggaagagcgatgggagagcagctctt<br>gccaggtaaaaagttttgggaaacagatgaatccagcaaagatggaccaaaaggaatattc<br>ctgggtgatcaatggcgagacagtgcctggggaacatcagatcattcagtttcccagccaat<br>catggtgcagagaagacctggtcagagtttccatgtgaacagtgaggtcaattctgtactgtc<br>cccacgatcggagagtgggggactaggcgttagcatggtggagtatgtgttgagctcatcc<br>ccgggcgattcctgtctaagaaaaggaggatttggcccaagggatgcagacagtgatgaaa<br>acgacaaaggtgaaaagaagaacaagggtacgtttgatggagataagctaggagatttgaa<br>ggaggagggtgatgtgatggacaagaccaatggtttaccagtgcagaatgggattgatgca<br>gacgtcaaagattttagccgtaccccctggtaattgccagaactctgctaatgaagtggatcttc<br>tgggtccaaaccagaatggttctgagggcttagcccagctgaccagcaccaatggtgccaa<br>gcctgtggaggatttctccaacatggagtcccagagtgtccccttggaccccatggaacatg<br>tgggcatggagcctcttcagtttgattattcaggcacgcaggtacctgtggactcagcagcag<br>caactgtgggacttttgactacaattctcaacaacagctgttccaaagacctaatgcgcttgct<br>gtccagcagttgacagctgctcagcagcagcagtatgcactggcagctgctcatcagccgc<br>acatcggtttagctcccgctgcgtttgtccccaatccatacatcatcagcgctgctcccccag<br>ggacggacccctacacagctggattggctgcagcagcgacactaggcccagctgtggtcc<br>ctcaccagtattatggagttactccctggggagtctaccctgccagtcttttccagcagcaagc<br>tgccgctgccgctgcagcaactaattcagctaatcaacagaccaccccacaggctcagcaa<br>ggacagcagcaggttctccgtggaggagccagccaacgtcctttgaccccaaaccagaac<br>cagcagggacagcaaacggatccccttgtggcagctgcagcagtgaattctgcccttgcatt<br>tggacaaggtctggcagcaggcatgccaggttatccggtgttggctcctgctgcttactatga<br>ccaaactggtgcccttgtagtgaatgcaggcgcgagaaatggtcttggagctcctgttcgact<br>tgtagctcctgccccagtcatcattagttcctcagctgcacaagcagctgttgcagcagccgc<br>agcttcagcaaatggagcagctggtggtcttgctggaacaacaaatggaccatttcgcccttt<br>aggaacacagcagcctcagccccagccccagcagcagcccaataacaacctggcatcca<br>gttctttctacggcaacaactctctgaacagcaattcacagagcagctccctcttctcccaggg<br>ctctgcccagcctgccaacacatccttgggattcggaagtagcagttctctcggcgccaccc<br>tgggatccgcccttggagggtttggaacagcagttgcaaactccaacactggcagtggctc<br>ccgccgtgactccctgactggcagcagtgacctttataagaggacatcgagcagcttgacc<br>cccattggacacagtttttataacggccttagcttttcctcctctcctggacccgtgggcatgcc<br>tctccctagtcagggaccaggacattcacagacaccacctccttccctctcttcacatggatc<br>ctcttcaagcttaaacctgggaggactcacgaatggcagtggaagatacatctctgctgctcc<br>aggcgctgaagccaagtaccgcagtgcaagcagcgcctccagcctcttcagcccgagca<br>gcactcttttctcttcctctcgtttgcgatatggaatgtctgatgtcatgccttctggcaggagca<br>ggcttttggaagattttcgaaacaaccggtaccccaatttacaactgcgggagattgctggac<br>atataatggaattttcccaagaccagcatgggtccagattcattcagctgaaactggagcgtg<br>ccacaccagctgagcgccagcttgtcttcaatgaaatcctccaggctgcctaccaactcatg<br>gtggatgtgtttggtaattacgtcattcagaagttctttgaatttggcagtcttgaacagaagctg<br>gctttggcagaacggattcgaggccacgtcctgtcattggcactacagatgtatggctgccgt<br>gttatccagaaagctcttgagtttattccttcagaccagcaggtaattaatgagatggttcggg<br>aactagatggccatgtcttgaagtgtgtgaaagatcagaatggcaatcacgtggttcagaaat<br>gcattgaatgtgtacagccccagtctttgcaatttatcatcgatgcgtttaagggacaggtattt<br>gccttatccacacatccttatggctgccgagtgattcagagaatcctggagcactgtctccctg<br>accagacactccctattttagaggagcttcaccagcacacagagcagcttgtacaggatcaa | 18 |

TABLE 1 -continued

| Colon Cancer Biomarker/Housekeeper Sequence Informatton | | | |
|---|---|---|---|
| Gene Name | RefSeq Accession | Sequence | SEQ ID NO: |
| | | tatggaaattatgtaatccaacatgtactggagcacggtcgtcctgaggataaaagcaaaatt<br>gtagcagaaatccgaggcaatgtacttgtattgagtcagcacaaatttgcaagcaatgttgtg<br>gagaagtgtgttactcacgcctcacgtacggagcgcgctgtgctcatcgatgaggtgtgcac<br>catgaacgacggtccccacagtgccttatacaccatgatgaaggaccagtatgccaactac<br>gtggtccagaagatgattgacgtggcggagccaggccagcggaagatcgtcatgcataag<br>atccggccccacatcgcaactcttcgtaagtacacctatggcaagcacattctggccaagct<br>ggagaagtactacatgaagaacggtgttgacttagggcccatctgtggccccctaatggta<br>tcatctgaggcagtgtcacccgctgttccctcattcccgctgacctcactggcccactggcaa<br>atccaaccagcaaccagaaatgttctagtgtagagtctgagacgggcaagtggttgctccag<br>gattactccctcctccaaaaaaggaatcaaatccacgagtggaaaagcctttgtaaatttaattt<br>tattacacataacatgtactattttattaattgactaattgccctgctgttttactggtgtataggat<br>acttgtacataggtaaccaatgtacatgggaggccacatattttgttcactgttgtatctatatttc<br>acatgtggaaactttcagggtggttggtttaacaaaaaaaaaaagctttaaaaaaaaaagaaa<br>aaaaggaaaaggtattagctcatttgcctggccggcaagttttgcaaatagctcttccccacc<br>tcctcattttagtaaaaaacaaacaaaaacaaaaaaacctgagaagtttgaattgtagttaaat<br>gaccccaaactggcatttaacactgtttataaaaaatatatatatatatatatatatatataatgaa<br>aaaggtttcagagttgctaaagcttcagtttgtgacattaagtttatgaaattctaaaaaatgcct<br>tttttggagactatattatgctgaagaaggctgttcgtgaggaggagatgcgagcacccaga<br>acgtcttttgaggctgggcgggtgtgattgtttactgcctactggatttttttctattaacattgaa<br>aggtaaaatctgattatttagcatgagaaaaaaaaatccaactctgcttttggtcttgcttctata<br>aatatatagtgtatacttggtgtagactttgcatatatacaaatttgtagtattttcttgttttgatgtc<br>taatctgtatctataatgtaccctagtagtcgaacatacttttgattgtacaattgtacatttgtata<br>cctgtaatgtaaatgtggagaagtttgaatcaacataaacacgtttttttggtaagaaaagagaa<br>ttagccagccctgtgcattcagtgtatattctcaccttttatggtcgtagcatatagtgttgtatatt<br>gtaaattgtaatttcaaccagaagtaaattttttttcttttgaaggaataaatgttctttatacagcct<br>agttaatgtttaaaaagaaaaaaatagcttggttttatttgtcatctagtctcaagtatagcgaga<br>ttctttctaaatgttattcaagattgagttctcactagtgtttttttaatcctaaaaaagtaatgttttg<br>attttgtgacagtcaaaaggacgtgcaaaagtctagccttgcccgagctttccttacaatcaga<br>gcccctctcaccttgtaaagtgtgaatcgcccttccctttttgtacagaagatgaactgtattttgc<br>attttgtctacttgtaagtgaatgtaacatactgtcaattttccttgtttgaatatagaattgtaacac<br>tacacggtgtacatttccagagccttgtgtatatttccaatgaactttttttgcaagcacacttgtaa<br>ccatatgtgtataattaacaaacctgtgtatgcttatgcctgggcaactatttttttgtaactcttgtg<br>tagattgtctctaaacaatgtgtgatctttattttgaaaaatacagaactttggaatctgaaaaaa<br>aaaaaaaaaaaaaaaaaaaaaaaa | |
| ACTB | NM_001101.4 | gagtgagcggcgcggggccaatcagcgtgcgccgttccgaaagttgccttttatggctcga<br>gcggccgcggcggcgccctataaaacccagcggcgcgacgcgccaccaccgccgaga<br>ccgcgtccgccccgcgagcacagagcctcgcctttgccgatccgccgcccgtccacaccc<br>gccgccagctcaccatggatgatgatatcgccgcgctcgtcgtcgacaacggctccggcat<br>gtgcaaggccggcttcgcgggcgacgatgccccccgggccgtcttcccctccatcgtggg<br>gcgccccaggcaccagggcgtgatggtgggcatgggtcagaaggattcctatgtgggcga<br>cgaggcccagagcaagagaggcatcctcaccctgaagtaccccatcgagcacggcatcgt<br>caccaactgggacgacatggagaaaatctggcaccacaccttctacaatgagctgcgtgtg<br>gctcccgaggagcaccccgtgctgctgaccgaggcccccctgaaccccaaggccaaccg<br>cgagaagatgacccagatcatgtttgagaccttcaacaccccagccatgtacgttgctatcca<br>ggctgtgctatccctgtacgcctctggccgtaccactggcatcgtgatggactccggtgacg<br>gggtcacccacactgtgcccatctacgaggggtatgccctcccccatgccatcctgcgtctg<br>gacctggctggccgggacctgactgactacctcatgaagatcctcaccgagcgcggctaca<br>gcttcaccaccacggccgagcgggaaatcgtgcgtgacattaaggagaagctgtgctacgt<br>cgccctggacttcgagcaagagatggccacggctgcttccagctcctccctggagaagag<br>ctacgagctgcctgacggccaggtcatcaccattggcaatgagcggttccgctgccctgag<br>gcactcttccagccttccttcctgggcatggagtcctgtggcatccacgaaactaccttcaact<br>ccatcatgaagtgtgacgtggacatccgcaaagacctgtacgccaacacagtgctgtctgg<br>cggcaccaccatgtaccctggcattgccgacaggatgcagaaggagatcactgccctggc<br>acccagcacaatgaagatcaagatcattgctcctcctgagcgcaagtactccgtgtggatcg<br>gcggctccatcctggcctcgctgtccaccttccagcagatgtggatcagcaagcaggagtat<br>gacgagtccggccccctccatcgtccaccgcaaatgcttctaggcggactatgacttagttgc<br>gttacaccctttcttgacaaaacctaacttgcgcagaaaacaagatgagattggcatggcttta<br>tttgtttttttgttttgttttggtttttttttttttttggcttgactcaggatttaaaaactggaacggtg<br>aaggtgacagcagtcggttggagcgagcatcccccaaagttcacaatgtggccgaggactt<br>tgattgcacattgttgttttttaatagtcattccaaatatgagatgcgttgttacaggaagtccctt<br>gccatcctaaaagccaccccacttctctctaaggagaatggcccagtcctctcccaagtcca<br>cacaggggaggtgatagcattgctttcgtgtaaattatgtaatgcaaaatttttttaatcttcgcct<br>taatactttttttattttgttttattttgaatgatgagccttcgtgccccccttccccctttttttgtcccc<br>caacttgagatgtatgaaggcttttggtctccctgggagtgggtggaggcagccagggctta<br>cctgtacactgacttgagaccagttgaataaaagtgcacaccttaaaaatgaggaaaaaaaa<br>aaaaaaaaaa | 19 |
| GAPD | NM_002046.6 | gctctctgctcctcctgttcgacagtcagccgcatcttcttttgcgtcgccagccgagccacat<br>cgctcagacaccatggggaaggtgaaggtcggagtcaacggatttggtcgtattgggcgcc<br>tggtcaccagggctgcttttaactctggtaaagtggatattgttgccatcaatgaccccttcatt<br>gacctcaactacatggtttacatgttccaatatgattccacccatggcaaattccatggcaccg<br>tcaaggctgagaacgggaagcttgtcatcaatggaaatcccatcaccatcttccaggagcga<br>gatccctccaaaatcaagtggggcgatgctggcgctgagtacgtcgtggagtccactggcg | 20 |

TABLE 1 -continued

Colon Cancer Biomarker/Housekeeper Sequence Informatton

| Gene Name | RefSeq Accession | Sequence | SEQ ID NO: |
|---|---|---|---|
| | | tcttcaccaccatggagaaggctggggctcatttgcaggggggagccaaaagggtcatcat<br>ctctgccccctctgctgatgcccccatgttcgtcatgggtgtgaaccatgagaagtatgacaa<br>cagcctcaagatcatcagcaatgcctcctgcaccaccaactgcttagcacccctggccaag<br>gtcatccatgacaactttggtatcgtggaaggactcatgaccacagtccatgccatcactgcc<br>acccagaagactgtggatggcccctccgggaaactgtggcgtgatggccgcggggctctc<br>cagaacatcatccctgcctctactggcgctgccaaggctgtgggcaaggtcatccctgagct<br>gaacgggaagctcactggcatggccttccgtgtccccactgccaacgtgtcagtggtggac<br>ctgacctgccgtctagaaaaacctgccaaatatgatgacatcaagaaggtggtgaagcagg<br>cgtcggagggcccctcaagggcatcctgggctacactgagcaccaggtggtctcctctga<br>cttcaacagcgacacccactcctccacctttgacgctggggctggcattgccctcaacgacc<br>actttgtcaagctcatttcctggtatgacaacgaatttggctacagcaacagggtggtggacct<br>catggcccacatggcctccaaggagtaagacccctggaccaccagccccagcaagagca<br>caagaggaagagagagaccctcactgctggggagtccctgccacactcagtcccccacca<br>cactgaatctcccctcctcacagttgccatgtagaccccttgaagaggggaggggcctagg<br>gagccgcaccttgtcatgtaccatcaataaagtaccctgtgctcaaccagttaaaaaaaaaaa<br>aaaaaaaaaa | |
| GUSB | NM_000181.3 | gtcctcaaccaagatggcgcggatggcttcaggcgcatcacgacaccggcgcgtcacgcg<br>acccgccctacgggcacctcccgcgcttttcttagcgccgcagacggtggccgagcgggg<br>gaccgggaagcatggcccgggggtcggcggttgcctgggcggcgctcgggccgttgttg<br>tggggctgcgcgctggggctgcagggcgggatgctgtaccccaggagagcccgtcgcg<br>ggagtgcaaggagctggacggcctctggagcttccgcgccgacttctctgacaaccgacg<br>ccggggcttcgaggagcagtggtaccggcggccgctgtgggagtcaggccccaccgtgg<br>acatgccagttccctccagcttcaatgacatcagccaggactggcgtctgcggcattttgtcg<br>gctgggtgtggtacgaacgggaggtgatcctgccggagcgatggacccaggacctgcgc<br>acaagagtggtgctgaggattggcagtgcccattcctatgccatcgtgtgggtgaatggggt<br>cgacacgctagagcatgagggggctacctccccttcgaggccgacatcagcaacctggt<br>ccaggtggggcccctgccctcccggctccgaatcactatcgccatcaacaacacactcacc<br>cccaccaccctgccaccagggaccatccaatacctgactgacacctccaagtatcccaagg<br>gttactttgtccagaacacatattttgactttttcaactacgctggactgcagcggtctgtacttct<br>gtacacgacacccaccacctacatcgatgacatcaccgtcaccaccagcgtggagcaaga<br>cagtgggctggtgaattaccagatctctgtcaagggcagtaacctgttcaagttggaagtgc<br>gtcttttggatgcagaaaacaaagtcgtggcgaatgggactgggacccagggccaacttaa<br>ggtgccaggtgtcagcctctggtggccgtacctgatgcacgaacgccctgcctatctgtattc<br>attggaggtgcagctgactgcacagacgtcactggggcctgtgtctgacttctacacactcc<br>ctgtggggatccgcactgtggctgtcaccaagagccagttcctcatcaatgggaaacctttct<br>atttccacggtgtcaacaagcatgaggatgcggacatccgagggaagggcttcgactggcc<br>gctgctggtgaaggacttcaacctgcttcgctggcttggtgccaacgctttccgtaccagcca<br>ctacccctatgcagaggaagtgatgcagatgtgtgaccgctatgggattgtggtcatcgatg<br>agtgtcccggcgtgggcctggcgctgccgcagttcttcaacaacgtttctctgcatcaccaca<br>tgcaggtgatggaagaagtggtgcgtagggacaagaaccaccccgcggtcgtgatgtggt<br>ctgtggccaacgagcctgcgtcccacctagaatctgctggctactacttgaagatggtgatc<br>gctcacaccaaatccttggacccctcccggcctgtgacctttgtgagcaactctaactatgca<br>gcagacaaggggctccgtatgtggatgtgatctgtttgaacagctactactcttggtatcac<br>gactacgggcacctggagttgattcagctgcagctggccacccagtttgagaactggtataa<br>gaagtatcagaagcccattattcagagcgagtatggagcagaaacgattgcagggtttcacc<br>aggatccacctctgatgttcactgaagagtaccagaaaagtctgctagagcagtaccatctg<br>ggtctggatcaaaaacgcagaaaatacgtggttggagagctcatttggaattttgccgatttca<br>tgactgaacagtcaccgacgagagtgctggggaataaaaaggggatcttcactcggcaga<br>gacaaccaaaaagtgcagcgttccttttgcgagagagatactggaagattgccaatgaaacc<br>aggtatccccactcagtagccaagtcacaatgtttggaaaacagcctgtttacttgagcaaga<br>ctgataccacctgcgtgtcccttcctccccgagtcagggcgacttccacagcagcagaaca<br>agtgcctcctggactgttcacggcagaccagaacgtttctggcctgggttttgtggtcatctatt<br>ctagcagggaacactaaaggtggaaataaaagattttctattatggaaataaagagttggcat<br>gaaagtggctactgaaaaaaaaaaaaaaaaaaaaaaaaa | 21 |
| RPLPO | NM_001002.3 | gtctgacgggcgatggcgcagccaatagacaggagcgctatccgcggtttctgattggcta<br>ctttgttcgcattataaaaggcacgcgcgggcgcgaggcccttctctcgccaggcgtcctcg<br>tggaagtgacatcgtctttaaaccctgcgtggcaatccctgacgcaccgccgtgatgcccag<br>ggaagacagggcgacctggaagtccaactacttccttaagatcatccaactattggatgatta<br>tccgaaatgtttcattgtgggagcagacaatgtgggctccaagcagatgcagcagatccgca<br>tgtcccttcgcgggaaggctgtggtgctgatgggcaagaacaccatgatgcgcaaggccat<br>ccgagggcacctggaaaacaacccagctctggagaaactgctgcctcatatccgggggaa<br>tgtgggctttgtgttcaccaaggaggacctcactgagatcagggacatgttgctggccaataa<br>ggtgccagctgctgcccgtgctggtgccattgccccatgtgaagtcactgtgccagcccag<br>aacactggtctcgggcccgagaagacctcctttttccaggctttaggtatcaccactaaaatct<br>ccaggggcaccattgaaatcctgagtgatgtgcagctgatcaagactggagacaaagtggg<br>agccagcgaagccacgctgctgaacatgctcaacatctccccctcctctccttgggctggtcat<br>ccagcaggtgttcgacaatggcagcatctacaaccctgaagtgcttgatatcacagaggaaa<br>ctctgcattctcgcttcctggagggtgtccgcaatgttgccagtgtctgtctgcagattggctac<br>ccaactgttgcatcagtaccccattctatcatcaacgggtacaaacgagtcctggccttgtctg<br>tggagacggattacaccttcccacttgctgaaaaggtcaaggccttcttggctgatccatctg<br>cctttgtggctgctgcccctgtggctgctgccaccacagctgctcctgctgctgctgcagccc<br>cagctaaggttgaagccaaggaagagtcggaggagtcggacgaggatatgggatttggtc | 22 |

TABLE 1 -continued

| Gene Name | RefSeq Accession | Colon Cancer Biomarker/Housekeeper Sequence Informatton<br>Sequence | SEQ ID NO: |
|---|---|---|---|
| | | tctttgactaatcaccaaaaagcaaccaacttagccagttttatttgcaaaacaaggaaataaa ggcttacttctttaaaaagtaaaaaaaaaaaaaaaaaaaaaaaa | |
| TFRC | NM_003234.3 | agagcgtcgggatatcgggtggcggctcgggacggaggacgcgctagtgtgagtgcggg cttctagaactacaccgaccctcgtgtcctcccttcatcctgcggggctggctggagcggcc gctccggtgctgtccagcagccatagggagccgcacggggagcgggaaagcggtcgcg gccccaggcggggcggccgggatggagcggggccgcgagcctgtggggaaggggct gtggcggcgcctcgagcggctgcaggttcttctgtgtggcagttcagaatgatggatcaagc tagatcagcattctctaacttgtttggtggagaaccattgtcatatacccggttcagcctggctc ggcaagtagatggcgataacagtcatgtggagatgaaacttgctgtagatgaagaagaaaa tgctgacaataacacaaaggccaatgtcacaaaaccaaaaaggtgtagtggaagtatctgct atgggactattgctgtgatcgtctttttcttgattggatttatgattggctacttgggctattgtaaa ggggtagaaccaaaaactgagtgtgagagactggcaggaaccgagtctccagtgaggga ggagccaggagaggacttccctgcagcacgtcgcttatattgggatgacctgaagagaaag ttgtcggagaaactggacagcacagacttcaccggcaccatcaagctgctgaatgaaaattc atatgtccctcgtgaggctggatctcaaaaagatgaaaatcttgcgttgtatgttgaaaatcaat ttcgtgaatttaaactcagcaaagtctggcgtgatcaacattttgttaagattcaggtcaaagac agcgctcaaaactcggtgatcatagttgataagaacggtagacttgtttacctggtggagaat cctgggggttatgtggcgtatagtaaggctgcaacagttactggtaaactggtccatgctaatt ttggtactaaaaaagattttgaggatttatacactcctgtgaatggatctatagtgattgtcagag cagggaaaatcacctttgcagaaaaggttgcaaatgctgaaagcttaaatgcaattggtgtgt tgatatacatggaccagactaaatttcccattgttaacgcagaactttcattctttggacatgctc atctggggacaggtgacccttacacacctggattcccttccttcaatcacactcagtttccacc atctcggtcatcaggattgcctaatatacctgtccagacaatctccagagctgctgcagaaaa gctgtttgggaatatggaaggagactgtccctctgactggaaaacagactctacatgtaggat ggtaacctcagaaagcaagaatgtgaagctcactgtgagcaatgtgctgaaagagataaaa attcttaacatctttggagttattaaaggctttgtagaaccagatcactatgttgtagttggggcc cagagagatgcatggggccctggagctgcaaaatccggtgtaggcacagctctcctattga aacttgcccagatgttctcagatatggtcttaaaagatgggtttcagcccagcagaagcattat ctttgccagttggagtgctggagactttggatcggttggtgccactgaatggctagagggata cctttcgtccctgcatttaaaggctttcacttatattaatctggataaagcggttcttggtaccag caacttcaaggtttctgccagcccactgttgtatacgcttattgagaaaacaatgcaaaatgtg aagcatccggttactgggcaatttctatatcaggacagcaactgggccagcaaagttgagaa actcactttagacaatgctgctttcccttttccttgcatattctggaatcccagcagtttctttctgttt ttgcgaggacacagattatccttatttgggtaccaccatggacacctataaggaactgattga gaggattcctgagttgaacaaagtggcacgagcagctgcagaggtcgctggtcagttcgtg attaaactaacccatgatgttgaattgaacctggactatgagaggtacaacagccaactgcttt catttgtgagggatctgaaccaatacagagcagacataaaggaaatgggcctgagtttacag tggctgtattctgctcgtggagacttcttccgtgctacttccagactaacaacagatttcgggaa tgctgagaaaacagacagatttgtcatgaagaaactcaatgatcgtgtcatgagagtggagt atcacttcctctctccctacgtatctccaaaagagtctcctttccgacatgtcttctggggctccg gctctcacacgctgccagctttactggagaacttgaaactgcgtaaacaaaataacggtgctt ttaatgaaacgctgttcagaaaccagttggctctagctacttggactattcagggagctgcaa atgccctctctggtgacgtttgggacattgacaatgagttttaaatgtgatacccatagcttcca tgagaacagcagggtagtctggtttctagacttgtgctgatcgtgctaaattttcagtagggct acaaaacctgatgttaaaattccatcccatcatcttggtactactagatgtctttaggcagcagc ttttaatacagggtagataacctgtacttcaagttaaagtgaataaccacttaaaaaatgtccat gatggaatattcccctatctctagaattttaagtgctttgtaatgggaactgcctctttcctgttgtt gttaatgaaaatgtcagaaaccagttatgtgaatgatctctctgaatcctaagggctggtctctg ctgaaggttgtaagtggtcgcttactttgagtgatcctccaacttcatttgatgctaaataggag ataccaggttgaaagaccttctccaaatgagatctaagcctttccataaggaatgtagctggtt tcctcattcctgaaagaaacagttaactttcagaagagatgggcttgttttcttgccaatgaggt ctgaaatggaggtccttctgctggataaaatgaggttcaactgttgattgcaggaataaggcc ttaatatgttaacctcagtgtcatttatgaaaagaggggaccagaagccaaagacttagtatat tttcttttcctctgtcccttcccccataagcctccatttagttctttgttattttttgtttcttccaaagca cattgaaagagaaccagtttcaggtgtttagttgcagactcagtttgtcagactttaaagaataa tatgctgccaaattttggccaaagtgttaatcttaggggagagctttctgtccttttggcactga gatatttattgtttatttatcagtgacagagttcactataaatggtgtttttttaatagaatataattat cggaagcagtgccttccataattatgacagttatactgtcggtttttttaaataaaagcagcatc tgctaataaaacccaacagatactggaagttttgcatttatggtcaacacttaagggttttagaa aacagccgtcagccaaatgtaattgaataaagttgaagctaagatttagagatgaattaaattt aattaggggttgctaagaagcgagcactgaccagataagaatgctggttttcctaaatgcagt gaattgtgaccaagttataaatcaatgtcacttaaaggctgtggtagtactcctgcaaaattttat agctcagtttatccaaggtgtaactctaattcccatttgcaaaatttccagtacctttgtcacaat cctaacacattatcgggagcagtgtcttccataatgtataaagaacaaggtagtttttacctacc acagtgtctgtatcggagacagtgatctccatatgttacactaagggtgtaagtaattatcggg aacagtgtttcccataatttttcttcatgcaatgacatcttcaaagcttgaagatcgttagtatctaa catgtatcccaactcctataattccctatcttttagttttagttgcagaaacattttgtggtcattaa gcattgggtgggtaaattcaaccactgtaaaatgaaattactacaaaatttgaaatttagcttgg gtttttgttacctttatggtttctccaggtcctctacttaatgagatagtagcatacatttataatgttt gctattgacaagtcattttaactttatcacattatttgcatgttacctcctataaacttagtgcggac aagttttaatccagaattgaccttttgacttaaagcagagggactttgtatagaaggtttggggg ctgtggggaaggagagtcccctgaaggtctgacacgtctgcctacccattcgtggtgatcaa ttaaatgtaggtatgaataagttcgaagctccgtgagtgaaccatcattataaacgtgatgatc | 23 |

TABLE 1 -continued

Colon Cancer Biomarker/Housekeeper Sequence Informatton

| Gene Name | RefSeq Accession | Sequence | SEQ ID NO: |
|---|---|---|---|
| | | agctgtttgtcatagggcagttggaaacggcctcctagggaaaagttcatagggtctcttcag<br>gttcttagtgtcacttacctagatttacagcctcacttgaatgtgtcactactcacagtctctttaat<br>cttcagttttatctttaatctcctcttttatcttggactgacatttagcgtagctaagtgaaaaggtc<br>atagctgagattcctggttcgggtgttacgcacacgtacttaaatgaaagcatgtggcatgttc<br>atcgtataacacaatatgaatacagggcatgcattttgcagcagtgagtctcttcagaaaacc<br>cttttctacagttagggttgagttacttcctatcaagccagtacgtgctaacaggctcaatattcc<br>tgaatgaaatatcagactagtgacaagctcctggtcttgagatgtcttctcgttaaggagatgg<br>gccttttggaggtaaaggataaaatgaatgagttctgtcatgattcactattctagaacttgcat<br>gacctttactgtgttagctctttgaatgttcttgaaattttagactttctttgtaaacaaatgatatgt<br>ccttatcattgtataaaagctgttatgtgcaacagtgtggagattccttgtctgatttaataaaata<br>cttaaacactgaaaaaaaaaaa | |
| 18S | X03205.1 | tacctggttgatcctgccagtagcatatgcttgtctcaaagattaagccatgcatgtctaagtac<br>gcacggccggtacagtgaaactgcgaatggctcattaaatcagttatggttcctttggtcgctc<br>gctcctctcccacttggataactgtggtaattctagagctaatacatgccgacgggcgctgac<br>cccttcgcggggggggatgcgtgcatttatcagatcaaaaccaacccggtcagcccctctcc<br>ggccccggccgggggggcgggcgccggcggctttggtgactctagataacctcgggccga<br>tcgcacgccccccgtggcggcgacgacccattcgaacgtctgccctatcaactttcgatggt<br>agtcgccgtgcctaccatggtgaccacgggtgacggggaatcagggttcgattccggaga<br>gggagcctgagaaacggctaccacatccaaggaaggcagcaggcgcgcaaattacccac<br>tcccgacccggggaggtagtgacgaaaaataacaatacaggactctttcgaggccctgtaa<br>ttggaatgagtccactttaaatcctttaacgaggatccattggagggcaagtctggtgccagc<br>agccgcggtaattccagctccaatagcgtatattaaagttgctgcagttaaaaagctcgtagtt<br>ggatcttgggagcgggcgggcggtccgccgcgaggcgagccaccgcccgtccccgccc<br>cttgcctctcggcgccccctcgatgctcttagctgagtgtcccgcggggcccgaagcgttta<br>ctttgaaaaaattagagtgttcaaagcaggcccgagccgcctggataccgcagctaggaat<br>aatggaataggaccgcggttctattttgttggttttcggaactgaggccatgattaagagggac<br>ggccgggggcattcgtattgcgccgctagaggtgaaattcttggaccggcgcaagacgga<br>ccagagcgaaagcatttgccaagaatgttttcattaatcaagaacgaaagtcggaggttcga<br>agacgatcagataccgtcgtagttccgaccataaacgatgccgaccggcgatgcggcggc<br>gttattcccatgacccgccgggcagcttccgggaaaccaaagtctttgggttccggggggga<br>gtatggttgcaaagctgaaacttaaaggaattgacggaagggcaccaccaggagtggagc<br>ctgcggcttaatttgactcaacacgggaaacctcacccggcccggacacggacaggattga<br>cagattgatagctctttctcgattccgtgggtggtggtgcatggccgttcttagttggtggagc<br>gatttgtctggttaattccgataacgaacgagactctggcatgctaactagttacgcgacccccc<br>gagcggtcggcgtcccccaacttcttagagggacaagtggcgttcagccacccgagattga<br>gcaataacaggtctgtgatgcccttagatgtccggggctgcacgcgcgctacactgactgg<br>ctcagcgtgtgcctaccctacgccggcaggcgcgggtaacccgttgaaccccattcgtgat<br>ggggatcggggattgcaattattccccatgaacgaggaattcccagtaagtgcgggtcataa<br>gcttgcgttgattaagtccctgccctttgtacacaccgcccgtcgctactaccgattggatggtt<br>tagtgaggccctcggatcggccccgccggggtcggcccacggccctggcggagcgctga<br>gaagacggtcgaacttgactatctagaggaagtaaaagtcgtaacaaggtttccgtaggtga<br>acctgcggaaggatcatta | 24 |
| PPIA | NM_021130.4 | ggggccgaacgtggtataaaaggggcgggaggccaggctcgtgccgttttgcagacgcc<br>accgccgaggaaaaccgtgtactattagccatggtcaaccccaccgtgttcttcgacattgcc<br>gtcgacggcgagcccttgggccgcgtctcctttgagctgtttgcagacaaggtcccaaaga<br>cagcagaaaattttcgtgctctgagcactggagagaaaggatttggttataagggttcctgctt<br>tcacagaattattccagggtttatgtgtcagggtggtgacttcacacgccataatggcactggt<br>ggcaagtccatctatggggagaaatttgaagatgagaacttcatcctaaagcatacgggtcct<br>ggcatcttgtccatggcaaatgctggacccaacacaaatggttcccagtttttcatctgcactg<br>ccaagactgagtggttggatggcaagcatgtggtgtttggcaaagtgaaagaaggcatgaa<br>tattgtggaggccatggagcgctttgggtccaggaatggcaagaccagcaagaagatcacc<br>attgctgactgtggacaactcgaataagtttgacttgtgttttatcttaaccaccagatcattcctt<br>ctgtagctcaggagagcacccctccaccccatttgctcgcagtatcctagaatctttgtgctct<br>cgctgcagttccctttgggttccatgttttccttgttccctcccatgcctagctggattgcagagt<br>taagtttatgattatgaaataaaaactaaataacaattgtcctcgtttgagttaagagtgttgatgt<br>aggctttattttaagcagtaatgggttacttctgaaacatcacttgtttgcttaattctacacagta<br>cttagatttattactttccagtcccaggaagtgtcaatgtttgttgagtggaatattgaaaatgta<br>ggcagcaactgggcatggtggctcactgtctgtaatgtattacctgaggcagaagaccacct<br>gagggtaggagtcaagatcagcctgggcaacatagtgagacgctgtctctacaaaaaataa<br>ttagcctggcctggtggtgcatgcctagtcctagctgatctggaggctgacgtgggaggatt<br>gcttgagcctagagtgagctattatcatgccactgtacagcctgggtgttcacagatcttgtgt<br>ctcaaaggtaggcagaggcaggaaaagcaaggagccagaattaagaggttgggtcagtct<br>gcagtgagttcatgcatttagaggtgttcttcaagatgactaatgtcaaaaattgagacatctgt<br>tgcggttttttttttttttttttcccctggaatgcagtggcgtgatctcagctcactgcagcctccgc<br>ctcctgggttcaagtgattctagtgcctcagcctcctgagtagctgggataatgggcgtgtgc<br>caccatgcccagctaattttttgtatttttagtatagatggggtttcatcattttgaccaggctggtc<br>tcaaactcttgacctcagctgatgcgcctgccttggcctcccaaactgctgagattacagatgt<br>gagccaccgcaccctacctcatttctgtaacaaagctaagcttgaacactgttgatgttcttga<br>gggaagcatattgggctttaggctgtaggtcaagtttatacatcttaattatggtggaattcctat<br>gtagagtctaaaaagccaggtacttggtgctacagtcagtctccctgcagagggttaaggcg<br>cagactacctgcagtgaggaggtactgcttgtagcatatagagcctctccctagctttggttat<br>ggaggctttgaggttttgcaaacctgaccaatttaagccataagatctggtcaaaggatacc | 25 |

TABLE 1 -continued

Colon Cancer Biomarker/Housekeeper Sequence Informatton

| Gene Name | RefSeq Accession | Sequence | SEQ ID NO: |
|---|---|---|---|
| | | cttcccactaaggacttggtttctcaggaaattatatgtacagtgcttgctggcagttagatgtc aggacaatctaagctgagaaaaccccttctctgcccaccttaacagacctctagggttcttaa cccagcaatcaagtttgcctatcctagaggtggcggatttgatcatttggtgtgttgggcaattt ttgttttactgtctggttccttctgcgtgaattaccaccaccaccacttgtgcatctcagtcttgtgt gttgtctggttacgtattccctgggtgataccattcaatgtcttaatgtacttgtggctcagacct gagtgcaaggtggaaataaacatcaaacatcttttcattatcccta | |
| PGK1 | NM_000291.3 | gagagcagcggccgggaaggggcggtgcgggaggcggggtgtggggcggtagtgtgg gccctgttcctgcccgcgcggtgttccgcattctgcaagcctccggagcgcacgtcggcag tcggctccctcgttgaccgaatcaccgacctctctccccagctgtatttccaaaatgtcgctttc taacaagctgacgctggacaagctggacgttaaagggaagcgggtcgttatgagagtcga cttcaatgttcctatgaagaacaaccagataacaaacaaccagaggattaaggctgctgtcc caagcatcaaattctgcttggacaatggagccaagtcggtagtccttatgagccacctaggc cggcctgatggtgtgcccatgcctgacaagtactccttagagccagttgctgtagaactcaaa tctctgctgggcaaggatgttctgttcttgaaggactgtgtaggcccagaagtggagaaagc ctgtgccaacccagctgctgggtctgtcatcctgctggagaacctccgctttcatgtggagga agaagggaagggaaaagatgcttctgggaacaaggttaaagccgagccagccaaaatag aagctttccgagcttcactttccaagctaggggatgtctatgtcaatgatgcttttggcactgct cacagagcccacagctccatggtaggagtcaatctgccacagaaggctggtgggtttttgat gaagaaggagctgaactactttgcaaaggccttggagagcccagagcgacccttcctggc catcctgggcggagctaaagttgcagacaagatccagctcatcaataatatgctggacaaag tcaatgagatgattattggtggtggaatggcttttaccttccttaaggtgctcaacaacatggag attggcacttctctgtttgatgaagagggagccaagattgtcaaagacctaatgtccaaagct gagaagaatggtgtgaagattaccttgcctgttgactttgtcactgctgacaagtttgatgaga atgccaagactggccaagccactgtggcttctggcatacctgctggctggatgggcttggac tgtggtcctgaaagcagcaagaagtatgctgaggctgtcactcgggctaagcagattgtgtg gaatggtcctgtgggggtatttgaatgggaagcttttgcccggggaaccaaagctctcatgg atgaggtggtgaaagccacttctagggggctgcatcaccatcataggtggtggagacactgc cacttgctgtgccaaatggaacacggaggataaagtcagccatgtgagcactgggggtggt gccagtttggagctcctggaaggtaaagtccttcctggggtggatgctctcagcaatatttagt actttcctgccttttagttcctgtgcacagcccctaagtcaacttagcatttctgcatctccactt ggcattagctaaaaccttccatgtcaagattcagctagtggccaagagatgcagtgccagga acccttaaacagttgcacagcatctcagctcatcttcactgcaccctggatttgcatacattctt caagatcccatttgaatttttagtgactaaaccattgtgcattctagagtgcatatatttatattttg cctgttaaaaagaaagtgagcagtgttagcttagttctcttttgatgtaggttattatgattagcttt gtcactgtttcactactcagcatggaaacaagatgaaattccatttgtaggtagtgagacaaaa ttgatgatccattaagtaaacaataaaagtgtccattgaaaccgtgattttttttttttttcctgtcata ctttgttaggaagggtgagaatagaatcttgaggaacggatcagatgtctatattgctgaatgc aagaagtggggcagcagcagtggagagatgggacaattagataaatgtccattctttatcaa gggcctactttatggcagacattgtgctagtgcttttattctaactttattttttatcagttacacatg atcataatttaaaaagtcaaggcttataacaaaaaagccccagcccattcctcccattcaagat tcccactccccagaggtgaccactttcaactcttgagtttttcaggtatatacctccatgtttcta agtaatatgcttatattgttcacttcttttttttttattttttaaagaaatctatttcataccatggagga aggctctgttccacatatatttccacttcttcattctctcggtatagttttgtcacaattatagattag atcaaaagtctacataactaatacagctgagctatgtagtatgctatgattaaatttacttatgta aaaaaaaaaaaaaaaaa | 26 |
| RPL13A | NM_012423.3 | cacttctgccgcccctgtttcaagggataagaaaccctgcgacaaaacctcctccttttccaa gcggctgccgaagatggcggaggtgcaggtcctggtgcttgatggtcgaggccatctcctg ggccgcctggcggccatcgtggctaaacaggtactgctgggccggaaggtggtggtcgta cgctgtgaaggcatcaacatttctggcaatttctacagaaacaagttgaagtacctggctttcc tccgcaagcggatgaacaccaacccttcccgaggcccctaccacttccgggcccccagcc gcatcttctggcggaccgtgcgaggtatgctgccccacaaaaccaagcgaggccaggccg ctctggaccgtctcaaggtgtttgacggcatcccaccgccctacgacaagaaaaagcggat ggtggttcctgctgccctcaaggtcgtgcgtctgaagcctacaagaaagtttgcctatctggg gcgcctggctcacgaggttggctggaagtaccaggcagtgacagccaccctggaggaga agaggaaagagaaagccaagatccactaccggaagaagaaacagctcatgaggctacgg aaacaggccgagaagaacgtggagaagaaaattgacaaatacacagaggtcctcaagac ccacggactcctggtctgagcccaataaagactgttaattcctcatgcgttgcctgcccttcct ccattgttgccctggaatgtacgggacccaggggcagcagcagtccaggtgccacaggca gccctgggacataggaagctgggagcaaggaaagggtcttagtcactgcctcccgaagtt gcttgaaagcactcggagaattgtgcaggtgtcatttatctatgaccaataggaagagcaacc agttactatgagtgaaagggagccagaagactgattggagggccctatcttgtgagtgggg catctgttggactttccacctggtcatatactctgcagctgttagaatgtgcaagcacttgggg acagcatgagcttgctgttgtacacagggtatttctagaagcagaaatagactgggaagatg cacaaccaaggggttacaggcatcgcccatgctcctcacctgtatttgtaatcagaaataaat tgcttttaaagaaaaaaaaaaaaaaaaaa | 27 |
| B2M | NM_004048.2 | aatataagtggaggcgtcgcgctggcgggcattcctgaagctgacagcattcgggccgag atgtctcgctccgtggccttagctgtgctcgcgctactctctctttctggcctggaggctatcca gcgtactccaaagattcaggtttactcacgtcatccagcagagaatggaaagtcaaatttcct gaattgctatgtgtctgggtttcatccatccgacattgaagttgacttactgaagaatggagag agaattgaaaaagtggagcattcagacttgtctttcagcaaggactggtctttctatctcttgta ctacactgaattcacccccactgaaaaagatgagtatgcctgccgtgtgaaccatgtgacttt | 28 |

TABLE 1 -continued

Colon Cancer Biomarker/Housekeeper Sequence Informatton

| Gene Name | RefSeq Accession | Sequence | SEQ ID NO: |
| --- | --- | --- | --- |
| | | gtcacagcccaagatagttaagtgggatcgagacatgtaagcagcatcatggaggtttgaa<br>gatgccgcatttggattggatgaattccaaattctgcttgcttgctttttaatattgatatgcttata<br>cacttacactttatgcacaaaatgtagggttataataatgttaacatggacatgatcttctttataa<br>ttctactttgagtgctgtctccatgtttgatgtatctgagcaggttgctccacaggtagctctagg<br>agggctggcaacttagaggtggggagcagagaattctcttatccaacatcaacatcttggtc<br>agatttgaactcttcaatctcttgcactcaaagcttgttaagatagttaagcgtgcataagttaac<br>ttccaatttacatactctgcttagaatttggggggaaaatttagaaatataattgacaggattattg<br>gaaatttgttataatgaatgaaacattttgtcatataagattcatatttacttcttatacatttgataa<br>agtaaggcatggttgtggttaatctggtttatttttgttccacaagttaaataaatcataaaacttg<br>atgtgttatctctta | |
| YWHAZ | NM_003406.3 | ctttctccttccccttcttccgggctcccgtcccggctcatcacccggcctgtggcccactccc<br>accgccagctggaaccctggggactacgacgtccctcaaaccttgcttctaggagataaaa<br>agaacatccagtcatggataaaaatgagctggttcagaaggccaaactggccgagcaggct<br>gagcgatatgatgacatggcagcctgcatgaagtctgtaactgagcaaggagctgaattatc<br>caatgaggagaggaatcttctctcagttgcttataaaaatgttgtaggagcccgtaggtcatct<br>tggagggtcgtctcaagtattgaacaaaagacggaaggtgctgagaaaaaacagcagatg<br>gctcgagaatacagagagaaaattgagacggagctaagagatatctgcaatgatgtactgtc<br>tcttttggaaaagttcttgatccccaatgcttcacaagcagagagcaaagtcttctatttgaaaa<br>tgaaaggagattactaccgttacttggctgaggttgccgctggtgatgacaagaaagggatt<br>gtcgatcagtcacaacaagcataccaagaagcttttgaaatcagcaaaaaggaaatgcaac<br>caacacatcctatcagactgggtctggcccttaacttctctgtgttctattatgagattctgaact<br>ccccagagaaagcctgctctcttgcaaagacagcttttgatgaagccattgctgaacttgata<br>cattaagtgaagagtcatacaaagacagcacgctaataatgcaattactgagagacaacttg<br>acattgtggacatcggatacccaaggagacgaagctgaagcaggagaaggaggggaaaa<br>ttaaccggccttccaactttttgtctgcctcattctaaaatttacacagtagaccatttgtcatccat<br>gctgtcccacaaatagtttttttgtttacgatttatgacaggtttatgttacttctatttgaatttctata<br>tttcccatgtggtttttatgtttaatattaggggagtagagccagttaacatttagggagttatctg<br>ttttcatcttgaggtggccaatatggggatgtggaattttttatacaagttataagtgtttggcata<br>gtacttttggtacattgtggcttcaaaagggccagtgtaaaactgcttccatgtctaagcaaag<br>aaaactgcctacatactggtttgtcctggcggggaataaaagggatcattggttccagtcaca<br>ggtgtagtaattgtgggtactttaaggtttggagcacttacaaggctgtggtagaatcataccc<br>catggataccacatattaaaccatgtatatctgtggaatactcaatgtgtacacctttgactaca<br>gctgcagaagtgttcctttagacaaagttgtgacccattttactctggataagggcagaaacg<br>gttcacattccattatttgtaaagttacctgctgttagctttcattatttttgctacactcattttatttg<br>tatttaaatgttttaggcaacctaagaacaaatgtaaaagtaaagatgcaggaaaaatgaattg<br>cttggtattcattacttcatgtatatcaagcacagcagtaaaacaaaaacccatgtatttaactttt<br>ttttaggattttgcttttgtgatttttttttttttttgatacttgcctaacatgcatgtgctgtaaaaatagt<br>taacagggaaataacttgagatgatggctagattgtttaatgtcttatgaaattttcatgaacaa<br>tccaagcataattgttaagaacacgtgtattaaattcatgtaagtggaataaaagttttatgaatg<br>gacttttcaactactttctctacagcttttcatgtaaattagtcttggttctgaaacttctctaaagg<br>aaattgtacatttttttgaaatttattccttattccctcttggcagctaatgggctcttaccaagtttaa<br>acacaaaatttatcataacaaaaatactactaatataactactgtttccatgtcccatgatcccct<br>ctcttcctccccaccctgaaaaaaatgagttcctatttttttctgggagagggggggattgatta<br>gaaaaaaatgtagtgtgttccatttaaaattttggcatatggcatttctaacttaggaagccaca<br>atgttcttggcccatcatgacattgggtagcattaactgtaagttttgtgcttccaaatcactttt<br>ggtttttaagaatttcttgatactcttatagcctgccttcaatttgatcctttattctttctatttgtca<br>ggtgcacaagattaccttcctgttttagccttctgtcttgtcaccaaccattcttacttggtggcc<br>atgtacttggaaaaaggccgcatgatctttctggctccactcagtgtctaaggcaccctgcttc<br>ctttgcttgcatcccacagactatttccctcatcctatttactgcagcaaatctctccttagttgat<br>gagactgtgtttatctccctttaaaaccctacctatcctgaatggtctgtcattgtctgcctttaaa<br>atccttcctctttcttcctcctctattctctaaataatgatggggctaagttatacccaaagctcac<br>tttacaaaatatttcctcagtactttgcagaaaacaccaaacaaaaatgccattttaaaaaaggt<br>gtatttttttcttttagaatgtaagctcctcaagagcagggacaatgttttctgtatgttctattgtgc<br>ctagtacactgtaaatgctcaataaatattgatgatgggaggcagtgagtcttgatgataagg<br>gtgagaaactgaaatcccaaacactgttttgttgcttgttttattatgacctcagattaaattggg<br>aaatattggcccttttgaataattgtcccaaatattacattcaaataaaagtgcaatggagaaaa<br>aaaaaaa | 29 |
| SDHA | NM_004168.3 | actgcagccccgctcgactccggcgtggtgcgcaggcgcggtatcccccctcccccgcca<br>gctcgaccccggtgtggtgcgcaggcgcagtctgcgcagggactggcgggactgcgcgg<br>cggcaacagcagacatgtcggggtccggggcctgtcgcggctgctgagcgctcggcgc<br>ctggcgctggccaaggcgtggccaacagtgttgcaaacaggaacccgaggttttcacttca<br>ctgttgatgggaacaagagggcatctgctaaagtttcagattccatttctgctcagtatccagta<br>gtggatcatgaatttgatgcagtggtggtaggcgctggaggggcaggcttgcgagctgcatt<br>tggcctttctgaggcagggtttaatacagcatgtgttaccaagctgtttcctaccaggtcacac<br>actgttgcagcacagggaggaatcaatgctgctctggggaacatggaggaggacaactgg<br>aggtggcatttctacgacaccgtgaagggctccgactggctgggggaccaggatgccatc<br>cactacatgacggagcaggcccccgccgccgtggtcgagctagaaaattatggcatgccg<br>tttagcagaactgaagatgggaagatttatcagcgtgcatttggtggacagagcctcaagttt<br>ggaaagggcgggcaggcccatcggtgctgctgtgtggctgatcggactggccactcgcta<br>ttgcacaccttatatggaaggtctctgcgatatgataccagctatttgtggagtattttgccttg<br>gatctcctgatggagaatggggagtgccgtggtgtcatcgcactgtgcatagaggacgggt<br>ccatccatcgcataagagcaaagaacactgttgttgccacaggaggctacgggcgcaccta | 30 |

TABLE 1 -continued

Colon Cancer Biomarker/Housekeeper Sequence Informatton

| Gene Name | RefSeq Accession | Sequence | SEQ ID NO: |
|---|---|---|---|
| | | cttcagctgcacgtctgcccacaccagcactggcgacggcacggccatgatcaccagggc<br>aggccttccttgccaggacctagagtttgttcagttccaccctacaggcatatatggtgctggt<br>tgtctcattacggaaggatgtcgtggagagggaggcattctcattaacagtcaaggcgaaag<br>gtttatggagcgatacgcccctgtcgcgaaggacctggcgtctagagatgtggtgtctcggt<br>ccatgactctggagatccgagaaggaagaggctgtggccctgagaaagatcacgtctacct<br>gcagctgcaccacctacctccagagcagctggccacgcgcctgcctggcatttcagagac<br>agccatgatcttcgctggcgtggacgtcacgaaggagccgatccctgtcctccccaccgtg<br>cattataacatgggcggcattcccaccaactacaaggggcaggtcctgaggcacgtgaatg<br>gccaggatcagattgtgcccggcctgtacgcctgtggggaggccgcctgtgcctcggtaca<br>tggtgccaaccgcctcggggcaaactcgctcttggacctggttgtctttggtcgggcatgtgc<br>cctgagcatcgaagagtcatgcaggcctggagataaagtccctccaattaaaccaaacgct<br>ggggaagaatctgtcatgaatcttgacaaattgagatttgctgatggaagcataagaacatcg<br>gaactgcgactcagcatgcagaagtcaatgcaaaatcatgctgccgtgttccgtgtgggaag<br>cgtgttgcaagaaggttgtgggaaaatcagcaagctctatggagacctaaagcacctgaag<br>acgttcgaccggggaatggtctggaacacggacctggtggagaccctggagctgcagaac<br>ctgatgctgtgtgcgctgcagaccatctacggagcagaggcacggaaggagtcacgggg<br>cgcgcatgccagggaagactacaaggtgcggattgatgagtacgattactccaagcccatc<br>caggggcaacagaagaagccctttgaggagcactggaggaagcacaccctgtcctatgtg<br>gacgttggcactgggaaggtcactctggaatatagacccgtgatcgacaaaactttgaacga<br>ggctgactgtgccaccgtcccgccagccattcgctcctactgatgagacaagatgtggtgat<br>gacagaatcagcttttgtaattatgtataatagctcatgcatgtgtccatgtcataactgtcttcat<br>acgcttctgcactctggggaagaaggagtacattgaagggagattggcacctagtggctgg<br>gagcttgccaggaacccagtggccagggagcgtggcacttacctttgtcccttgcttcattctt<br>gtgagatgataaaactgggcacagctcttaaataaaatataaatgaacaaactttcttttatttcc<br>aaatccatttgaaatattttactgttgtgactttagtcatatttgttgacctaaaaatcaaatgtaat<br>ctttgtattgtgttacatcaaaatccagatattttgtatagtttcttttttctttttcttttctttttttttttttg<br>agacaggatcggtgcagtagtacaatcacagctcactgcagcctcaaactcctgggcagct<br>caggtgatcttcctgactcagccttctgagtagttggggctacaggtgtgcaccaccatgccc<br>agctcatttattttgtaattgtagggacagggtctcactgtgttgcctaggctggtctcaagtgat<br>cctccctccttggcctcccaaggtgctggaattataggtgtgaacaaaccaaaaaaaaaaaa<br>aa | |
| HPRT1 | NM_000194.2 | ggcggggcctgcttctcctcagcttcaggcggctgcgacgagccctcaggcgaacctctcg<br>gctttcccgcgcggcgccgcctcttgctgcgcctccgcctcctcctctgctccgccaccggc<br>ttcctcctcctgagcagtcagcccgcgcgccggccggctccgttatggcgacccgcagccc<br>tggcgtcgtgattagtgatgatgaaccaggttatgaccttgatttattttgcatacctaatcattat<br>gctgaggatttggaaagggtgtttattcctcatggactaattatggacaggactgaacgtcttg<br>ctcgagatgtgatgaaggagatgggaggccatcacattgtagccctctgtgtgctcaaggg<br>gggctataaattctttgctgacctgctggattacatcaaagcactgaatagaaatagtgataga<br>tccattcctatgactgtagattttatcagactgaagagctattgtaatgaccagtcaacagggg<br>acataaaagtaattggtggagatgatctctcaactttaactggaaagaatgtcttgattgtggaa<br>gatataattgacactggcaaaacaatgcagactttgctttccttggtcaggcagtataatccaa<br>agatggtcaaggtcgcaagcttgctggtgaaaaggaccccacgaagtgttggatataagcc<br>agactttgttggatttgaaattccagacaagtttgttgtaggatatgcccttgactataatgaata<br>cttcagggatttgaatcatgtttgtgtcattagtgaaactggaaaagcaaaatacaaagcctaa<br>gatgagagttcaagttgagtttggaaacatctggagtcctattgacatcgccagtaaaattatc<br>aatgttctagttctgtggccatctgcttagtagagcttttgcatgtatcttctaagaattttatctgt<br>tttgtactttagaaatgtcagttgctgcattcctaaactgtttatttgcactatgagcctatagacta<br>tcagttccctttgggcggattgttgtttaacttgtaaatgaaaaaattctcttaaaccacagcact<br>attgagtgaaacattgaactcatatctgtaagaaataaagagaagatatattagtttttttaattgg<br>tattttaatttttatatatgcaggaaagaatagaagtgattgaatattgttaattataccaccgtgtg<br>ttagaaaagtaagaagcagtcaattttcacatcaaagacagcatctaagaagttttgttctgtcc<br>tggaattattttagtagtgtttcagtaatgttgactgtattttccaacttgttcaaattattaccagtg<br>aatctttgtcagcagttcccttttaaatgcaaatcaataaattcccaaaaatttaaaaaaaaaaaa<br>aaaaaaaaaa | 31 |

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

As used herein, the terms "polynucleotide" and "nucleic acid molecule" are used interchangeably to mean a polymeric form of nucleotides of at least 10 bases or base pairs in length, either ribonucleotides or deoxynucleotides or a modified form of either type of nucleotide, and is meant to include single and double stranded forms of DNA. As used herein, a nucleic acid molecule or nucleic acid sequence that serves as a probe in a microarray analysis preferably comprises a chain of nucleotides, more preferably DNA and/or RNA. In other aspects, a nucleic acid molecule or nucleic acid sequence comprises other kinds of nucleic acid structures such a for instance a DNA/RNA helix, peptide nucleic acid (PNA), locked nucleic acid (LNA) and/or a ribozyme. Hence, as used herein the term "nucleic acid molecule" also encompasses a chain comprising non-natural nucleotides, modified nucleotides and/or non-nucleotide building blocks which exhibit the same function as natural nucleotides.

As used herein, the terms "hybridize," "hybridizing", "hybridizes," and the like, used in the context of polynucleotides, are meant to refer to conventional hybridization conditions, such as hybridization in 50% formamide/6×SSC/

0.1% SDS/100 μg/ml ssDNA, in which temperatures for hybridization are above 37 degrees centigrade and temperatures for washing in 0.1×SSC/0.1% SDS are above 55 degrees C., and preferably to stringent hybridization conditions.

As used herein, the term "normalization" or "normalizer" refers to the expression of a differential value in terms of a standard value to adjust for effects which arise from technical variation due to sample handling, sample preparation, and measurement methods rather than biological variation of biomarker concentration in a sample. For example, when measuring the expression of a differentially expressed protein, the absolute value for the expression of the protein can be expressed in terms of an absolute value for the expression of a standard protein that is substantially constant in expression.

The terms "diagnosis" and "diagnostics" also encompass the terms "prognosis" and "prognostics", respectively, as well as the applications of such procedures over two or more time points to monitor the diagnosis and/or prognosis over time, and statistical modeling based thereupon. Furthermore, the term diagnosis includes: a. prediction (determining if a patient will likely develop aggressive disease (hyperproliferative/invasive)), b. prognosis (predicting whether a patient will likely have a better or worse outcome at a pre-selected time in the future), c. therapy selection, d. therapeutic drug monitoring, and e. relapse monitoring.

"Accuracy" refers to the degree of conformity of a measured or calculated quantity (a test reported value) to its actual (or true) value. Clinical accuracy relates to the proportion of true outcomes (true positives (TP) or true negatives (TN)) versus misclassified outcomes (false positives (FP) or false negatives (FN)), and may be stated as a sensitivity, specificity, positive predictive values (PPV) or negative predictive values (NPV), or as a likelihood, odds ratio, among other measures.

The term "biological sample" as used herein refers to any sample of biological origin potentially containing one or more biomarkers. Examples of biological samples include tissue, organs, or bodily fluids such as whole blood, plasma, serum, tissue, lavage or any other specimen used for detection of disease.

The term "subject" as used herein refers to a mammal, preferably a human. In some aspects, a subject can have at least one colon cancer symptom. In some aspects, a subject can have a predisposition or familial history for developing a colon cancer. A subject can also have been previously diagnosed with a colon cancer and is tested for cancer recurrence.

"Treating" or "treatment" as used herein with regard to a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

Biomarker levels may change due to treatment of the disease. The changes in biomarker levels may be measured by the present disclosure. Changes in biomarker levels may be used to monitor the progression of disease or therapy.

"Altered", "changed" or "significantly different" refer to a detectable change or difference from a reasonably comparable state, profile, measurement, or the like. Such changes may be all or none. They may be incremental and need not be linear. They may be by orders of magnitude. A change may be an increase or decrease by 5%, 10%, 20%, 30%, 40%, 50%, 60%, 70%, 80%, 90%, 95%, 99%, 100%, or more, or any value in between 0% and 100%. Alternatively, the change may be 1-fold, 1.5-fold, 2-fold, 3-fold, 4-fold, 5-fold or more, or any values in between 1-fold and five-fold. The change may be statistically significant with a p value of 0.1, 0.05, 0.001, or 0.0001.

The term "stable disease" refers to a diagnosis for the presence of a colon cancer, however the colon cancer has been treated and remains in a stable condition, i.e. one that that is not progressive, as determined by imaging data and/or best clinical judgment.

The term "progressive disease" refers to a diagnosis for the presence of a highly active state of a colon cancer, i.e. one has not been treated and is not stable or has been treated and has not responded to therapy, or has been treated and active disease remains, as determined by imaging data and/or best clinical judgment.

The term "neoplastic disease" refers to any abnormal growth of cells or tissues being either benign (non-cancerous) or malignant (cancerous). For example, the neoplastic disease can be a colon cancer.

The term "neoplastic tissue" refers to a mass of cells that grow abnormally.

The term "non-neoplastic tissue" refers to a mass of cells that grow normally.

The term "immunotherapy" can refer to activating immunotherapy or suppressing immunotherapy. As will be appreciated by those in the art, activating immunotherapy refers to the use of a therapeutic agent that induces, enhances, or promotes an immune response, including, e.g., a T cell response while suppressing immunotherapy refers to the use of a therapeutic agent that interferes with, suppresses, or inhibits an immune response, including, e.g., a T cell response. Activating immunotherapy may comprise the use of checkpoint inhibitors. Activating immunotherapy may comprise administering to a subject a therapeutic agent that activates a stimulatory checkpoint molecule. Stimulatory checkpoint molecules include, but are not limited to, CD27, CD28, CD40, CD122, CD137, OX40, GITR and ICOS. Therapeutic agents that activate a stimulatory checkpoint molecule include, but are not limited to, MEDI0562, TGN1412, CDX-1127, lipocalin.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. An antibody that binds to a target refers to an antibody that is capable of binding the target with sufficient affinity such that the antibody is useful as a diagnostic and/or therapeutic agent in targeting the target. In one embodiment, the extent of binding of an anti-target antibody to an unrelated, non-target protein is less than about 10% of the binding of the antibody to target as measured, e.g., by a radioimmunoassay (RIA) or biacore assay. In certain embodiments, an antibody that binds to a target has a dissociation constant (Kd) of <1 μM, <100 nM, <10 nM, <1 nM, <0.1 nM, <0.01 nM, or <0.001 nM (e.g. 108 M or less, e.g. from 108 M to 1013 M, e.g., from 109 M to 1013 M). In certain embodiments, an anti-target antibody binds to an epitope of a target that is conserved among different species.

A "blocking antibody" or an "antagonist antibody" is one that partially or fully blocks, inhibits, interferes, or neutralizes a normal biological activity of the antigen it binds. For example, an antagonist antibody may block signaling through an immune cell receptor (e.g., a T cell receptor) so as to restore a functional response by T cells (e.g., proliferation, cytokine production, target cell killing) from a dysfunctional state to antigen stimulation.

An "agonist antibody" or "activating antibody" is one that mimics, promotes, stimulates, or enhances a normal biological activity of the antigen it binds. Agonist antibodies can also enhance or initiate signaling by the antigen to which it binds. In some embodiments, agonist antibodies cause or activate signaling without the presence of the natural ligand. For example, an agonist antibody may increase memory T cell proliferation, increase cytokine production by memory T cells, inhibit regulatory T cell function, and/or inhibit regulatory T cell suppression of effector T cell function, such as effector T cell proliferation and/or cytokine production.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

Administering chemotherapy to a subject can comprise administering a therapeutically effective dose of at least one chemotherapeutic agent. Chemotherapeutic agents include, but are not limited to, 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abemaciclib, Abiraterone acetate, Abraxane, Accutane, Actinomycin-D, Adcetris, Ado-Trastuzumab Emtansine, Adriamycin, Adrucil, Afatinib, Afinitor, Agrylin, Ala-Cort, Aldesleukin, Alemtuzumab, Alecensa, Alectinib, Alimta, Alitretinoin, Alkaban-AQ, Alkeran, All-transretinoic Acid, Alpha Interferon, Altretamine, Alunbrig, Amethopterin, Amifostine, Aminoglutethimide, Anagrelide, Anandron, Anastrozole, Apalutamide, Arabinosylcytosine, Ara-C, Aranesp, Aredia, Arimidex, Aromasin, Arranon, Arsenic Trioxide, Arzerra, Asparaginase, Atezolizumab, Atra, Avastin, Avelumab, Axicabtagene Ciloleucel, Axitinib, Azacitidine, Bavencio, Bcg, Beleodaq, Belinostat, Bendamustine, Bendeka, Besponsa, Bevacizumab, Bexarotene, Bexxar, Bicalutamide, Bicnu, Blenoxane, Bleomycin, Blinatumomab, Blincyto, Bortezomib, Bosulif, Bosutinib, Brentuximab Vedotin, Brigatinib, Busulfan, Busulfex, C225, Cabazitaxel, Cabozantinib, Calcium Leucovorin, Campath, Camptosar, Camptothecin-11, Capecitabine, Caprelsa, Carac, Carboplatin, Carfilzomib, Carmustine, Carmustine Wafer, Casodex, CCI-779, Ccnu, Cddp, Ceenu, Ceritinib, Cerubidine, Cetuximab, Chlorambucil, Cisplatin, Citrovorum Factor, Cladribine, Clofarabine, Clolar, Cobimetinib, Cometriq, Cortisone, Cosmegen, Cotellic, Cpt-11, Crizotinib, Cyclophosphamide, Cyramza, Cytadren, Cytarabine, Cytarabine Liposomal, Cytosar-U, Cytoxan, Dabrafenib, Dacarbazine, Dacogen, Dactinomycin, Daratumumab, Darbepoetin Alfa, Darzalex, Dasatinib, Daunomycin, Daunorubicin, Daunorubicin Cytarabine (Liposomal), daunorubicin-hydrochloride, Daunorubicin Liposomal, DaunoXome, Decadron, Decitabine, Degarelix, Delta-Cortef, Deltasone, Denileukin Diftitox, Denosumab, DepoCyt, Dexamethasone, Dexamethasone Acetate, Dexamethasone Sodium Phosphate, Dexasone, Dexrazoxane, Dhad, Dic, Diodex, Docetaxel, Doxil, Doxorubicin, Doxorubicin Liposomal, Droxia, DTIC, Dtic-Dome, Duralone, Durvalumab, Eculizumab, Efudex, Ellence, Elotuzumab, Eloxatin, Elspar, Eltrombopag, Emcyt, Empliciti, Enasidenib, Enzalutamide, Epirubicin, Epoetin Alfa, Erbitux, Eribulin, Erivedge, Erleada, Erlotinib, Erwinia L-asparaginase, Estramustine, Ethyol, Etopophos, Etoposide, Etoposide Phosphate, Eulexin, Everolimus, Evista, Exemestane, Fareston, Farydak, Faslodex, Femara, Filgrastim, Firmagon, Floxuridine, Fludara, Fludarabine, Fluoroplex, Fluorouracil, Fluorouracil (cream), Fluoxymesterone, Flutamide, Folinic Acid, Folotyn, Fudr, Fulvestrant, G-Csf, Gazyva, Gefitinib, Gemcitabine, Gemtuzumab ozogamicin, Gemzar, Gilotrif, Gleevec, Gleostine, Gliadel Wafer, Gm-Csf, Goserelin, Granix, Granulocyte-Colony Stimulating Factor, Granulocyte Macrophage Colony Stimulating Factor, Halaven, Halotestin, Herceptin, Hexadrol, Hexalen, Hexamethylmelamine, Hmm, Hycamtin, Hydrea, Hydrocort Acetate, Hydrocortisone, Hydrocortisone Sodium Phosphate, Hydrocortisone Sodium Succinate, Hydrocortone Phosphate, Hydroxyurea, Ibrance, Ibritumomab, Ibritumomab Tiuxetan, Ibrutinib, Iclusig, Idamycin, Idarubicin, Idelalisib, Idhifa, Ifex, IFN-alpha, Ifosfamide, IL-11, IL-2, Imbruvica, Imatinib Mesylate, Imfinzi, Imidazole Carboxamide, Imlygic, Inlyta, Inotuzumab Ozogamicin, Interferon-Alfa, Interferon Alfa-2b (PEG Conjugate), Interleukin-2, Interleukin-11, Intron A (interferon alfa-2b), Ipilimumab, Iressa, Irinotecan, Irinotecan (Liposomal), Isotretinoin, Istodax, Ixabepilone, Ixazomib, Ixempra, Jakafi, Jevtana, Kadcyla, Keytruda, Kidrolase, Kisqali, Kymriah, Kyprolis, Lanacort, Lanreotide, Lapatinib, Lartruvo, L-Asparaginase, Lbrance, Lcr, Lenalidomide, Lenvatinib, Lenvima, Letrozole, Leucovorin, Leukeran, Leukine, Leuprolide, Leurocristine, Leustatin, Liposomal Ara-C, Liquid Pred, Lomustine, Lonsurf, L-PAM, L-Sarcolysin, Lupron, Lupron Depot, Lynparza, Marqibo, Matulane, Maxidex, Mechlorethamine, Mechlorethamine Hydrochloride, Medralone, Medrol, Megace, Megestrol, Megestrol Acetate, Mekinist, Mercaptopurine, Mesna, Mesnex, Methotrexate, Methotrexate Sodium, Methylprednisolone, Meticorten, Midostaurin, Mitomycin, Mitomycin-C, Mitoxantrone, M-Prednisol, MTC, MTX, Mustargen, Mustine, Mutamycin, Myleran, Mylocel, Mylotarg, Navelbine, Necitumumab, Nelarabine, Neosar, Neratinib, Nerlynx, Neulasta, Neumega, Neupogen, Nexavar, Nilandron, Nilotinib, Nilutamide, Ninlaro, Nipent, Niraparib, Nitrogen Mustard, Nivolumab, Nolvadex, Novantrone, Nplate, Obinutuzumab, Octreotide, Octreotide Acetate, Odomzo, Ofatumumab, Olaparib, Olaratumab, Omacetaxine, Oncospar, Oncovin, Onivyde, Ontak, Onxal, Opdivo, Oprelvekin, Orapred, Orasone, Osimertinib, Otrexup, Oxaliplatin, Paclitaxel, Paclitaxel Protein-bound, Palbociclib, Pamidronate, Panitumumab, Panobinostat, Panretin, Paraplatin, Pazopanib, Pediapred, Peg Interferon, Pegaspargase, Pegfilgrastim, Peg-Intron, PEG-L-asparaginase, Pembrolizumab, Pemetrexed, Pentostatin, Perj eta, Pertuzumab, Phenylalanine Mustard, Platinol, Platinol-AQ, Pomalidomide, Pomalyst, Ponatinib, Portrazza, Pralatrexate, Prednisolone, Prednisone, Prelone, Procarbazine, Procrit, Proleukin, Prolia, Prolifeprospan 20 with Carmustine Implant, Promacta, Provenge, Purinethol, Radium 223 Dichloride, Raloxifene, Ramucirumab, Rasuvo, Regorafenib, Revlimid, Rheumatrex, Ribociclib, Rituxan, Rituxan Hycela, Rituximab, Rituximab Hyalurodinase, Roferon-A (Interferon Alfa-2a), Romidepsin, Romiplostim, Rubex, Rubidomycin Hydrochloride, Rubraca, Rucaparib, Ruxolitinib, Rydapt, Sandostatin, Sandostatin LAR, Sargramostim, Siltuximab, Sipuleucel-T, Soliris, Solu-Cortef, Solu-Medrol, Somatuline, Sonidegib, Sorafenib, Sprycel, Sti-571, Stivarga, Streptozocin, SU11248, Sunitinib, Sutent, Sylvant, Synribo, Tafinlar, Tagrisso, Talimogene Laherparepvec, Tamoxifen, Tarceva, Targretin, Tasigna, Taxol, Taxotere, Tecentriq, Temodar, Temozolomide, Temsirolimus, Teniposide, Tespa, Thalidomide, Thalomid, TheraCys, Thioguanine, Thioguanine Tabloid, Thiophosphoamide, Thioplex, Thiotepa, Tice, Tisagenlecleucel, Toposar, Topotecan, Toremifene, Torisel, Tositumomab, Trabectedin, Trametinib, Trastuzumab, Treanda, Trelstar, Tretinoin, Trexall, Trifluridine/Tipiricil, Triptorelin pamoate, Trisenox, Tspa, T-VEC, Tykerb, Valrubicin, Valstar, Vandetanib, VCR, Vectibix, Velban, Velcade, Vemurafenib, Venclexta, Venetoclax, VePesid, Verzenio, Vesanoid, Viadur, Vidaza, Vinblastine, Vinblastine Sulfate, Vincasar Pfs, Vincristine, Vincristine Liposomal, Vinorelbine, Vinorelbine Tartrate, Vismodegib, Vlb, VM-26, Vorinostat, Votrient, VP-16, Vumon, Vyxeos, Xalkori Capsules, Xeloda, Xgeva, Xofigo, Xtandi, Yervoy, Yescarta, Yondelis, Zaltrap, Zanosar, Zarxio, Zejula, Zelboraf, Zevalin, Zinecard, Ziv-aflibercept, Zoladex, Zoledronic Acid, Zolinza, Zometa, Zydelig, Zykadia, Zytiga, or any combination thereof.

The terms “effective amount” and “therapeutically effective amount” of an agent or compound are used in the broadest sense to refer to a nontoxic but sufficient amount of an active agent or compound to provide the desired effect or benefit.

The term “benefit” is used in the broadest sense and refers to any desirable effect and specifically includes clinical benefit as defined herein. Clinical benefit can be measured by assessing various endpoints, e.g., inhibition, to some extent, of disease progression, including slowing down and complete arrest; reduction in the number of disease episodes and/or symptoms; reduction in lesion size; inhibition (i.e., reduction, slowing down or complete stopping) of disease cell infiltration into adjacent peripheral organs and/or tissues; inhibition (i.e. reduction, slowing down or complete stopping) of disease spread; decrease of auto-immune response, which may, but does not have to, result in the regression or ablation of the disease lesion; relief, to some extent, of one or more symptoms associated with the disorder; increase in the length of disease-free presentation following treatment, e.g., progression-free survival; increased overall survival; higher response rate; and/or decreased mortality at a given point of time following treatment.

The terms “cancer” and “cancerous” refer to or describe the physiological condition in mammals that is typically characterized by unregulated cell growth. Included in this definition are benign and malignant cancers. Examples of cancer include but are not limited to, carcinoma, lymphoma, blastoma, sarcoma, and leukemia. More particular examples of such cancers include adrenocortical carcinoma, bladder urothelial carcinoma, breast invasive carcinoma, cervical squamous cell carcinoma, endocervical adenocarcinoma, cholangiocarcinoma, colon adenocarcinoma, lymphoid neoplasm diffuse large B-cell lymphoma, esophageal carcinoma, glioblastoma multiforme, head and neck squamous cell carcinoma, kidney chromophobe, kidney renal clear cell carcinoma, kidney renal papillary cell carcinoma, acute myeloid leukemia, brain lower grade glioma, liver hepatocellular carcinoma, lung adenocarcinoma, lung squamous cell carcinoma, mesothelioma, ovarian serous cystadenocarcinoma, pancreatic adenocarcinoma, pheochromocytoma, paraganglioma, prostate adenocarcinoma, rectum adenocarcinoma, sarcoma, skin cutaneous melanoma, stomach adenocarcinoma, testicular germ cell tumors, thyroid carcinoma, thymoma, uterine carcinosarcoma, uveal melanoma. Other examples include breast cancer, lung cancer, lymphoma, melanoma, liver cancer, colorectal cancer, ovarian cancer, bladder cancer, renal cancer or gastric cancer. Further examples of cancer include neuroendocrine cancer, non-small cell lung cancer (NSCLC), small cell lung cancer, thyroid cancer, endometrial cancer, biliary cancer, esophageal cancer, anal cancer, salivary, cancer, vulvar cancer or cervical cancer.

The term “tumor” refers to all neoplastic cell growth and proliferation, whether malignant or benign, and all pre-cancerous and cancerous cells and tissues. The terms “cancer,” “cancerous,” “cell proliferative disorder,” “proliferative disorder” and “tumor” are not mutually exclusive as referred to herein.

EXAMPLES

The disclosure is further illustrated by the following examples, which are not to be construed as limiting this disclosure in scope or spirit to the specific procedures herein described. It is to be understood that the examples are provided to illustrate certain aspects and that no limitation to the scope of the disclosure is intended thereby. It is to be further understood that resort may be had to various other aspects, embodiments, modifications, and equivalents thereof which may suggest themselves to those skilled in the art without departing from the spirit of the present disclosure and/or scope of the appended claims.

Example 1. Derivation of a 13-Marker Gene Panel

Figure 1B:
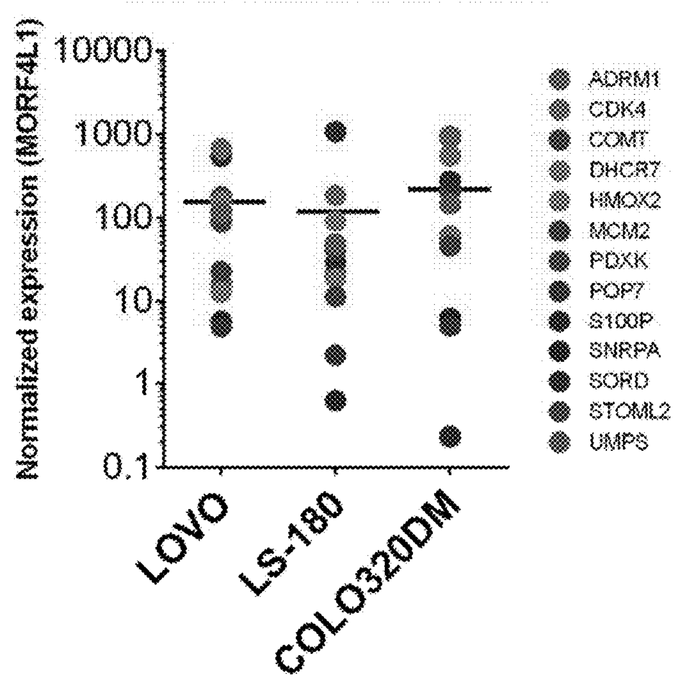

Raw probe intensities from n=24 colon cancer tumor tissue samples were compared to n=22 control colon mucosa to identify genes that best discriminated between disease using the transcriptional profile of E-MTAB-57. Gene co-expression networks were generated to identify temporal patterns of gene regulation associated with colon cancer. A total of 513 nodes with 53,786 links were identified. Differential expression analysis identified 103 genes were upregulated in tumor tissue compared to blood. To identify blood-specific colon cancer gene biomarkers, we evaluated expression of the 103 genes in peripheral blood transcriptomes (n=7). Thirty-three (32%) of the 103 genes were below the level of detection in blood identifying these as candidate genes. Evaluation of transcripts in a preliminary dataset of blood samples from colon cancer (n=20) and matched normal blood (n=20) identified thirteen genes and one house-keeping gene as markers of colon cancer (Table 2). These genes were demonstrated to be highly expressed in colon cancer tumor tissue compared to normal mucosa and in three different colon cancer cell lines, LOVO (metastatic, hyperdiploid, MSI unstable cell line), LS-180 (derived from a Duke’s B, colorectal adenocarcinoma) and Colo 320DM (derived from a Duke’s C, colorectal adenocarcinoma). These data demonstrate target transcripts are produced by neoplastically transformed colon mucosal cells (FIGS. 1A-1B).

An artificial intelligence model of colon cancer disease was built using normalized gene expression of these 13 markers in whole blood from Controls (n=120) and Colon Cancers (n=272) samples. The dataset was randomly split into training and testing partitions for model creation and validation respectively. Twelve algorithms were evaluated (XGB, RF, glmnet, cforest, CART, treebag, knn, nnet, SVM-radial, SVM-linear, NB and mlp). The top performing algorithm (XGB—“gradient boosting”) best predicted the training data. In the test set, XGB produced probability scores that predicted the sample. Each probability score reflects the “certainty” of an algorithm that an unknown sample belongs to either “Control” or “Colon Cancer” class. For example, an unknown sample Si can have the following probability vector [Control=20%, Colon Cancer=80%]. This sample would be considered a colon cancer sample.

Example 2. Clinical Utility

Figure 2A:
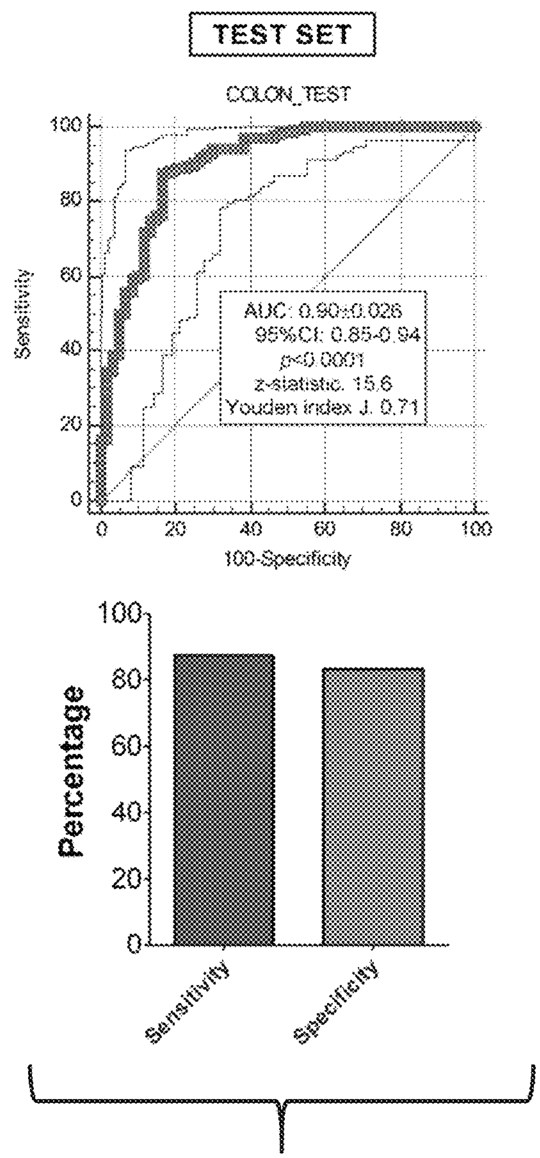
FIGS. 2A-2B are graphs showing receiver operator curve analysis of the test set (FIG. 2A) and independent set (FIG. 2B). Each cohort included 136 cancers and 60 controls. The AUROC in the test set was 0.9 and the Youden J index was 0.71. In the independent set the AUROC was 0.86 with a Youden index of 0.6. Z-statistics ranged 11.2-15.6 and were highly significant ($p<0.0001$). The sensitivity and specificity of the test ranged 85-87.5% and 75-83%, respectively.
Figure 2B:
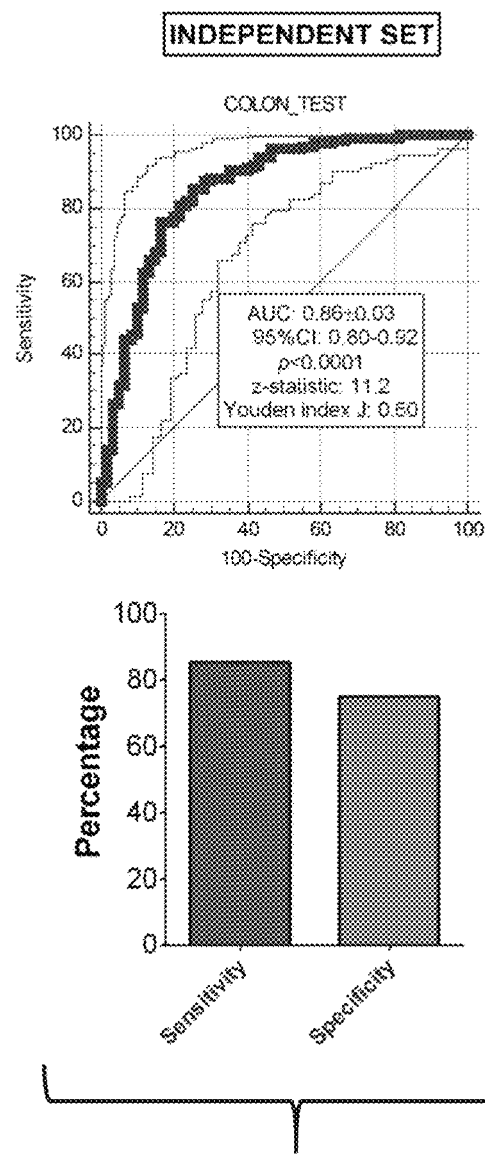

The data (receiver operator cuver analysis and metrics) for the utility of the test to differentiate patients with colon cancer (n=136) from controls (n=60) in the training and test sets are included in FIGS. 2A-2B. The score exhibited an area under the curve (AUC) of 0.90 (training) and 0.86 (test set). The metrics are: sensitivity: 85.3-87.5% and specificity: 75-83.3%.

Figure 3A:
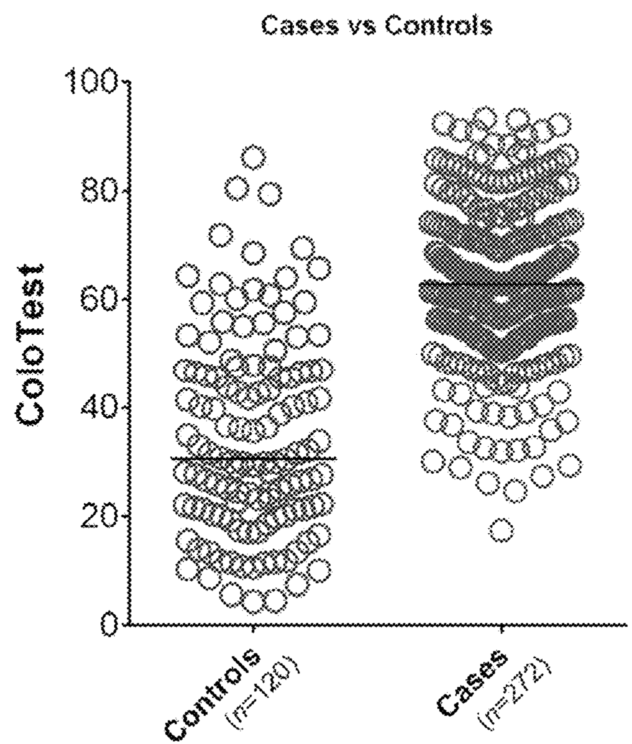
FIGS. 3A-3B are graphs showing that gene expression in the entire cohort (controls: n=120; colon cancer cases: n=272) identified levels were significantly ($p<0.0001$) elevated in cases (62.7±14%) versus controls (34.6±18%) (FIG. 3A). The AUROC was 0.88, $p<0.0001$ (FIG. 3B). Horizontal lines identify median expression of the normalized 13 gene signature (ColoTest).
Figure 3B:
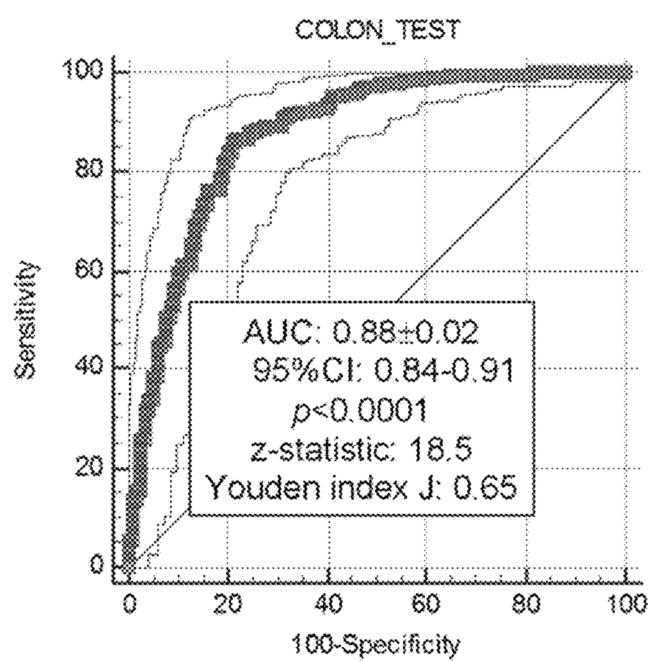

Overall, ColoTest scores were significantly elevated in cancers (63±1%) and controls (34±2%) (FIGS. 3A-3B). The overall accuracy (training and test cohort) is 84%, with an AUC: 0.88. The z-statistic for differentiating controls was 18.5.

Figure 4A:
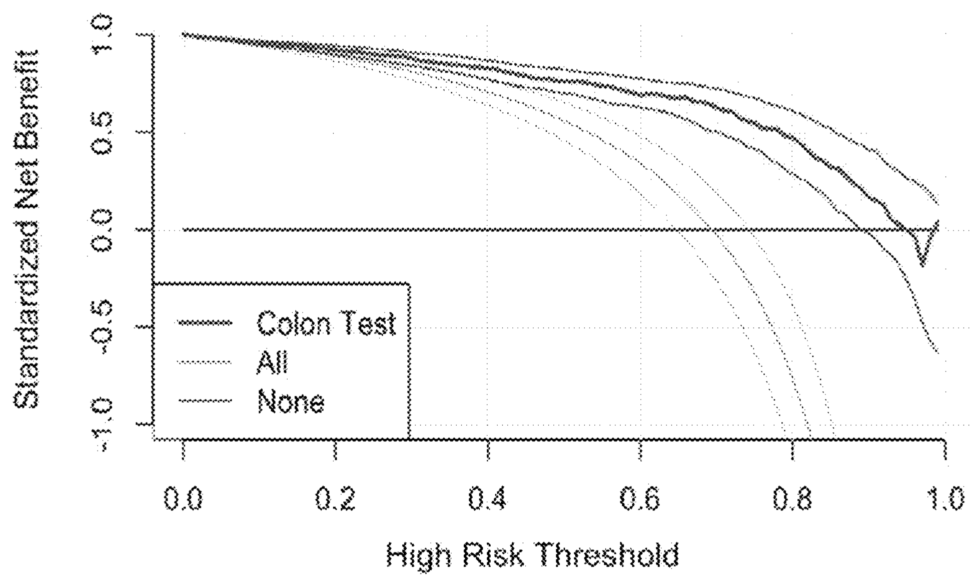
FIGS. 4A-4B are graphs showing decision curve analysis (FIG. 4A) and risk analysis (FIG. 4B) for the ColoTest. This exhibited >50% standardized predictive benefit up to a risk threshold of 80%. The probit risk assessment plot identified a ColoTest score>50% was 75% accurate for predicting colon cancer in a blood sample. This was increased to >80% at a ColoTest score>60%.
Figure 4B:
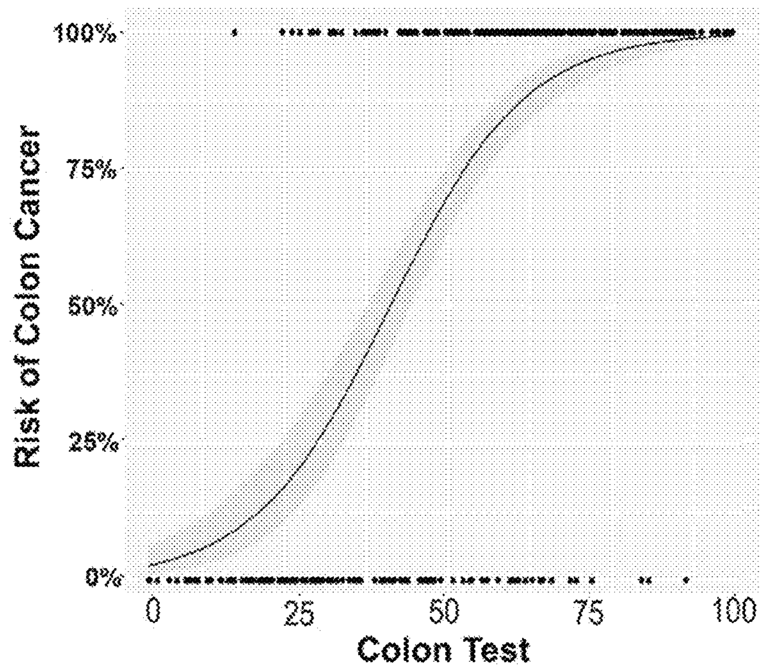

A decision curve analysis was used to quantify the clinical benefit of the diagnostic test (FIGS. 4A-4B). The ColoTest exhibited >50% standardized predictive benefit up to a risk threshold of 80%. The probit risk assessment plot identified a ColoTest score>50% was 75% accurate for predicting colon cancer in a blood sample. This was increased to >80% at a ColoTest score≥60%. The tool can therefore accurately differentiate between controls and colon cancer disease.

Figure 5:
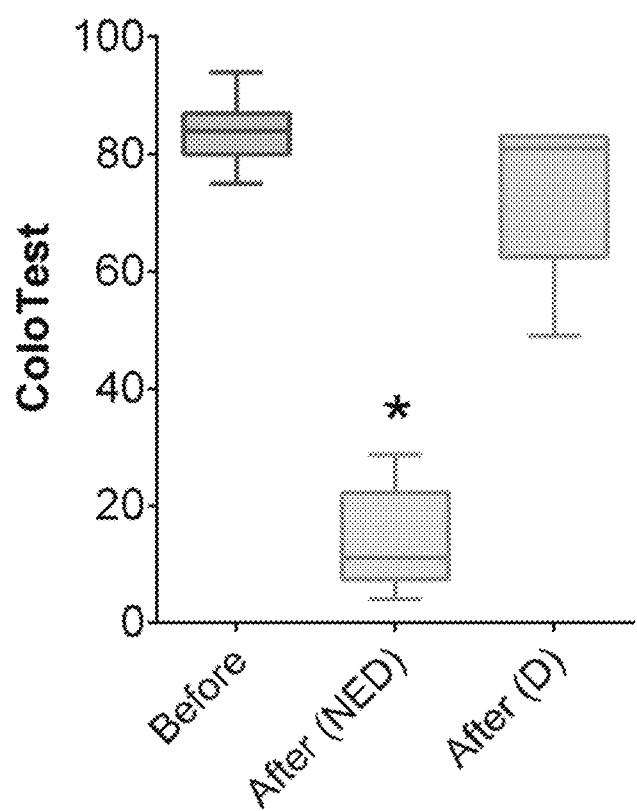
FIG. 5 is a graph showing the effect of surgery on the ColoTest. Levels prior to surgery are elevated (84±6%). In those with no evidence of disease (NED) levels were reduced by surgery to 14±9% (*p=0.0001). In those with disease (D) remaining after surgery, levels remained similar to pre-surgical values (74±4%).

Specific evaluation of a colon cancer cohort before and after surgery identified that complete removal of a tumor and no evidence of disease was associated with a significant decrease (p<0.0001) in the ColoTest (FIG. 5). Levels were not significantly different in those with evidence of residual disease.

Figure 6A:
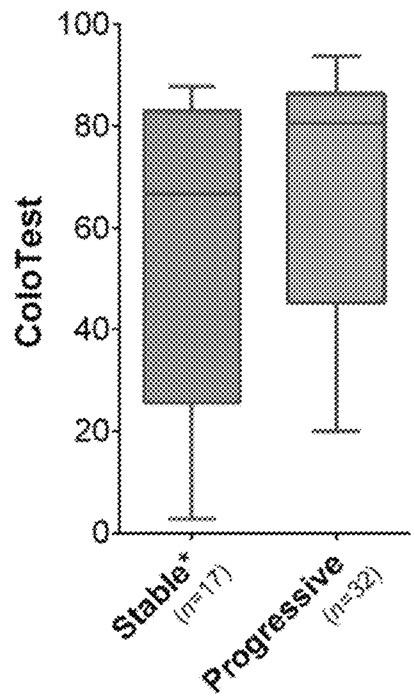
FIGS. 6A-6C are graphs showing ColoTest scores in stable and progressive disease. Test scores were not significantly different between those identified as stable and those with progressive disease at the time of assessment (FIG. 6A). Of the 17 with stable disease, 12 exhibited disease progression in the 3 month follow-up. Levels in those who truly had demonstrable stable disease were low (16±10%) (FIG. 6B). In those who did progress in the 3 months levels were not different to those that had progressive disease (73±16% vs. 68±25%). The AUROC for differentiating stable from progressing/progressive disease was 0.97, $p<0.0001$ (FIG. 6C).
Figure 6B:
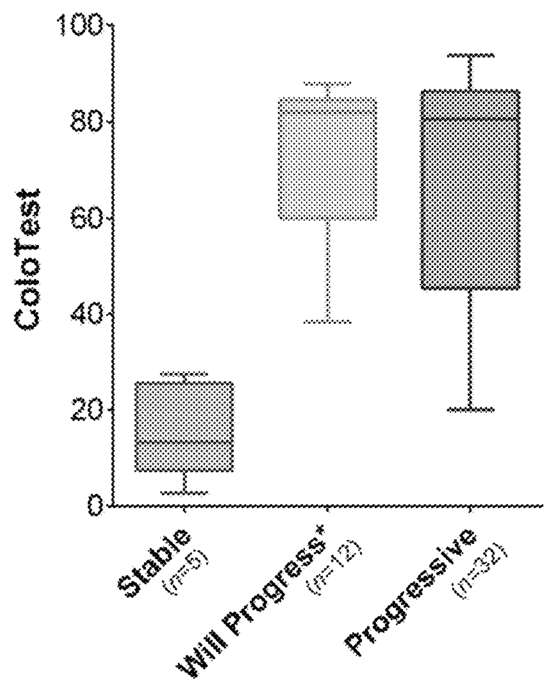
Figure 6C:
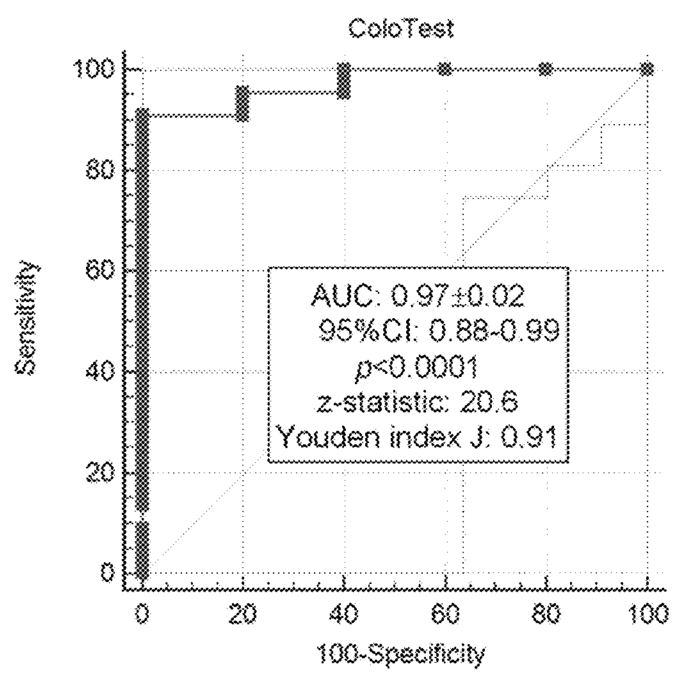
Figure 7:
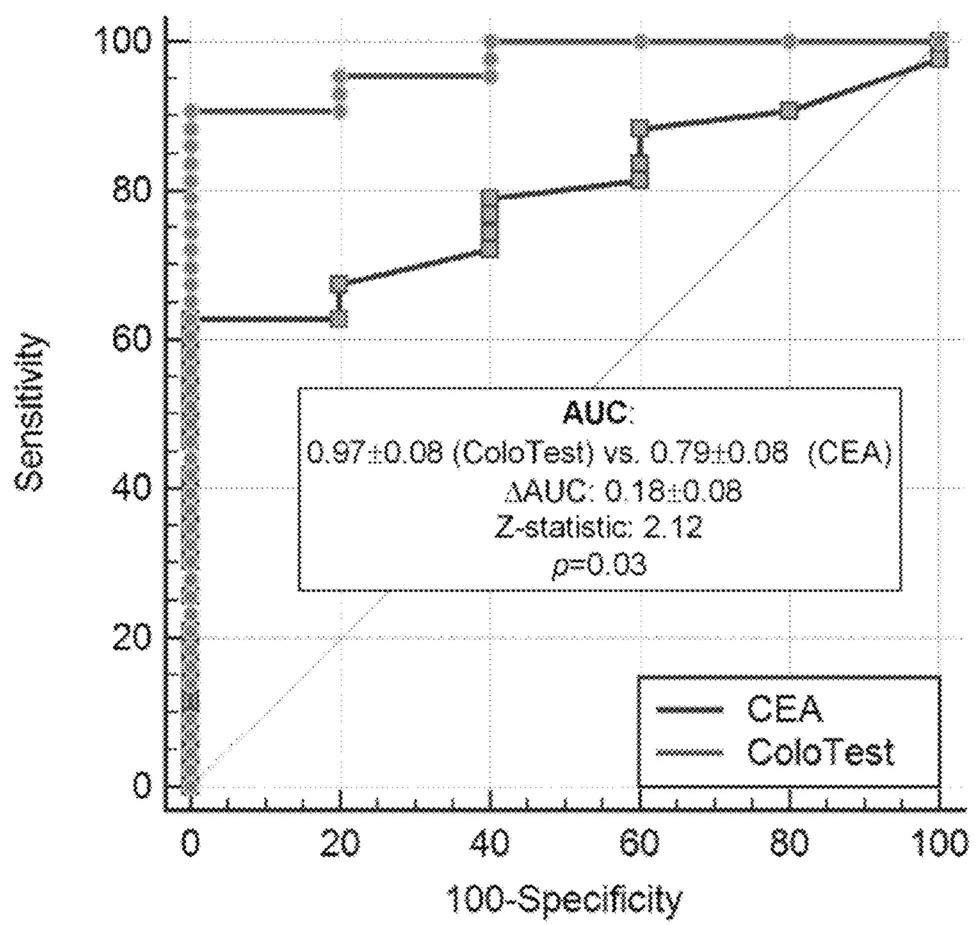
FIG. 7 is a graph showing comparison of AUROC between the ColoTest and CEA for differentiating stable from progressive disease. The ColoTest was significantly more sensitive than CEA (difference in AUC: 0.18, z-statistic: 2.1, p=0.03).

Examination of a separate colon cancer cohort by disease status (clinical evaluation at time of blood-draw) identified that the ColoTest was not significantly different between stable (n=17: 56±7%) and progressive disease (n=32: 68±4%) (FIGS. 6A-6C). However, 12 of the 17 patients progressed with 3 months of blood collection. Those that did progress exhibited elevated ColoTest scores at time of blood draw (n=12: 73±4%) that were not different to those with progressive disease at time of blood draw (n=32: 68±4%) (FIGS. 6A-6C). Levels in patients with stable disease were significantly lower (n=5: 16±4%, p<0.0001). A direct comparison between the ColoTest and CEA in these samples identified that the gene expression assay was significantly more sensitive (p<0.05) than CEA for predicting disease progression (FIG. 7). The ColoTest tool can therefore accurately predict progressive colon cancer disease.

Figure 8:
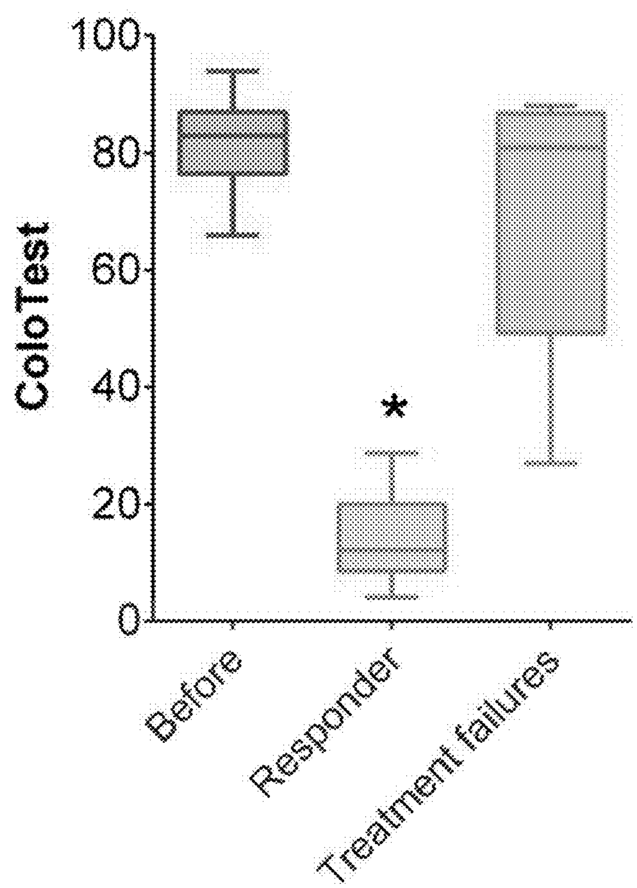
FIG. 8 is a graph showing the effect of treatment on the ColoTest. Levels prior to treatment are elevated (82±9%). In those who responded to therapy with disease stabilization, levels were reduced to 14±7% (*$p<0.0001$). In those that exhibited disease progression because of treatment failure, levels were elevated (69±21%).

ROC analysis identified the ColoTest had an AUC: 0.97 for differentiating stable from progressive disease. The z-statistic for differentiating controls was 20.6. Further evaluation of this cohort identified that patients who exhibited disease progression despite therapy exhibited higher scores than those responding to therapy (FIG. 8). Therapies included bevacizumab, chemotherapy and EGFR TKI inhibitors. The tool can therefore accurately identify treatment failure in colon cancer disease.

TABLE 2

| Colon Cancer Biomarker or Housekeeping Genes | | NCBI Chromosome | | | Amplicon | Exon | Assay |
|---|---|---|---|---|---|---|---|
| Symbol | Name | location | UniGene ID | RefSeq | length | Boundary | Location |
| ADRM1 | adhesion regulating molecule 1 | Chr.20: 62302056-62308862 | Hs.90107 | NM_007002.3 | 60 | 3-4 | 486 |
| CDK4 | cyclin dependent kinase 4 | Chr.12: 57747727-57752447 | Hs.95577 | NM_000075.3 | 65 | 5-6 | 928 |
| COMT | catechol-O-methyltransferase | Chr.22: 19941740-19969975 | Hs.370408 | NM_000754.3 | 118 | 5-6 | 864 |
| DHCR7 | 7-dehydrocholesterol reductase | Chr.11: 71434411-71448431 | Hs.503134 | NM_001163817.1 | 74 | 3-4 | 351 |
| HMOX2 | heme oxygenase 2 | Chr.16: 4474697-4510347 | Hs.284279 | NM_001127204.1 | 81 | 5-6 | 1002 |
| MCM2 | minichromosome maintenance complex component 2 | Chr.3: 127598357-127622436 | Hs.477481 | NM_004526.3 | 67 | 13-14 | 2374 |
| MORF4L1 (housekeeping gene) | mortality factor 4 like 1 | Chr.15: 78872781-78897739 | Hs.374503 | NM_001265603.1 | 62 | 1 | 116 |
| PDXK | pyridoxal (pyridoxine, vitamin B6) kinase | Chr.21: 43719097-43762307 | Hs.284491 | NM_003681.4 | 103 | 9-10 | 959 |
| POP7 | POP7 homolog, ribonuclease P/MRP subunit | Chr.7: 100706053-100707500 | Hs.416994 | NM_005837.2 | 136 | 2 | 828 |
| S100P | S100 calcium binding protein P | Chr.4: 6693839-6697170 | Hs.2962 | NM_005980.2 | 73 | 1-2 | 234 |
| SNRPA | small nuclear ribonucleoprotein polypeptide A | Chr.19: 40750854-40765392 | Hs.466775 | NM_004596.4 | 123 | 3-4 | 986 |
| SORD | sorbitol dehydrogenase | Chr.15: 45023104-45075089 | Hs.878 | NM_003104.5 | 72 | 4-5 | 601 |
| STOML2 | stomatin like 2 | Chr.9: 35099776-35103195 | Hs.3439 | NM_001287031.1 | 68 | 2-3 | 290 |
| UMPS | uridine monophosphate synthetase | Chr.3: 124730366-124749273 | Hs.2057 | NM_000373.3 | 85 | 3-4 | 1082 |

REFERENCES

1. Siegel R L, Miller K D, Jemal A. Cancer Statistics, 2017. CA Cancer J Clin. 2017; 67: 7-30. doi: 10.3322/caac.21387. Epub 2017 Jan. 5.

2. Ferlay J, Steliarova-Foucher E, Lortet-Tieulent J, Rosso S, Coebergh J W, Comber H, Forman D, Bray F. Cancer incidence and mortality patterns in Europe: estimates for 40 countries in 2012. Eur J Cancer. 2013; 49: 1374-403.

3. Fritzmann J, Morkel M, Besser D, Budczies J, Kosel F, Brembeck F H, Stein U, Fichtner I, Schlag P M, Birchmeier W. A colorectal cancer expression profile that includes transforming growth factor beta inhibitor BAMBI predicts metastatic potential. Gastroenterology. 2009; 137: 165-75.
4. Chen V W, Hsieh M C, Charlton M E, Ruiz B A, Karlitz J, Altekruse S F, Ries L A, Jessup J M. Analysis of stage and clinical/prognostic factors for colon and rectal cancer from SEER registries: AJCC and collaborative stage data collection system. Cancer. 2014; 120: 3793-806.
5. Heald R J, Lockhart-Mummery H E. The lesion of the second cancer of the large bowel. Br J Surg. 1972; 59: 16-9.
6. Mokhles S, Macbeth F, Farewell V, Fiorentino F, Williams N R, Younes R N, Takkenberg J J, Treasure T. Meta-analysis of colorectal cancer follow-up after potentially curative resection. Br J Surg. 2016; 103: 1259-68.
7. Thomas S N, Zhu F, Schnaar R L, Alves C S, Konstantopoulos K. Carcinoembryonic antigen and CD44 variant isoforms cooperate to mediate colon carcinoma cell adhesion to E- and L-selectin in shear flow. J Biol Chem. 2008; 283: 15647-55.
8. Amri R, Bordeianou L G, Sylla P, Berger D L. Preoperative carcinoembryonic antigen as an outcome predictor in colon cancer. J Surg Oncol. 2013; 108: 14-8.
9. Jansen N, Coy J F. Diagnostic use of epitope detection in monocytes blood test for early detection of colon cancer metastasis. Future Oncol. 2013; 9: 605-9.
10. Locker G Y, Hamilton S, Harris J, Jessup J M, Kemeny N, Macdonald J S, Somerfield M R, Hayes D F, Bast R C, Jr. ASCO 2006 update of recommendations for the use of tumor markers in gastrointestinal cancer. J Clin Oncol. 2006; 24: 5313-27.
11. Warren J D, Xiong W, Bunker A M, Vaughn C P, Furtado L V, Roberts W L, Fang J C, Samowitz W S, Heichman K A. Septin 9 methylated DNA is a sensitive and specific blood test for colorectal cancer. BMC Med. 2011; 9:133.: 10.1186/741-7015-9-133.
12. Mead R, Duku M, Bhandari P, Cree I A. Circulating tumour markers can define patients with normal colons, benign polyps, and cancers. Br J Cancer. 2011; 105: 239-45.
13. Molnar B, Floro L, Sipos F, Toth B, Sreter L, Tulassay Z. Elevation in peripheral blood circulating tumor cell number correlates with macroscopic progression in UICC stage I V colorectal cancer patients. Dis Markers. 2008; 24: 141-50. doi:
14. Mishaeli M, Klein B, Sadikov E, Bayer I, Koren R, Gal R, Rakowsky E, Levin I, Kfir B, Schachter J, Klein T. Initial TPS serum level as an indicator of relapse and survival in colorectal cancer. Anticancer Res. 1998; 18: 2101-5.
15. Piepoli A, Cotugno R, Merla G, Gentile A, Augello B, Quitadamo M, Merla A, Panza A, Carella M, Maglietta R, D'Addabbo A, Ancona N, Fusilli S, et al. Promoter methylation correlates with reduced NDRG2 expression in advanced colon tumour. BMC Med Genomics. 2009; 2:11.: 10.1186/755-8794-2-11.

EQUIVALENTS

While the present invention has been described in conjunction with the specific aspects set forth above, many alternatives, modifications and other variations thereof will be apparent to those of ordinary skill in the art. All such alternatives, modifications and variations are intended to fall within the spirit and scope of the present invention.

The invention claimed is:

1. A method of treating colon cancer in a subject comprising:

determining the expression level of at least 14 biomarkers from a test sample from a subject by contacting the test sample with a plurality of agents specific to detect the expression of the at least 14 biomarkers, wherein the 14 biomarkers comprise ADRM1, CDK4, COMT, DHCR7, HMOX2, MCM2, PDXK, POP7, S100P, SNRPA, SORD, STOML2, UMPS, and a housekeeping gene, wherein the housekeeping gene is MORF4L1;

normalizing the expression level of each of ADRM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADRM1, CDK4, COMT, DHCR7, HMOX2, MCM2, PDXK, POP7, S100P, SNRPA, SORD, STOML2, and UMPS;

inputting each normalized expression level into an algorithm to generate a score, wherein the algorithm is a product of a model of colon cancer disease derived using the XGB algorithm;

comparing the score with a predetermined cutoff value; and determining that the score is equal to or greater than the predetermined cutoff value, thereby identifying the subject as having colon cancer; and administering to the subject identified as having colon cancer a therapy, wherein the therapy comprises surgery.

2. The method of claim 1, wherein the predetermined cutoff value is at least 50% on a scale of 0-100%.

3. The method of claim 1, wherein the predetermined cutoff value is at least 60% on a scale of 0-100%.

4. The method of claim 1, wherein the predetermined cutoff value has a sensitivity of identifying the subject as having colon cancer that is greater than 85%.

5. The method of claim 1, wherein the predetermined cutoff value has a specificity of identifying the subject as having colon cancer that is greater than 75%.

6. The method of claim 1, wherein at least one of the at least 14 biomarkers is RNA, cDNA or protein.

7. The method of claim 6, wherein when the biomarker is RNA, the RNA is reverse transcribed to produce cDNA, and the produced cDNA expression level is detected.

8. The method of claim 1, wherein the predetermined cutoff value is derived from a plurality of reference samples obtained from subjects not having or not diagnosed with a colon cancer.

9. The method of claim 1, wherein the surgery comprises removing a polyp during a colonoscopy, endoscopic mucosal resection, a partial colectomy, an ostomy, removing at least one cancerous lesion from the liver, or any combination thereof.

* * * * *

SEQUENCE LISTING

```
<160> NUMBER OF SEQ ID NOS: 31

<210> SEQ ID NO 1
<211> LENGTH: 1496
<212> TYPE: DNA
<213> ORGANISM: Homo sapiens

<400> SEQUENCE: 1

gttagagccg gctgcgcggc ttacggggct caatcggcgg cgagagcggc aggcggggcg     60

ggccgaacgc gggtttccgg cggggcccgg caggcgccga ggaggaagag cgagcccgga    120

cggcgcctct cgaacgagtg tgggcgcgag gcaggatgac gacctcaggc gcgctctttc    180

caagcctggt gccaggctct cggggcgcct ccaacaagta cttggtggag tttcgggcgg    240

gaaagatgtc cctgaagggg accaccgtga ctccggataa gcggaaaggg ctggtgtaca    300

ttcagcagac ggacgactcg cttattcact tctgctggaa ggacaggacg tccgggaacg    360

tggaagacga cttgatcatc ttccctgacg actgtgagtt caagcgggtg ccgcagtgcc    420

ccagcgggag ggtctacgtg ctgaagttca aggcagggtc caagcggctt ttcttctgga    480

tgcaggaacc caagacagac caggatgagg agcattgccg gaaagtcaac gagtatctga    540

acaacccccc gatgcctggg gcgctggggg ccagcggaag cagcggccac gaactctctg    600

cgctaggcgg tgagggtggc ctgcagagcc tgctgggaaa catgagccac agccagctca    660

tgcagctcat cggaccagcc ggcctcggag gactgggtgg gctgggggcc ctgactggac    720

ctggcctggc cagcttactg gggagcagtg ggcctccagg gagcagctcc tcctccagct    780
```

```
cccggagcca gtcggcagcg gtcaccccgt catccaccac ctcttccacc cgtgccaccc    840

cagccccttc tgctccagca gctgcctcag caactagccc gagccccgcg cccagttccg    900

ggaatggagc cagcacagca gccagcccga cccagcccat ccagctgagc gacctccaga    960

gcatcctggc cacgatgaac gtaccagccg ggccagcagg cggccagcaa gtggacctgg   1020

ccagtgtgct gacgccggag ataatggctc ccatcctcgc caacgcggat gtccaggagc   1080

gcctgcttcc ctacttgcca tctggggagt cgctgccgca gaccgcggat gagatccaga   1140

ataccctgac ctcgccccag ttccagcagg ccctgggcat gttcagcgca gccttggcct   1200

cggggcagct gggcccctc atgtgccagt tcggtctgcc tgcagaggct gtggaggccg   1260

ccaacaaggg cgatgtggaa gcgtttgcca aagccatgca gaacaacgcc aagcccgagc   1320

agaaagaggg cgacacgaag gacaagaagg acgaagagga ggacatgagc ctggactgag   1380

ccacgcgccg tcctccgagg aactgggcgc ttgcagtgcg ttgcacaccc tcacctccca   1440

cccactgatt attaataaag tcttttcttt tacctgccaa aaaaaaaaaa aaaaaa       1496
```

<210> SEQ ID NO 2
<211> LENGTH: 2020
<212> TYPE: DNA
<213> ORGANISM: Homo sapiens

<400> SEQUENCE: 2

```
cacctcctgt ccgcccctca gcgcatgggt ggcggtcacg tgcccagaac gtccggcgtt     60

cgccccgccc tcccagtttc cgcgcgcctc tttggcagct ggtcacatgg tgagggtggg    120

ggtgaggggg cctctctagc ttgcggcctg tgtctatggt cgggccctct gcgtccagct    180

gctccggacc gagctcgggt gtatggggcc gtaggaaccg gctccggggc cccgataacg    240

ggccgccccc acagcacccc gggctggcgt gagggtctcc cttgatctga gaatggctac    300

ctctcgatat gagccagtgg ctgaaattgg tgtcggtgcc tatgggacag tgtacaaggc    360

ccgtgatccc cacagtggcc actttgtggc cctcaagagt gtgagagtcc ccaatggagg    420

aggaggtgga ggaggccttc ccatcagcac agttcgtgag gtggctttac tgaggcgact    480

ggaggctttt gagcatccca atgttgtccg gctgatggac gtctgtgcca catcccgaac    540

tgaccgggag atcaaggtaa ccctggtgtt tgagcatgta gaccaggacc taaggacata    600

tctggacaag gcacccccac caggcttgcc agccgaaacg atcaaggatc tgatgcgcca    660

gtttctaaga ggcctagatt tccttcatgc caattgcatc gttcaccgag atctgaagcc    720

agagaacatt ctggtgacaa gtggtggaac agtcaagctg gctgactttg gcctggccag    780

aatctacagc taccagatgg cacttacacc cgtggttgtt acactctggt accgagctcc    840

cgaagttctt ctgcagtcca catatgcaac acctgtggac atgtggagtg ttggctgtat    900

ctttgcagag atgtttcgtc gaaagcctct cttctgtgga aactctgaag ccgaccagtt    960

gggcaaaatc tttgacctga ttgggctgcc tccagaggat gactggcctc gagatgtatc   1020

cctgccccgt ggagcctttc cccccagagg gccccgccca gtgcagtcgg tggtacctga   1080

gatggaggag tcgggagcac agctgctgct ggaaatgctg acttttaacc cacacaagcg   1140

aatctctgcc tttcgagctc tgcagcactc ttatctacat aaggatgaag gtaatccgga   1200

gtgagcaatg gagtggctgc catggaagga agaaaagctg ccatttccct tctggacact   1260

gagagggcaa tctttgcctt tatctctgag gctatggagg gtcctcctcc atctttctac   1320

agagattact ttgctgcctt aatgacattc cctcccacc tctccttttg aggcttctcc   1380

ttctccttcc catttctcta cactaagggg tatgttccct cttgtccctt tccctacctt   1440
```

```
tatatttggg gtcctttttt atacaggaaa aacaaaacaa agaaataatg gtcttttttt   1500
tttttttaat gtttcttcct ctgtttggct ttgccattgt gcgatttgga aaaaccactt   1560
ggaagaaggg actttcctgc aaaaccttaa agactggtta aattacaggg cctaggaagt   1620
cagtggagcc ccttgactga caaagcttag aaaggaactg aaattgcttc tttgaatatg   1680
gattttaggc ggggcgtggt ggctcacgcc tataatccca gcacgttggg aggccaacgc   1740
gggtggatca cctgaggtca ggagttcgag accagcctga ctaacatggt gaaaccctgt   1800
ctctactaaa aatacaaaat tagtcaggcg tggtggtgca cacctgtaat cccagctact   1860
tgggagactg aggcaggagg atcgcttgaa cccgggaggc agaggttgcg gtgagccgag   1920
atcatgccat tgcactccag cctgggcaac agagcaagac tctgtgtcaa aaaaaaaaaa   1980
agaatataga tttttaaatg gcaaaaaaaa aaaaaaaaaa                         2020
```

<210> SEQ ID NO 3
<211> LENGTH: 2304
<212> TYPE: DNA
<213> ORGANISM: Homo sapiens

<400> SEQUENCE: 3

```
cggcctgcgt ccgccaccgg aagcgccctc ctaatccccg cagcgccacc gccattgccg     60
ccatcgtcgt ggggcttctg gggcagctag ggctgcccgc cgcgctgcct gcgccggacc    120
ggggcgggtc cagtcccggg cgggccgtcg cgggagagaa ataacatctg ctttgctgcc    180
gagctcagag gagaccccag acccctcccg cagccagagg gctggagcct gctcagaggt    240
gctttgaaga tgccggaggc cccgcctctg ctgttggcag ctgtgttgct gggcctggtg    300
ctgctggtgg tgctgctgct gcttctgagg cactggggct ggggcctgtg ccttatcggc    360
tggaacgagt tcatcctgca gcccatccac aacctgctca tgggtgacac caaggagcag    420
cgcatcctga accacgtgct gcagcatgcg gagcccggga acgcacagag cgtgctggag    480
gccattgaca cctactgcga gcagaaggag tgggccatga acgtgggcga caagaaaggc    540
aagatcgtgg acgccgtgat tcaggagcac cagccctccg tgctgctgga gctgggggcc    600
tactgtggct actcagctgt gcgcatggcc cgcctgctgt caccaggggc gaggctcatc    660
accatcgaga tcaaccccga ctgtgccgcc atcacccagc ggatggtgga tttcgctggc    720
gtgaaggaca aggtcaccct tgtggttgga gcgtcccagg acatcatccc ccagctgaag    780
aagaagtatg atgtggacac actggacatg gtcttcctcg accactggaa ggaccggtac    840
ctgccggaca cgcttctctt ggaggaatgt ggcctgctgc ggaaggggac agtgctactg    900
gctgacaacg tgatctgccc aggtgcgcca gacttcctag cacacgtgcg cgggagcagc    960
tgctttgagt gcacacacta ccaatcgttc ctggaataca gggaggtggt ggacggcctg   1020
gagaaggcca tctacaaggg cccaggcagc gaagcagggc cctgactgcc cccccggccc   1080
ccctctcggg ctctctcacc cagcctggta ctgaaggtgc cagacgtgct cctgctgacc   1140
ttctgcggct ccgggctgtg tcctaaatgc aaagcacacc tcggccgagg cctgcgccct   1200
gacatgctaa cctctctgaa ctgcaacact ggattgttct tttttaagac tcaatcatga   1260
cttctttact aacactggct agctatatta tcttatatac taatatcatg ttttaaaaat   1320
ataaaataga aattaagaat ctaaatattt agatataact cgacttagta catccttctc   1380
aactgccatt cccctgctgc ccttgacttg ggcaccaaac attcaaagct ccccttgacg   1440
gacgctaacg ctaagggcgg ggcccctagc tggctgggtt ctgggtggca cgcctggccc   1500
```

```
actggcctcc cagccacagt ggtgcagagg tcagccctcc tgcagctagg ccaggggcac   1560

ctgttagccc catggggacg actgccggcc tgggaaacga agaggagtca gccagcattc   1620

acacctttct gaccaagcag gcgctgggga caggtggacc ccgcagcagc accagcccct   1680

ctgggcccca tgtggcacag agtggaagca tctccttccc tactccccac tgggccttgc   1740

ttacagaaga ggcaatggct cagaccagct cccgcatccc tgtagttgcc tccctggccc   1800

atgagtgagg atgcagtgct ggtttctgcc cacctacacc tagagctgtc cccatctcct   1860

ccaaggggtc agactgctag ccacctcaga ggctccaagg gcccagttcc caggcccagg   1920

acaggaatca accctgtgct agctgagttc acctgcaccg agaccagccc ctagccaaga   1980

ttctactcct gggctcaagg cctggctagc cccagccag cccactccta tggatagaca   2040

gaccagtgag cccaagtgga caagtttggg gccacccagg gaccagaaac agagcctctg   2100

caggacacag cagatgggca cctgggacca cctccaccca gggccctgcc ccagacgcgc   2160

agaggcccga cacaagggag aagccagcca cttgtgccag acctgagtgg cagaaagcaa   2220

aaagttcctt tgctgcttta atttttaaat tttcttacaa aaatttaggt gtttaccaat   2280

agtcttattt tggcttattt ttaa                                          2304
```

<210> SEQ ID NO 4
<211> LENGTH: 2642
<212> TYPE: DNA
<213> ORGANISM: Homo sapiens

<400> SEQUENCE: 4

```
aatcgctgac atcatccggg ggcgggcgcc cctgccctgc gggtgactcc gacccctggc     60

tagagggtag gcggcgtgga gcagcgcgcg caagcgaggc caggggaagg tgggcgcagg    120

actttagccg gttgagaagg atcaagcagg catttggagc acaggtgtct agaaactttt    180

aaggggccgg ttcaagaagg aaaagttccc ttctgctgtg aaactatttg gcaagaggct    240

ggagggccca atggctgcaa aatcgcaacc caacattccc aaagccaaga gtctagatgg    300

cgtcaccaat gacagaaccg catctcaagg gcagtggggc cgtgcctggg aggtggactg    360

gttttcactg gcgagcgtca tcttcctact gctgttcgcc cccttcatcg tctactactt    420

catcatggct tgtgaccagt acagctgcgc cctgactggc cctgtggtgg acatcgtcac    480

cggacatgct cggctctcgg acatctgggc caagactcca cctataacga ggaaagccgc    540

ccagctctat accttgtggg tcaccttcca ggtgcttctg tacacgtctc tccctgactt    600

ctgccataag tttctacccg gctacgtagg aggcatccag gagggggccg tgactcctgc    660

aggggttgtg aacaagtatc agatcaatgg cctgcaagcc tggctcctca cgcacctgct    720

ctggtttgca aacgctcatc tcctgtcctg gttctcgccc accatcatct tcgacaactg    780

gatcccactg ctgtggtgcg ccaacatcct tggctatgcc gtctccacct tcgccatggt    840

caagggctac ttcttcccca ccagcgccag agactgcaaa ttcacaggca atttctttta    900

caactacatg atgggcatcg agtttaaccc tcggatcggg aagtggtttg acttcaagct    960

gttcttcaat gggcgccccg ggatcgtcgc ctggaccctc atcaacctgt ccttcgcagc   1020

gaagcagcgg gagctccaca gccatgtgac caatgccatg gtcctggtca acgtcctgca   1080

ggccatctac gtgattgact tcttctggaa cgaaacctgg tacctgaaga ccattgacat   1140

ctgccatgac cacttcgggt ggtacctggg ctggggcgac tgtgtctggc tgccttatct   1200

ttacacgctg cagggtctgt acttggtgta ccaccccgtg cagctgtcca ccccgcacgc   1260

cgtgggcgtc ctgctgctgg gcctggtggg ctactacatc ttccgggtgg ccaaccacca   1320
```

```
gaaggacctg ttccgccgca cggatgggcg ctgcctcatc tggggcagga agcccaaggt   1380

catcgagtgc tcctacacat ccgccgatgg gcagaggcac cacagcaagc tgctggtgtc   1440

gggcttctgg ggcgtggccc gccacttcaa ctacgtcggc gacctgatgg gcagcctggc   1500

ctactgcctg gcctgtggcg gcggccacct gctgccctac ttctacatca tctacatggc   1560

catcctgctg acccaccgct gcctccggga cgagcaccgc tgcgccagca agtacggccg   1620

ggactgggag cgctacaccg ccgcagtgcc ttaccgcctg ctgcctggaa tcttctaagg   1680

gcacgcccta gggagaagcc ctgtggggct gtcaagagcg tgttctgcca ggtccatggg   1740

ggctggcatc ccagctccaa ctcgaggagc ctcagtttcc tcatctgtaa actggagaga   1800

gcccagcact tggcaggtgt ccagtaccta atcacgctct gttccttgct tttgccttca   1860

agggaattcc gagtgtccag cactgccgta ttgccagcac agacggattt tctctaatca   1920

gtgtccctgg ggcaggagga tgacccagtc acctttacta gtcctttgga gacaatttac   1980

ctgtattagg agcccaggcc acgctacact ctgcccacac tggtgagcag gaggtcttcc   2040

cacgccctgt cattaggctg catttactct tgctaaataa aagtgggagt ggggcgtgcg   2100

cgttatccat gtattgcctt tcagctctag atccccctcc cctgcctgct ctgcagtcgt   2160

gggtggggcc cgtgcgccgt ttctccttgg tagcgtgcac ggtgttgaac tgggacactg   2220

gggagaaagg ggctttcatg tcgtttcctt cctgctcctg ctgcacagct gccaggagtg   2280

ctctgcctgg agtctgcaga cctcagagag gtcccagcac cggctgtggc ctttcaggtg   2340

taggcaggtg ggctctgctt cccgattccc tgtgagcgcc caccctctcg aaagaatttt   2400

ctgcttgccc tatgactgtg cagactctgg ctcgagcaac ccggggaact tcaccctcag   2460

gggcctccca caccttctcc agcgaggagg tctcagtccc agcctcggga gggcacctcc   2520

ttttctgtgc tttcttccct gaggcattct tcctcatccc tagggtgttg tgtagaactc   2580

tttttaaact ctatgctccg agtagagttc atctttatat taaacttccc ctgttcaaat   2640

aa                                                                  2642
```

<210> SEQ ID NO 5
<211> LENGTH: 1872
<212> TYPE: DNA
<213> ORGANISM: Homo sapiens

<400> SEQUENCE: 5

```
catctctagg ccccgccccg cgctgcgtgc ccacgttgcg ccggcctcgc gccagtccgc     60

tgggctgcag ggactgcggc gcctgaggga gtcgctgacg ggcacgctga ctggaggctg    120

gcggacaggc gacagcgacc tgcggcagag tcttgctgcg acacccaggc tggagtgcaa    180

tggcgctatc tcggctcact gcaacctccg cttcccggat tcaagcgatt ctcctgcctc    240

agcctcccga gtaggtggga ctacaggacc agaggagcga gagcagcaag aaccacaccc    300

agcagcaatg tcagcggaag tggaaacctc agagggggta gacgagtcag aaaaaaagaa    360

ctctggggcc ctagaaaagg agaaccaaat gagaatggct gacctctcgg agctcctgaa    420

ggaagggacc aaggaagcac acgaccgggc agaaaacacc cagtttgtca aggacttctt    480

gaaaggcaac attaagaagg agctgtttaa gctggccacc acggcacttt acttcacata    540

ctcagccctc gaggaggaaa tggagcgcaa caaggaccat ccagcctttg cccctttgta    600

cttccccatg gagctgcacc ggaaggaggc gctgaccaag gacatggagt atttctttgg    660

tgaaaactgg gaggagcagg tgcagtgccc caaggctgcc cagaagtacg tggagcggat    720
```

```
ccactacata gggcagaacg agccggagct actggtggcc catgcataca cccgctacat    780
gggggatctc tcgggggccc aggtgctgaa gaaggtggcc cagcgagcac tgaaactccc    840
cagcacaggg gaagggaccc agttctacct gtttgagaat gtggacaatg cccagcagtt    900
caagcagctc taccgggcca ggatgaacgc cctggacctg aacatgaaga ccaaagagag    960
gatcgtggag gaggccaaca aggcttttga gtataacatg cagatattca atgaactgga   1020
ccaggccggc tccacactgg ccagagagac cttggaggat gggttccctg tacacgatgg   1080
gaaaggagac atgcgtaaat gccctttcta cgctgctgaa caagacaaag gtgccctgga   1140
gggcagcagc tgtcccttcc gaacagctat ggctgtgctg aggaagccca gcctccagtt   1200
catcctggcc gctggtgtgg ccctagctgc tggactcttg gcctggtact acatgtgaag   1260
cacccatcat gccacaccgg taccctcctc ccgactgacc actggcctac ccctttctcc   1320
agccctgact aaactaccac ctcaggtgac tttttaaaaa atgctgggtt taagaaaggc   1380
aaccaataaa agccagatgc tagagcctct gcctgacagc atcctctcta tgggccatat   1440
tccgcactgg gcacaggccg tcaccctggg agcagtcggc acagtgcagc aagcctggcc   1500
cccgacccag ctctactcca ggcttccaca cttctgggcc ctaggctgct tccggtagtc   1560
cctgtttttg cagtacatgg gtgactatct cccctgttgg aggtgagtgg cctgtaagtc   1620
caagctgtgc gagggggcct tgctggatgc tgctgtacaa cttctgggcc tctcttggac   1680
cctgggagtg agggtgggtg tgggtggaag cctcagaggc cttgggagct catccctctc   1740
acccagaatc cctctaaccc cttgggtgcg gtttgctcag ccccagctta tctcctcctc   1800
cgcgctgtgt aaatgctcca gcactcaata aagtgggctt tgcaagctaa aaaaaaaaaa   1860
aaaaaaaaaa aa                                                       1872
```

<210> SEQ ID NO 6
<211> LENGTH: 3504
<212> TYPE: DNA
<213> ORGANISM: Homo sapiens

<400> SEQUENCE: 6

```
atgacgtcgc gttccgtagg gctcttcccg ggctttggtg ggtcacgtga accacttttc     60
gcgcgaaacc tggttgttgc tgtagtggcg gagaggatcg tggtactgct atggcggaat    120
catcggaatc cttcaccatg gcatccagcc cggcccagcg tcggcgaggc aatgatcctc    180
tcacctccag ccctggccga agctcccggc gtactgatgc cctcacctcc agccctggcc    240
gtgaccttcc accatttgag gatgagtccg aggggctcct aggcacagag ggggcccctgg   300
aggaagaaga ggatggagag gagctcattg gagatggcat ggaaagggac taccgcgcca    360
tcccagagct ggacgcctat gaggccgagg gactggctct ggatgatgag gacgtagagg    420
agctgacggc cagtcagagg gaggcagcag agcgggccat gcggcagcgt gaccgggagg    480
ctggccgggg cctgggccgc atgcgccgtg ggctcctgta tgacagcgat gaggaggacg    540
aggagcgccc tgcccgcaag cgccgccagg tggagcgggc cacggaggac ggcgaggagg    600
acgaggagat gatcgagagc atcgagaacc tggaggatct caaaggccac tctgtgcgcg    660
agtgggtgag catggcgggc ccccggctgg agatccacca ccgcttcaag aacttcctgc    720
gcactcacgt cgacagccac ggccacaacg tcttcaagga gcgcatcagc gacatgtgca    780
aagagaaccg tgagagcctg gtggtgaact atgaggactt ggcagccagg gagcacgtgc    840
tggcctactt cctgcctgag gcaccggcgg agctgctgca gatctttgat gaggctgccc    900
tggaggtggt actggccatg taccccaagt acgaccgcat caccaaccac atccatgtcc    960
```

-continued

```
gcatctccca cctgcctctg gtggaggagc tgcgctcgct gaggcagctg catctgaacc   1020

agctgatccg caccagtggg gtggtgacca gctgcactgg cgtcctgccc cagctcagca   1080

tggtcaagta caactgcaac aagtgcaatt tcgtcctggg tcctttctgc cagtcccaga   1140

accaggaggt gaaaccaggc tcctgtcctg agtgccagtc ggccggcccc tttgaggtca   1200

acatggagga gaccatctat cagaactacc agcgtatccg aatccaggag agtccaggca   1260

aagtggcggc tggccggctg ccccgctcca aggacgccat tctcctcgca gatctggtgg   1320

acagctgcaa gccaggagac gagatagagc tgactggcat ctatcacaac aactatgatg   1380

gctccctcaa cactgccaat ggcttccctg tctttgccac tgtcatccta gccaaccacg   1440

tggccaagaa ggacaacaag gttgctgtag gggaactgac cgatgaagat gtgaagatga   1500

tcactagcct ctccaaggat cagcagatcg gagagaagat ctttgccagc attgctcctt   1560

ccatctatgg tcatgaagac atcaagagag gcctggctct ggccctgttc ggaggggagc   1620

ccaaaaaccc aggtggcaag cacaaggtac gtggtgatat caacgtgctc ttgtgcggag   1680

accctggcac agcgaagtcg cagtttctca agtatattga gaaagtgtcc agccgagcca   1740

tcttcaccac tggccagggg gcgtcggctg tgggcctcac ggcgtatgtc cagcggcacc   1800

ctgtcagcag ggagtggacc ttggaggctg gggccctggt tctggctgac cgaggagtgt   1860

gtctcattga tgaatttgac aagatgaatg accaggacag aaccagcatc catgaggcca   1920

tggagcaaca gagcatctcc atctcgaagg ctggcatcgt cacctccctg caggctcgct   1980

gcacggtcat tgctgccgcc aaccccatag gagggcgcta cgacccctcg ctgactttct   2040

ctgagaacgt ggacctcaca gagcccatca tctcacgctt tgacatcctg tgtgtggtga   2100

gggacaccgt ggacccagtc caggacgaga tgctggcccg cttcgtggtg ggcagccacg   2160

tcagacacca ccccagcaac aaggaggagg aggggctggc caatggcagc gctgctgagc   2220

ccgccatgcc caacacgtat ggcgtggagc ccctgcccca ggaggtcctg aagaagtaca   2280

tcatctacgc caaggagagg gtccacccga agctcaacca gatggaccag gacaaggtgg   2340

ccaagatgta cagtgacctg aggaaagaat ctatggcgac aggcagcatc cccattacgg   2400

tgcggcacat cgagtccatg atccgcatgg cggaggccca cgcgcgcatc catctgcggg   2460

actatgtgat cgaagacgac gtcaacatgg ccatccgcgt gatgctggag agcttcatag   2520

acacacagaa gttcagcgtc atgcgcagca tgcgcaagac ttttgcccgc tacctttcat   2580

tccggcgtga caacaatgag ctgttgctct tcatactgaa gcagttagtg gcagagcagg   2640

tgacatatca gcgcaaccgc tttggggccc agcaggacac tattgaggtc cctgagaagg   2700

acttggtgga taaggctcgt cagatcaaca tccacaacct ctctgcattt tatgacagtg   2760

agctcttcag gatgaacaag ttcagccacg acctgaaaag gaaaatgatc ctgcagcagt   2820

tctgaggccc tatgccatcc ataaggattc cttgggattc tggtttgggg tggtcagtgc   2880

cctctgtgct ttatggacac aaaaccagag cacttgatga actcggggta ctagggtcag   2940

ggcttatagc aggatgtctg gctgcacctg gcatgactgt ttgtttctcc aagcctgctt   3000

tgtgcttctc acctttgggt gggatgcctt gccagtgtgt cttacttggt tgctgaacat   3060

cttgccacct ccgagtgctt tgtctccact cagtaccttg gatcagagct gctgagttca   3120

ggatgcctgc gtgtggttta ggtgttagcc ttcttacatg gatgtcagga gagctgctgc   3180

cctcttggcg tgagttgcgt attcaggctg cttttgctgc ctttggccag agagctggtt   3240

gaagatgttt gtaatcgttt tcagtctcct gcaggtttct gtgcccctgt ggtggaagag   3300
```

ggcacgacag tgccagcgca gcgttctggg ctcctcagtc gcaggggtgg gatgtgagtc 3360
atgcggatta tccactcgcc acagttatca gctgccattg ctccctgtct gtttccccac 3420
tctcttattt gtgcattcgg tttggtttct gtagttttaa tttttaataa agttgaataa 3480
aatataaaaa aaaaaaaaaa aaaa 3504

<210> SEQ ID NO 7
<211> LENGTH: 7390
<212> TYPE: DNA
<213> ORGANISM: Homo sapiens

<400> SEQUENCE: 7
cggaactcgc gggttcggag ccgcccgctg aggtcagaag gaggcgtctg cgctgatcgg 60
gtccgccgcg cgccagagcc agagtcgcag ccgaggggag ccggggccgg agcccgagcc 120
cgagccgagc cggagcccga gcgagcggcg gagaccgtgc ccccgcctcg gccccgcgcc 180
gccgcggcca ggcccggcat ggaggaggag tgccgggtgc tctccataca gagccacgtc 240
atccgcggct acgtgggcaa ccgggcggcc acgttcccgc tgcaggtttt gggatttgag 300
attgacgcgg tgaactctgt ccagttttca aaccacacag gctatgccca ctggaagggc 360
caagtgctga attcagatga gctccaggag ttgtacgaag gcctgaggct gaacaacatg 420
aataaatatg actacgtgct cacaggttat acgagggaca agtcgttcct ggccatggtg 480
gtggacattg tgcaggagct gaagcagcag aaccccaggc tggtgtacgt gtgtgatcca 540
gtcttgggtg acaagtggga cggcgaaggc tcgatgtacg tcccggagga cctccttccc 600
gtctacaaag aaaaagtggt gccgcttgca gacattatca cgcccaacca gtttgaggcc 660
gagttactga gtggccggaa gatccacagc caggaggaag ccttgcgggt gatggacatg 720
ctgcactcta tgggccccga caccgtggtc atcaccagct ccgacctgcc ctccccgcag 780
ggcagcaact acctgattgt gctggggagt cagaggagga ggaatcccgc tggctccgtg 840
gtgatggaac gcatccggat ggacattcgc aaagtggacg ccgtctttgt gggcactggg 900
gacctgtttg ctgccatgct cctggcgtgg acacacaagc accccaataa cctcaaggtg 960
gcctgtgaga agaccgtgtc taccttgcac cacgttctgc agaggaccat ccagtgtgca 1020
aaagcccagg ccggggaagg agtgaggccc agccccatgc agctggagct gcggatggtg 1080
cagagcaaaa gggacatcga ggacccagag atcgtcgtcc aggccacggt gctgtgaggg 1140
ccccgccgct tgcccgtgac acgcagcgcg ttggtgtctc cgtgtttgtc cctgtgaaaa 1200
catgtaacgt ctgccttaga gccatgaccg aaacttgata ttttttttctt tcatgagtgt 1260 ccggcatctg ctggtcttca ttgtgaaacg tgccagtcgt gctttgtgaa aaataacaaa 1320
gtggtcacag aaatttgtga tctgaaaacc cggctccctt ccccacaagg ctcctgggcc 1380
tccgggaaga cgggcccctg tttgccatct cgggggtgtt ccctgtggga gggtgagtgg 1440
gtgaggccga gcctgctgcg tgtggagcct cgagtgggcc ctggctgcca ctaccgtaca 1500
gaggccgtgt cgcgctgggc tgggcctggg tggcctctgt ctttgcatct ctgagaagga 1560
gtcgggtggt aacggttggg gtcaggaaga attctgccaa gtatctttac tgtcattctg 1620
accatagcct ctttgttccc gcattcgaac ttttggttct tactttgctg ctcgtttagt 1680
ccctggggat ttcagatctt aggctgttgt ttcaccgtat gggagggttg atgtgagctt 1740
gcttggagac acacggtgca gcatcaggga ccttcccagg ccccagcaaa ttcaagtcgg 1800
tctgcagacc tctcagctac ccgcgggacc tcttgtaacc catcggcatc ttccaggaat 1860
ccgccgagtg acttgaggaa gatgctaacg cagtaaggtc tgtgctgggc caagagcagc 1920

```
tttgaagctc cagagaacca ccccgtcagg ttccttgtgg aagctcccct catccgtggt   1980
gcagcaggct gagcactgcg cgtttgccac gtgctgcccg tgacagcaca ttgagccaca   2040
gcatttgtag acaggacaga ggggtgcctg cccccctgccc ctgctggcac atttaaccct   2100
tgtcccctga cctcagttct gtgccccacc aaatgcccag gggcaagagg ccaccctgga   2160
agctgccaat cttccaaggt gggtgtgggg cacggtgggg gcgggcagct cccaggccct   2220
tgggcaggct ggggtgacgg cagaggccac agcaccagct ctgacaagtc ctatcatcct   2280
ctgctcagca gtgacctccc tggccccact ttgcccagag tttggggtcc ccccaggtat   2340
agctataggc ggcagtgcct gtccctggcc tgccttgatt tcagccacac ccctgcagcc   2400
ctgcatccca gctctggggt gtgcagaggt ttgtgtctcc agggaaccca cggctggaga   2460
gaaataggga gatgcaggaa gtgggggccc atggggcccc caagaagcgg actctccaag   2520
gggtaccccc accccgctac cttccccacg gacgggcccc tcctggagcc cataccctcc   2580
tgtgaggcca ttccagtgtc ttctagaaag actcgcttgc caggagtgcg ttctttgttg   2640
aaaaatgccc tgaagcgaaa agatgcaggt ttatatggaa cccccacccc ctcccccact   2700
ctcccactct gttcgttctg aatgtcttca cgagcgtgca tcagggcgcc tggctccccc   2760
acctcagcca gtgagtcaga cacgggtttc gcagccatgt ttcctggctc cgaggacacg   2820
ggtggcaggc ccgttgcagc ccagagccac tggtccctac agggcgccgc cacaccagca   2880
ggaaggagga tggctgtgtc cggagcctgg cggggaggcg gcctccccag tatgtgagtg   2940
cagggatctg ccagaaccac ctggccctct gtagggcgtt taactggaaa taccctcact   3000
gccaagtgga gactggggcg tgtgccacat tgccagccac caggaaagct ttcttttttc   3060
ttttttttt ttttttaaac accaagagca cgtatagcat gggggaaaga acctaaatgt   3120
ctctctgtcc tgtgagctgg tgaaaaaccc agcatgagaa cgcagtgtca ggtgtgggac   3180
tccttctgcc cctgcagtgg gtgttacggg cggtgtgccc tggcgagcaa gctttgattc   3240
ttggttcttt gagctcgttt cagaggctga gtccccacat cagctttagt tcttggactt   3300
ccctgtatta agcaagaatt aggagaatgg ctgtccctgc aggcgcctcc cgtaaatcct   3360
gagctctctg gcgcaatctg aaacttctct tctgttttct ttggctgtat cagccgaacc   3420
aggagaggcc tgggctgcga ctaaggagaa agaaatcggg ggtttctgag agcagatggt   3480
gcctttgtgg gtgcagggct tttgtggaaa ttgtcagcct ctacgggcag agtccggcat   3540
cccctcccca gactgcctgc tgtcaaacca cggagcagct ggagcctgcc ctgtccacgg   3600
cccgtttcca cccgggcatg ttcgtctctc atgacttcgg cagaggcccc tggtggcctt   3660
cagtttcagt ttctcatcca ggaaggtaac cttgggcatt ggcagtgggt ttccctatgg   3720
cttggatcca gattagaatt gatctttgtt ttcactttcc atagttaata acatgcaaaa   3780
taatgagaag aatttatttt aaggtgacag ctatactggt ccaacatcgc ctgcttattg   3840
tcagggtaca gaagtttaat actttcttaa tccagttttt caaacttctc cctgtagacc   3900
gtaaggatga attccacaat aggatccttt ttaaaatcga ttttaaattg ttgcctagtc   3960
ctgccaaggt tattatgtgc atctgttatt tttccaatac atgtaaacag ttgcagcatg   4020
atgctttgtt taatgtcctg ttcttaagct cgttagagcc agttttgaaa cgtttggtct   4080
taccgtgaac ggaggctggc ttggcttagc cacgctgatg agtaagtgag ggatgtctcc   4140
atcttgagat caccaggcaa gagagttgcc tgcaccaggt aagaggccaa agcccctggg   4200
gtaacagtcc ccaccgctac ccgaggtaaa acaataaaag ctatgtggtt gagctcaggc   4260
```

```
ctctcgtgcc tggtgtcaga gaaggcagag cccacagtag gtgcacggtg caaggccctg   4320
ggagggcact ggccagggaa ggtggtatag atggccctca gattgcgggg ccccgagcag   4380
ctccccactc tgcccgtcca ccttccctgg ctccagcctc attctctctt tagtttaact   4440
atgcaaagag aggaggttga gagtgttctg gcagctggag ctcttttcct tgtccttcct   4500
gccctccgat ggggccacct gtgtcggggc agcagtgtcc atgtttatgg agatcagagg   4560
tgtccccact gtgtggctgg actgtactct gctgcccggg tagccaggag tctctccctc   4620
tctcccctgc cgcctgcctg gtctcatggg cctccttcac acacccctcc ctgtggatcg   4680
cctgcctggg cccagagcag gggaactgga gtttgtgagt gagcagagca ggttatgtgc   4740
agacagggaa acgagaactt tggacctggc tttctgagtc caggtgagag ctgtgtggcc   4800
ccccgatgcc actctgcccg ccggagggat gtgcctgctg agccttttcc ttccacgccg   4860
cctctcactg ccaggccagc ggcttccgct gagactcgct ggagaggcgg ctcccgtgtc   4920
cgtccaccga gcactcagat ggatgctgat caccagggcc gagggggctc ccagaaggac   4980
cccaggccct ggggagggtg gctgtgggag gccaagtcca ctgcccggaa gtcttgtcag   5040
ccctaagcca gggaagcctg gagcgtggcc tggcgggtct gggtggacac cgtccccact   5100
ccggactccc agcacagggg aggatacctg agcctgtatg gccctgtagc cctgggcaga   5160
gctgggcctg tcgtgtgttc ctgcctggca ggtgcaggtg ctggccatct gcaggtggaa   5220
ggaggtggga atcttggatt ttttgttttt ttttgttttt ttttttttga gatgaagtct   5280
cgctctgaca cccaggctgg cgtgcagtgg tgtgatctcg gctcactgca aactccgctt   5340
cctgggttca agtggttctc ctgccccagc ctcccaagta gctgggatta caggcatgcg   5400
ccaccacgct cagctgattt ttgtattttt agtagagatg ggtttcacc atgttggcca    5460
agctggtctc aaactcctga cctcaagtga tctgcccgcc tcggcctccc agagtgctgg   5520
gattacaggc atgagccagt gcacccggcg gaatcttgga atttttatag acagcacctc   5580
agtttctgac tccagccgca cacctcctgc ctctgccagc aggggttgcc gccagaccag   5640
agccagggcc aggtccctgc gtccatcccc cccggtagga tggacgtgag ccatccttct   5700
aggggacttt tttcagtgtg cgactcgtct ctgttaggtg gtaggagcca gtttgtgtgg   5760
cctgtgccac gctccacagt gcgtggctgg gctctgtgtg tggcctgtgt cccctgtccc   5820
tgcaggaccc agcaggcatc gtggcgtgac agctgtgtcc aagccactgc ccgggcatcc   5880
catcacccac cagggtgcac ggtctctcct gctgggggct ttctgtcgca tgtgtgtctc   5940
ctgtcgactc tgcagtttgt tctcagagca gaatgtttcc tgttctcagt gcacaaagac   6000
actggttttc aatcggcgtc taaaaccacg ttcctgcctt tcattgcaac acggtgtgtt   6060
catttgttta aaacagttta atgagtaagt ttagatgact ggtcaatatc ttaaaaatgt   6120
atattagtaa gaagttcttc ctggaatttt tctttcgatt ctggcagaat aaacaggtgt   6180
ttttagtttt cccactgtct gagccaagca ggaccctgtc ccagagcaag agatgtcccc   6240
ttccatctct gacccttgcc tgggacaagc tttgatgggg ggccccagct tcaaggctgt   6300
ggtgggaaca gcacccccaa atgccagcct ctcctttctt cccatccacc agtatactgc   6360
ggggccattt ctggtctttg tccaacagga aacccatttc tggtgggata tgccttccag   6420
tgccacaggg ccactcaccc catgcatctc tgtcctgccc gtcagtgctg ggacggacag   6480
caagggcaag cccagtgtct ggcggatagg tgggtgggaa cagagagggg agaatgccgt   6540
cctaagcttc tgcttgggga tcccccacac gacctgggta ctgcctggga aacctgtcct   6600
aagtaaaact atggacctcg cctcgcccac cggcctgcga agccagcatc tccgtgaagg   6660
```

```
tggatggaag cgcctttgtc ctcattttga gctgcaagct gggtcagcgg ctctgaagcc   6720

ctcgagtgac tttctaaccc aagacccagc ccctggcagg aggagggtgg gtgcagggct   6780

ggtgggacaa aaagaggcct cagcaggcct ggaagaccct tccagtacat cccacagcgt   6840

gtcgagcagc tgggagaacc tgtgtcaagc tcgagccgtc ataggtcccc atgaggtgtc   6900

tgaagcccct tcttggtgat gggaggcaga ggtgctgacg ttctggagca tggacgtgag   6960

tcctcagctg gctccgcgtg ggcccttgga gggtgccagg tgtgtggtga ccttctggat   7020

gcctttaact tcatggctgc gtcattcctg atttagaact ttaaccggag cttcatctag   7080

tgattgcaaa actggaccaa tgggaggacg gcggcgcagc ccgctccctc cgtggaatgg   7140

agctcagctc ttcggaggca tcaaagcacc tgtcgcctcc gtggtccccc tgctgaggga   7200

gtgcggcctc tgcaaggttc gggggtggct tcgtttgcct ggagtggccg gccctgcttg   7260

tgccatgtgg atgtttgtga gcctcggtcc tacagcactg tgtaggctgc atctgtttcg   7320

tgctggtcct gttgacttgt atgatatcca caaataaata ttttcatggc ggtcgtgttg   7380

aaaaaaaaaa                                                          7390
```

<210> SEQ ID NO 8
<211> LENGTH: 949
<212> TYPE: DNA
<213> ORGANISM: Homo sapiens

<400> SEQUENCE: 8

```
ggaaggggcg gggcgaacgg aagccgggaa ggcgattcat agctcgcggg gtacgggcgc     60

gcgtgcgcac tccgcagccc gttcaggacc ccggcgcggg cagggcgccc acgagctggc    120

tggctgcttg cacccacatc cttctttctc tgggacctgg ggtcgcggtt acttgggctg    180

gccggcgaac ccttgagtgg cctggcgggg agcgggcctc gcgcgcctgg agggccctgt    240

ggaacgaaga gaggcacaca gcatggcaga aaaccgagag ccccgcggtg ctgtggaggc    300

tgaactggat ccagtggaat acacccttag gaaaaggctt cccagccgcc tgccccggag    360

acccaatgac atttatgtca acatgaagac ggactttaag gcccagctgg cccgctgcca    420

gaagctgctg gacggagggg cccggggtca gaacgcgtgc tctgagatct acattcacgg    480

cttgggcctg gccatcaacc gcgccatcaa catcgcgctg cagctgcagg cgggcagctt    540

cgggtccttg caggtggctg ccaatacctc caccgtggag cttgttgatg agctggagcc    600

agagaccgac acacgggagc cactgactcg gatccgcaac aactcagcca tccacatccg    660

agtcttcagg gtcacaccca agtaattgaa aagacactcc tccacttatc ccctccgtga    720

tatggctctt cgcatgctga gtactggacc tcggaccaga gccatgtaag aaaaggcctg    780

ttccctggaa gcccaaagga ctctgcattg agggtggggg taattgtctc ttggtgggcc    840

cagttagtgg gccttcctga gtgtgtgtat gcggtctgta actattgcca tataaataaa    900

aaatcctgtt gcactagtgt cctgccatcc caaaaaaaaa aaaaaaaaa               949
```

<210> SEQ ID NO 9
<211> LENGTH: 510
<212> TYPE: DNA
<213> ORGANISM: Homo sapiens

<400> SEQUENCE: 9

```
tgaggctgcc ttataaagca ccaagaggct gccagtggga cattttctcg gccctgccag     60

cccccaggag gaaggtgggt ctgaatctag caccatgacg gaactagaga cagccatggg    120
```

```
catgatcata gacgtctttt cccgatattc gggcagcgag ggcagcacgc agaccctgac    180

caagggggag ctcaaggtgc tgatggagaa ggagctacca ggcttcctgc agagtggaaa    240

agacaaggat gccgtggata aattgctcaa ggacctggac gccaatggag atgcccaggt    300

ggacttcagt gagttcatcg tgttcgtggc tgcaatcacg tctgcctgtc acaagtactt    360

tgagaaggca ggactcaaat gatgccctgg agatgtcaca gattcctggc agagccatgg    420

tcccaggctt cccaaaagtg tttgttggca attattcccc taggctgagc ctgctcatgt    480

acctctgatt aataaatgct tatgaaatga                                     510
```

```
<210> SEQ ID NO 10
<211> LENGTH: 1646
<212> TYPE: DNA
<213> ORGANISM: Homo sapiens

<400> SEQUENCE: 10

ggcggggcca ggagagaaag ctttgtggtt tggtctcagg gaagtagcag gcgccggttg     60

agagaactac ggccctgtcg gaaggtaacc tccggtgcaa acgaccatcg gcggcaggcg    120

agcggtacgc ttggcgtccg ggccttcctg ggcccgtctg aggaaacttg ctgctcgagg    180

ccaggctgcc taggacctgt ccctttttc tatactggct cccacatccg ggtttttct    240

ccgggacggc ccttcggatg cttgggccaa tgggaatcgc catttagggt gctccgccca    300

ccgggtcgcg tagagcatcc tggaagtcgt agtaaatctc tcgagagttc tctccgcacg    360

cgggctggag aagcgggtcc tacgcacgct ttgttgtcgc gctttgcctc cgtccttgcc    420

cctactcccg ccttacctga cttccttttc ggaggaagat ccttgagcag ccgacgttgg    480

gacaaaggat ttggagaaac ccagggctaa agtcacgttt ttcctccttt aagacttacc    540

tcaacacttc actccatggc agttcccgag acccgcccta accacactat ttatatcaac    600

aacctcaatg agaagatcaa gaaggatgag ctaaaaaagt ccctgtacgc catcttctcc    660

cagtttggcc agatcctgga tatcctggta tcacggagcc tgaagatgag ggccaggcc    720

tttgtcatct tcaaggaggt cagcagcgcc accaacgccc tgcgctccat gcagggtttc    780

cctttctatg acaaacctat gcgtatccag tatgccaaga ccgactcaga tatcattgcc    840

aagatgaaag gcaccttcgt ggagcgggac cgcaagcggg agaagaggaa gcccaagagc    900

caggagaccc cggccaccaa gaaggctgtg caaggcgggg gagccacccc cgtggtgggg    960

gctgtccagg ggcctgtccc gggcatgccg ccgatgactc aggcgccccg cattatgcac   1020

cacatgccgg gccagccgcc ctacatgccg cccccctggta tgatcccccc gccaggcctt   1080

gcacctggcc agatcccacc aggggccatg cccccgcagc agcttatgcc aggacagatg   1140

ccccctgccc agcctctttc tgagaatcca ccgaatcaca tcttgttcct caccaacctg   1200

ccagaggaga ccaacgagct catgctgtcc atgcttttca atcagttccc tggcttcaag   1260

gaggtccgtc tggtacccgg gcggcatgac atcgccttcg tggagtttga caatgaggta   1320

caggcagggg cagctcgcga tgccctgcag ggctttaaga tcacgcagaa caacgccatg   1380

aagatctcct ttgccaagaa gtagcacctt ttccccccat gcctgcccct tcccctgttc   1440

tggggccacc cctttccccc ttggctcagc cccctgaagg taagtccccc cttgggggcc   1500

ttcttggagc cgtgtgtgag tgagtggtcg ccacacagca ttgtacccag agtctgtccc   1560

cagacattgc acctggcgct gttaggccgg aattaaagtg gcttttttgag gtttggtttt   1620

tcacaatcaa aaaaaaaaaa aaaaaa                                        1646
```

<210> SEQ ID NO 11
<211> LENGTH: 2813
<212> TYPE: DNA
<213> ORGANISM: Homo sapiens

<400> SEQUENCE: 11

```
ctccacgcta gcgccgccca ggctggcaca aaggaggaag cctagtcccg cccctgcgtg     60

cggcgcttct cccaggcccc accttccatc cagtgccctg gaccctcggc tgggtagcgc    120

caccagagcg accaaacgtc ccgcgccttc caggccgcac tccagagcca aaagagctcc    180

atggcggcgg cggccaagcc caacaacctt tccctggtgg tgcacggacc gggggacttg    240

cgcctggaga actatcctat ccctgaacca ggcccaaatg aggtcttgct gaggatgcat    300

tctgttggaa tctgtggctc agatgtccac tactgggagt atggtcgaat tgggaatttt    360

attgtgaaaa agcccatggt gctgggacat gaagcttcgg gaacagtcga aaaagtggga    420

tcatcggtaa agcacctaaa accaggtgat cgtgttgcca tcgagcctgg tgctccccga    480

gaaaatgatg aattctgcaa gatgggccga tacaatctgt caccttccat cttcttctgt    540

gccacgcccc ccgatgacgg gaacctctgc cggttctata agcacaatgc agccttttgt    600

tacaagcttc ctgacaatgt cacctttgag gaaggcgccc tgatcgagcc actttctgtg    660

gggatccatg cctgcaggag aggcggagtt accctgggac acaaggtcct tgtgtgtgga    720

gctgggccaa tcgggatggt cactttgctc gtggccaaag caatgggagc agctcaagta    780

gtggtgactg atctgtctgc tacccgattg tccaaagcca aggagattgg ggctgattta    840

gtcctccaga tctccaagga gagccctcag gaaatcgcca ggaaagtaga aggtcagctg    900

gggtgcaagc cggaagtcac catcgagtgc acgggggcag aggcctccat ccaggcgggc    960

atctacgcca ctcgctctgg tgggaacctc gtgcttgtgg ggctgggctc tgagatgacc   1020

accgtacccc tactgcatgc agccatccgg gaggtggata tcaagggcgt gtttcgatac   1080

tgcaacacgt ggccagtggc gatttcgatg cttgcgtcca agtctgtgaa tgtaaaaccc   1140

ctcgtcaccc ataggtttcc tctggagaaa gctctggagg cctttgaaac atttaaaaag   1200

ggattggggt tgaaaatcat gctcaagtgt gaccccagtg accagaatcc ctgatgttaa   1260

tgggctctgc cctcatcccc acagtcttgg gatctcaggg cacaatggct ggacatgggt   1320

gggctctgat gcagaacttt ctcttttgaa tgttaagaat aactaataca attcattgtg   1380

aacagaagtc cttaagcaga ggaattggtg tgccttaaag atacaatctg ggatagtttg   1440

ggggaacttg tagccagaat gccctgttca tgctgagcaa agttcagcaa gtagagcaga   1500

gtttggcagg caggtgccag gaactcccct tcttcctgga gtgccttcat tgaggaagga   1560

aatctggccc ttgggtttcc tggttccact gctactgacc cagaggggaa tgagggctga   1620

gttatgaaaa gataacttca tgaagactta actggcccag aagctgattt tcatgaaaat   1680

ctgccactca gggtctggga tgaaggcttg tcagcacttc cagtttagaa cgcaatgttt   1740

ctagagacat attggctgtt tgttttgatg ataaaaggag aataagaaaa ggcatcactt   1800

tcctggatcc aggataattt ttaaaccaat caaatgaaaa aaacaaacaa acaaaaaagg   1860

aaatgtcatg tgaggttaaa ccagtttgca ttcccctaat gtggaaaaag taagaggact   1920

actcagcact gtttgaagat tgcctcttct acagcttctg agaattgtgt tatttcactt   1980

gccaagtgaa ggacccctc cccaacatgc cccagcccac ccctaagcat ggtcccttgt    2040

caccaggcaa ccaggaaact gctacttgtg gacctcacca gagaccagga gggtttggtt   2100

agctcacagg acttccccca ccccagaaga ttagcatccc atactagact catactcaac   2160
```

```
tcaactaggc tcatactcaa ttgatggtta ttagacaatt ccatttcttt ctggttatta   2220

taaacagaaa atctttcctc ttctcattac cagtaaaggc tcttggtatc tttctgttgg   2280

aatgatttct atgaacttgt cttattttaa tggtgggttt tttttctggt aagatttaga   2340

cctaaatcgc atcatgccaa cttgtgactt tgagactatt catcaagaat gaggatatag   2400

tagccatgac atagcttgag ctatagcctt taattcctta ctttggctat gggtggaggg   2460

tgagtttgaa gaggttctga ttttcttgta acctgggaaa gccatgacct tgtgcccgat   2520

tctttcagat tgctttgggt aataaatatt ggtggtggta tctgactcat gctgctgttt   2580

atggtcctgt ttagtgggga atggactcag gttacccatt tcccagaggg aaggatccca   2640

ggatttttga aggttacata ttttctgtac caaatataat ttcattgaca tgaattatct   2700

ctaatcctca tgacaagcca catacacaat cattttgtag ataaagaaga tataaatgcc   2760

agaggagacc ttaagattgt cttacaacac aacccttcag ttaacgagag agg           2813
```

<210> SEQ ID NO 12
<211> LENGTH: 1296
<212> TYPE: DNA
<213> ORGANISM: Homo sapiens

<400> SEQUENCE: 12

```
tccgggggag cggaactgca agaggaaagg ctcgggtagg cttctgggag cgaccgctcc     60

gctcgtctcg ttggttccgg aggtcgctgc ggcggtggga aatgctggcg cgcgcggcgc    120

ggggcactgg ggcccttttg ctgaggggct ctctactggc ttctggccgc gctccgcgcc    180

gcgcctcctc tggattgccc cgaaacaccg tggtactgtt cgtgccgcag caggaggcct    240

gggtggtgga gcgaatgggc cgattccacc ggatcctgga gcctggtttg aacatcctca    300

tccctgtgtt agaccggatc cgatatgtgc agagtctcaa ggaaattgtc atcaacgtgc    360

ctgagcagtc ggctgtgact ctcgacaatg taactctgca aatcgatgga gtcctttacc    420

tgcgcatcat ggacccttac aaggcaagct acggtgtgga ggaccctgag tatgccgtca    480

cccagctagc tcaaacaacc atgagatcag agctcggcaa actctctctg gacaaagtct    540

tccgggtgga ggcagagcgg cggaaacggg ccacagttct agagtctgag gggacccgag    600

agtcggccat caatgtggca gaagggaaga aacaggccca gatcctggcc tccgaagcag    660

aaaaggctga acagataaat caggcagcag gagaggccag tgcagttctg gcgaaggcca    720

aggctaaagc tgaagctatt cgaatcctgg ctgcagctct gacacaacat aatggagatg    780

cagcagcttc actgactgtg gccgagcagt atgtcagcgc gttctccaaa ctggccaagg    840

actccaacac tatcctactg ccctccaacc ctggcgatgt caccagcatg gtggctcagg    900

ccatgggtgt atatggagcc ctcaccaaag ccccagtgcc agggactcca gactcactct    960

ccagtgggag cagcagagat gtccagggta cagatgcaag tcttgatgag gaacttgatc   1020

gagtcaagat gagttagtgg agctgggctt ggccagggag tctgggaaca aggaagcaga   1080

ttttcctgat tctggctcta gcttccctgc caagattttg gtttttattt ttttatttga   1140

actttagtcg tgtaataaac tcaccagtgg caaaccagaa actgtcctct ttgattgggg   1200

aatgaagttg ggaaagtcac tagcattttc cttggatcca gtcctgtcag catgatgcct   1260

ccatgaataa gagtgaactt cttgtaaagt gaaact                             1296
```

<210> SEQ ID NO 13
<211> LENGTH: 6738
<212> TYPE: DNA
<213> ORGANISM: Homo sapiens

<400> SEQUENCE: 13

```
ctgcagacga ggcaggcgga agaggcggga cttcgcgggt gacgtcatcg gggcgccgga     60
ggcccggggc gcctgggaat ttgaagcaaa caggcagcgc gcgacaatgg cggtcgctcg    120
tgcagctttg gggccattgg tgacgggtct gtacgacgtg caggctttca agtttgggga    180
cttcgtgctg aagagcgggc tttcctcccc catctacatc gatctgcggg gcatcgtgtc    240
tcgaccgcgt cttctgagtc aggttgcaga tattttattc caaactgccc aaaatgcagg    300
catcagtttt gacaccgtgt gtggagtgcc ttatacagct ttgccattgg ctacagttat    360
ctgttcaacc aatcaaattc caatgcttat tagaaggaaa gaaacaaagg attatggaac    420
taagcgtctt gtagaaggaa ctattaatcc aggagaaacc tgtttaatca ttgaagatgt    480
tgtcaccagt ggatctagtg ttttggaaac tgttgaggtt cttcagaagg agggcttgaa    540
ggtcactgat gccatagtgc tgttggacag agagcaggga ggcaaggaca agttgcaggc    600
gcacgggatc cgcctccact cagtgtgtac attgtccaaa atgctggaga ttctcgagca    660
gcagaaaaaa gttgatgctg agacagttgg gagagtgaag aggtttattc aggagaatgt    720
ctttgtggca gcgaatcata atggttctcc cctttctata aaggaagcac ccaaagaact    780
cagcttcggt gcacgtgcag agctgcccag gatccaccca gttgcatcga agcttctcag    840
gcttatgcaa aagaaggaga ccaatctgtg tctatctgct gatgtttcac tggccagaga    900
gctgttgcag ctagcagatg ctttaggacc tagtatctgc atgctgaaga ctcatgtaga    960
tattttgaat gattttactc tggatgtgat gaaggagttg ataactctgg caaaatgcca   1020
tgagttcttg atatttgaag accggaagtt tgcagatata ggaaacacag tgaaaaagca   1080
gtatgaagga ggtatcttta aaatagcttc ctgggcagat ctagtaaatg ctcacgtggt   1140
gccaggctca ggagttgtga aaggcctgca agaagtgggc ctgcctttgc atcgggggtg   1200
cctccttatt gcggaaatga gctccaccgg ctccctggcc actggggact acactagagc   1260
agcggttaga atggctgagg agcactctga atttgttgtt ggttttattt ctggctcccg   1320
agtaagcatg aaaccagaat ttcttcactt gactccagga gttcagttgg aagcaggagg   1380
agataatctt ggccaacagt acaatagccc acaagaagtt attggcaaac gaggttccga   1440
tatcatcatt gtaggtcgtg gcataatctc agcagctgat cgtctggaag cagcagagat   1500
gtacagaaaa gctgcttggg aagcgtattt gagtagactt ggtgtttgag tgcttcagat   1560
acatttttca gatacaatgt gaagacattg aagatatgtg gtcctcctga aagtcactgg   1620
ctggaaataa tccaattatt cctgcttgga ttcttccaca gggcctgtgt aagaatgggt   1680
tctggagttc tcatggtctt taggaaatat tgagtaattt gtaatcaccg cattgatact   1740
ataataagtt cattcttaag cttgcttttt ttgagactgg tgtttgttag acagccacag   1800
tcctgtctgg gttagggtct tccacatttg aggatccttc ctatctctcc atgggactag   1860
actgctttgt tattctattt attttttaat ttttttcgag acaggatctc actctgttgc   1920
ccaggatgga gtgcagtggt gagatcacgg ctcattgcag cctcgacctc ccaggtgatc   1980
ctcccacctc agcttccaga ttagctggtg ctataggcat gcaccaccac gtccatctaa   2040
atttctttat tatttgtaga gatgaggtct tgccatgtta cccaggctgg tctcaactcc   2100
tgggctcaag cgatcctcct gcctcagtct ctcaaagtgc tgggattaca ggtgtgagcc   2160
actgtgccca gcctaattgc agtaagacaa aaattctagg gcaccaagag gctaaagtca   2220
gcacagcttt tcttgtgtcc tgtattctct gtctaatgtg ttgcccaaat aatacctaat   2280
```

```
tgttagccat tcccctccat ctctggccta aaagtgatag tccaggtatc cacatgggct   2340
ggttcccaga actgccattg ctcactctcc aaagagggga aggtggggaa ggggaaggtg   2400
actatagctc agctcctgag ctagtatctg gctgttattt caacaaccgg agttggggtt   2460
tgggctcatt ttttccccta gccagcaatt atggaccagt agtaacacaa gtgacagctt   2520
cctgtgactg acttcacaat taggaggtct aagattccat ttgggtattt gcttaaggat   2580
cccacataat tgtcccaacg gtcattagta gaggggaggt aagccttcat taataataaa   2640
gagaaagccc acattcaagg tggtgtttga gcaggggcag ggtgagggct gtcccggtgc   2700
tcattgcacc agcacactca cattccttct catttggggc ccacctgcag gaagtggcac   2760
aggatcagcc atttccccac ccttgtcagc tgatggccca ctgttcttta atgactcaga   2820
ggaatgccta ggattttttt ttttttttga gacagaatct cactgtcgcc caggctggag   2880
ttcagtggca cgatctcggc tcactgcaac ttctgcctct ctggttcaag cagttctcct   2940
gcctcagcct cccgagtagc tgggactaca agcctaggat ttttaactca ggtttttatt   3000
atattccctc ctgaagtttt tacttcaaga gcttctgctc taaagtccaa tttgggcttc   3060
atgtccccag tgctgcatct ccagggaaat gctgtctgtg ggagagacca actctcaagg   3120
aagaagtggc cacagaagga gcaggaaggg agttggccct cagggctact ctggggaagc   3180
caaaagtcat gaaggggaga agaattttct gacaaaaact tgcaggaatc tcttaggtgt   3240
cttcagtgtt ggagtgatat gttgagaggc ctttggagtg atgtgctgag gtctcaggcg   3300
cccacctccc tggctgtcac ttccatgtgt cagtggttct cccactttag caggtatcag   3360
agtcacctgg agtcttgtca aaacaggtac cagccccacc cgcagcgttt ctgactctgg   3420
gtagctctgg gatggggctt gagaatttgc gtttccaaaa aggtcccagg tgatgctgcg   3480
gttgcctgcg cagggactgg actttgagaa ccacttcact ggttattcac atttctgcct   3540
ctgcagtgag acagccttga ggtctgcctc ctgctaagag tcacatgctc ctgtccttta   3600
gaaatgtggg ctcctgccat ctccaggacg caggcactgt tcctgttgat gaaccctatt   3660
tcacaggacc cctgctaagg tgatttgagg ggaaatgaga ggaggctcaa ataatcaccc   3720
agcccctgcc acttactgaa agtgtaggtc cttgtgcccc acaccatcag agtttctgcg   3780
ttagcagatt tgtggtttgc ccagcagcct gggcgtgtgc atttctaatg ggtgcctcaa   3840
gtgatctgtt tctgatttgt atttctattg tgaagagtca gcccagtact gcaggcctct   3900
tacctaagca gaatcccagt ctggcatcaa agctttagag gacaagttga ttcaggcaga   3960
gaagaacttg ggctatacaa gcgctgttct tcagcattga agtattttgg aggcattaga   4020
tagtttaacc ctttctcagt caaggaatat ttacagaaca tgatctctgg gcattgtaac   4080
tcctggtctt agtggggaat atagggaccc catgtctcca tggggtgcac agaatgtctg   4140
tgagactgat ggagtggaga acgccatccc ccagcctctc cagctactcg aggcattctg   4200
tagaacataa gcccatagat tgtgtgtgtg tgtgtgtgtg tgtgtgtgtg tgtgtgtgtg   4260
tgcatgcgcg cgcgtgcgca ctggaggaac ctaagaaact atttggtgca cttcctctta   4320
ttttagagct cccaaagtgt agctccagaa tcgtaaaggg atatgctcag tctcacagcc   4380
agcctgtgga tctcagtccc aacactcacc cttgtgctac tgagtcagct ctaagaaaat   4440
ctgccaaaag taggccgagg gctggttttt tgttttgttt tgtttgtttg atacagggtc   4500
ttcactctgt tgcccaggct ggagtatatc atggctcact gcaaccttga cttgggctca   4560
agcgatccgc tcaagtagct ggaactactc tcaagtagct ctcaagagcc tctcgagtgg   4620
ctggaactac aggcgtgcac caccacagct ggttaatttt taaaattttt tgtagagacg   4680
```

```
gtggaggagg ttctcactgt gactcagtgt gtgcccgaca gcagagccca caccactcca   4740
gttgcagtgg ttgccatctg ggtcatcaga cctggctgtc aggggtgcag ccacaggaga   4800
gccaacagca gagggtgctg gccgctgagc tagctgctaa tgctggcctg ggtgcagttc   4860
tcatccaaag tacccggtgg gtgggagtca ctcagtacca gttccgagcc tgaacccaaa   4920
ctctcgtgtt tctgctcacc cctctctggc ttctgccacc acatgggaag aatatgccct   4980
ggttagccca tggcttctga agagcaagag aaagtagagc agagcctact ccagcctccc   5040
ccgtccaatg tatgaaagcc ccagctgatc tgtaagcctg ggagcgtgat aaatgcttag   5100
tagtgcatgc catggagttc cagggtggtt tattacacgg caatatctag ctaaatacat   5160
ttaacttgct gcagctctct ggatccagcc tggttaccag gaagacaaaa actgggctcc   5220
accaggaacc agtcttctgc cttcccaacc atcacctctg gctgcatcag cgatctctcc   5280
cagcgaaata gctgcttggt cttgtgtgaa tcctgtactt taacacagtg gaccaagtgt   5340
cagtcattga aaatgaccat gagtaaccct gtggactctc tgcagcttgg ttcctttgcc   5400
ccttaacagg tgggtatgaa tcgtgtcttc agtgccaggg ctgaatgaga aagggcattc   5460
ctttttgaag gaatctgata ctaaacacaa agcatgagaa aaatcaggac ttgttggagt   5520
tatattttta aaatatatat tttaacagtt atatatatta gatataatat ataatagtat   5580
atataaataa tactatattg cccaggctgg tctcgaactc cttagctcaa gtgatcctcc   5640
tgccttggct tcccaaagtg ctaggattac aggtgtgagc cactgctccc ggcctgttgg   5700
agttctttac atttatttta taatcaatgc tgttttatta aatgcggatt ttattttgga   5760
ttacaggatg tagaatgcca tatttttctt agatcatagg gcctttcaca tttgtaattt   5820
ggccttgtat gagttaccct gcaatccctt tgttttcccc ataacccttc caaaggaagg   5880
ccgcaataga aatacaaaga gaaacaaaat aattagaata ttttttaact tctaaagttc   5940
aaggttttgg cataagtctg gtttagaagc acatttgcct agccctttcc ttcccaccaa   6000
gggggaaagt cttcctctag acaagaggca gagggctcct cagagtcaga tcctggtgtg   6060
ggctctcacg tgctgctgct gaatcccagg gaaggaggga ggaagggcag ttgacaccca   6120
aaataagggt ggggaactgt cagcagagga ggtctgtgtc atgtttttca gcgctggggt   6180
tggggggagc ccaggagagc aggaagatcc agagatccct cgccccagct cggccatgtg   6240
tgtctgggac agagcctgag gtggcctgag cttcctgtgg ctccagagta acattataga   6300
gaagctgaat tctcctgttt ttctgaaaag ggcatgggag ttagctgaga agcagacctg   6360
gtgggcctga gagtctcaat cgtcaggtaa ggacagtcag tgggaagtgg acgggccgca   6420
caaccaaggt tctcatgagg acaaccatgt cttcgggggt gcccttgtgc acagacagct   6480
ccatagtcct gcctccaatg tcccaacact gcattgtctc cctgcactta gcagccctgc   6540
agggtgagac ttggggagga tcctgaaatg attgtattta acaagacatg ctgtccttgt   6600
ttacctggaa cctagcaatg ttgttttctg ccacaacttg aatagatact tgaagcagag   6660
atgatgttga gttaaaaaaa atatatacat aaaaatatgg gttcttttca acctgaatag   6720
atggcctaaa aattcaaa                                                 6738
```

<210> SEQ ID NO 14
<211> LENGTH: 1779
<212> TYPE: DNA
<213> ORGANISM: Homo sapiens

<400> SEQUENCE: 14

```
cggcgtgccc tggggcggcg cgggcgcagg ggcgcgtgcg cggcgggctg tcgttggctg     60
gagcagcggc tgcgcgggtc gcggtgctgt gaggtctgcg ggcgctggca aatccggccc    120
aggatgtaga gctggcagtg cctgacggcg cgtctgacgc ggagttgggt ggggtagaga    180
gtagggggcg gtagtcgggg gtggtgggag aaggaggagg cggcgaatca cttataaatg    240
gcgccgaagc aggacccgaa gcctaaattc caggaggttg ggatgaatgg gttccggaga    300
gcagagtact caaatacgtg gacaccaatt tgcagaaaca gcgagaactt caaaaagcca    360
atcaggagca gtatgcagag gggaagatga gaggggctgc cccaggaaag aagacatctg    420
gtctgcaaca gaaaaatgtt gaagtgaaaa cgaaaaagaa caaacagaaa acacctggaa    480
atggagatgg tggcagtacc agtgagaccc ctcagcctcc tcggaagaaa agggcccggg    540
tagatcctac tgttgaaaat gaggaaacat tcatgaacag agttgaagtt aaagtaaaga    600
ttcctgaaga gctaaaaccg tggcttgttg atgactggga cttaattacc aggcaaaaac    660
agctctttta tcttcctgcc aagaagaatg tggattccat tcttgaggat tatgcaaatt    720
acaagaaatc tcgtggaaac acagataata aggagtatgc ggttaatgaa gttgtggcag    780
ggataaaaga atacttcaac gtaatgttgg gtacccagct actctataaa tttgagagac    840
cacagtatgc tgaaattctt gcagatcatc ccgatgcacc catgtcccag gtgtatggag    900
cgccacatct cctgagatta tttgtacgaa ttggagcaat gttggcttat acacctctgg    960
atgagaagag ccttgcttta ttactcaatt atcttcacga tttcctaaag tacctggcaa   1020
agaattctgc aactttgttc agtgccagcg attatgaagt ggctcctcct gagtaccatc   1080
ggaaagctgt gtgagaggca ctctcactca cttatgtttg gatctccgta aacacatttt   1140
tgttcttagt ctatctcttg tacaaacgat gtgctttgaa gatgttagtg tataacaatt   1200
gatgtttgtt ttctgtttga ttttaaacag agaaaaaata aaagggggta atagctcctt   1260
ttttcttctt tctttttttt tttcatttca aaattgctgc cagtgttttc aatgatggac   1320
aacagaggga tatgctgtag agtgttttat tgcctagttg acaaagctgc ttttgaatgc   1380
tggtggttct attcctttga cactacgcac ttttataata catgttaatg ctatatgaca   1440
aaatgctctg attcctagtg ccaaaggttc aattcagtgt atataactga acacactcat   1500
ccatttgtgc ttttgttttt ttttatggtg cttaaagtaa agagcccatc ctttgcaagt   1560
catccatgtt gttacttagg cattttatct tggctcaaat tgttgaagaa tggtggcttg   1620
tttcatggtt tttgtatttg tgtctaatgc acgttttaac atgatagacg caatgcattg   1680
tgtagctagt tttctggaaa agtcaatctt ttaggaattg tttttcagat cttcaataaa   1740
tttttttcttt aaatttcaaa gaacaaaaaa aaaaaaaaa                          1779
```

<210> SEQ ID NO 15
<211> LENGTH: 7827
<212> TYPE: DNA
<213> ORGANISM: Homo sapiens

<400> SEQUENCE: 15

```
gtagtcttga cgtgagctag ctggcatggc ggcctgcatt gcagcggggc actgggctgc     60
aatgggccta ggccggagtt tccaagccgc caggactctg ctccccccgc cggcctctat    120
cgcctgcagg gtccacgcgg ggcctgtccg gcagcagagc actgggcctt ccgagcccgg    180
tgcgttccaa ccgccgccga aaccggtcat cgtggacaag caccgccccg tggaaccgga    240
acgcaggttc ttgagtcctg aattcattcc tcgaagggga agaacagatc ctctgaaatt    300
tcaaatagaa agaaaagata tgttagaaag gagaaaagta ctccacattc cagagttcta    360
```

```
tgttggaagt attcttcgtg ttactacagc tgacccatat gccagtggaa aaatcagcca    420
gtttctgggg atttgcattc agagatcagg aagaggactt ggagctactt tcatccttag    480
gaatgttatc gaaggacaag gtgtcgagat ttgctttgaa ctttataatc ctcgggtcca    540
ggagattcag gtggtcaaat tagagaaacg gctggatgat agcttgctat acttacgaga    600
tgcccttcct gaatatagca cttttgatgt gaatatgaag ccagtagtac aagagcctaa    660
ccaaaaagtt cctgttaatg agctgaaagt aaaaatgaag cctaagccct ggtctaaacg    720
ctgggaacgt ccaaatttta atattaaagg aatcagattt gatctttgtt taactgaaca    780
gcaaatgaaa gaagctcaga agtggaatca gccatggctt gaatttgata tgatgaggga    840
atatgatact tcaaaaattg aagctgcaat atggaaggaa attgaagcgt cgaaaaggtc    900
ttgattctga gaatgaattt ggttagttgc agaagataca ttggctctaa gaggatatat    960
tttgagacca atttaatttc atttataaga acatagtaat taagtgaact aagcattcat   1020
tgttttatta atactttttt tctaaaataa aacttgtaca ccagtttatt actctaaaaa   1080
gagaattaca catgccaaat ggaccaatgt ccatttgctt attggaggca aagctacaat   1140
agaagtcaga gcatcaccag aatggtcttt aatgagcatg gaacctgagc aaagggaata   1200
ggtgggatga attttttttt taattgtgaa acaattcata agcacaatat gatttacaga   1260
ataataaaca ttcatgtacc cactatcagg ttaagaaata gaacatttat taatatgtag   1320
gaatgttaag aaataaaaca tttaataaga tctcagaaga ctccagtaaa tctgcaattg   1380
tatctctctc ctttttaaat gtaaatatca tcttgacttg ttaattattc ccttgcattt   1440
cttttagttt actgccaaca catatattct tcaacaatat atttaatttt gaaaaacctg   1500
aaaaaaaaaa cctgttagca agtataaagg ggcagtatta ctattattgc atgaaggctt   1560
caagggaaac gttacagtct ttgggtcata gtctggcttc agcttcctct gagagtttac   1620
agaggccaat tttgagcaaa ttcatggcta aggttatgag tgagttctgc taaacagaag   1680
gctcaccaca aggtatctgg caggattata ctgggtagct ggatgttgca gaaatgtggt   1740
tagaggaagt aaactgtttt ttgatgctca cagcatgatg aatcaaactc tgtatcttag   1800
gattaggtta aaacaatacc tttggtatga tatgagtgtt gttgctgatc catgcagcat   1860
ggattggaaa gctggggtat aagcacacat gctaaagaaa aacatgtaat ttggtccata   1920
ctcacctgga tatactgttc ctcaggttaa aaaatacagt actatcctaa atcttgaagg   1980
caactctcag cctatccatt gagttacctt cagatctgcc ctctggttcc tagctgtctt   2040
gggactaact tctttcctgc gctcagctgt tttctggatt ccatgttttc cattttattg   2100
agtactaact tgttttgctg cagcacatcc tttggtagct tctagaggaa gtttgtgtgg   2160
aggtaaaatt tttgagacct tgcatgtctc atgtttgatt gatactttat acgtttaggt   2220
aggaggtaat tttccttcag gactttaaaa atattgttgc tccattttct ttgtttctat   2280
tgttgtattg agaaatccaa tgccattttg atttccccat cataaatttc atgatgatgt   2340
gtcttggtgt gggtctatat ttatccattg tattgggttt taggtgaacc cttccagata   2400
gtaactcatt tctgtcagtt ctgggaaaca cttagcattg gttgatgatt tattctctgc   2460
tgctttgttc tcccaactat tatttggatg ttggatatcc agcactgggt atctattttc   2520
ttacctccct cccttgaccc cagtctctgt tttttagctc tttagctcaa tcttccaact   2580
ctttgctatt gtattttaaa atcttaagac cccttcttga tttgtagaag ttccttttct   2640
tacaaccaaa aagcctttat ctatggattt gttcacagat aaggggtatt caatatagtg   2700
```

```
tattttttt tcatttaaaa ttgtttgcgc atctatttcc tccaaatttc tttctgtatt   2760
tattttttgt tgtctatatt tcagactttt ccaggatatc tgataatctt tggctgtctt   2820
cttatggttg aaagagggac taaaaagctt ggaaagcctt tgggttgtgg gaaggggctg   2880
tctttaggat tatctgaatg ggctttttg ggagtcccct cctccacatg aatattttgg   2940
ttttgtcaga ttccctagaa tagaggcttc caatctcctt cctggagggg tctgtccagg   3000
aaggagattg tctaggggtc tgtcagacag cagctttcag ctacttcctt gatctttttc   3060
actaatgatt atatagtcat ctaactactg tcaacaagta atagatatcc tatccttcac   3120
ttgtttagat tatttgctga gataacctct caaaagaacc tctcaaaata aaaggttaac   3180
aagagcctat atcttatatt tttcttctct ttatcttgtt agaagatagc tattaaaacc   3240
tgttcttttt ctgtcttgat aaacacactt caatcttggt agaatggtag atgggacagt   3300
atattttagg acctaaagct ctgcaaatgt atgatcagct tgtaagtaca ggtgctcaaa   3360
aacatgtaaa caatcatgct ttttactctg taggaatatc tttaaaattc ttgtgaattt   3420
ttccccagaa gtaaagcaaa tcttccccca gaaataaaat taaatgtgca taatctaaag   3480
cttttttttt ttattgtggt aggatatata tataaaacat aatttgccat tgtaaacatt   3540
ttaaatttac aagtcagagg cattaattac atcacaatgt tgtgaaatta ttactactat   3600
ttccaaaatt ttctcatcac cccaaactga aactctgtaa ctgttgagca ataacctcat   3660
tcctgtatct ctcccaaccc caggtaacct caaatctttc tttttatctt tgagacaagg   3720
tctcattcta tcactcaggt aggagtgcag tggtgtgatc atagctcatt gcagcctcaa   3780
aatcctgggc tcaagcaatc ctccttgagt agctaagact ataggcacac attaactgcg   3840
cctggctgat tttgtttttt gtagagatgt ggtcttgcta tgtttcccat gctggtcttg   3900
agttcctggc ctcaagcagt ccttaagatt catccatgtt gtggcatgtg tcagaatttc   3960
atttgttttt atgactaaat aatattccat tgtatgtata tacattttgt tcatccatct   4020
tctgatgaac actgggatat gtctaccttt tggctattgt gaataatgct gcagtaaaca   4080
ttgacataac aagtatgtat ttgattgcct gtttctaagt tcttttgggt atacatcttg   4140
agtagaattg ctagataatg tcatgtttta tttctcttgt gatttcttct tcgatcccct   4200
ggttgagtgt gttaatttct acatgtttat gaatttccca ctgttttttt gttattgatt   4260
tccaagttca ttccattgtg attagagaag atacttagta tgattttaat gtttttgaga   4320
attggtgtgt ggcctgatag atggtctgtc ctggagaatg ttcctcatac acttgagcaa   4380
aatatttatc atgctattgt tgactgtagt tttctatatg tctcttaggt caaggtggtt   4440
tacaatgtgt taaggttctc tttttttaaa aaaatttttg cacagagtat ctttttctat   4500
gtgttccatg tatttgtgtc tttggagcta tagtctcttg tagacagcat atcactatct   4560
tgttttgttt tgtttttttct gtccattctg ccaatttctg ccttttgatt ggaaaattta   4620
atccatttgc atttaaagta attaaggaag gactttcttc taccatttaa cacttcttct   4680
atatgtcata tactttttttg gcccctcatt tcctctttat ggccttcttt tctgtttttt   4740
tgtagtgaac tagtctgatt ctctttccac tccccttttgt gtatatttgt tagatgtttt   4800
atttgtggtt gctatgggga ttatagttaa catcctacac ttaaaacaat ctaatttaaa   4860
ctgataccaa tttaccttca atagcataca aaatctctac tcctgtaaag ctctgcccct   4920
gcccccctta tgttattgat ggcacaaatt gcctaataaa taatttatag ttatttgtat   4980
gagtttgtct tttaaatcat ttaggaaata aaaagtggag ttagaaaaca gtatgatagt   5040
aatactgact tttatatttg tcaatatatt tatcttattt tggatcctta tttcattata   5100
```

```
tagatttgag ttactgtcta gtgcccttcc atttcggccc aaaggattcc cttatgcatt   5160
tcttgcaggg caagtctaat tgtaataaac tccctcagct tttgttttat ctgagaatgt   5220
cttgatttct cccttatttt tgatggataa ttttgccaga tacatgaatt tttggtaaca   5280
gtatttttct ttcagcactt taaatatgtc atcccactac cttctgactt catggtttct   5340
catgagatat tagatgttat aaaatttgag gattcctcat tcttgatgag tcagttctgt   5400
cttattgctt ttcggatttg ctcagctttt gtcttttgac agtttgatta taacgcggct   5460
cagtgtgggt ctctgagttt atcccactta gagtttgttg agtttcttgg agtcatagat   5520
ttatgtcttt tatcaaattt tggacatatt tggctattat ttcttcaatt tttttcactg   5580
cttctttctt ttccttctga aatattctta atgtatatgt tggtctgttt gatgctgtct   5640
caccagtttc ttaggctgtg ttctcttttg ttcctcagac ttgattattg cagttgccct   5700
tctttttatt tttttcaagt ttgttgattc ttctccctgt tcagatcaac tgttgaactc   5760
ctctagtgaa tttatttcag ttactgtact tttcagctcc aagatttatc tttggttcct   5820
ttttataacg tctgtgtctt tattgatatt ctcattttgt tcatatgtct ctttcttcct   5880
ttagttcttt gtccatgttt tcctttagct ctttgggctt atttaagaca attgtttaaa   5940
gtctttgcat agtaagtcca atgtctgtgt ttcttcaggg atggttttca ttattttgtt   6000
ttcaatgagc catactttcc tgtgtctttg tatgctgtct ttttgttgtt gaaaactgta   6060
tgtttgaaca tcataacgtg gtggccctga aaatcagata ttcccccctt cctgagagtt   6120
agttttattt ttattattga agattgtagc agtctattgc tacatgtgca gtcatttcca   6180
aactattttt gcaaagactg tattccttct gtgtgtcatc actgaagtct ctgttcctta   6240
gtttgtgttt aatagtttga catagatttc cttgaaagga gttaaaacta gcagaaaaat   6300
ctctctccca gtctttccag tctttgtaga ttggttctgt gctgggcttt tccattaata   6360
cttagccagg cttgtactga gcctaacaat caggcccaaa agcgtagggt ctttgcagat   6420
cttgtctgag catgcttctt gctgtgtatg cacgtagttt tctaaatctc cctgtatgtg   6480
ctgttgaata ttctaatttc ccaaagaaac tcctttgcag ctttttctca cagaacatag   6540
atggtttttt ggatatcttg accatagtct ttcgacccag gtgtttgcgg ttgttagttc   6600
accttacact tttttcaagc attgcctact gcttacgatg agtgctctgt caatccttta   6660
agtagcccca gacaggctac cagagactta aacaagaatt tgtaagttct gctcagcttc   6720
ctctagaaat ggggatcagg gtccaagaca gaatgcagtt gctgatttca agactgctgc   6780
aacaccaggg agcttgtggg ggaagggcaa gcagaaatgt cacaaagctt tcttgccatt   6840
ttaaagttgc ctgttcttga ctcagcattt gcttcattgc tataaacttt ttactgtttt   6900
tcagagttct gataaaattg gctatgcctg ttcctgcttt aaaaaaatata tatatatttt   6960
ttagggattg gggtctcact atactgacca ggctggtctt gaacttctgg cctcaagcca   7020
tcctctcatt tcagcttccc aaagtgctgc aattacacgc gtgaaccacc acacccagcc   7080
cctgcttgtt tttcaatgtg cctactccac catgttgctc aagtatgtat attttctaaa   7140
ctaccttgta gtgttgtgat gggaaataaa tccctgagcc ttttgaataa ctcagagaga   7200
tcaaaaactt agtttatcct attcgaagga ttagaaaaat gatatatctt tcactttttc   7260
agggataggc tcctcattag aaggctccta tgtgccgatg ctgtacaaga catttcattt   7320
ctcttaatgt ttacaacaag cttgttgcca aggctgatct tgaactcctg gcctcaaacg   7380
atcctcccag ctcagtctca caaagtgttg ggatgtctgg ccaactaatg actatcttaa   7440
```

```
ctcttgtgtt tcaatgttta tgccttcttt tatcttgact gattgtatga ctatgtcttc   7500

tagaacaatg ttgaacagaa atggtgagag cagacatcct tgctttaata tttcaccatt   7560

atatatgatg ttaggtatag atttttctca cagatgcctt ttatcagatt gaggaattta   7620

tattcctact ttgccgaaag gtttttgtag tatgaggggg tgctgaattt tgtcaaacac   7680

tttttcggta ataattgaga tgattggttc tgcagtcatc gagatgtgga ttttctcctt   7740

tattctgttc gtgagtgatt acactggttg actaatgtta aaacaacctt actttccagg   7800

aataaaccct attatctttt ttataca                                       7827


<210> SEQ ID NO 16
<211> LENGTH: 1821
<212> TYPE: DNA
<213> ORGANISM: Homo sapiens

<400> SEQUENCE: 16

tgcgggtacg gacagcgcat gagcttatgt tgagggcgga gcccagacca gcccttcgtc     60

ctatcctgcc cttccagcac ctctcagccg taacttaaac tacacttccc agaagcctcc    120

tcagccaggg acttccgttg tcgtcagcgg aagcggtgac agatcatccc aggccacaca    180

gaggccggct tggtcactat ggaggagata ggcatcttgg tggagaaggc tcaggatgag    240

atcccagcac tgtccgtgtc ccggccccag accggcctgt ccttcctggg ccctgagcct    300

gaggacctgg aggacctgta cagccgctac aaggaggagg tgaagcgaat ccaaagcatc    360

ccgctggtca tcggacaatt tctggaggct gtggatcaga atacagccat cgtgggctct    420

accacaggct ccaactatta tgtgcgcatc ctgagcacca tcgatcggga gctgctcaag    480

cccaacgcct cagtggccct ccacaagcac agcaatgcac tggtggacgt gctgcccccc    540

gaagccgaca gcagcatcat gatgctcacc tcagaccaga agccagatgt gatgtacgcg    600

gacatcggag gcatggacat ccagaagcag gaggtgcggg aggccgtgga gctcccgctc    660

acgcatttcg agctctacaa gcagatcggc atcgatcccc cccgaggcgt cctcatgtat    720

ggcccacctg gctgtgggaa gaccatgttg gcaaaggcgg tggcacatca cacaacagct    780

gcattcatcc gggtcgtggg ctcggagttt gtacagaagt atctgggtga gggcccccgc    840

atggtccggg atgtgttccg cctggccaag gagaatgcac ctgccatcat cttcatagac    900

gagattgatg ccatcgccac caagagattc gatgctcaga caggggccga cagggaggtt    960

cagaggatcc tgctggagct gctgaatcag atggatggat ttgatcagaa tgtcaatgtc   1020

aaggtaatca tggccacaaa cagagcagac accctggatc cggccctgct acggccagga   1080

cggctggacc gtaaaattga atttccactt cctgaccgcc gccagaagag attgattttc   1140

tccactatca ctagcaagat gaacctctct gaggaggttg acttggaaga ctatgtggcc   1200

cggccagata agatttcagg agctgatatt aactccatct gtcaggagag tggaatgttg   1260

gctgtccgtg aaaaccgcta cattgtcctg gccaaggact tcgagaaagc atacaagact   1320

gtcatcaaga aggacgagca ggagcatgag ttttacaagt gacccttccc ttccctccac   1380

cacaccactc aggggctggg gcttctctcg caccccccagc acctctgtcc caaaacctca   1440

ttcccttttt tctttaccca ggattggttt cttcaataaa tagataagat cgaatccatt   1500

taatttcttc ttagaagttt aactcctttg gagaatgtgg gccttgaata ggatcctctg   1560

ggtccctctt aatctgacag atgagcagac gaggtgcatg gcctgggttg cagcttgaga   1620

gaaccaaaat attcaaacca gatgacttcc aaaatgtggg gaaagggatg gaaaatgaac   1680

ctgagatgga gtccttaatc acgggataaa gccctgtgca tctccctcat ttcctacagg   1740
```

```
taaaagacag taaagaaatt caggtcacag gccttgggag ttcataggaa ggagatgtcc   1800

agtgctgtcc agtagaactt t                                             1821
```

<210> SEQ ID NO 17
<211> LENGTH: 5159
<212> TYPE: DNA
<213> ORGANISM: Homo sapiens

<400> SEQUENCE: 17

```
ggtcccggaa gtgcgccagt cgtaccttcg cggccgcaac tcgctcggcc gccgccatct     60

tgcgagctcg tcgtactgac cgagcgggga ggctgtcttg aggcggcacc gctcaccgac    120

accgaggcgg actggcagcc ctgagcgtcg cagtcatgcc ggccggaccc gtgcaggcgg    180

tgcccccgcc gccgcccgtg cccacggagc ccaaacagcc cacagaagaa gaagcatctt    240

caaaggagga ttctgcacct tctaagccag ttgtggggat tatttaccct cctccagagg    300

tcagaaatat tgttgacaag actgccagct ttgtggccag aaacgggcct gaatttgaag    360

ctaggatccg acagaacgag atcaacaacc ccaagttcaa ctttctgaac cccaatgacc    420

cttaccatgc ctactaccgc cacaaggtca gcgagttcaa ggaagggaag gctcaggagc    480

cgtccgccgc catccccaag gtcatgcagc agcagcagca gaccacccag cagcagctgc    540

cccagaaggt ccaagcccaa gtaatccaag agaccatcgt gcccaaagag cctcctcctg    600

agtttgagtt cattgctgat cctccctcta tctcagcctt cgacttggat gtggtgaagc    660

tgacggctca gtttgtggcc aggaatgggc gccagtttct gacccagctg atgcagaaag    720

agcagcgcaa ctaccagttt gactttctcc gcccacagca cagcctcttc aactacttca    780

cgaagctagt ggaacagtac accaagatct tgattccacc caaaggttta ttttcaaagc    840

tcaagaaaga ggctgaaaac ccccgagaag ttttggatca ggtgtgttac cgagtggaat    900

gggccaaatt ccaggaacgt gagaggaaga aggaagaaga ggagaaggag aaggagcggg    960

tggcctatgc tcagatcgac tggcatgatt ttgtggtggt ggaaacagtg gacttccaac   1020

ccaatgagca agggaacttc cctcccccca ccacgccaga ggagctgggg gcccgaatcc   1080

tcattcagga gcgctatgaa aagtttgggg agagtgagga agttgagatg gaggtcgagt   1140

ctgatgagga ggatgacaaa caggagaagg cggaggagcc tccttcccag ctggaccagg   1200

acacccaagt acaagatatg gatgagggtt cagatgatga agaagaaggg cagaaagtgc   1260

ccccaccccc agagacaccc atgcctccac ctctgccccc aactccagac caagtcattg   1320

tccgcaagga ttatgatccc aaagcctcca agcccttgcc tccagcccct gctccagatg   1380

agtatcttgt gtcccccatt actggggaga agatccccgc cagcaaaatg caggaacaca   1440

tgcgcattgg acttcttgac cctcgctggc tggagcagcg ggatcgctcc atccgtgaga   1500

agcagagcga tgatgaggtg tacgcaccag gtctggatat tgagagcagc ttgaagcagt   1560

tggctgagcg gcgtactgac atcttcggtg tagaggaaac agccattggt aagaagatcg   1620

gtgaggagga gatccagaag ccagaggaaa aggtgacctg ggatggccac tcaggcagca   1680

tggcccggac ccagcaggct gcccaggcca acatcaccct ccaggagcag attgaggcca   1740

ttcacaaggc caaaggcctg gtgccagagg atgacactaa agagaagatt ggccccagca   1800

agcccaatga aatccctcaa cagccaccgc caccatcttc agccaccaac atccccagct   1860

cggctccacc catcacttca gtgccccgac cacccacaat gccacctcca gttcgtacta   1920

cagttgtctc cgcagtaccc gtcatgcccc ggcccccaat ggcatctgtg gtccggctgc   1980
```

-continued

```
ccccaggctc agtgatcgcc cccatgccgc ccatcatcca cgcgcccaga atcaacgtgg   2040
tgcccatgcc tccctcggcc cctcctatta tggcccccg cccacccccc atgattgtgc   2100
caacagcctt tgtgcctgct ccacctgtgg cacctgtccc agctccagcc ccaatgcccc   2160
ctgtgcatcc cccacctccc atggaagatg agcccacctc caaaaaactg aagacagagg   2220
acagcctcat gccagaggag gagttcctgc gcagaaacaa gggtccagtg tccatcaaag   2280
tccaggtgcc caacatgcag gataagacgg aatggaaact gaatgggcag gtgctggtct   2340
tcaccctccc actcacggac caggtctctg tcattaaggt gaagattcat gaagccacag   2400
gcatgcctgc agggaaacag aagctacagt atgagggtat cttcatcaaa gattccaact   2460
cactggctta ctacaacatg gccaatggcg cagtcatcca cctggccctc aaggagagag   2520
gcgggaggaa gaagtagaca agaggaacct gctgtcaagt ccctgccatt ttgcctctcc   2580
tgtctcccac cccctgcccc agacccagga gcccccctga ggctttgcct tgcctgcata   2640
tttgtttcgc tcttactcag tttgggaatt caaattgtcc tgcagaggtt cattcccctg   2700
accctttccc cacattggta agagtagctg ggttttctaa gccactctct ggaatctctt   2760
tgtgttaggg tctcgatttg aggacattca tttcttcagc agcccattag caactgagag   2820
cccagggatg tcctacagga tagtttcata gtgacaggtg gcacttggct aatagaatat   2880
ggctgatatt gtcattaatc attttgtacc ttgacatggg ttgtctaata aaactcggac   2940
ccttcttgtg aaatcagtta aataagactt gtctcggtca cctgtgccct gtccagactc   3000
gaggcagtgg taacactgca cagtgctatg tggcttctct ttgaggattt ttgggttttg   3060
taactaaatt cttgctgccc tcatactttt tatgtattag aatcatattc gtattgccct   3120
tttaaaacat tgggatcctc caaaggcctg ccccatgtat ttaacagtaa tacaggaagc   3180
atggcaggca ccatgcaaac caaggatgga tggtgcagtc cctgtgtcag tgggcggtgg   3240
tttcctgctg gcctggaatc actcatcacc tgattgattg gctctgtggt cctgggcagg   3300
tgcctcatag gtgtgtggat atgatgacgt ttctttaaaa tgtatgtatt taacaaatac   3360
ttaattgtat taaggtcatg taccaaggat ttgataaagt ttaaataatt tactctctac   3420
ttttatccat tttatccatt ttaactcatg taatcctcat gtgagtattc ctgtttaaca   3480
cttgagtaaa ctgaggcaca gagaacataa gttgcatgcc atagtcacac actgtgaaag   3540
tgaaaagaga atgtgtgcaa aacacgtcac agtcctggtt tctgagtaaa ggcaggctgt   3600
tatctttaga atcaagctat cacagggaga taggcaatgc tgtgggtgtt ggaggaaggt   3660
gagagcctgt tgctaacaat ttcctggttt taaagctaag gctgatttta ttgggaagat   3720
ctcacatgtg tgtggcccct gagagttccc agtgcctttt atttgcagtc cttccatttg   3780
gacctcctag ctgccccatc aggtcatctc cagggctcag aggggtgaga ccatttccca   3840
aggtcacaga accagctctc tagtcaccac cctgcctctc cctctcaccc agagtcagta   3900
ccagttttat ggctttatta caaactgctg ggtccctccc attttcaact tgattgatgg   3960
gatgtcatcc cttatcctgt ctgacatttg cctctggcct ggttgctaga agtttgcccc   4020
aggggcaaga gttgaaattt ggcttcctga ggtgggcttt gtggtttgcg tccctaaagt   4080
gagcccacta ctggttgctt gtccatggcc aacaccagaa atcccctgag cactacctgg   4140
gtctcattcc aagaaggaag agggtcagga gacctgggga gtctcatatt ccaagttctt   4200
ctttctttct gggagcagtg ggcagttcat ggtgttaggg cactcacccc cacagactgg   4260
caaaccctgc aggacttccg tggctgaggc tgtgaccgga ggccaggaat gccgttgggt   4320
ggattgtgag tgaatgggcc ctttgagctg ccctctagag agcaaatcca gtttcctgga   4380
```

```
gctcctgaat gaatatctgt actggctcgc tcagatgcag aagctccatt gaccatgagg   4440
ccttgtgaac atcagtggcc acaggcccag tgtgctgctt ggcactgcac tagtttagga   4500
cctgcagcat gtaggtagcg tcctagtgtt tataatacaa agctgctctg cacagctttt   4560
ctgattcttc ttgcaatctc ctgaggatta tctgccccat ttttaaaacg aggtggaata   4620
cccaaggtca tgtagccagt gagtgctctg gaaagccaaa gcagctcatc ccttcctggg   4680
gaccacactg ctctgctcca ccagaccaca ctatgaaata ggaataagtg ctcctgttgc   4740
aggactgctg ggaaaacagg tggtgtggga cttaagtcac cataattttg aagacttgca   4800
tgcagagggc tccaggaatt gtagacatta aggaatttca ctttcagttc tacccactac   4860
ttaagtactt gtcatgtact cttagaggag gccagtaatg atcagaacca ttttacttta   4920
aaattaataa tattgtatta gagaatatat taaatggtta tattgggtta tgttaggata   4980
tatacttgaa tggaaataca tgtactatta gcaatcatat ttcatttatc cctgtaatta   5040
gacaagaaag cataatatag ctctactcat gggtacacat accagtgtat aagattttta   5100
gaagtttact ttttaaaaat aaaagcaaaa tgtaagatct taaaaaaaaa aaaaaaaaa    5159
```

<210> SEQ ID NO 18
<211> LENGTH: 5416
<212> TYPE: DNA
<213> ORGANISM: Homo sapiens

<400> SEQUENCE: 18

```
agtgggccgc catgttgtcg gagtgaaagg taagggggag cgagagcgcc agagagagaa     60
gatcgggggg ctgaaatcca tcttcatcct accgctccgc ccgtgttggt ggaatgagcg    120
ttgcatgtgt cttgaagaga aaagcagtgc tttggcagga ctctttcagc cccccacctga    180
aacatcaccc tcaagaacca gctaatccca acatgcctgt tgttttgaca tctggaacag    240
ggtcgcaagc gcagccacaa ccagctgcaa atcaggctct tgcagctggg actcactcca    300
gccctgtccc aggatctata ggagttgcag gccgttccca ggacgacgct atggtggact    360
acttctttca gaggcagcat ggtgagcagc ttgggggagg aggaagtgga ggaggcggct    420
ataataatag caaacatcga tggcctactg gggataacat tcatgcagaa catcaggtgc    480
gttccatgga tgaactgaat catgattttc aagcacttgc tctggaggga agagcgatgg    540
gagagcagct cttgccaggt aaaaagtttt gggaaacaga tgaatccagc aaagatggac    600
caaaaggaat attcctgggt gatcaatggc gagacagtgc ctggggaaca tcagatcatt    660
cagtttccca gccaatcatg gtgcagagaa gacctggtca gagtttccat gtgaacagtg    720
aggtcaattc tgtactgtcc ccacgatcgg agagtggggg actaggcgtt agcatggtgg    780
agtatgtgtt gagctcatcc ccgggcgatt cctgtctaag aaaaggagga tttggcccaa    840
gggatgcaga cagtgatgaa aacgacaaag gtgaaaagaa gaacaagggt acgtttgatg    900
gagataagct aggagatttg aaggaggagg gtgatgtgat ggacaagacc aatggtttac    960
cagtgcagaa tgggattgat gcagacgtca aagattttag ccgtacccct ggtaattgcc   1020
agaactctgc taatgaagtg gatcttctgg gtccaaacca gaatggttct gagggcttag   1080
cccagctgac cagcaccaat ggtgccaagc ctgtggagga tttctccaac atggagtccc   1140
agagtgtccc cttggacccc atggaacatg tgggcatgga gcctcttcag tttgattatt   1200
caggcacgca ggtacctgtg gactcagcag cagcaactgt gggacttttt gactacaatt   1260
ctcaacaaca gctgttccaa agacctaatg cgcttgctgt ccagcagttg acagctgctc   1320
```

-continued

```
agcagcagca gtatgcactg gcagctgctc atcagccgca catcggttta gctcccgctg   1380
cgtttgtccc caatccatac atcatcagcg ctgctccccc agggacggac ccctacacag   1440
ctggattggc tgcagcagcg acactaggcc cagctgtggt ccctcaccag tattatggag   1500
ttactccctg gggagtctac cctgccagtc ttttccagca gcaagctgcc gctgccgctg   1560
cagcaactaa ttcagctaat caacagacca ccccacaggc tcagcaagga cagcagcagg   1620
ttctccgtgg aggagccagc caacgtcctt tgaccccaaa ccagaaccag cagggacagc   1680
aaacggatcc ccttgtggca gctgcagcag tgaattctgc ccttgcattt ggacaaggtc   1740
tggcagcagg catgccaggt tatccggtgt tggctcctgc tgcttactat gaccaaactg   1800
gtgcccttgt agtgaatgca ggcgcgagaa atggtcttgg agctcctgtt cgacttgtag   1860
ctcctgcccc agtcatcatt agttcctcag ctgcacaagc agctgttgca gcagccgcag   1920
cttcagcaaa tggagcagct ggtggtcttg ctggaacaac aaatggacca tttcgccctt   1980
taggaacaca gcagcctcag ccccagcccc agcagcagcc caataacaac ctggcatcca   2040
gttctttcta cggcaacaac tctctgaaca gcaattcaca gagcagctcc ctcttctccc   2100
agggctctgc ccagcctgcc aacacatcct tgggattcgg aagtagcagt tctctcggcg   2160
ccaccctggg atccgccctt ggagggtttg gaacagcagt tgcaaactcc aacactggca   2220
gtggctcccg ccgtgactcc ctgactggca gcagtgacct ttataagagg acatcgagca   2280
gcttgacccc cattggacac agtttttata acggccttag cttttcctcc tctcctggac   2340
ccgtgggcat gcctctccct agtcagggac caggacattc acagacacca cctccttccc   2400
tctcttcaca tggatcctct tcaagcttaa acctgggagg actcacgaat ggcagtggaa   2460
gatacatctc tgctgctcca ggcgctgaag ccaagtaccg cagtgcaagc agcgcctcca   2520
gcctcttcag cccgagcagc actcttttct cttcctctcg tttgcgatat ggaatgtctg   2580
atgtcatgcc ttctggcagg agcaggcttt tggaagattt tcgaaacaac cggtacccca   2640
atttacaact gcgggagatt gctggacata taatggaatt ttcccaagac cagcatgggt   2700
ccagattcat tcagctgaaa ctggagcgtg ccacaccagc tgagcgccag cttgtcttca   2760
atgaaatcct ccaggctgcc taccaactca tggtggatgt gtttggtaat tacgtcattc   2820
agaagttctt tgaatttggc agtcttgaac agaagctggc tttggcagaa cggattcgag   2880
gccacgtcct gtcattggca ctacagatgt atggctgccg tgttatccag aaagctcttg   2940
agtttattcc ttcagaccag caggtaatta atgagatggt tcgggaacta gatggccatg   3000
tcttgaagtg tgtgaaagat cagaatggca atcacgtggt tcagaaatgc attgaatgtg   3060
tacagcccca gtctttgcaa tttatcatcg atgcgtttaa gggacaggta tttgccttat   3120
ccacacatcc ttatggctgc cgagtgattc agagaatcct ggagcactgt ctccctgacc   3180
agacactccc tattttagag gagcttcacc agcacacaga gcagcttgta caggatcaat   3240
atggaaatta tgtaatccaa catgtactgg agcacggtcg tcctgaggat aaaagcaaaa   3300
ttgtagcaga aatccgaggc aatgtacttg tattgagtca gcacaaattt gcaagcaatg   3360
ttgtggagaa gtgtgttact cacgcctcac gtacggagcg cgctgtgctc atcgatgagg   3420
tgtgcaccat gaacgacggt ccccacagtg ccttatacac catgatgaag gaccagtatg   3480
ccaactacgt ggtccagaag atgattgacg tggcggagcc aggccagcgg aagatcgtca   3540
tgcataagat ccggccccac atcgcaactc ttcgtaagta cacctatggc aagcacattc   3600
tggccaagct ggagaagtac tacatgaaga acggtgttga cttagggccc atctgtggcc   3660
cccctaatgg tatcatctga ggcagtgtca cccgctgttc cctcattccc gctgacctca   3720
```

```
ctggcccact ggcaaatcca accagcaacc agaaatgttc tagtgtagag tctgagacgg   3780

gcaagtggtt gctccaggat tactccctcc tccaaaaaag gaatcaaatc cacgagtgga   3840

aaagcctttg taaatttaat tttattacac ataacatgta ctattttttt taattgacta   3900

attgccctgc tgttttactg gtgtatagga tacttgtaca taggtaacca atgtacatgg   3960

gaggccacat attttgttca ctgttgtatc tatatttcac atgtggaaac tttcagggtg   4020

gttggtttaa caaaaaaaaa aagctttaaa aaaaaaagaa aaaaaggaaa aggtttttag   4080

ctcatttgcc tggccggcaa gttttgcaaa tagctcttcc ccacctcctc attttagtaa   4140

aaaacaaaca aaaacaaaaa aacctgagaa gtttgaattg tagttaaatg accccaaact   4200

ggcatttaac actgtttata aaaaatatat atatatatat atatatatat aatgaaaaag   4260

gtttcagagt tgctaaagct tcagtttgtg acattaagtt tatgaaattc taaaaaatgc   4320

ctttttttgga gactatatta tgctgaagaa ggctgttcgt gaggaggaga tgcgagcacc   4380

cagaacgtct tttgaggctg ggcgggtgtg attgtttact gcctactgga tttttttcta   4440

ttaacattga aaggtaaaat ctgattattt agcatgagaa aaaaaaatcc aactctgctt   4500

ttggtcttgc ttctataaat atatagtgta tacttggtgt agactttgca tatatacaaa   4560

tttgtagtat tttcttgttt tgatgtctaa tctgtatcta taatgtaccc tagtagtcga   4620

acatactttt gattgtacaa ttgtacattt gtatacctgt aatgtaaatg tggagaagtt   4680

tgaatcaaca taaacacgtt ttttggtaag aaaagagaat tagccagccc tgtgcattca   4740

gtgtatattc tcacctttta tggtcgtagc atatagtgtt gtatattgta aattgtaatt   4800

tcaaccagaa gtaaattttt ttcttttgaa ggaataaatg ttctttatac agcctagtta   4860

atgtttaaaa agaaaaaaat agcttggttt tatttgtcat ctagtctcaa gtatagcgag   4920

attctttcta aatgttattc aagattgagt tctcactagt gttttttttaa tcctaaaaaa   4980

gtaatgtttt gattttgtga cagtcaaaag gacgtgcaaa agtctagcct tgcccgagct   5040

ttccttacaa tcagagcccc tctcaccttg taaagtgtga atcgcccttc ccttttgtac   5100

agaagatgaa ctgtattttg cattttgtct acttgtaagt gaatgtaaca tactgtcaat   5160

tttccttgtt tgaatataga attgtaacac tacacggtgt acatttccag agccttgtgt   5220

atatttccaa tgaacttttt tgcaagcaca cttgtaacca tatgtgtata attaacaaac   5280

ctgtgtatgc ttatgcctgg gcaactattt tttgtaactc ttgtgtagat tgtctctaaa   5340

caatgtgtga tctttatttt gaaaaataca gaactttgga atctgaaaaa aaaaaaaaaa   5400

aaaaaaaaaa aaaaaa                                                    5416
```

```
<210> SEQ ID NO 19
<211> LENGTH: 1940
<212> TYPE: DNA
<213> ORGANISM: Homo sapiens

<400> SEQUENCE: 19

gagtgagcgg cgcggggcca atcagcgtgc gccgttccga aagttgcctt ttatggctcg     60

agcggccgcg gcggcgccct ataaaaccca gcggcgcgac gcgccaccac cgccgagacc    120

gcgtccgccc cgcgagcaca gagcctcgcc tttgccgatc cgccgcccgt ccacacccgc    180

cgccagctca ccatggatga tgatatcgcc gcgctcgtcg tcgacaacgg ctccggcatg    240

tgcaaggccg gcttcgcggg cgacgatgcc ccccgggccg tcttcccctc catcgtgggg    300

cgccccaggc accagggcgt gatggtgggc atgggtcaga aggattccta tgtgggcgac    360
```

```
gaggcccaga gcaagagagg catcctcacc ctgaagtacc ccatcgagca cggcatcgtc    420

accaactggg acgacatgga gaaaatctgg caccacacct tctacaatga gctgcgtgtg    480

gctcccgagg agcaccccgt gctgctgacc gaggcccccc tgaaccccaa ggccaaccgc    540

gagaagatga cccagatcat gtttgagacc ttcaacaccc cagccatgta cgttgctatc    600

caggctgtgc tatccctgta cgcctctggc cgtaccactg gcatcgtgat ggactccggt    660

gacggggtca cccacactgt gcccatctac gaggggtatg ccctccccca tgccatcctg    720

cgtctggacc tggctggccg ggacctgact gactacctca tgaagatcct caccgagcgc    780

ggctacagct tcaccaccac ggccgagcgg gaaatcgtgc gtgacattaa ggagaagctg    840

tgctacgtcg ccctggactt cgagcaagag atggccacgg ctgcttccag ctcctccctg    900

gagaagagct acgagctgcc tgacggccag gtcatcacca ttggcaatga gcggttccgc    960

tgccctgagg cactcttcca gccttccttc ctgggcatgg agtcctgtgg catccacgaa   1020

actaccttca actccatcat gaagtgtgac gtggacatcc gcaaagacct gtacgccaac   1080

acagtgctgt ctggcggcac caccatgtac cctggcattg ccgacaggat gcagaaggag   1140

atcactgccc tggcacccag cacaatgaag atcaagatca ttgctcctcc tgagcgcaag   1200

tactccgtgt ggatcggcgg ctccatcctg gcctcgctgt ccaccttcca gcagatgtgg   1260

atcagcaagc aggagtatga cgagtccggc ccctccatcg tccaccgcaa atgcttctag   1320

gcggactatg acttagttgc gttacaccct ttcttgacaa aacctaactt gcgcagaaaa   1380

caagatgaga ttggcatggc tttatttgtt ttttttgttt tgttttggtt tttttttttt   1440

ttttggcttg actcaggatt taaaaactgg aacggtgaag gtgacagcag tcggttggag   1500

cgagcatccc ccaaagttca caatgtggcc gaggactttg attgcacatt gttgtttttt   1560

taatagtcat tccaaatatg agatgcgttg ttacaggaag tcccttgcca tcctaaaagc   1620

caccccactt ctctctaagg agaatggccc agtcctctcc caagtccaca caggggaggt   1680

gatagcattg ctttcgtgta aattatgtaa tgcaaaattt ttttaatctt cgccttaata   1740

ctttttttatt ttgttttatt ttgaatgatg agccttcgtg cccccccttc cccctttttt   1800

gtcccccaac ttgagatgta tgaaggcttt tggtctccct gggagtgggt ggaggcagcc   1860

agggcttacc tgtacactga cttgagacca gttgaataaa agtgcacacc ttaaaaatga   1920

ggaaaaaaaa aaaaaaaaaa                                                1940
```

<210> SEQ ID NO 20
<211> LENGTH: 1309
<212> TYPE: DNA
<213> ORGANISM: Homo sapiens

<400> SEQUENCE: 20

```
gctctctgct cctcctgttc gacagtcagc cgcatcttct tttgcgtcgc cagccgagcc     60

acatcgctca gacaccatgg ggaaggtgaa ggtcggagtc aacggatttg gtcgtattgg    120

gcgcctggtc accagggctg cttttaactc tggtaaagtg gatattgttg ccatcaatga    180

ccccttcatt gacctcaact acatggttta catgttccaa tatgattcca cccatggcaa    240

attccatggc accgtcaagg ctgagaacgg gaagcttgtc atcaatggaa atcccatcac    300

catcttccag gagcgagatc cctccaaaat caagtggggc gatgctggcg ctgagtacgt    360

cgtggagtcc actggcgtct tcaccaccat ggagaaggct ggggctcatt tgcagggggg    420

agccaaaagg gtcatcatct ctgcccccctc tgctgatgcc cccatgttcg tcatgggtgt    480

gaaccatgag aagtatgaca acagcctcaa gatcatcagc aatgcctcct gcaccaccaa    540
```

```
ctgcttagca cccctggcca aggtcatcca tgacaacttt ggtatcgtgg aaggactcat    600
gaccacagtc catgccatca ctgccaccca gaagactgtg gatggcccct ccgggaaact    660
gtggcgtgat ggccgcgggg ctctccagaa catcatccct gcctctactg gcgctgccaa    720
ggctgtgggc aaggtcatcc ctgagctgaa cgggaagctc actggcatgg ccttccgtgt    780
ccccactgcc aacgtgtcag tggtggacct gacctgccgt ctagaaaaac ctgccaaata    840
tgatgacatc aagaaggtgg tgaagcaggc gtcggagggc cccctcaagg gcatcctggg    900
ctacactgag caccaggtgg tctcctctga cttcaacagc gacacccact cctccacctt    960
tgacgctggg gctggcattg ccctcaacga ccactttgtc aagctcattt cctggtatga   1020
caacgaattt ggctacagca acagggtggt ggacctcatg gcccacatgg cctccaagga   1080
gtaagacccc tggaccacca gccccagcaa gagcacaaga ggaagagaga gaccctcact   1140
gctggggagt ccctgccaca ctcagtcccc caccacactg aatctcccct cctcacagtt   1200
gccatgtaga ccccttgaag aggggagggg cctagggagc cgcaccttgt catgtaccat   1260
caataaagta ccctgtgctc aaccagttaa aaaaaaaaaa aaaaaaaaa               1309
```

<210> SEQ ID NO 21
<211> LENGTH: 2321
<212> TYPE: DNA
<213> ORGANISM: Homo sapiens

<400> SEQUENCE: 21

```
gtcctcaacc aagatggcgc ggatggcttc aggcgcatca cgacaccggc gcgtcacgcg     60
acccgcccta cgggcacctc ccgcgctttt cttagcgccg cagacggtgg ccgagcgggg    120
gaccgggaag catggcccgg gggtcggcgg ttgcctgggc ggcgctcggg ccgttgttgt    180
ggggctgcgc gctggggctg cagggcggga tgctgtaccc ccaggagagc ccgtcgcggg    240
agtgcaagga gctggacggc ctctggagct tccgcgccga cttctctgac aaccgacgcc    300
ggggcttcga ggagcagtgg taccggcggc cgctgtggga gtcaggcccc accgtggaca    360
tgccagttcc ctccagcttc aatgacatca gccaggactg gcgtctgcgg cattttgtcg    420
gctgggtgtg gtacgaacgg gaggtgatcc tgccggagcg atggacccag gacctgcgca    480
caagagtggt gctgaggatt ggcagtgccc attcctatgc catcgtgtgg gtgaatgggg    540
tcgacacgct agagcatgag gggggctacc tccccttcga ggccgacatc agcaacctgg    600
tccaggtggg gcccctgccc tcccggctcc gaatcactat cgccatcaac aacacactca    660
cccccaccac cctgccacca gggaccatcc aatacctgac tgacacctcc aagtatccca    720
agggttactt tgtccagaac acatattttg actttttcaa ctacgctgga ctgcagcggt    780
ctgtacttct gtacacgaca cccaccacct acatcgatga catcaccgtc accaccagcg    840
tggagcaaga cagtgggctg gtgaattacc agatctctgt caagggcagt aacctgttca    900
agttggaagt gcgtcttttg gatgcagaaa acaaagtcgt ggcgaatggg actgggaccc    960
agggccaact taaggtgcca ggtgtcagcc tctggtggcc gtacctgatg cacgaacgcc   1020
ctgcctatct gtattcattg gaggtgcagc tgactgcaca gacgtcactg gggcctgtgt   1080
ctgacttcta cacactccct gtggggatcc gcactgtggc tgtcaccaag agccagttcc   1140
tcatcaatgg gaaacctttc tatttccacg gtgtcaacaa gcatgaggat gcggacatcc   1200
gagggaaggg cttcgactgg ccgctgctgg tgaaggactt caacctgctt cgctggcttg   1260
gtgccaacgc tttccgtacc agccactacc cctatgcaga ggaagtgatg cagatgtgtg   1320
```

```
accgctatgg gattgtggtc atcgatgagt gtcccggcgt gggcctggcg ctgccgcagt   1380

tcttcaacaa cgtttctctg catcaccaca tgcaggtgat ggaagaagtg gtgcgtaggg   1440

acaagaacca ccccgcggtc gtgatgtggt ctgtggccaa cgagcctgcg tcccacctag   1500

aatctgctgg ctactacttg aagatggtga tcgctcacac caaatccttg gacccctccc   1560

ggcctgtgac ctttgtgagc aactctaact atgcagcaga caagggggct ccgtatgtgg   1620

atgtgatctg tttgaacagc tactactctt ggtatcacga ctacgggcac ctggagttga   1680

ttcagctgca gctggccacc cagtttgaga actggtataa gaagtatcag aagcccatta   1740

ttcagagcga gtatggagca gaaacgattg cagggtttca ccaggatcca cctctgatgt   1800

tcactgaaga gtaccagaaa agtctgctag agcagtacca tctgggtctg gatcaaaaac   1860

gcagaaaata cgtggttgga gagctcattt ggaattttgc cgatttcatg actgaacagt   1920

caccgacgag agtgctgggg aataaaaagg ggatcttcac tcggcagaga caaccaaaaa   1980

gtgcagcgtt ccttttgcga gagagatact ggaagattgc caatgaaacc aggtatcccc   2040

actcagtagc caagtcacaa tgtttggaaa acagcctgtt tacttgagca agactgatac   2100

cacctgcgtg tcccttcctc cccgagtcag ggcgacttcc acagcagcag aacaagtgcc   2160

tcctggactg ttcacggcag accagaacgt ttctggcctg ggttttgtgg tcatctattc   2220

tagcagggaa cactaaaggt ggaaataaaa gattttctat tatggaaata aagagttggc   2280

atgaaagtgg ctactgaaaa aaaaaaaaaa aaaaaaaaaa a                       2321
```

<210> SEQ ID NO 22
<211> LENGTH: 1229
<212> TYPE: DNA
<213> ORGANISM: Homo sapiens

<400> SEQUENCE: 22

```
gtctgacggg cgatggcgca gccaatagac aggagcgcta tccgcggttt ctgattggct     60

actttgttcg cattataaaa ggcacgcgcg ggcgcgaggc ccttctctcg ccaggcgtcc    120

tcgtggaagt gacatcgtct ttaaaccctg cgtggcaatc cctgacgcac cgccgtgatg    180

cccagggaag acagggcgac ctggaagtcc aactacttcc ttaagatcat ccaactattg    240

gatgattatc cgaaatgttt cattgtggga gcagacaatg tgggctccaa gcagatgcag    300

cagatccgca tgtcccttcg cgggaaggct gtggtgctga tgggcaagaa caccatgatg    360

cgcaaggcca tccgagggca cctggaaaac aacccagctc tggagaaact gctgcctcat    420

atccggggga atgtgggctt tgtgttcacc aaggaggacc tcactgagat cagggacatg    480

ttgctggcca ataaggtgcc agctgctgcc cgtgctggtg ccattgcccc atgtgaagtc    540

actgtgccag cccagaacac tggtctcggg cccgagaaga cctccttttt ccaggcttta    600

ggtatcacca ctaaaatctc caggggcacc attgaaatcc tgagtgatgt gcagctgatc    660

aagactggag acaaagtggg agccagcgaa gccacgctgc tgaacatgct caacatctcc    720

cccttctcct ttgggctggt catccagcag gtgttcgaca atggcagcat ctacaaccct    780

gaagtgcttg atatcacaga ggaaactctg cattctcgct tcctggaggg tgtccgcaat    840

gttgccagtg tctgtctgca gattggctac ccaactgttg catcagtacc ccattctatc    900

atcaacgggt acaaacgagt cctggccttg tctgtggaga cggattacac cttcccactt    960

gctgaaaagg tcaaggcctt cttggctgat ccatctgcct ttgtggctgc tgcccctgtg   1020

gctgctgcca ccacagctgc tcctgctgct gctgcagccc cagctaaggt tgaagccaag   1080

gaagagtcgg aggagtcgga cgaggatatg ggatttggtc tctttgacta atcaccaaaa   1140
```

```
agcaaccaac ttagccagtt ttatttgcaa aacaaggaaa taaaggctta cttctttaaa   1200

aagtaaaaaa aaaaaaaaaa aaaaaaaaa                                     1229


<210> SEQ ID NO 23
<211> LENGTH: 5234
<212> TYPE: DNA
<213> ORGANISM: Homo sapiens

<400> SEQUENCE: 23

agagcgtcgg gatatcgggt ggcggctcgg gacggaggac gcgctagtgt gagtgcgggc     60

ttctagaact acaccgaccc tcgtgtcctc ccttcatcct gcggggctgg ctggagcggc    120

cgctccggtg ctgtccagca gccataggga gccgcacggg gagcgggaaa gcggtcgcgg    180

ccccaggcgg ggcggccggg atggagcggg gccgcgagcc tgtggggaag gggctgtggc    240

ggcgcctcga gcggctgcag gttcttctgt gtggcagttc agaatgatgg atcaagctag    300

atcagcattc tctaacttgt ttggtggaga accattgtca tatacccggt tcagcctggc    360

tcggcaagta gatggcgata acagtcatgt ggagatgaaa cttgctgtag atgaagaaga    420

aaatgctgac aataacacaa aggccaatgt cacaaaaacca aaaaggtgta gtggaagtat   480

ctgctatggg actattgctg tgatcgtctt tttcttgatt ggatttatga ttggctactt    540

gggctattgt aaaggggtag aaccaaaaac tgagtgtgag agactggcag gaaccgagtc    600

tccagtgagg gaggagccag gagaggactt ccctgcagca cgtcgcttat attgggatga    660

cctgaagaga aagttgtcgg agaaactgga cagcacagac ttcaccggca ccatcaagct    720

gctgaatgaa aattcatatg tccctcgtga ggctggatct caaaaagatg aaaatcttgc    780

gttgtatgtt gaaaatcaat ttcgtgaatt taaactcagc aaagtctggc gtgatcaaca    840

ttttgttaag attcaggtca aagacagcgc tcaaaactcg gtgatcatag ttgataagaa    900

cggtagactt gtttacctgg tggagaatcc tgggggttat gtggcgtata gtaaggctgc    960

aacagttact ggtaaactgg tccatgctaa ttttggtact aaaaaagatt ttgaggattt   1020

atacactcct gtgaatggat ctatagtgat tgtcagagca gggaaaatca cctttgcaga   1080

aaaggttgca aatgctgaaa gcttaaatgc aattggtgtg ttgatataca tggaccagac   1140

taaatttccc attgttaacg cagaactttc attctttgga catgctcatc tggggacagg   1200

tgacccttac acacctggat tcccttcctt caatcacact cagtttccac catctcggtc   1260

atcaggattg cctaatatac ctgtccagac aatctccaga gctgctgcag aaaagctgtt   1320

tgggaatatg gaaggagact gtccctctga ctggaaaaca gactctacat gtaggatggt   1380

aacctcagaa agcaagaatg tgaagctcac tgtgagcaat gtgctgaaag agataaaaat   1440

tcttaacatc tttggagtta ttaaaggctt tgtagaacca gatcactatg ttgtagttgg   1500

ggcccagaga gatgcatggg gccctggagc tgcaaaatcc ggtgtaggca cagctctcct   1560

attgaaactt gcccagatgt tctcagatat ggtcttaaaa gatgggtttc agcccagcag   1620

aagcattatc tttgccagtt ggagtgctgg agactttgga tcggttggtg ccactgaatg   1680

gctagaggga tacctttcgt ccctgcattt aaaggctttc acttatatta atctggataa   1740

agcggttctt ggtaccagca acttcaaggt ttctgccagc ccactgttgt atacgcttat   1800

tgagaaaaca atgcaaaatg tgaagcatcc ggttactggg caatttctat atcaggacag   1860

caactgggcc agcaaagttg agaaactcac tttagacaat gctgctttcc ctttccttgc   1920

atattctgga atcccagcag tttctttctg tttttgcgag gacacagatt atccttattt   1980
```

```
gggtaccacc atggacacct ataaggaact gattgagagg attcctgagt tgaacaaagt   2040
ggcacgagca gctgcagagg tcgctggtca gttcgtgatt aaactaaccc atgatgttga   2100
attgaacctg gactatgaga ggtacaacag ccaactgctt tcatttgtga gggatctgaa   2160
ccaatacaga gcagacataa aggaaatggg cctgagttta cagtggctgt attctgctcg   2220
tggagacttc ttccgtgcta cttccagact aacaacagat ttcgggaatg ctgagaaaac   2280
agacagattt gtcatgaaga aactcaatga tcgtgtcatg agagtggagt atcacttcct   2340
ctctccctac gtatctccaa aagagtctcc tttccgacat gtcttctggg gctccggctc   2400
tcacacgctg ccagctttac tggagaactt gaaactgcgt aaacaaaata acggtgcttt   2460
taatgaaacg ctgttcagaa accagttggc tctagctact tggactattc agggagctgc   2520
aaatgccctc tctggtgacg tttgggacat tgacaatgag ttttaaatgt gatacccata   2580
gcttccatga gaacagcagg gtagtctggt ttctagactt gtgctgatcg tgctaaattt   2640
tcagtagggc tacaaaacct gatgttaaaa ttccatccca tcatcttggt actactagat   2700
gtctttaggc agcagctttt aatacagggt agataacctg tacttcaagt taaagtgaat   2760
aaccacttaa aaaatgtcca tgatggaata ttcccctatc tctagaattt taagtgcttt   2820
gtaatgggaa ctgcctcttt cctgttgttg ttaatgaaaa tgtcagaaac cagttatgtg   2880
aatgatctct ctgaatccta agggctggtc tctgctgaag gttgtaagtg gtcgcttact   2940
ttgagtgatc ctccaacttc atttgatgct aaataggaga taccaggttg aaagaccttc   3000
tccaaatgag atctaagcct ttccataagg aatgtagctg gtttcctcat tcctgaaaga   3060
aacagttaac tttcagaaga gatgggcttg ttttcttgcc aatgaggtct gaaatggagg   3120
tccttctgct ggataaaatg aggttcaact gttgattgca ggaataaggc cttaatatgt   3180
taacctcagt gtcatttatg aaaagagggg accagaagcc aaagacttag tatattttct   3240
tttcctctgt cccttccccc ataagcctcc atttagttct ttgttatttt tgtttcttcc   3300
aaagcacatt gaaagagaac cagtttcagg tgtttagttg cagactcagt ttgtcagact   3360
ttaaagaata atatgctgcc aaattttggc caaagtgtta atcttagggg agagctttct   3420
gtccttttgg cactgagata tttattgttt atttatcagt gacagagttc actataaatg   3480
gtgttttttt aatagaatat aattatcgga agcagtgcct tccataatta tgacagttat   3540
actgtcggtt ttttttaaat aaaagcagca tctgctaata aaacccaaca gatactggaa   3600
gttttgcatt tatggtcaac acttaagggt tttagaaaac agccgtcagc caaatgtaat   3660
tgaataaagt tgaagctaag atttagagat gaattaaatt taattagggg ttgctaagaa   3720
gcgagcactg accagataag aatgctggtt ttcctaaatg cagtgaattg tgaccaagtt   3780
ataaatcaat gtcacttaaa ggctgtggta gtactcctgc aaaattttat agctcagttt   3840
atccaaggtg taactctaat tcccattttg caaaatttcc agtacctttg tcacaatcct   3900
aacacattat cgggagcagt gtcttccata atgtataaag aacaaggtag tttttaccta   3960
ccacagtgtc tgtatcggag acagtgatct ccatatgtta cactaagggt gtaagtaatt   4020
atcgggaaca gtgtttccca taattttctt catgcaatga catcttcaaa gcttgaagat   4080
cgttagtatc taacatgtat cccaactcct ataattccct atcttttagt tttagttgca   4140
gaaacatttt gtggtcatta agcattgggt gggtaaattc aaccactgta aaatgaaatt   4200
actacaaaat ttgaaattta gcttgggttt ttgttacctt tatggtttct ccaggtcctc   4260
tacttaatga gatagtagca tacatttata atgtttgcta ttgacaagtc attttaactt   4320
tatcacatta tttgcatgtt acctcctata aacttagtgc ggacaagttt taatccagaa   4380
```

```
ttgacctttt gacttaaagc agagggactt tgtatagaag gtttgggggc tgtggggaag   4440
gagagtcccc tgaaggtctg acacgtctgc ctacccattc gtggtgatca attaaatgta   4500
ggtatgaata agttcgaagc tccgtgagtg aaccatcatt ataaacgtga tgatcagctg   4560
tttgtcatag ggcagttgga aacggcctcc tagggaaaag ttcatagggt ctcttcaggt   4620
tcttagtgtc acttacctag atttacagcc tcacttgaat gtgtcactac tcacagtctc   4680
tttaatcttc agttttatct ttaatctcct cttttatctt ggactgacat ttagcgtagc   4740
taagtgaaaa ggtcatagct gagattcctg gttcgggtgt tacgcacacg tacttaaatg   4800
aaagcatgtg gcatgttcat cgtataacac aatatgaata cagggcatgc attttgcagc   4860
agtgagtctc ttcagaaaac ccttttctac agttagggtt gagttacttc ctatcaagcc   4920
agtacgtgct aacaggctca atattcctga atgaaatatc agactagtga caagctcctg   4980
gtcttgagat gtcttctcgt taaggagatg ggccttttgg aggtaaagga taaaatgaat   5040
gagttctgtc atgattcact attctagaac ttgcatgacc tttactgtgt tagctctttg   5100
aatgttcttg aaattttaga ctttctttgt aaacaaatga tatgtcctta tcattgtata   5160
aaagctgtta tgtgcaacag tgtggagatt ccttgtctga tttaataaaa tacttaaaca   5220
ctgaaaaaaa aaaa                                                     5234
```

<210> SEQ ID NO 24
<211> LENGTH: 1869
<212> TYPE: DNA
<213> ORGANISM: Homo sapiens

<400> SEQUENCE: 24

```
tacctggttg atcctgccag tagcatatgc ttgtctcaaa gattaagcca tgcatgtcta     60
agtacgcacg gccggtacag tgaaactgcg aatggctcat taaatcagtt atggttcctt    120
tggtcgctcg ctcctctccc acttggataa ctgtggtaat tctagagcta atacatgccg    180
acgggcgctg acccccttcg cggggggggat gcgtgcattt atcagatcaa aaccaacccg    240
gtcagcccct ctccggcccc ggccgggggg cgggcgccgg cggctttggt gactctagat    300
aacctcgggc cgatcgcacg ccccccgtgg cggcgacgac ccattcgaac gtctgcccta    360
tcaactttcg atggtagtcg ccgtgcctac catggtgacc acgggtgacg gggaatcagg    420
gttcgattcc ggagagggag cctgagaaac ggctaccaca tccaaggaag gcagcaggcg    480
cgcaaattac ccactcccga cccggggagg tagtgacgaa aaataacaat acaggactct    540
ttcgaggccc tgtaattgga atgagtccac tttaaatcct ttaacgagga tccattggag    600
ggcaagtctg gtgccagcag ccgcggtaat tccagctcca atagcgtata ttaaagttgc    660
tgcagttaaa aagctcgtag ttggatcttg ggagcgggcg ggcggtccgc cgcgaggcga    720
gccaccgccc gtccccgccc cttgcctctc ggcgccccct cgatgctctt agctgagtgt    780
cccgcggggc ccgaagcgtt tactttgaaa aaattagagt gttcaaagca ggcccgagcc    840
gcctggatac cgcagctagg aataatggaa taggaccgcg gttctatttt gttggttttc    900
ggaactgagg ccatgattaa gagggacggc cgggggcatt cgtattgcgc cgctagaggt    960
gaaattcttg gaccggcgca agacggacca gagcgaaagc atttgccaag aatgttttca   1020
ttaatcaaga acgaaagtcg gaggttcgaa gacgatcaga taccgtcgta gttccgacca   1080
taaacgatgc cgaccggcga tgcggcggcg ttattcccat gacccgccgg gcagcttccg   1140
ggaaaccaaa gtctttgggt tccgggggga gtatggttgc aaagctgaaa cttaaaggaa   1200
```

```
ttgacggaag ggcaccacca ggagtggagc ctgcggctta atttgactca acacgggaaa   1260

cctcacccgg cccggacacg gacaggattg acagattgat agctctttct cgattccgtg   1320

ggtggtggtg catggccgtt cttagttggt ggagcgattt gtctggttaa ttccgataac   1380

gaacgagact ctggcatgct aactagttac gcgacccccg agcggtcggc gtcccccaac   1440

ttcttagagg gacaagtggc gttcagccac ccgagattga gcaataacag gtctgtgatg   1500

cccttagatg tccggggctg cacgcgcgct acactgactg gctcagcgtg tgcctaccct   1560

acgccggcag gcgcgggtaa cccgttgaac cccattcgtg atggggatcg gggattgcaa   1620

ttattcccca tgaacgagga attcccagta agtgcgggtc ataagcttgc gttgattaag   1680

tccctgccct ttgtacacac cgcccgtcgc tactaccgat tggatggttt agtgaggccc   1740

tcggatcggc cccgccgggg tcggcccacg gccctggcgg agcgctgaga agacggtcga   1800

acttgactat ctagaggaag taaaagtcgt aacaaggttt ccgtaggtga acctgcggaa   1860

ggatcatta                                                           1869
```

<210> SEQ ID NO 25
<211> LENGTH: 2288
<212> TYPE: DNA
<213> ORGANISM: Homo sapiens

<400> SEQUENCE: 25

```
ggggccgaac gtggtataaa aggggcggga ggccaggctc gtgccgtttt gcagacgcca     60

ccgccgagga aaaccgtgta ctattagcca tggtcaaccc caccgtgttc ttcgacattg    120

ccgtcgacgg cgagcccttg ggccgcgtct cctttgagct gtttgcagac aaggtcccaa    180

agacagcaga aaattttcgt gctctgagca ctggagagaa aggatttggt tataagggtt    240

cctgctttca cagaattatt ccagggttta tgtgtcaggg tggtgacttc acacgccata    300

atggcactgg tggcaagtcc atctatgggg agaaatttga agatgagaac ttcatcctaa    360

agcatacggg tcctggcatc ttgtccatgg caaatgctgg acccaacaca aatggttccc    420

agtttttcat ctgcactgcc aagactgagt ggttggatgg caagcatgtg gtgtttggca    480

aagtgaaaga aggcatgaat attgtggagg ccatggagcg ctttgggtcc aggaatggca    540

agaccagcaa gaagatcacc attgctgact gtggacaact cgaataagtt tgacttgtgt    600

tttatcttaa ccaccagatc attccttctg tagctcagga gagcacccct ccaccccatt    660

tgctcgcagt atcctagaat ctttgtgctc tcgctgcagt tccctttggg ttccatgttt    720

tccttgttcc ctcccatgcc tagctggatt gcagagttaa gtttatgatt atgaaataaa    780

aactaaataa caattgtcct cgtttgagtt aagagtgttg atgtaggctt tattttaagc    840

agtaatgggt tacttctgaa acatcacttg tttgcttaat tctacacagt acttagattt    900

tttttacttt ccagtcccag gaagtgtcaa tgtttgttga gtggaatatt gaaaatgtag    960

gcagcaactg ggcatggtgg ctcactgtct gtaatgtatt acctgaggca gaagaccacc   1020

tgagggtagg agtcaagatc agcctgggca acatagtgag acgctgtctc tacaaaaaat   1080

aattagcctg gcctggtggt gcatgcctag tcctagctga tctggaggct gacgtgggag   1140

gattgcttga gcctagagtg agctattatc atgccactgt acagcctggg tgttcacaga   1200

tcttgtgtct caaaggtagg cagaggcagg aaaagcaagg agccagaatt aagaggttgg   1260

gtcagtctgc agtgagttca tgcatttaga ggtgttcttc aagatgacta atgtcaaaaa   1320

ttgagacatc tgttgcggtt tttttttttt ttttttcccc tggaatgcag tggcgtgatc   1380

tcagctcact gcagcctccg cctcctgggt tcaagtgatt ctagtgcctc agcctcctga   1440
```

gtagctggga taatgggcgt gtgccaccat gcccagctaa tttttgtatt tttagtatag 1500
atggggtttc atcattttga ccaggctggt ctcaaactct tgacctcagc tgatgcgcct 1560
gccttggcct cccaaactgc tgagattaca gatgtgagcc accgcaccct acctcatttt 1620
ctgtaacaaa gctaagcttg aacactgttg atgttcttga gggaagcata ttgggcttta 1680
ggctgtaggt caagtttata catcttaatt atggtggaat tcctatgtag agtctaaaaa 1740
gccaggtact tggtgctaca gtcagtctcc ctgcagaggg ttaaggcgca gactacctgc 1800
agtgaggagg tactgcttgt agcatataga gcctctccct agctttggtt atggaggctt 1860
tgaggttttg caaacctgac caatttaagc cataagatct ggtcaaaggg ataccettcc 1920 cactaaggac ttggtttctc aggaaattat atgtacagtg cttgctggca gttagatgtc 1980
aggacaatct aagctgagaa aaccccttct ctgcccacct taacagacct ctagggttct 2040
taacccagca atcaagtttg cctatcctag aggtggcgga tttgatcatt tggtgtgttg 2100
ggcaattttt gttttactgt ctggttcctt ctgcgtgaat taccaccacc accacttgtg 2160
catctcagtc ttgtgtgttg tctggttacg tattccctgg gtgataccat tcaatgtctt 2220
aatgtacttg tggctcagac ctgagtgcaa ggtggaaata aacatcaaac atcttttcat 2280
tatcccta 2288

<210> SEQ ID NO 26
<211> LENGTH: 2439
<212> TYPE: DNA
<213> ORGANISM: Homo sapiens

<400> SEQUENCE: 26
gagagcagcg gccgggaagg ggcggtgcgg gaggcggggt gtggggcggt agtgtgggcc 60
ctgttcctgc ccgcgcggtg ttccgcattc tgcaagcctc cggagcgcac gtcggcagtc 120
ggctccctcg ttgaccgaat caccgacctc tctccccagc tgtatttcca aaatgtcgct 180
ttctaacaag ctgacgctgg acaagctgga cgttaaaggg aagcgggtcg ttatgagagt 240
cgacttcaat gttcctatga agaacaacca gataacaaac aaccagagga ttaaggctgc 300
tgtcccaagc atcaaattct gcttggacaa tggagccaag tcggtagtcc ttatgagcca 360
cctaggccgg cctgatggtg tgcccatgcc tgacaagtac tccttagagc cagttgctgt 420
agaactcaaa tctctgctgg gcaaggatgt tctgttcttg aaggactgtg taggcccaga 480
agtggagaaa gcctgtgcca acccagctgc tgggtctgtc atcctgctgg agaacctccg 540
ctttcatgtg gaggaagaag ggaagggaaa agatgcttct gggaacaagg ttaaagccga 600
gccagccaaa atagaagctt tccgagcttc actttccaag ctaggggatg tctatgtcaa 660
tgatgctttt ggcactgctc acagagccca cagctccatg gtaggagtca atctgccaca 720
gaaggctggt gggtttttga tgaagaagga gctgaactac tttgcaaagg ccttggagag 780
cccagagcga cccttcctgg ccatcctggg cggagctaaa gttgcagaca agatccagct 840
catcaataat atgctggaca aagtcaatga gatgattatt ggtggtggaa tggcttttac 900
cttccttaag gtgctcaaca acatggagat tggcacttct ctgtttgatg aagagggagc 960
caagattgtc aaagacctaa tgtccaaagc tgagaagaat ggtgtgaaga ttaccttgcc 1020
tgttgacttt gtcactgctg acaagtttga tgagaatgcc aagactggcc aagccactgt 1080
ggcttctggc atacctgctg gctggatggg cttggactgt ggtcctgaaa gcagcaagaa 1140
gtatgctgag gctgtcactc gggctaagca gattgtgtgg aatggtcctg tgggggtatt 1200

```
tgaatgggaa gcttttgccc ggggaaccaa agctctcatg gatgaggtgg tgaaagccac   1260
ttctaggggc tgcatcacca tcataggtgg tggagacact gccacttgct gtgccaaatg   1320
gaacacggag gataaagtca gccatgtgag cactgggggt ggtgccagtt tggagctcct   1380
ggaaggtaaa gtccttcctg ggtggatgc tctcagcaat atttagtact ttcctgcctt   1440
ttagttcctg tgcacagccc ctaagtcaac ttagcatttt ctgcatctcc acttggcatt   1500
agctaaaacc ttccatgtca agattcagct agtggccaag agatgcagtg ccaggaaccc   1560
ttaaacagtt gcacagcatc tcagctcatc ttcactgcac cctggatttg catacattct   1620
tcaagatccc atttgaattt tttagtgact aaaccattgt gcattctaga gtgcatatat   1680
ttatattttg cctgttaaaa agaaagtgag cagtgttagc ttagttctct tttgatgtag   1740
gttattatga ttagctttgt cactgtttca ctactcagca tggaaacaag atgaaattcc   1800
atttgtaggt agtgagacaa aattgatgat ccattaagta aacaataaaa gtgtccattg   1860
aaaccgtgat tttttttttt ttcctgtcat actttgttag gaagggtgag aatagaatct   1920
tgaggaacgg atcagatgtc tatattgctg aatgcaagaa gtggggcagc agcagtggag   1980
agatgggaca attagataaa tgtccattct ttatcaaggg cctactttat ggcagacatt   2040
gtgctagtgc ttttattcta acttttattt ttatcagtta cacatgatca taatttaaaa   2100
agtcaaggct tataacaaaa aagccccagc ccattcctcc cattcaagat tcccactccc   2160
cagaggtgac cactttcaac tcttgagttt ttcaggtata tacctccatg tttctaagta   2220
atatgcttat attgttcact tctttttttt ttatttttta aagaaatcta tttcatacca   2280
tggaggaagg ctctgttcca catatatttc cacttcttca ttctctcggt atagttttgt   2340
cacaattata gattagatca aaagtctaca taactaatac agctgagcta tgtagtatgc   2400
tatgattaaa tttacttatg taaaaaaaaa aaaaaaaaa                           2439
```

```
<210> SEQ ID NO 27
<211> LENGTH: 1196
<212> TYPE: DNA
<213> ORGANISM: Homo sapiens

<400> SEQUENCE: 27

cacttctgcc gcccctgttt caagggataa gaaaccctgc gacaaaacct cctccttttc     60
caagcggctg ccgaagatgg cggaggtgca ggtcctggtg cttgatggtc gaggccatct    120
cctgggccgc ctggcggcca tcgtggctaa acaggtactg ctgggccgga aggtggtggt    180
cgtacgctgt gaaggcatca acatttctgg caatttctac agaaacaagt tgaagtacct    240
ggctttcctc cgcaagcgga tgaacaccaa cccttcccga ggcccctacc acttccgggc    300
ccccagccgc atcttctggc ggaccgtgcg aggtatgctg ccccacaaaa ccaagcgagg    360
ccaggccgct ctggaccgtc tcaaggtgtt tgacggcatc ccaccgccct acgacaagaa    420
aaagcggatg gtggttcctg ctgccctcaa ggtcgtgcgt ctgaagccta caagaaagtt    480
tgcctatctg ggcgcgcctgg ctcacgaggt tggctggaag taccaggcag tgacagccac    540
cctggaggag aagaggaaag agaaagccaa gatccactac cggaagaaga aacagctcat    600
gaggctacgg aaacaggccg agaagaacgt ggagaagaaa attgacaaat acacagaggt    660
cctcaagacc cacggactcc tggtctgagc ccaataaaga ctgttaattc ctcatgcgtt    720
gcctgccctt cctccattgt tgccctggaa tgtacgggac ccaggggcag cagcagtcca    780
ggtgccacag gcagccctgg gacataggaa gctgggagca aggaaagggt cttagtcact    840
gcctcccgaa gttgcttgaa agcactcgga gaattgtgca ggtgtcattt atctatgacc    900
```

aataggaaga gcaaccagtt actatgagtg aaagggagcc agaagactga ttggagggcc 960
ctatcttgtg agtggggcat ctgttggact ttccacctgg tcatatactc tgcagctgtt 1020
agaatgtgca agcacttggg gacagcatga gcttgctgtt gtacacaggg tatttctaga 1080
agcagaaata gactgggaag atgcacaacc aaggggttac aggcatcgcc catgctcctc 1140
acctgtattt tgtaatcaga aataaattgc ttttaaagaa aaaaaaaaaa aaaaaa 1196

<210> SEQ ID NO 28
<211> LENGTH: 987
<212> TYPE: DNA
<213> ORGANISM: Homo sapiens

<400> SEQUENCE: 28
aatataagtg gaggcgtcgc gctggcgggc attcctgaag ctgacagcat tcgggccgag 60
atgtctcgct ccgtggcctt agctgtgctc gcgctactct ctctttctgg cctggaggct 120
atccagcgta ctccaaagat tcaggtttac tcacgtcatc cagcagagaa tggaaagtca 180
aatttcctga attgctatgt gtctgggttt catccatccg acattgaagt tgacttactg 240
aagaatggag agagaattga aaaagtggag cattcagact tgtctttcag caaggactgg 300
tctttctatc tcttgtacta cactgaattc acccccactg aaaaagatga gtatgcctgc 360
cgtgtgaacc atgtgacttt gtcacagccc aagatagtta agtgggatcg agacatgtaa 420
gcagcatcat ggaggtttga agatgccgca tttggattgg atgaattcca aattctgctt 480
gcttgctttt taatattgat atgcttatac acttacactt tatgcacaaa atgtagggtt 540
ataataatgt taacatggac atgatcttct ttataattct actttgagtg ctgtctccat 600
gtttgatgta tctgagcagg ttgctccaca ggtagctcta ggagggctgg caacttagag 660
gtggggagca gagaattctc ttatccaaca tcaacatctt ggtcagattt gaactcttca 720
atctcttgca ctcaaagctt gttaagatag ttaagcgtgc ataagttaac ttccaattta 780
catactctgc ttagaatttg ggggaaaatt tagaaatata attgacagga ttattggaaa 840
tttgttataa tgaatgaaac attttgtcat ataagattca tatttacttc ttatacattt 900
gataaagtaa ggcatggttg tggttaatct ggtttatttt tgttccacaa gttaaataaa 960
tcataaaact tgatgtgtta tctctta 987

<210> SEQ ID NO 29
<211> LENGTH: 3003
<212> TYPE: DNA
<213> ORGANISM: Homo sapiens

<400> SEQUENCE: 29
ctttctcctt ccccttcttc cgggctcccg tcccggctca tcacccggcc tgtggcccac 60
tcccaccgcc agctggaacc ctggggacta cgacgtccct caaaccttgc ttctaggaga 120
taaaaagaac atccagtcat ggataaaaat gagctggttc agaaggccaa actggccgag 180
caggctgagc gatatgatga catggcagcc tgcatgaagt ctgtaactga gcaaggagct 240
gaattatcca atgaggagag gaatcttctc tcagttgctt ataaaaatgt tgtaggagcc 300
cgtaggtcat cttggagggt cgtctcaagt attgaacaaa agacggaagg tgctgagaaa 360
aaacagcaga tggctcgaga atacagagag aaaattgaga cggagctaag agatatctgc 420
aatgatgtac tgtctctttt ggaaaagttc ttgatcccca atgcttcaca agcagagagc 480
aaagtcttct atttgaaaat gaaaggagat tactaccgtt acttggctga ggttgccgct 540

-continued

```
ggtgatgaca agaaagggat tgtcgatcag tcacaacaag cataccaaga agcttttgaa    600
atcagcaaaa aggaaatgca accaacacat cctatcagac tgggtctggc ccttaacttc    660
tctgtgttct attatgagat tctgaactcc ccagagaaag cctgctctct tgcaaagaca    720
gcttttgatg aagccattgc tgaacttgat acattaagtg aagagtcata caaagacagc    780
acgctaataa tgcaattact gagagacaac ttgacattgt ggacatcgga tacccaagga    840
gacgaagctg aagcaggaga aggaggggaa aattaaccgg ccttccaact tttgtctgcc    900
tcattctaaa atttacacag tagaccattt gtcatccatg ctgtcccaca aatagttttt    960
tgtttacgat ttatgacagg tttatgttac ttctatttga atttctatat ttcccatgtg   1020
gtttttatgt ttaatattag gggagtagag ccagttaaca tttagggagt tatctgtttt   1080
catcttgagg tggccaatat ggggatgtgg aatttttata caagttataa gtgtttggca   1140
tagtactttt ggtacattgt ggcttcaaaa gggccagtgt aaaactgctt ccatgtctaa   1200
gcaaagaaaa ctgcctacat actggtttgt cctggcgggg aataaaaggg atcattggtt   1260
ccagtcacag gtgtagtaat tgtgggtact ttaaggtttg gagcacttac aaggctgtgg   1320
tagaatcata ccccatggat accacatatt aaaccatgta tatctgtgga atactcaatg   1380
tgtacacctt tgactacagc tgcagaagtg ttcctttaga caaagttgtg acccatttta   1440
ctctggataa gggcagaaac ggttcacatt ccattatttg taaagttacc tgctgttagc   1500
tttcattatt tttgctacac tcattttatt tgtatttaaa tgttttaggc aacctaagaa   1560
caaatgtaaa agtaaagatg caggaaaaat gaattgcttg gtattcatta cttcatgtat   1620
atcaagcaca gcagtaaaac aaaaacccat gtatttaact ttttttagg atttttgctt    1680
ttgtgatttt ttttttttg atacttgcct aacatgcatg tgctgtaaaa atagttaaca    1740
gggaaataac ttgagatgat ggctagcttt gtttaatgtc ttatgaaatt ttcatgaaca   1800
atccaagcat aattgttaag aacacgtgta ttaaattcat gtaagtggaa taaaagtttt   1860
atgaatggac ttttcaacta ctttctctac agcttttcat gtaaattagt cttggttctg   1920
aaacttctct aaaggaaatt gtacattttt tgaaatttat tccttattcc ctcttggcag   1980
ctaatgggct cttaccaagt ttaaacacaa aatttatcat aacaaaaata ctactaatat   2040
aactactgtt tccatgtccc atgatcccct ctcttcctcc ccaccctgaa aaaaatgagt   2100
tcctattttt tctgggagag ggggggattg attagaaaaa aatgtagtgt gttccattta   2160
aaattttggc atatggcatt ttctaactta ggaagccaca atgttcttgg cccatcatga   2220
cattgggtag cattaactgt aagttttgtg cttccaaatc actttttggt ttttaagaat   2280
ttcttgatac tcttatagcc tgccttcaat tttgatcctt tattctttct atttgtcagg   2340
tgcacaagat taccttcctg ttttagcctt ctgtcttgtc accaaccatt cttacttggt   2400
ggccatgtac ttggaaaaag gccgcatgat ctttctggct ccactcagtg tctaaggcac   2460
cctgcttcct ttgcttgcat cccacagact atttccctca tcctatttac tgcagcaaat   2520
ctctccttag ttgatgagac tgtgtttatc tccctttaaa accctaccta tcctgaatgg   2580
tctgtcattg tctgccttta aaatccttcc tctttcttcc tcctctattc tctaaataat   2640
gatggggcta agttataccc aaagctcact ttacaaaata tttcctcagt actttgcaga   2700
aaacaccaaa caaaaatgcc attttaaaaa aggtgtattt tttcttttag aatgtaagct   2760
cctcaagagc agggacaatg ttttctgtat gttctattgt gcctagtaca ctgtaaatgc   2820
tcaataaata ttgatgatgg gaggcagtga gtcttgatga taagggtgag aaactgaaat   2880
cccaaacact gttttgttgc ttgttttatt atgacctcag attaaattgg gaaatattgg   2940
```

ccccttttgaa taattgtccc aaatattaca ttcaaataaa agtgcaatgg agaaaaaaaa 3000
aaa 3003

<210> SEQ ID NO 30
<211> LENGTH: 2803
<212> TYPE: DNA
<213> ORGANISM: Homo sapiens

<400> SEQUENCE: 30
actgcagccc cgctcgactc cggcgtggtg cgcaggcgcg gtatcccccc tcccccgcca 60
gctcgacccc ggtgtggtgc gcaggcgcag tctgcgcagg gactggcggg actgcgcggc 120
ggcaacagca gacatgtcgg gggtccgggg cctgtcgcgg ctgctgagcg ctcggcgcct 180
ggcgctggcc aaggcgtggc caacagtgtt gcaaacagga acccgaggtt ttcacttcac 240
tgttgatggg aacaagaggg catctgctaa agtttcagat tccatttctg ctcagtatcc 300
agtagtggat catgaatttg atgcagtggt ggtaggcgct ggaggggcag gcttgcgagc 360
tgcatttggc ctttctgagg cagggtttaa tacagcatgt gttaccaagc tgtttcctac 420
caggtcacac actgttgcag cacagggagg aatcaatgct gctctgggga acatggagga 480
ggacaactgg aggtggcatt tctacgacac cgtgaagggc tccgactggc tgggggacca 540
ggatgccatc cactacatga cggagcaggc ccccgccgcc gtggtcgagc tagaaaatta 600
tggcatgccg tttagcagaa ctgaagatgg gaagatttat cagcgtgcat ttggtggaca 660
gagcctcaag tttggaaagg gcgggcaggc ccatcggtgc tgctgtgtgg ctgatcggac 720
tggccactcg ctattgcaca ccttatatgg aaggtctctg cgatatgata ccagctattt 780
tgtggagtat tttgccttgg atctcctgat ggagaatggg gagtgccgtg gtgtcatcgc 840
actgtgcata gaggacgggt ccatccatcg cataagagca aagaacactg ttgttgccac 900
aggaggctac gggcgcacct acttcagctg cacgtctgcc cacaccagca ctggcgacgg 960
cacggccatg atcaccaggg caggccttcc ttgccaggac ctagagtttg ttcagttcca 1020
ccctacaggc atatatggtg ctggttgtct cattacggaa ggatgtcgtg gagagggagg 1080
cattctcatt aacagtcaag gcgaaaggtt tatggagcga tacgcccctg tcgcgaagga 1140
cctggcgtct agagatgtgg tgtctcggtc catgactctg gagatccgag aaggaagagg 1200
ctgtggccct gagaaagatc acgtctacct gcagctgcac cacctacctc cagagcagct 1260
ggccacgcgc ctgcctggca tttcagagac agccatgatc ttcgctggcg tggacgtcac 1320
gaaggagccg atccctgtcc tccccaccgt gcattataac atgggcggca ttcccaccaa 1380
ctacaagggg caggtcctga ggcacgtgaa tggccaggat cagattgtgc ccggcctgta 1440
cgcctgtggg gaggccgcct gtgcctcggt acatggtgcc aaccgcctcg ggcaaactc 1500 gctcttggac ctggttgtct ttggtcgggc atgtgccctg agcatcgaag agtcatgcag 1560
gcctggagat aaagtccctc caattaaacc aaacgctggg gaagaatctg tcatgaatct 1620
tgacaaattg agatttgctg atggaagcat aagaacatcg gaactgcgac tcagcatgca 1680
gaagtcaatg caaaatcatg ctgccgtgtt ccgtgtggga agcgtgttgc aagaaggttg 1740
tgggaaaatc agcaagctct atggagacct aaagcacctg aagacgttcg accggggaat 1800
ggtctggaac acggacctgg tggagaccct ggagctgcag aacctgatgc tgtgtgcgct 1860
gcagaccatc tacggagcag aggcacggaa ggagtcacgg ggcgcgcatg ccagggaaga 1920
ctacaaggtg cggattgatg agtacgatta ctccaagccc atccaggggc aacagaagaa 1980

```
gccctttgag gagcactgga ggaagcacac cctgtcctat gtggacgttg gcactgggaa   2040
ggtcactctg gaatatagac ccgtgatcga caaaactttg aacgaggctg actgtgccac   2100
cgtcccgcca gccattcgct cctactgatg agacaagatg tggtgatgac agaatcagct   2160
tttgtaatta tgtataatag ctcatgcatg tgtccatgtc ataactgtct tcatacgctt   2220
ctgcactctg gggaagaagg agtacattga agggagattg gcacctagtg gctgggagct   2280
tgccaggaac ccagtggcca gggagcgtgg cacttacctt tgtcccttgc ttcattcttg   2340
tgagatgata aaactgggca cagctcttaa ataaaatata aatgaacaaa ctttctttta   2400
tttccaaatc catttgaaat attttactgt tgtgacttta gtcatatttg ttgacctaaa   2460
aatcaaatgt aatctttgta ttgtgttaca tcaaaatcca gatattttgt atagtttctt   2520
ttttcttttt cttttctttt tttttttga gacaggatcg gtgcagtagt acaatcacag   2580
ctcactgcag cctcaaactc ctgggcagct caggtgatct tcctgactca gccttctgag   2640
tagttggggc tacaggtgtg caccaccatg cccagctcat ttattttgta attgtaggga   2700
cagggtctca ctgtgttgcc taggctggtc tcaagtgatc ctccctcctt ggcctcccaa   2760
ggtgctggaa ttataggtgt gaacaaacca aaaaaaaaaa aaa                      2803
```

```
<210> SEQ ID NO 31
<211> LENGTH: 1435
<212> TYPE: DNA
<213> ORGANISM: Homo sapiens

<400> SEQUENCE: 31

ggcggggcct gcttctcctc agcttcaggc ggctgcgacg agccctcagg cgaacctctc     60
ggctttcccg cgcggcgccg cctcttgctg cgcctccgcc tcctcctctg ctccgccacc    120
ggcttcctcc tcctgagcag tcagcccgcg cgccggccgg ctccgttatg gcgacccgca    180
gccctggcgt cgtgattagt gatgatgaac caggttatga ccttgattta ttttgcatac    240
ctaatcatta tgctgaggat ttggaaaggg tgtttattcc tcatggacta attatggaca    300
ggactgaacg tcttgctcga gatgtgatga aggagatggg aggccatcac attgtagccc    360
tctgtgtgct caaggggggc tataaattct ttgctgacct gctggattac atcaaagcac    420
tgaatagaaa tagtgataga tccattccta tgactgtaga ttttatcaga ctgaagagct    480
attgtaatga ccagtcaaca ggggacataa aagtaattgg tggagatgat ctctcaactt    540
taactggaaa gaatgtcttg attgtggaag atataattga cactggcaaa acaatgcaga    600
ctttgctttc cttggtcagg cagtataatc caaagatggt caaggtcgca agcttgctgg    660
tgaaaaggac cccacgaagt gttggatata agccagactt tgttggattt gaaattccag    720
acaagtttgt tgtaggatat gcccttgact ataatgaata cttcagggat ttgaatcatg    780
tttgtgtcat tagtgaaact ggaaaagcaa aatacaaagc ctaagatgag agttcaagtt    840
gagtttggaa acatctggag tcctattgac atcgccagta aaattatcaa tgttctagtt    900
ctgtggccat ctgcttagta gagctttttg catgtatctt ctaagaattt tatctgtttt    960
gtactttaga aatgtcagtt gctgcattcc taaactgttt atttgcacta tgagcctata   1020
gactatcagt tccctttggg cggattgttg tttaacttgt aaatgaaaaa attctcttaa   1080
accacagcac tattgagtga aacattgaac tcatatctgt aagaaataaa gagaagatat   1140
attagttttt taattggtat tttaattttt atatatgcag gaaagaatag aagtgattga   1200
atattgttaa ttataccacc gtgtgttaga aaagtaagaa gcagtcaatt ttcacatcaa   1260
agacagcatc taagaagttt tgttctgtcc tggaattatt ttagtagtgt ttcagtaatg   1320
```

-continued

```
ttgactgtat tttccaactt gttcaaatta ttaccagtga atctttgtca gcagttccct    1380

tttaaatgca aatcaataaa ttcccaaaaa tttaaaaaaa aaaaaaaaaa aaaaa         1435
```